United States Patent
Sagehashi et al.

(10) Patent No.: US 9,256,127 B2
(45) Date of Patent: Feb. 9, 2016

(54) MONOMER, POLYMER, RESIST COMPOSITION, AND PATTERNING PROCESS

(71) Applicant: Shin-Etsu Chemical Co., Ltd., Tokyo (JP)

(72) Inventors: Masayoshi Sagehashi, Joetsu (JP); Takayuki Fujiwara, Joetsu (JP); Koji Hasegawa, Joetsu (JP); Ryosuke Taniguchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/697,901

(22) Filed: Apr. 28, 2015

(65) Prior Publication Data

US 2015/0323865 A1     Nov. 12, 2015

(30) Foreign Application Priority Data

May 9, 2014   (JP) .................................. 2014-097347

(51) Int. Cl.
*C08F 24/00* (2006.01)
*C08F 28/06* (2006.01)
(Continued)

(52) U.S. Cl.
CPC ............ *G03F 7/0397* (2013.01); *C07D 307/83* (2013.01); *C07D 307/935* (2013.01);
(Continued)

(58) Field of Classification Search
None
See application file for complete search history.

(56) References Cited

U.S. PATENT DOCUMENTS 6,280,898 B1   8/2001   Hasegawa et al.
6,312,867 B1   11/2001   Kinsho et al.
(Continued)

FOREIGN PATENT DOCUMENTS

JP   3042618 B2    5/2000
JP   2000-336121 A  12/2000
(Continued)

*Primary Examiner* — Sin Lee
(74) *Attorney, Agent, or Firm* — Westerman, Hattori, Daniels & Adrian, LLP

(57) ABSTRACT

A polymer for resist use is obtainable from a monomer having formula (1) wherein $R^1$ is H, $CH_3$ or $CF_3$, $R^2$ and $R^3$ each are H or a monovalent hydrocarbon group, $X^1$ is a divalent hydrocarbon group, $k^1=0$ or 1, and Z forms a 5 or 6-membered alicyclic ring. A resist composition comprising the polymer is shelf stable and displays a high dissolution contrast, controlled acid diffusion and low roughness during both alkaline development and organic solvent development.

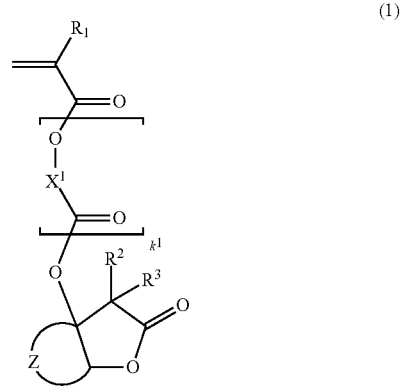

(1)

17 Claims, 1 Drawing Sheet

(51) Int. Cl.
*G03F 7/039* (2006.01)
*G03F 7/32* (2006.01)
*G03F 7/004* (2006.01)
*G03F 7/30* (2006.01)
*G03F 7/20* (2006.01)
*C07D 307/83* (2006.01)
*C07D 307/935* (2006.01)
*C07D 493/04* (2006.01)
*C07D 495/04* (2006.01)
*C08F 224/00* (2006.01)
*C08F 228/06* (2006.01)

(52) U.S. Cl.
CPC ............ *C07D493/04* (2013.01); *C07D 495/04* (2013.01); *C08F 24/00* (2013.01); *C08F 28/06* (2013.01); *C08F 224/00* (2013.01); *C08F 228/06* (2013.01); *G03F 7/0045* (2013.01); *G03F 7/0046* (2013.01); *G03F 7/2041* (2013.01); *G03F 7/30* (2013.01); *G03F 7/322* (2013.01); *G03F 7/325* (2013.01)

(56) References Cited

U.S. PATENT DOCUMENTS

| | | | |
|---|---|---|---|
| 7,339,014 B2 * | 3/2008 | Kamon | C07D 307/88 526/268 |
| 7,537,880 B2 | 5/2009 | Harada et al. | |
| 7,670,750 B2 | 3/2010 | Harada et al. | |
| 7,759,047 B2 | 7/2010 | Hatakeyama et al. | |
| 7,771,913 B2 | 8/2010 | Kaneko et al. | |
| 8,034,547 B2 | 10/2011 | Tsubaki et al. | |
| 8,114,571 B2 | 2/2012 | Ohashi et al. | |
| 8,241,840 B2 | 8/2012 | Tsubaki et al. | |
| 8,323,872 B2 | 12/2012 | Hatakeyama et al. | |
| 8,440,386 B2 | 5/2013 | Hatakeyama et al. | |
| 2008/0153030 A1 | 6/2008 | Kobayashi et al. | |
| 2011/0250539 A1 | 10/2011 | Sagehashi et al. | |
| 2012/0148945 A1 | 6/2012 | Hasegawa et al. | |
| 2013/0034813 A1 | 2/2013 | Ohsawa et al. | |
| 2014/0319552 A1 | 10/2014 | Komatsubara et al. | |

FOREIGN PATENT DOCUMENTS

| | | | |
|---|---|---|---|
| JP | 2006-146143 A | 6/2006 |
| JP | 3790649 B2 | 6/2006 |
| JP | 2007-25634 A | 2/2007 |
| JP | 3995575 B2 | 10/2007 |
| JP | 2007-297590 A | 11/2007 |
| JP | 2007-316448 A | 12/2007 |
| JP | 2008-3569 A | 1/2008 |
| JP | 2008-81716 A | 4/2008 |
| JP | 2008-111089 A | 5/2008 |
| JP | 2008-111103 A | 5/2008 |
| JP | 2008-122932 A | 5/2008 |
| JP | 2008-158339 A | 7/2008 |
| JP | 4131062 B2 | 8/2008 |
| JP | 2008-281974 A | 11/2008 |
| JP | 2008-281975 A | 11/2008 |
| JP | 2008-281980 A | 11/2008 |
| JP | 2009-158144 A | 7/2009 |
| JP | 2009-269953 A | 11/2009 |
| JP | 2011-221513 A | 11/2011 |
| JP | 2011-231312 A | 11/2011 |
| JP | 2012-128067 A | 7/2012 |
| JP | 2013-37092 A | 2/2013 |

* cited by examiner

MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2014-097347 filed in Japan on May 9, 2014, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the resist composition. The monomer is useful for the preparation of a polymer which is used as a base resin to formulate a radiation-sensitive resist composition having high transparency to radiation of wavelength 500 nm or less, especially 300 nm or less, typically KrF, ArF or $F_2$ laser radiation, and improved development properties.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

Besides the positive tone resist by alkaline development, a highlight is recently put on the negative tone resist by organic solvent development. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, alkaline development and organic solvent development is under study.

As the ArF resist composition for negative tone development with organic solvent, positive ArF resist compositions of the prior art design may be used. Such pattern forming processes are described in Patent Documents 1 to 3.

Independent of whether the resist material is subject to positive or negative tone development, methacrylate unit having an acid labile group is one of predominant constituent units relating to the basic function of the base resin in current chemically amplified resist materials. Likewise, lactone unit is an important unit that governs performance factors during resist pattern formation such as adhesion of base resin film to substrate. Heretofore, methacrylates of monocyclic lactone type such as butyrolactone ring or valerolactone ring and methacrylates of fused ring lactone units as typified by methacrylates of norbornane lactone have been proposed as disclosed in Patent Documents 4 to 6. Sultone units of cyclic sulfonic acid ester structure are also used for the same purpose as the lactone units (see Patent Document 7).

To meet the further miniaturization requirement, there is a desire to have a base resin unit capable of forming a fine size pattern of good profile with improved properties such as control of acid diffusion length and low roughness.

CITATION LIST

Patent Document 1: JP-A 2008-281974
Patent Document 2: JP-A 2008-281975
Patent Document 3: JP-A 2008-281980
Patent Document 4: JP 3042618
Patent Document 5: JP 4131062
Patent Document 6: JP-A 2006-146143
Patent Document 7: JP-A 2009-158144

DISCLOSURE OF INVENTION

In the current lithography for which further miniaturization is required, it is desired to meet controlled diffusion of acid generated upon exposure, good pattern profile, and low roughness. To this end, further collaboration must be made on the formulation of a base resin, typically of acid labile units and adhesive units, and the structure and function of additives including a photoacid generator and sensitivity adjustors such as a basic compound or quencher. In the negative tone development process under the recent study, the region which is retained after exposure and organic solvent development is the portion where acid labile units accounting for a large proportion in the base resin are deprotected so that the carbon density is reduced from that prior to the exposure. Then resistance during the etching step and the retention of pattern profile after etching become pending issues.

An object of the invention is to provide a resist composition which displays improved performance properties such as controlled acid diffusion and low roughness during both positive tone development and negative tone development. Specifically, an object of the invention is to provide a monomer, a polymer prepared from the monomer and suited for use in photoresist compositions, a resist composition comprising the polymer as a base resin, and a pattern forming process using the resist composition.

The inventors have found that a monomer having the general formula (1) defined below can be readily synthesized, and that a resist composition comprising a polymer resulting from the monomer as base resin is improved in performance properties such as acid diffusion control and roughness during both positive tone development and negative tone development.

A first embodiment of the invention provides a monomer having the general formula (1).

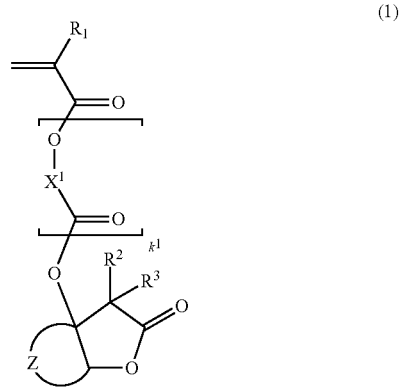

Herein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, and Z forms a 5 or 6-membered alicyclic group, which may contain a heteroatom, with the two carbon atoms to which it is attached.

A second embodiment provides a polymer comprising recurring units having the general formula (2).

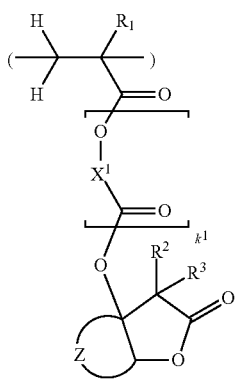

(2)

Herein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, and Z forms a 5 or 6-membered alicyclic group, which may contain a heteroatom, with the two carbon atoms to which it is attached.

The polymer may further comprise recurring units of at least one type selected from recurring units having the general formulae (A) to (E).

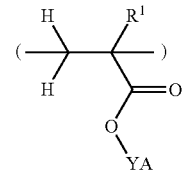

(A)

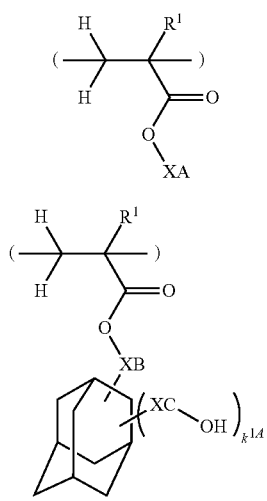

(B)

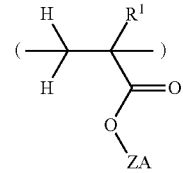

(C)

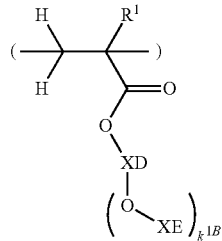

(D)

(E)

Herein $R^1$ is hydrogen, methyl or trifluoromethyl, XA is an acid labile group, XB and XC are each independently a single bond or a straight or branched, divalent hydrocarbon group of 1 to 4 carbon atoms, XD is a straight, branched or cyclic, di- to pentavalent aliphatic hydrocarbon group of 1 to 16 carbon atoms in which a constituent —$CH_2$— may be replaced by —O— or —C(=O)—, XE is an acid labile group, YA is a substituent group of lactone, sultone or carbonate structure, ZA is hydrogen, a fluoroalkyl group of 1 to 30 carbon atoms or a fluoroalcohol-containing group of 1 to 15 carbon atoms, $k^{1A}$ is an integer of 1 to 3, and $k^{1B}$ is an integer of 1 to 4.

The polymer may further comprise recurring units of at least one type selected from sulfonium salt units (d1) to (d3) represented by the following general formula.

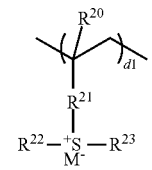

(d1)

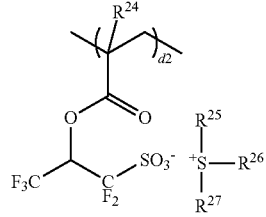

(d2)

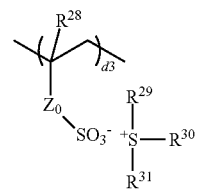

(d3)

Herein $R^{20}$, $R^{24}$, and $R^{28}$ each are hydrogen or methyl; $R^{21}$ is a single bond, phenylene, —O—$R^{33}$—, or —C(=O)—Y—

R—, wherein Y is oxygen or NH and $R^{33}$ is a straight, branched or cyclic $C_1$-$C_6$ alkylene group, alkenylene group or phenylene group, which may contain a carbonyl (—CO—), ester (—COO—), ether (—O—), or hydroxyl moiety; $R^{22}$, $R^{23}$, $R^{25}$, $R^{26}$, $R^{27}$, $R^{29}$, $R^{30}$, and $R^{31}$ each, independently a straight, branched or cyclic $C_1$-$C_{12}$ alkyl group which may contain a carbonyl, ester or ether moiety, a $C_6$-$C_{12}$ aryl group, a $C_7$-$C_{20}$ aralkyl group, or a thiophenyl group; $Z_0$ is a single bond, methylene, ethylene, phenylene, fluorinated phenylene, —O—$R^{32}$—, or —C(=O)—$Z_1$—$R^{32}$—, wherein $Z_1$ is oxygen or NH, and $R^{32}$ is a straight, branched or cyclic $C_1$-$C_6$ alkylene group, alkenylene group or phenylene group, which may contain a carbonyl, ester, ether or hydroxyl moiety; and $M^-$ is a non-nucleophilic counter ion.

A third embodiment provides a resist composition comprising a base resin containing the polymer defined above, an acid generator, and an organic solvent; or a resist composition comprising a base resin containing the polymer defined above, and an organic solvent.

A fourth embodiment provides a pattern forming process comprising the steps of applying the resist composition defined above onto a substrate, prebaking to form a resist film, exposing the resist film to high-energy radiation, baking, and developing the exposed resist film in a developer.

In a preferred embodiment, an aqueous alkaline solution is used as the developer in the developing step to form a positive pattern wherein the exposed region of resist film is dissolved away and the unexposed region of resist film is not dissolved.

In another preferred embodiment, an organic solvent is used as the developer in the developing step to form a negative pattern wherein the unexposed region of resist film is dissolved away and the exposed region of resist film is not dissolved. Preferably, the developer comprises at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Preferably, the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

A fifth embodiment provides a method for preparing a monomer having the general formula (1), comprising the steps of reacting a compound having the general formula (6) with a base or metal to form a metal enolate reagent, and reacting it with an acyloxyketone having the general formula (5).

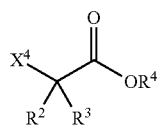

(6)

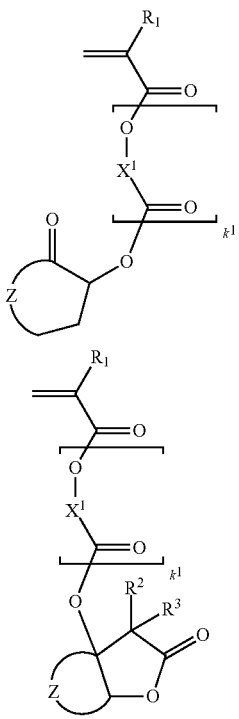

(5)

(1)

Herein $R^1$, $R^2$, $R^3$, $X^1$, $k^1$, and Z are as defined above, $X^4$ is hydrogen or halogen, and $R^4$ is a straight, branched or cyclic, monovalent hydrocarbon group of 1 to 10 carbon atoms.

A sixth embodiment provides a method for preparing a monomer having the general formula (1), comprising the steps of reacting a compound having the general formula (6) with a base or metal to form a metal enolate reagent, reacting it with an acyloxyketone having the general formula (5), isolating a hydroxy ester compound having the general formula (7b), and treating it with an acid.

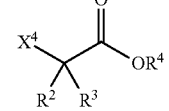

(6)

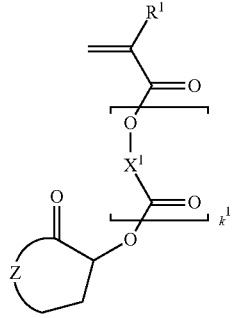

(5)

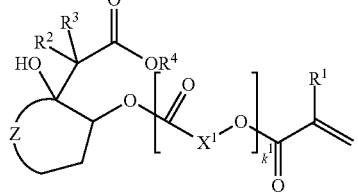

(7b)

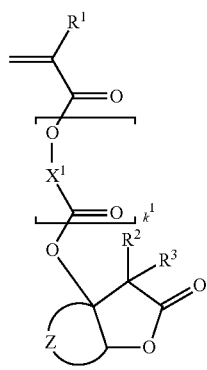
(1)

Herein $R^1$, $R^2$, $R^3$, $X^1$, $k^1$, Z, $X^4$ and $R^4$ are as defined above.

Preferably, the acyloxyketone having the general formula (5) is obtained by reacting a cycloalkanone compound having the general formula (3) with an esterifying agent having the general formula (4).

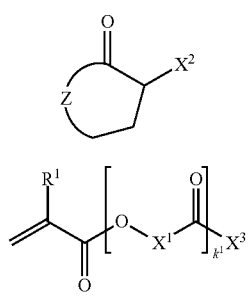
(3)
(4)

Herein $R^1$, $X^1$, Z and $k^1$ are as defined above, $X^2$ is halogen or hydroxyl, $X^3$ is —$OM^b$, halogen, hydroxyl or —$OR^{14}$, $M^b$ is Li, Na, K, $Mg_{1/2}$, $Ca_{1/2}$, or substituted or unsubstituted ammonium, and $R^{14}$ is methyl, ethyl or a group of the formula (9):

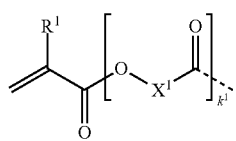
(9)

wherein $R^1$, $X^1$ and $k^1$ are as defined above, and the broken line denotes a valence bond.

A still further embodiment provides a method for preparing a monomer having the general formula (1), comprising the step of reacting a hydroxylactone compound having the general formula (66) with an esterifying agent having the general formula (88).

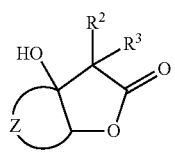
(66)

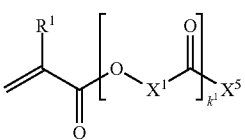
(88)

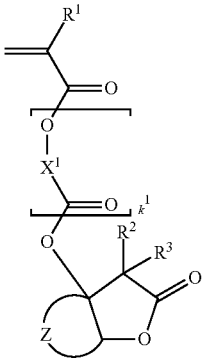
(1)

Herein $R^1$, $R^2$, $R^3$, $X^1$, $k^1$, and Z are as defined above, $X^5$ is halogen, hydroxyl or —$OR^{14}$, and $R^{14}$ is methyl, ethyl or a group of the formula (9):

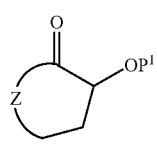
(9)

wherein $R^1$, $X^1$ and $k^1$ are as defined above, and the broken line denotes a valence bond.

Preferably, the hydroxylactone compound having the general formula (66) is obtained from reaction of a ketone compound of the general formula (33) wherein $P^1$ is a protective group with a compound having the general formula (6) and a base or metal to form a hydroxy ester compound having the general formula (44), deprotection of protective group $P^1$, and acid treatment.

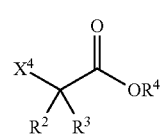
(33)

(6)

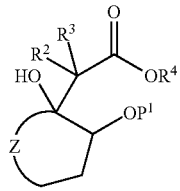
(44)

9

-continued

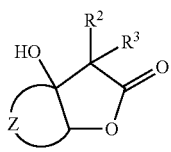
(66)

Herein $R^2$, $R^3$ and Z are as defined above, $P^1$ is a protective group, $X^4$ is hydrogen or halogen, and $R^4$ is a straight, branched or cyclic, monovalent hydrocarbon group of 1 to 10 carbon atoms.

Also preferably, the hydroxylactone compound having the general formula (66) is obtained from reaction of a ketone compound of the general formula (33) wherein $P^1$ is hydrogen with a compound having the general formula (6) and a base or metal:

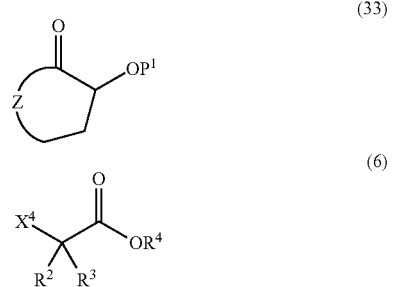

Herein $P^1$ is hydrogen, $R^2$, $R^3$, Z, $X^4$, and $R^4$ are as defined above.

ADVANTAGEOUS EFFECTS OF INVENTION

When a polymer comprising recurring units derived from the inventive monomer is used as base resin in a resist composition, the resulting resist composition is improved in acid diffusion control and roughness performance in either of positive tone development and negative tone development and is thus capable of forming a fine line-and-space pattern which is resistant to pattern collapse during formation and has improved etch resistance.

DESCRIPTION OF EMBODIMENTS

Figure 1A:
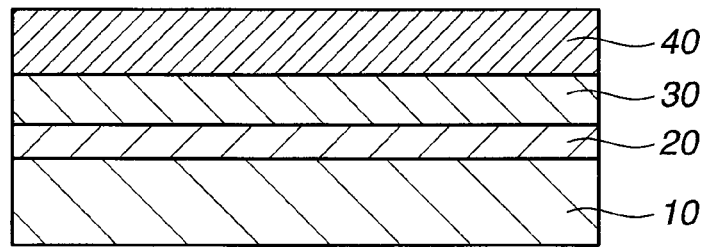
FIG. 1 schematically illustrates in cross-sectional views the pattern forming process of the invention, FIG. 1 (A) shows a photoresist film formed on a substrate, FIG. 1 (B) shows the photoresist film being exposed, and FIG. 1 (C) shows the photoresist film being developed in organic solvent.

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond; Me stands for methyl, Ph for phenyl, and Ac for acetyl.

The abbreviations and acronyms have the following meaning.

EB: electron beam
EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake
LWR: line width roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Monomer

In the first embodiment, the invention provides a monomer having the general formula (1).

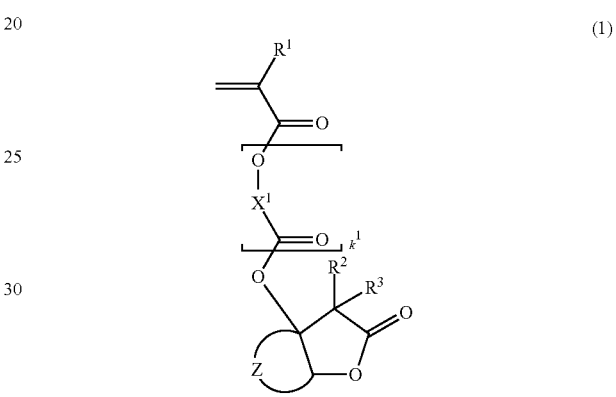

Herein $R^1$ is hydrogen, methyl or trifluoromethyl, $R^2$ and $R^3$ are each independently hydrogen or a straight, branched or cyclic $C_1$-$C_{10}$ monovalent hydrocarbon group, $R^2$ and $R^3$ may bond together to form a $C_5$-$C_{10}$ alicyclic group, which may be separated by an oxygen atom or have a carbon chain, with the carbon atom to which they are attached, $X^1$ is a straight, branched or cyclic $C_1$-$C_{20}$ divalent hydrocarbon group in which a constituent —$CH_2$— may be replaced by —O— or —C(=O)—, $k^1$ is 0 or 1, and Z forms a 5 or 6-membered alicyclic group, which may contain a heteroatom, with the two carbon atoms to which it is attached.

In formula (1), typical examples of the straight, branched or cyclic $C_1$-$C_{10}$ monovalent hydrocarbon group represented by $R^2$ and $R^3$ are straight, branched or cyclic alkyl groups including methyl, ethyl, propyl, isopropyl, n-butyl, sec-butyl, tert-butyl, cyclopentyl, cyclohexyl, 2-ethylhexyl, n-octyl, norbornyl, tricyclodecanyl, and adamantyl. When $R^2$ and $R^3$ bond together to form a $C_5$-$C_{10}$ alicyclic group with the carbon atom to which they are attached, examples of the alicyclic group which may be separated by an oxygen atom or have a carbon chain include 5 or 6-membered rings such as cyclopentane and cyclohexane rings as well as norbornane, oxanorbornane, and adamantane rings.

Examples of the straight, branched or cyclic $C_1$-$C_{20}$ divalent hydrocarbon group represented by $X^1$ are shown below.

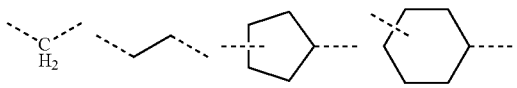

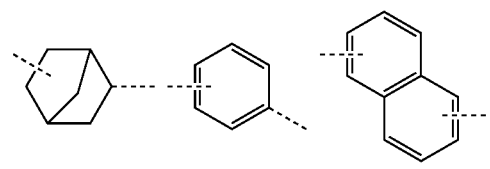
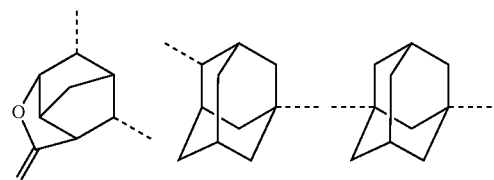
Examples of the optionally heteroatom-containing 5 or 6-membered alicyclic group represented by Z are shown below.
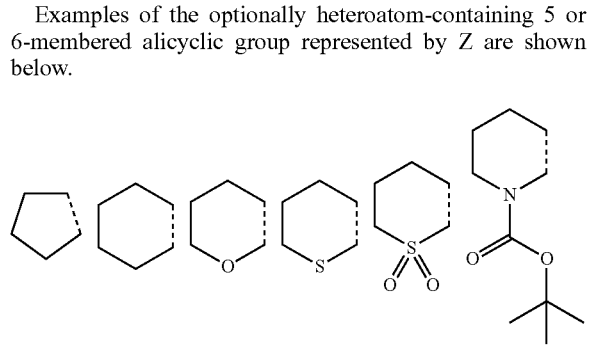
It is noted that the broken line denotes a bond between two carbon atoms to which Z is attached.
Examples of the monomer having formula (1) are given below.
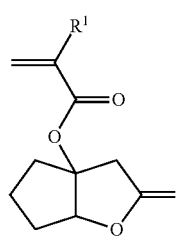
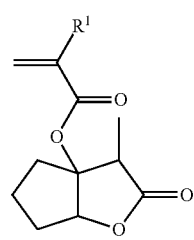
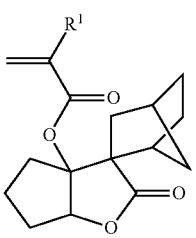
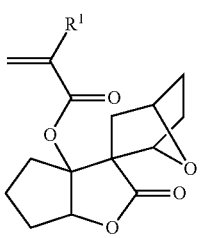

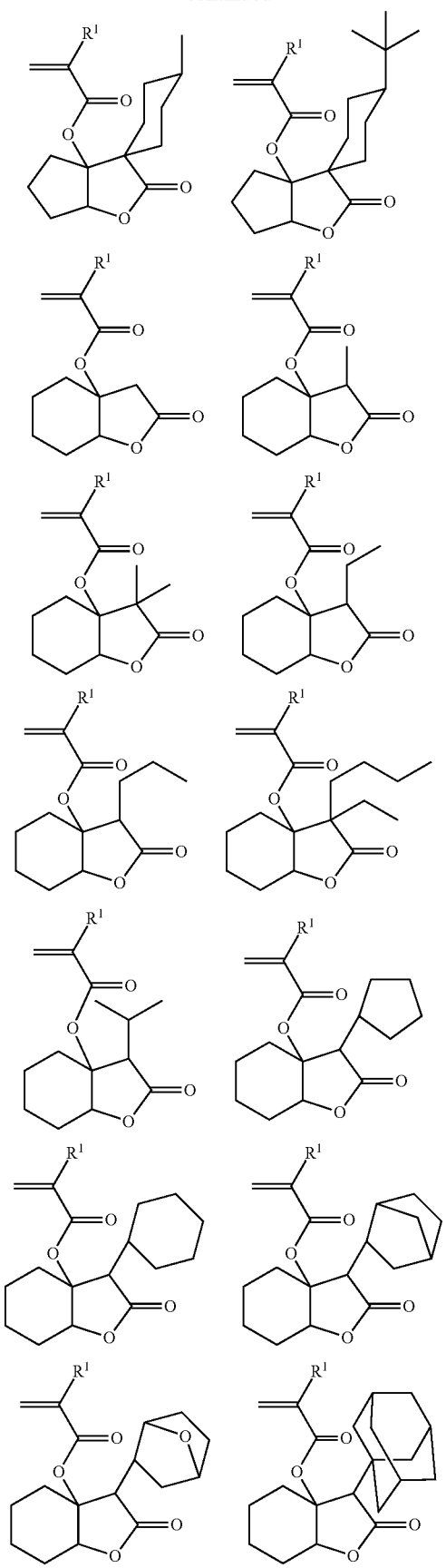
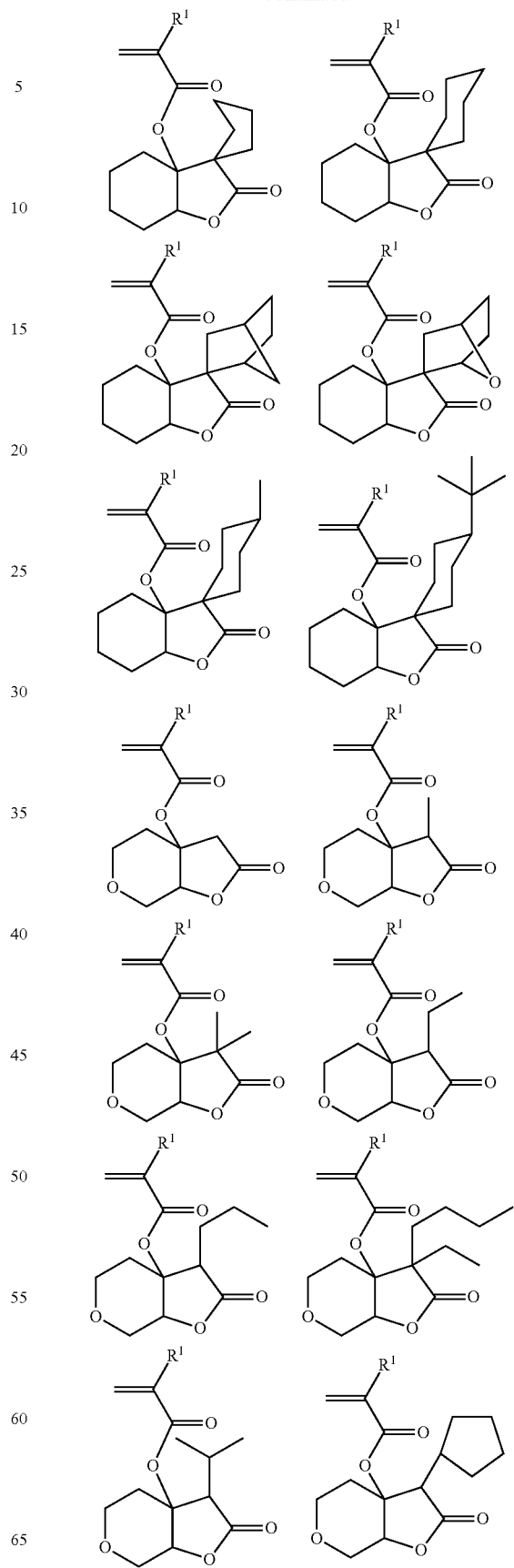

15
-continued
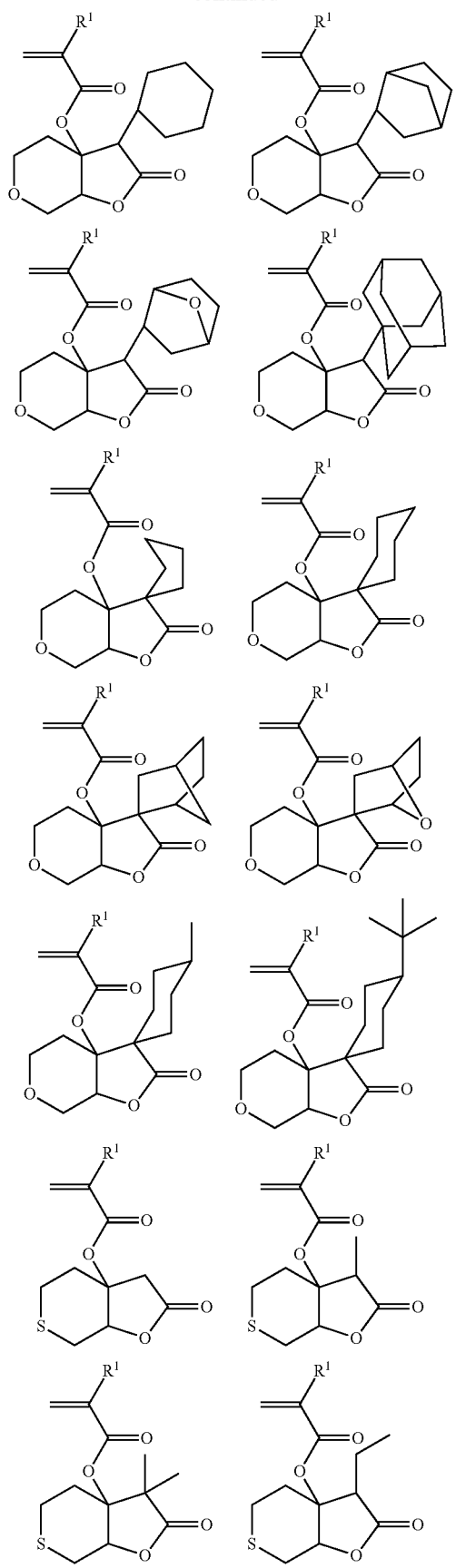
16
-continued
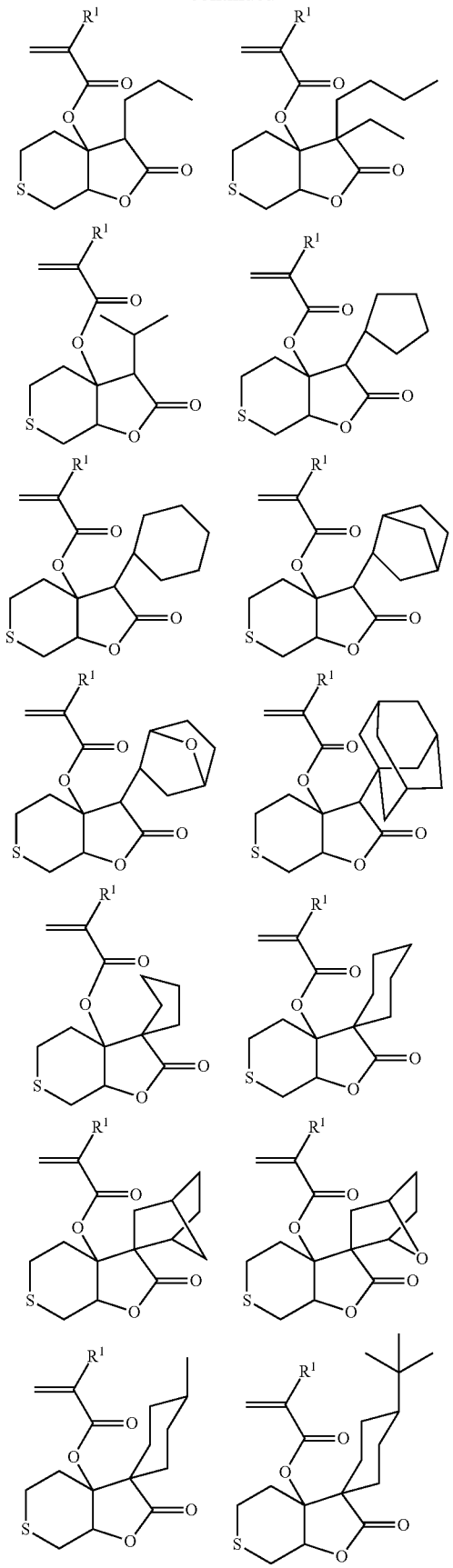

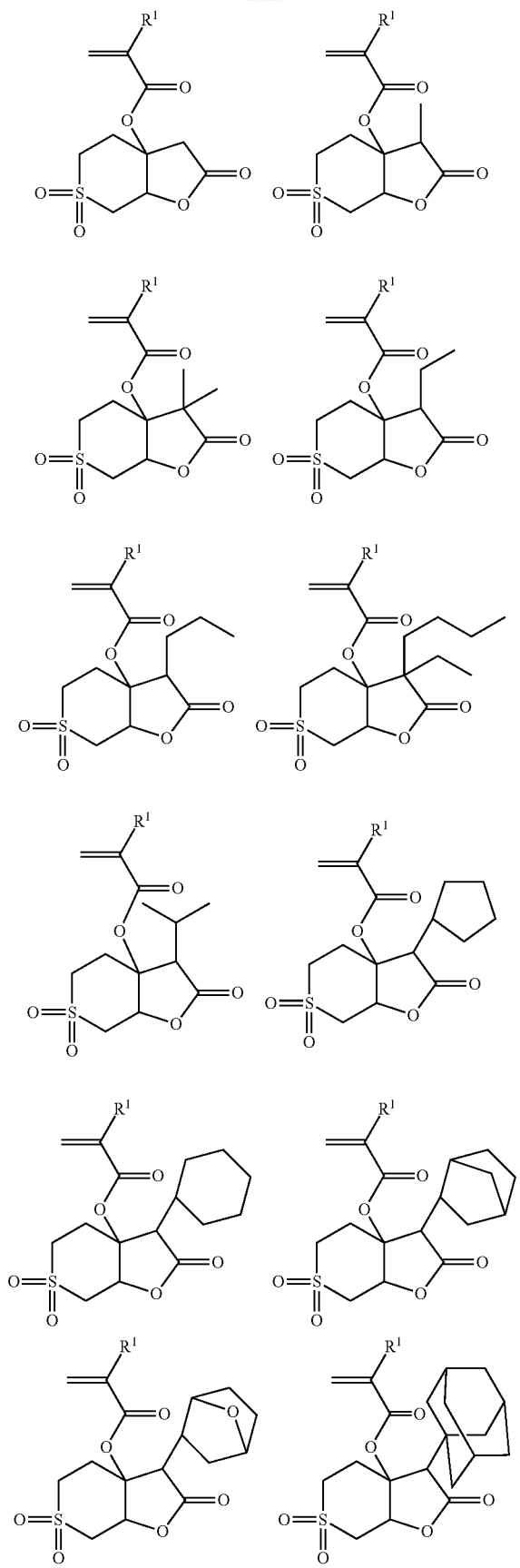
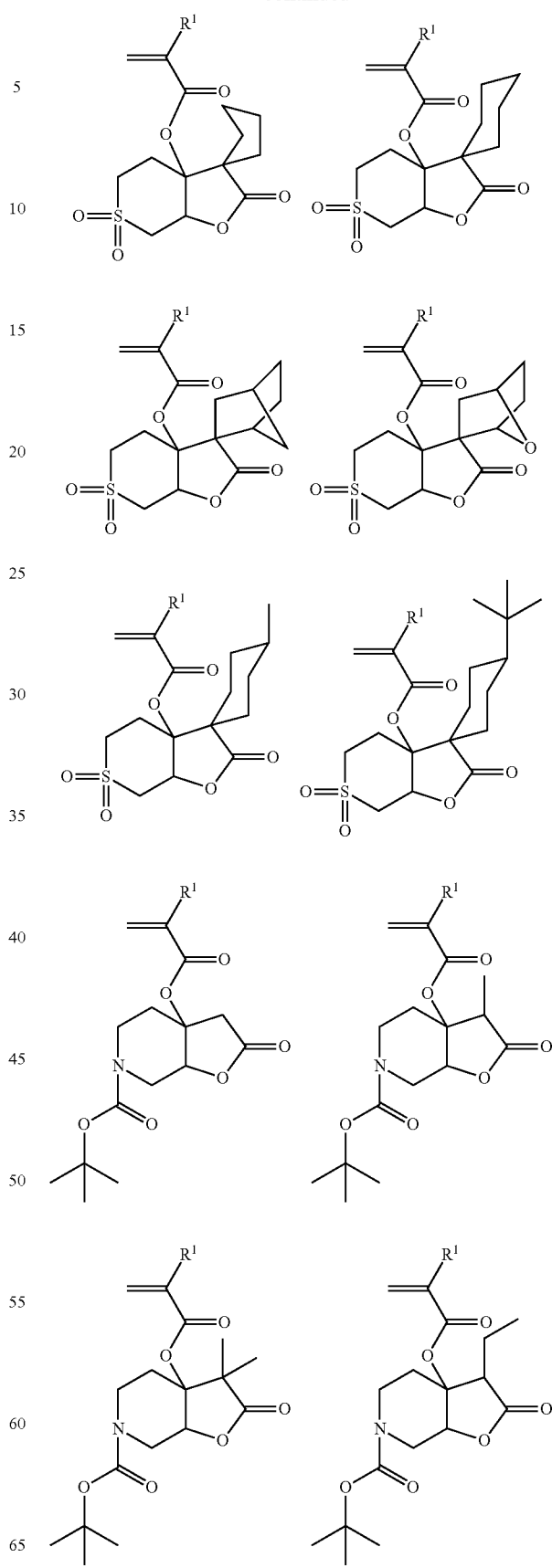

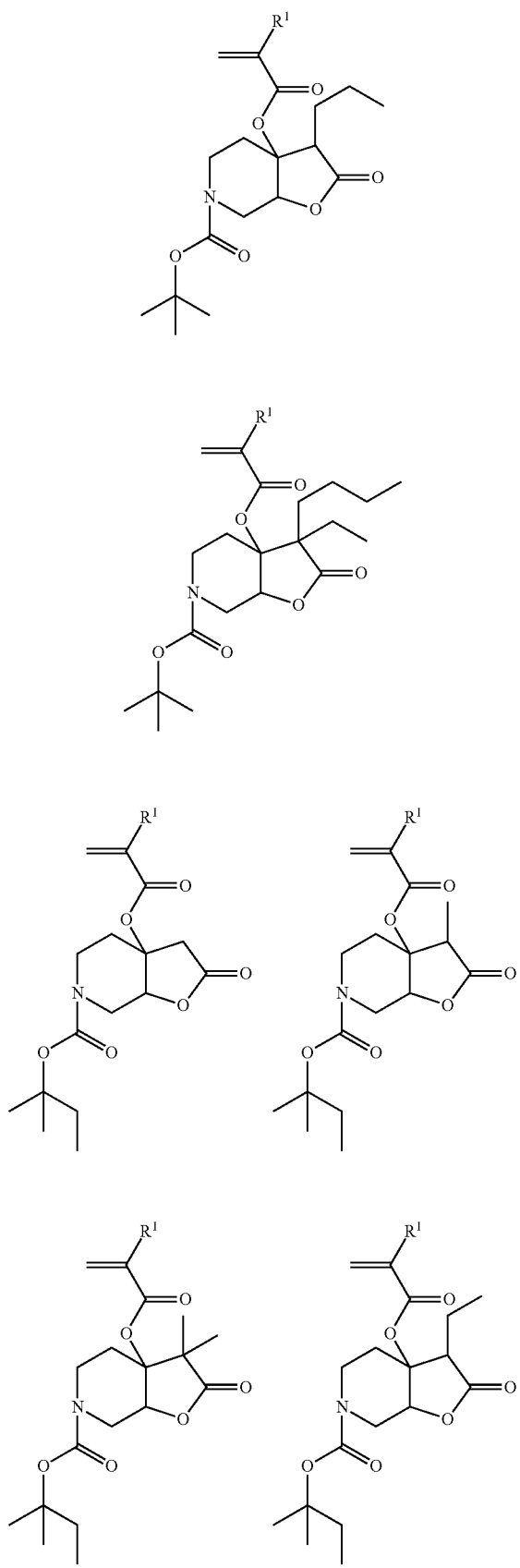

21
-continued
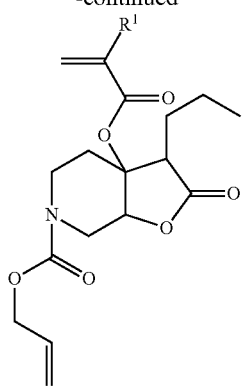
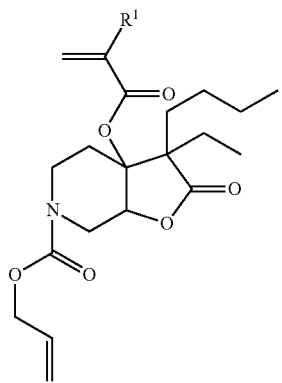
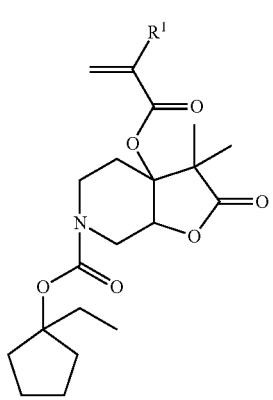 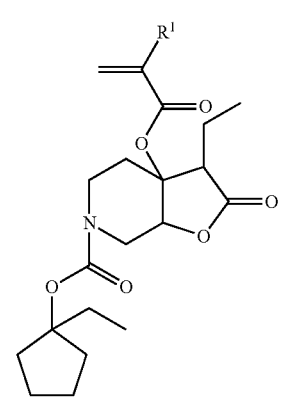
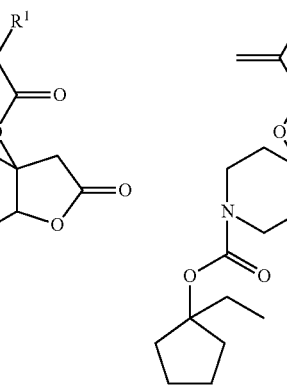
22
-continued
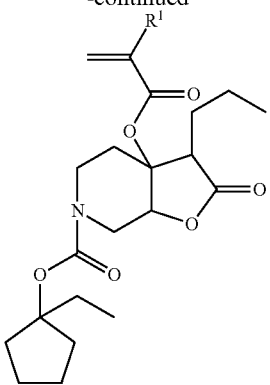
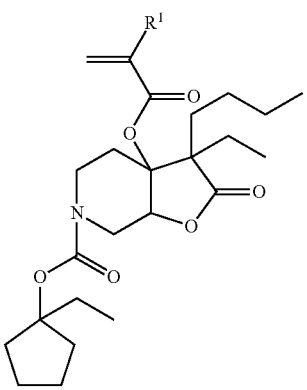
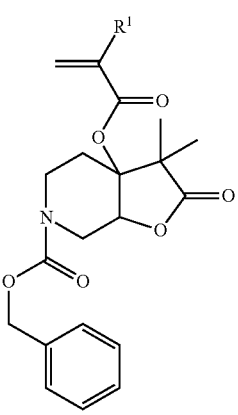 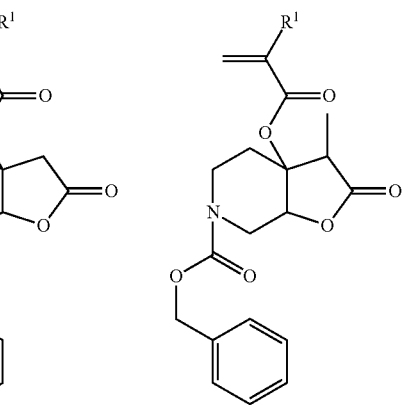
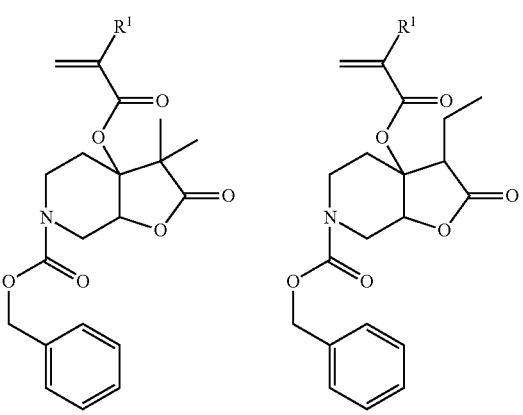

23
-continued
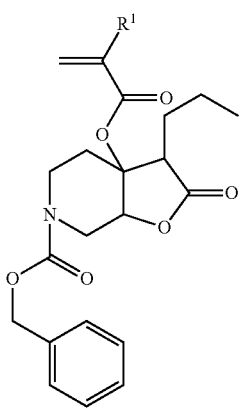
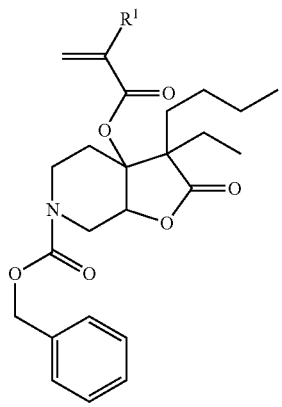
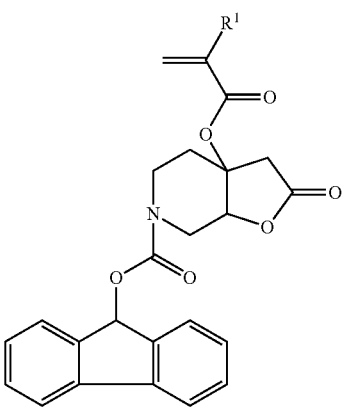
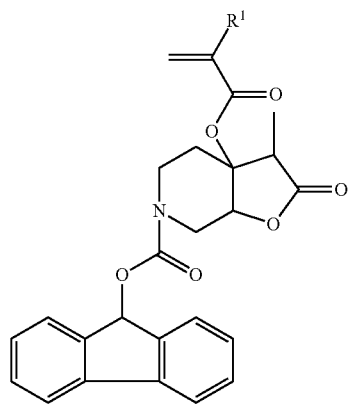
24
-continued
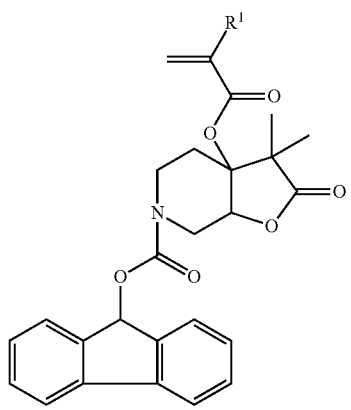
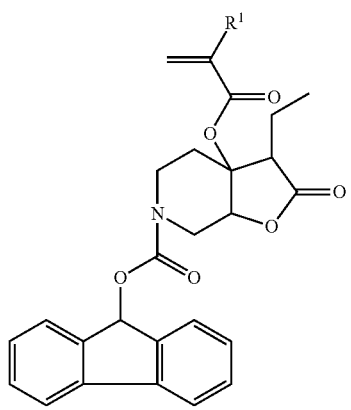
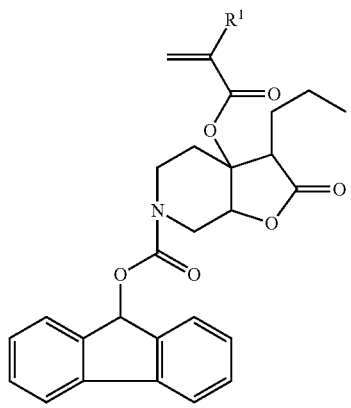
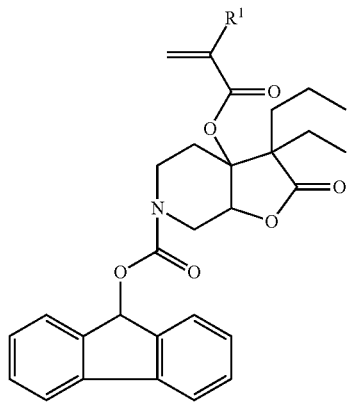

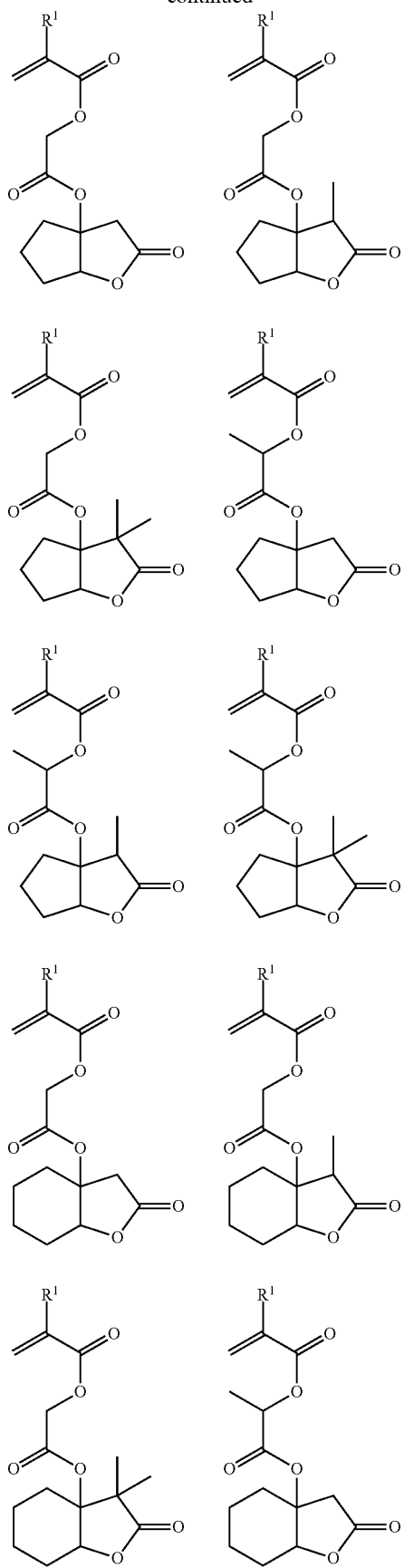
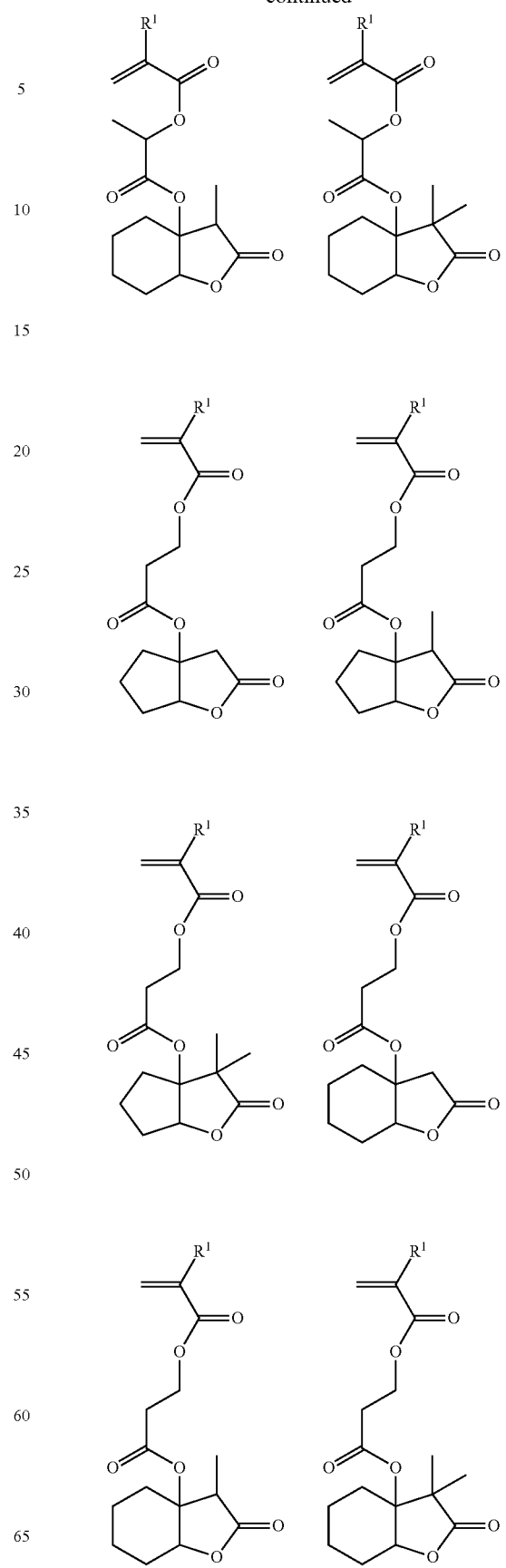

-continued
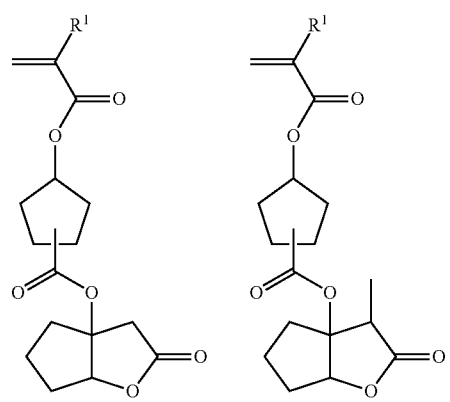
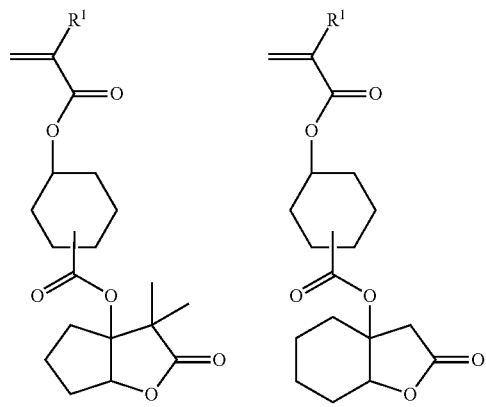
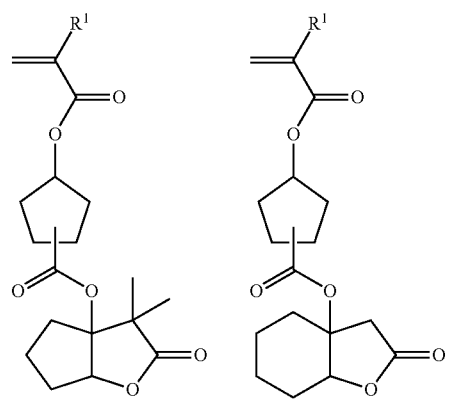
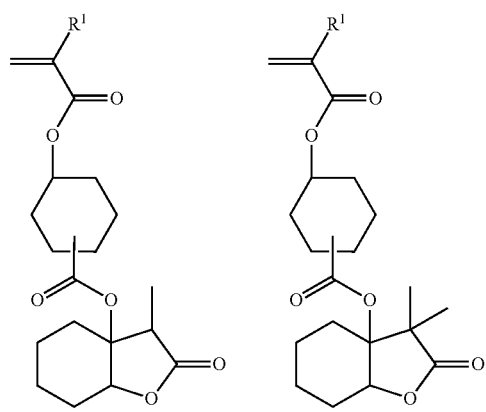
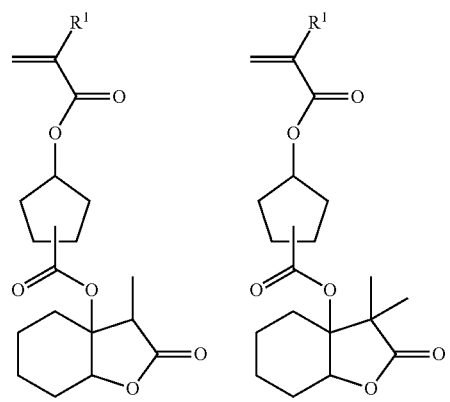
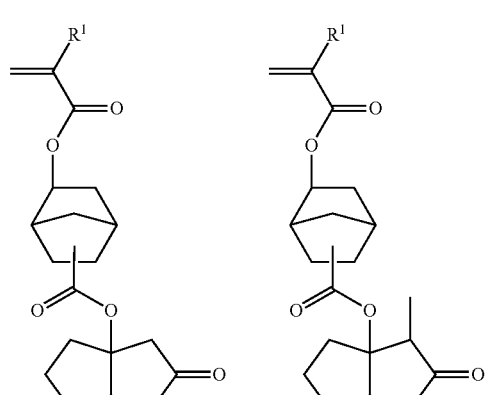
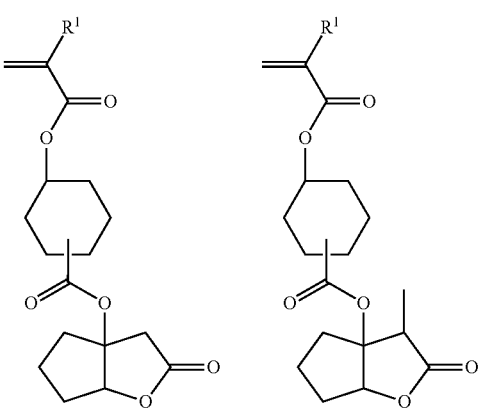
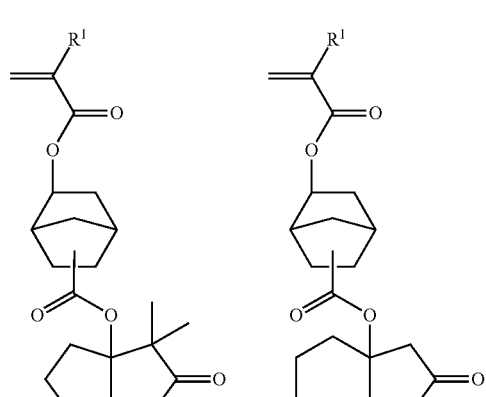

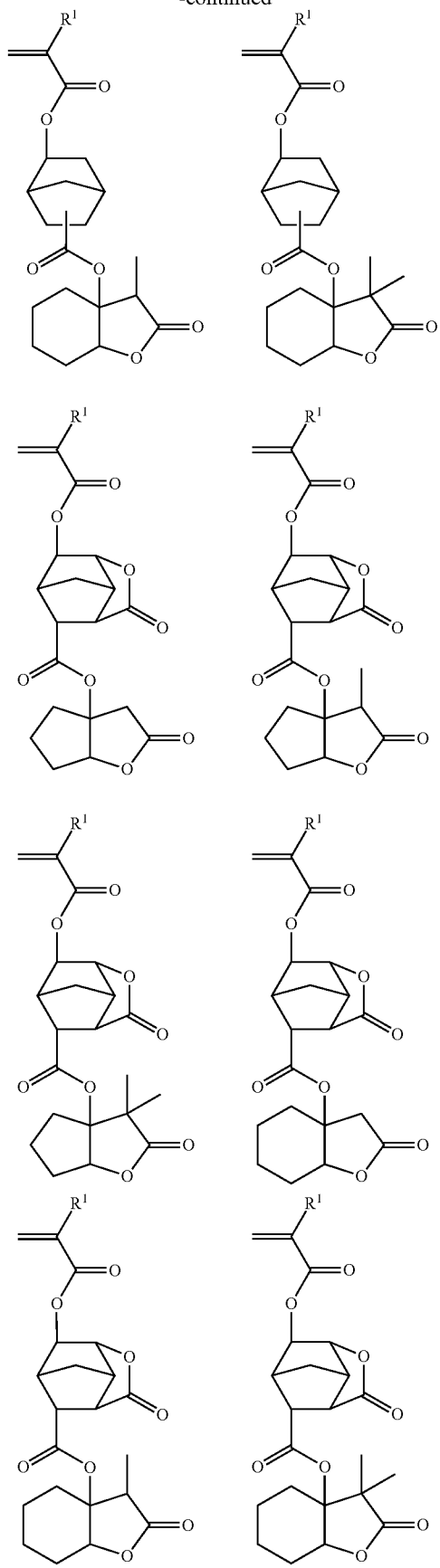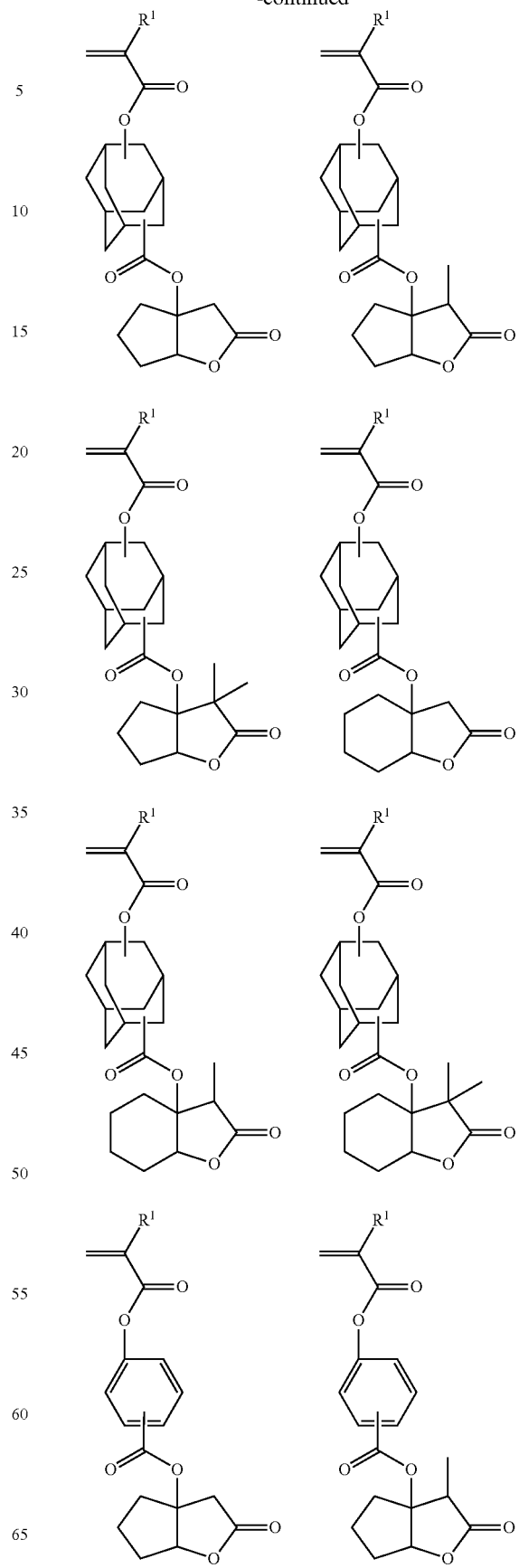

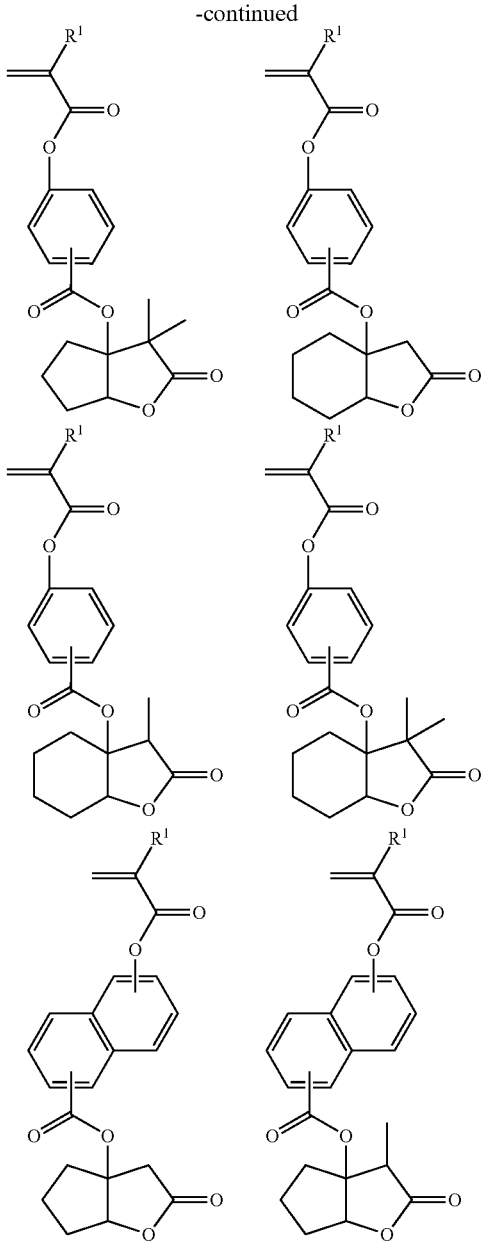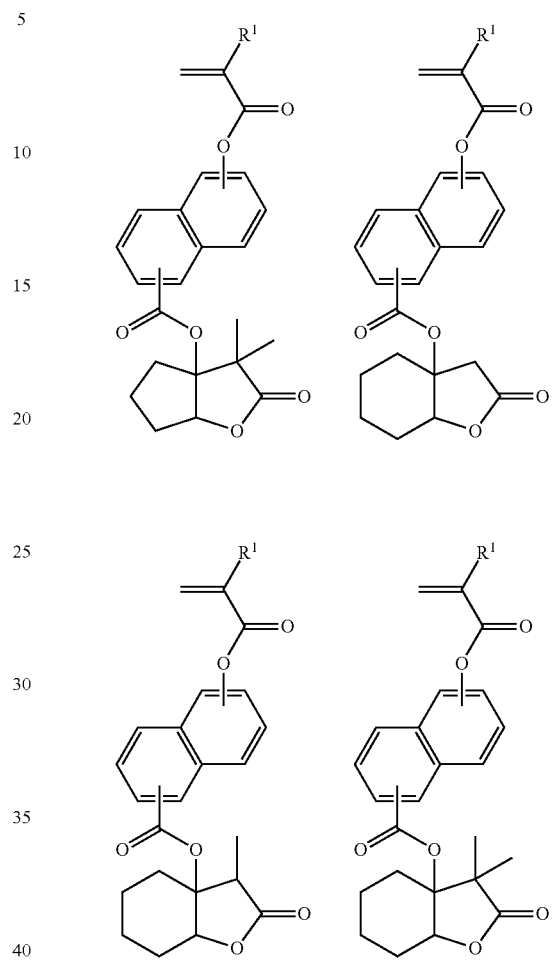
Herein $R^1$ is as defined above.
The monomer having formula (1) may be prepared according to the reaction scheme shown below although the synthesis route is not limited thereto.
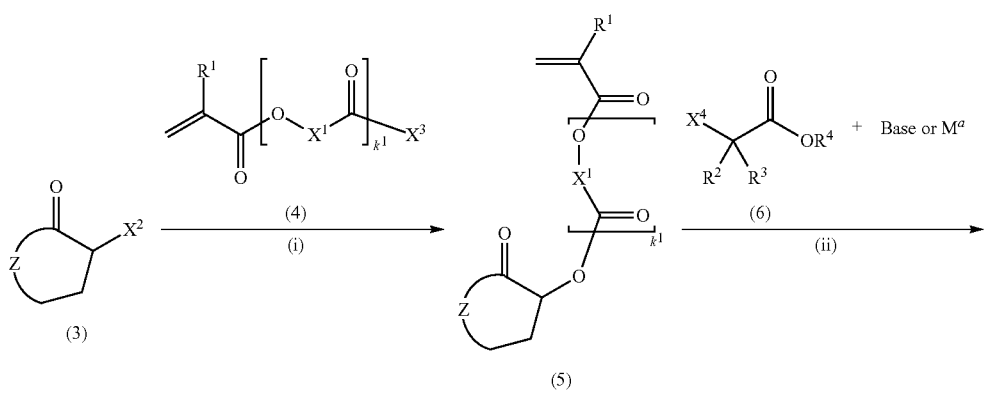

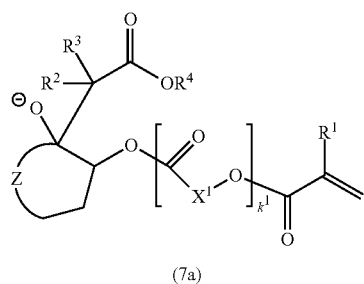

(7a)

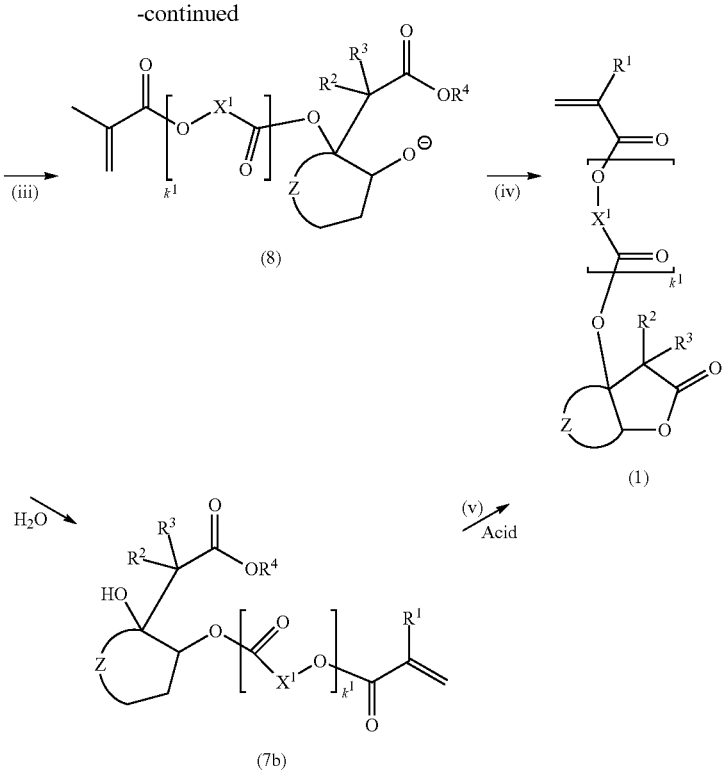

(8)

(1)

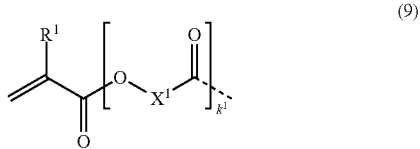

(7b)

Herein $R^1$ to $R^3$, $X^1$, z and $k^1$ are as defined above. $R^4$ is a straight, branched or cyclic $C_1$-$C_{10}$ monovalent hydrocarbon group. $X^2$ is halogen or hydroxyl. $X^3$ is —$OM^b$, halogen, hydroxyl or —$OR^{14}$. $M^b$ is Li, Na, K, $Mg_{1/2}$, $Ca_{1/2}$ or substituted or unsubstituted ammonium. $R^{14}$ is methyl, ethyl or a group of the formula (9):

$$\text{(9)}$$

wherein $R^1$, $X^1$ and $k^1$ are as defined above. $X^4$ is hydrogen or halogen. $M^a$ is a metal.

Described below is the method for preparing the monomer having formula (1) according to the above reaction scheme.

Step (i) is a reaction of cycloalkanone compound (3) with esterifying agent (4) to form acyloxy-ketone (5).

The reaction may readily run by a well-known procedure. As one reactant, cycloalkanone compound (3) which is substituted with substituent $X^2$ at α-position, wherein $X^2$ is halogen, for example, any of commercially available α-halocycloalkanones such as 2-chlorocyclopentanone, 2-chlorocyclohexanone, and 2-bromocyclohexanone may be used. Also useful are derivatives synthesized by chlorinating or brominating various cycloalkanones at α-position by standard technique. As the cycloalkanone compound (3) wherein $X^2$ is hydroxyl, commercially available alkanones such as 2-hydroxycyclohexanone may be used. For the availability of reactant, it is preferred that $X^2$ be halogen. Although the esterifying agent (4) varies with a particular cycloalkanone compound (3) used as one reactant, it is preferred that an α-halocycloalkanone of formula (3) wherein $X^2$ is halogen is reacted with a carboxylic acid salt compound of formula (4) wherein $X^3$ is —$OM^b$ because this compound is readily available. When a cycloalkanone compound (3) wherein $X^2$ is hydroxyl is used, the esterifying agent (4) is preferably selected from (meth)acrylic acid chloride, methyl (meth)acrylate, and (meth)acrylic acid, for example.

When a carboxylic acid salt compound acts as the esterifying agent on an α-halocycloalkanone, any of commercially available carboxylic acid salt compounds such as carboxylic acid metal salts may be used as such. Alternatively, a corresponding carboxylic acid such as methacrylic acid or acrylic acid and a base are added to a reaction system where a carboxylic acid salt compound is formed therefrom. An appropriate amount of esterifying agent (4) used is 0.5 to 10 moles, more preferably 1.0 to 3.0 moles per mole of cycloalkanone compound (3). If the esterifying agent is less than 0.5 mole, a large fraction of the reactant is left unreacted, with a substantial drop of yield. More than 10 moles of the esterifying agent may be uneconomical because of the increased amount of the agent and a lowering of pot yield. In the alternative where a carboxylic acid salt compound is formed in situ from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate; metals such as sodium; metal hydrides such as sodium hydride; metal alkoxides such as sodium methoxide and potassium tert-butoxide; organometallic compounds such as butyl lithium and ethylmagnesium bromide; and metal amides such as lithium diisopropylamide, which may be used alone or in admixture. An appropriate amount of the base used is 0.2 to 10 moles, more preferably 0.5 to 2.0 moles per mole of the corresponding carboxylic acid. If the base is less than 0.2 mole, a large fraction of the carboxylic acid may become waste, which is uneconomical. More than 10 moles of the base may promote side reactions, with a substantial drop of yield.

A solvent may be used for the reaction of step (i). Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. To the reaction system, a phase transfer catalyst such as tetrabutylammonium hydrogensulfate may be added. An appropriate amount of the phase transfer catalyst added is 0.0001 to 1.0 mole, more preferably 0.001 to 0.5 mole per mole of the alkanone compound. Less than 0.0001 mole of the phase transfer catalyst may fail to exert catalytic effect whereas more than 1.0 mole may be uneconomical because of the increased catalyst cost.

The esterification reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is especially preferred. Since substantial side reactions may occur at elevated temperatures, it is crucial in achieving high yields to carry out the reaction at a temperature as low as possible within the range where reaction proceeds at a practically acceptable rate. It is desired for higher yields that the reaction time be determined by monitoring the progress of reaction by thin-layer chromatography (TLC) or gas chromatography (GC). The reaction time is usually about 30 minutes to about 40 hours. The acyloxy-ketone (5) may be recovered from the reaction mixture by ordinary aqueous work-up. If necessary, it can be purified by any standard technique such as distillation, recrystallization or chromatography.

Steps (ii) to (iv) are to obtain monomer (1) in one-pot through reaction of a corresponding ester of formula (6) wherein $X^4$ is hydrogen or halo-ester wherein $X^4$ is halogen with a base or metal to form a metal enolate reagent, effecting nucleophilic addition reaction of the enolate to the ketone site of acyloxy-ketone (5), forming intermediate (7a) and then intermediate (8).

Examples of the base used herein include, but are not limited to, metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, magnesium diisopropylamide bromide; alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogencarbonate, lithium carbonate, and potassium carbonate; metal hydrides such as boran, alkylboran, sodium hydride, lithium hydride, potassium hydride, and calcium hydride; alkyl metal compounds such as trityl lithium, trityl sodium, trityl potassium, methyl lithium, phenyl lithium, sec-butyl lithium, tert-butyl lithium, and ethylmagnesium bromide; metals such as lithium, sodium, potassium, magnesium and zinc. It is noted that reaction using halo-ester and zinc is known as Reformatsky reaction. Among others, Reformatsky reaction is preferred because of possible preparation and handling of metal enolate reagent under mild temperature conditions and a high selectivity of reaction at the ketone site of acyloxyketone (5).

The Reformatsky reaction may be conducted by a well-known procedure. For example, a procedure of simultaneously adding dropwise halo-ester compound of formula (6) wherein $X^4$ is halogen, typically bromine, such as α-bromoester and acyloxy-ketone (5) to a suspension of metallic zinc in an ether such as tetrahydrofuran is preferred because monomer (1) is obtained in high yields. An appropriate amount of acyloxy-ketone (5) used is 0.5 to 10 moles, more preferably 0.8 to 3.0 moles per mole of the reactant, ester compound (6). If acyloxy-ketone (5) is less than 0.5 mole, a large fraction of the reactant may be left unreacted, with a substantial drop of yield. More than 10 moles of acyloxy-ketone (5) may be uneconomical because of an increase of material amount and a lowering of pot yield.

For the Reformatsky reaction, an appropriate reaction temperature may be selected in accordance with other reaction conditions. A temperature in the range of 40 to 65° C., especially 50 to 60° C. is preferred because at too low temperature, the reaction may stop at the stage of intermediate (7a) or step (ii).

It is believed that a series of reactions run such that an intermediate (7a) having organic zinc reagent added to the ketone site of acyloxy-ketone (5) forms in step (ii); then an intermediate (8) forms via rearrangement reaction of acyl group in step (iii); finally lactonization takes place in step (iv) to form the desired monomer (1).

The reaction time is determined as appropriate for yield improvement by monitoring the reaction process by thin-layer chromatography (TLC) or gas chromatography (GC). The reaction time is usually about 30 minutes to about 2 hours because long-term aging allows for anionic polymerization to invite a drop of monomer yield. Monomer (1) may be recovered from the reaction mixture by ordinary aqueous work-up. If necessary, the monomer may be purified by standard techniques like distillation, recrystallization and chromatography.

If the conversion rate of one-pot lactonization from intermediate (7a) to monomer (1) via intermediate (8) is low, an alternative route may be followed. Once addition product (7b) of step (ii) is isolated, step (v) of acid treatment is carried out to obtain monomer (1) in high yields. Since the reaction terminates at the stage of addition product (7a) where a bulky ester such as tert-butyl ester or tert-amyl ester is selected as ester compound (6), hydroxy-ester compound (7b) may be isolated from the reaction mixture by aqueous work-up.

Usually, hydroxy-ester compound (7b) is available in a sufficient purity for direct use in the subsequent step (v) of acid treatment. If necessary, it may be purified by standard techniques like distillation, recrystallization and chromatography.

Step (v) is acid treatment of hydroxy-ester compound (7b) into the desired monomer (1). Step (v) is carried out by diluting hydroxy-ester compound (7b) with a solvent, adding an acid catalyst, heating and stirring the mixture for reaction. Although the precise mechanism is not well understood, like steps (ii) to (iv), lactonization takes place through the mechanism that the acyl group of hydroxy-ester compound (7b) transfers to the adjacent tertiary hydroxyl group in the presence of the acid catalyst.

Examples of the solvent used in the acid treatment reaction include hydrocarbons such as toluene, xylene, hexane, and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. Notably, the reaction may also be conducted in a solventless system.

Suitable acid catalysts include mineral acids such as hydrochloric acid, sulfuric acid, nitric acid and perchloric acid, organic acids such as methanesulfonic acid, trifluoromethanesulfonic acid, p-toluenesulfonic acid, and benzenesulfonic acid, and Lewis acids such as boron trifluoride, trimethylsilyl triflate, aluminum chloride, and titanium chloride. An appropriate amount of the acid used is 0.01 to 3 moles, more preferably 0.05 to 0.5 mole per mole of the reactant, hydroxy-ester compound (7b). Less than 0.01 mole of the acid may invite an economic disadvantage because of a slow reaction rate and longer reaction time. More than 3 moles may incur side reactions due to strong acidity.

For the acid treatment, an appropriate reaction temperature may be selected in accordance with other reaction conditions. In most cases, a temperature of 40 to 60° C. is preferred because reaction does not take place at lower temperatures. The reaction time is determined as appropriate for yield improvement by monitoring the reaction process by thin-layer chromatography (TLC) or gas chromatography (GC). The reaction time is usually about 2 hours to about 1 day. At the end of reaction, monomer (1) may be recovered from the reaction mixture by ordinary aqueous work-up. If necessary, the monomer may be purified by standard techniques like distillation, recrystallization and chromatography.

The method for the synthesis of monomer (1) according to the reaction scheme illustrated above has advantages like short steps and simple reaction operation. In a certain case, however, a compound having a polymerizable acyloxy group is subject to reactions in many stages. Then any intermediate having a polymerizable group requires careful handling so as to prevent polymerization during reactions and storage until the desired monomer (1) is obtained.

Besides the synthesis method illustrated above, an alternative method may be used. That is, monomer (1) may be produced by introducing a polymerizable functional group at the final stage as shown by the reaction scheme below.

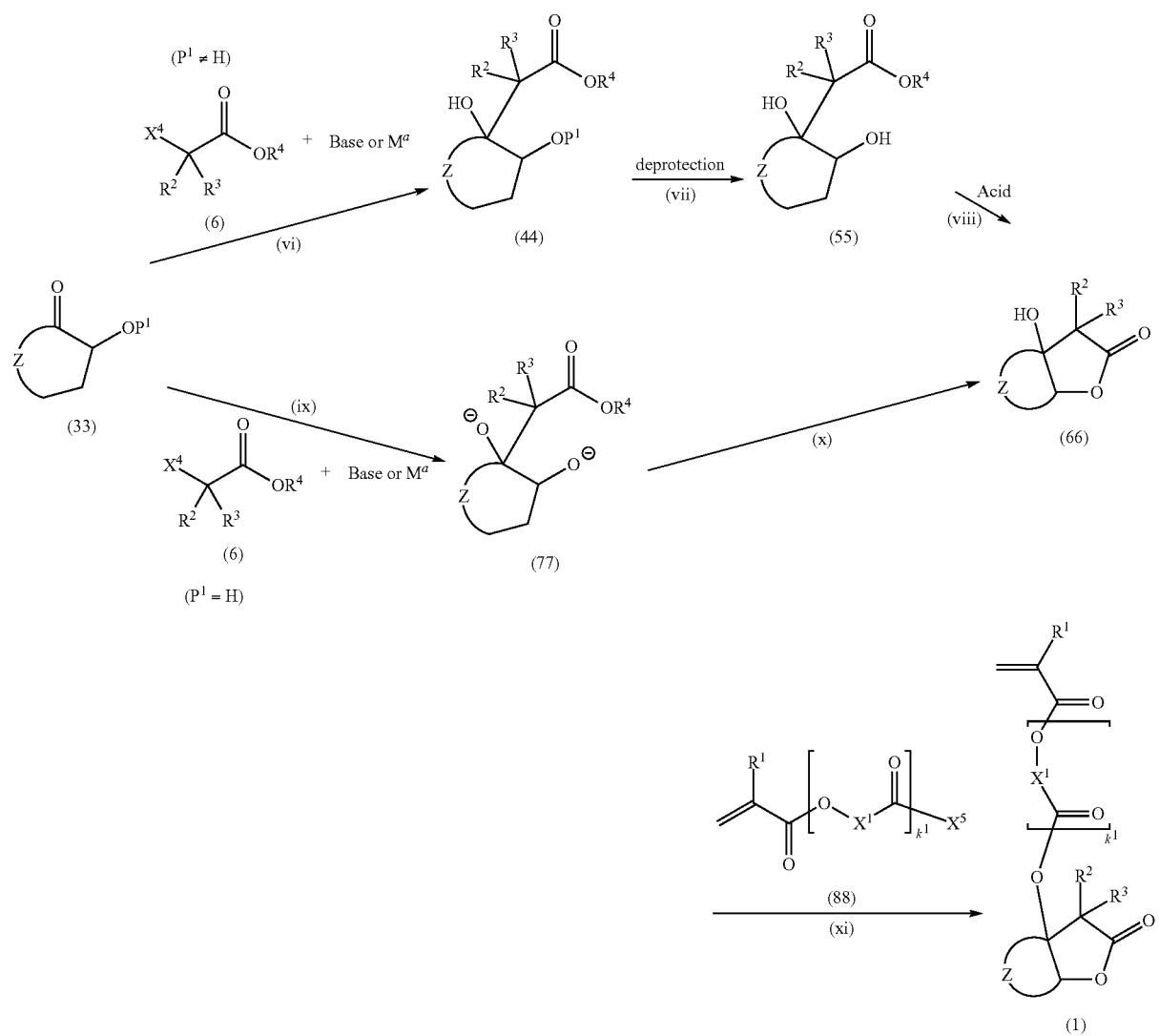

Herein $R^1$ to $R^4$, $X^1$, $X^4$, Z, $k^1$, and $M^a$ are as defined above, $X^5$ is halogen, hydroxyl or —$OR^{14}$, $R^{14}$ is as defined above, and $P^1$ is hydrogen or a protective group for hydroxyl.

When the method starts with compound (33) wherein $P^1$ is a protective group for hydroxyl, compound (33) is converted to hydroxy-lactone compound (66) via steps (vi) to (viii), and finally compound (66) is reacted with polymerizable acylating agent (88) in step (xi) to form monomer (1). These steps are described in detail.

The starting reactant is compound (33) wherein $P^1$ is a protective group. Suitable protective groups include silyl ether protective groups such as trimethylsilyl, triethylsilyl, tert-butyldimethylsilyl, triisopropylsilyl, and tert-butyldiphenylsilyl; ether protective groups such as benzyl and p-methoxybenzyl; acetal protective groups such as methoxymethyl, ethoxyethyl, tetrahydropyranyl, methylthiomethyl, benzyloxymethyl and methoxyethoxymethyl; and acyl protective groups such as acetyl, pivaloyl and benzoyl. Inter alia, protective groups which can be deprotected under acidic conditions such as silyl ether protective groups and acetal protective groups are preferred because steps (vii) and (viii) of deprotection of $P^1$ and lactonization can be carried out under identical reaction conditions.

Like step (ii) above, step (vi) is addition reaction of ketone compound (33) and ester compound (6) with the aid of a base or metal to form a corresponding hydroxy-ester compound (44). Particularly when $P^1$ is an acyl protective group, selective reaction between ketone compound (33) at its ketone site and ester compound (44) is necessary. Then Reformatsky reaction conditions as previously described for step (ii) are preferred. Once reaction is carried out under the same conditions as in step (ii), hydroxy-ester compound (44) may be recovered from the reaction mixture by ordinary aqueous work-up. If necessary, the compound may be purified by standard techniques like distillation, recrystallization and chromatography.

Next step (vii) is a reaction to deprotect the protective group $P^1$ on hydroxy-ester compound (44) to form dihydroxy-ester compound (55). Deprotection reaction may be carried out by any well-known technique for a particular protective group $P^1$.

In the case of hydroxy-ester compound (44) wherein $R^4$ is a bulky substituent group such as tert-butyl ester or tert-amyl ester, dihydroxy-ester compound (55) obtained after deprotection of $P^1$ may be isolated and optionally purified by standard techniques like distillation, recrystallization and chromatography. In most cases, there is no need for isolation and purification of dihydroxy-ester compound (55), that is, if the reaction mixture from the deprotection reaction is post-treated under acidic conditions, then the process will proceed all at once to lactonization of step (viii).

The acidic treatment following deprotection refers to the step of optionally diluting the crude product as post-treated of dihydroxy-ester compound (55) obtained after deprotection with a solvent, adding an acid catalyst to the crude product in the solvent or solventless system, and stirring the mixture for inducing reaction. Suitable solvents used herein include hydrocarbons such as toluene, xylene, hexane, and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. The reaction may also be conducted in a solventless system.

Suitable acids include mineral acids such as hydrochloric acid, sulfuric acid, nitric acid and perchloric acid, organic acids such as methanesulfonic acid, trifluoromethanesulfonic acid, p-toluenesulfonic acid, and benzenesulfonic acid, and Lewis acids such as boron trifluoride, trimethylsilyl triflate, aluminum chloride, and titanium chloride. An appropriate amount of the acid used is 0.01 to 3 moles, more preferably 0.05 to 0.5 mole per mole of the reactant prior to deprotection, hydroxy-ester compound (44). Less than 0.01 mole of the acid may invite an economic disadvantage because of a slow reaction rate and longer reaction time. More than 3 moles may invite an economic disadvantage since little merits are obtained with respect to reaction rate and reaction time. For this reason, a necessary sufficient amount of the acid is 0.01 to 3 moles. To the reaction system, a phase transfer catalyst such as tetrabutylammonium hydrogensulfate may be added. An appropriate amount of the phase transfer catalyst added is 0.0001 to 1.0 mole, more preferably 0.001 to 0.5 mole per mole of the alcohol compound. Less than 0.0001 mole of the phase transfer catalyst may fail to exert catalytic effect whereas more than 1.0 mole may be uneconomical because of the increased catalyst cost.

In step (viii), an appropriate reaction temperature may be selected in accordance with other reaction conditions. In most cases, a temperature of 0 to 60° C., more preferably 20 to 60° C. is preferred because reaction does not take place at lower temperatures. The reaction time is determined as appropriate for yield improvement by monitoring the reaction process by thin-layer chromatography (TLC) or gas chromatography (GC). The reaction time is usually about 30 minutes to about 72 hours. At the end of reaction, hydroxy-lactone compound (66) may be recovered from the reaction mixture by ordinary aqueous work-up. If necessary, the compound may be purified by standard techniques like distillation, recrystallization and chromatography.

As the protective group $P^1$ in hydroxy-ester compound (44), those protective groups which can be deprotected under acidic conditions such as silyl ether protective groups and acetal protective groups are most preferred because step (vii) of deprotection of $P^1$ and step (viii) of lactonization under acidic conditions can be carried out under identical reaction conditions.

Deprotection takes place when a catalytic amount of an acid is added to a system of hydroxy-ester compound (44) in water or an alcohol solvent such as methanol, ethanol, propanol or butanol. Suitable acids include mineral acids such as hydrochloric acid, sulfuric acid, nitric acid and perchloric acid, organic acids such as methanesulfonic acid, trifluoromethanesulfonic acid, p-toluenesulfonic acid, and benzenesulfonic acid, and Lewis acids such as boron trifluoride, trimethylsilyl triflate, aluminum chloride, and titanium chloride. Subsequent to deprotection, lactonization of the resulting hydroxyl group takes place under acidic conditions. In this way, hydroxy-lactone compound (66) is obtained in one-pot. This one-pot process achieves a great cost saving because it eliminates a need to replace the crude product as post-treated of dihydroxy-ester compound (55) obtained after deprotection of $P^1$ by a solvent for lactonization reaction.

For the deprotection reaction, an appropriate reaction temperature may be selected in accordance with other reaction conditions. In the lactonization step following deprotection, an optimum temperature is in the range of 0 to 60° C., more preferably 20 to 60° C. as above.

Step (xi) is a reaction of hydroxy-lactone compound (66) with esterifying agent (88) to form the desired monomer (1). The reaction may readily run by a well-known procedure. The preferred esterifying agent (88) is an acid chloride of formula

(88) wherein $X^5$ is chlorine, or a carboxylic anhydride of formula (88) wherein $X^5$ is $—OR^{14}$ and $R^{14}$ is a group having formula (9):

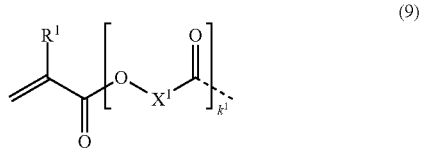

(9)

wherein $R^1$, $X^1$ and $k^1$ are as defined above.

When an acid chloride, typically carboxylic acid chloride such as methacrylic acid chloride is used as esterifying agent (88), the reaction may be conducted in a solventless system or in a solvent (e.g., methylene chloride, acetonitrile, toluene or hexane) by adding hydroxy-lactone compound (66), acid chloride, and a base (e.g., triethylamine, pyridine or 4-dimethylaminopyridine) in sequence or at the same time, and optional cooling or heating. When a carboxylic anhydride such as methacrylic anhydride is used as esterifying agent (88), the reaction may be conducted in a solventless system or in a solvent (e.g., methylene chloride, acetonitrile, toluene or hexane) by adding hydroxy-lactone compound (66), carboxylic anhydride, and a base (e.g., triethylamine, pyridine or 4-dimethylaminopyridine) in sequence or at the same time, and optional cooling or heating. When a carboxylic acid of formula (88) wherein $X^5$ is hydroxyl such as methacrylic acid is used as esterifying agent (88), the reaction may be conducted by heating hydroxy-lactone compound (66) and carboxylic acid in a solvent (e.g., toluene or hexane) in the presence of an acid catalyst and optionally removing water resulting from reaction out of the system. Examples of the acid catalyst used herein include mineral acids such as hydrochloric acid, sulfuric acid, nitric acid and perchloric acid and organic acids such as p-toluenesulfonic acid and benzenesulfonic acid.

The reaction time is determined as appropriate by monitoring the reaction process by thin-layer chromatography (TLC) or gas chromatography (GC) because it is desirable from the yield aspect to drive the reaction to completion. Usually the reaction time is about 30 minutes to about 48 hours. The desired monomer (1) may be recovered from the reaction mixture by ordinary aqueous work-up. If necessary, the monomer may be purified by standard techniques like distillation, recrystallization and chromatography.

When the alternative method starts with compound (33) wherein $P^1$ is hydrogen, compound (33) is converted to hydroxy-lactone compound (66) via steps (ix) and (x), and finally compound (66) is acylated in step (xi) as described above to form monomer (1). These steps are described in detail.

The starting reactant is a ketone compound of formula (33) wherein $P^1$ is hydrogen, that is a hydroxy-cycloalkanone compound. If addition reaction is carried out in step (ix) in the same way as in step (vi), then ketone compound (33) can be converted all at once to hydroxy-lactone compound (66) via intermediate (77) or step (x). As compared with the previous procedure passing steps (vi) to (viii), the procedure passing steps (ix) and (x) has the advantage of fewer steps because the deprotection of protective group $P^1$ is unnecessary.

Once a metal enolate reagent is prepared from ester compound (6) and a base or metal (as previously defined and exemplified) by any well-known technique, it may be used in step (ix). Since the metal enolate reagent is consumed by the hydroxyl group on ketone compound (33) as the reactant, the metal enolate reagent must be used in excess relative to ketone compound (33). An appropriate amount of the metal enolate reagent used is 1.2 to 10 moles, more preferably 1.5 to 5.0 moles per mole of the reactant, ketone compound (33). If the metal enolate reagent is less than 1.2 moles, a large fraction of the reactant is left unreacted, with a substantial drop of yield. More than 10 moles of the metal enolate reagent may be uneconomical because of an increase of material amount and a lowering of pot yield.

The reaction time of step (ix) is determined as appropriate by monitoring the reaction process by thin-layer chromatography (TLC) or gas chromatography (GC) because it is desirable from the yield aspect to drive the reaction to completion. Usually the reaction time is about 30 minutes to about 48 hours. Typically, the product is identified as hydroxy-lactone compound (66) throughout steps (ix) and (x). An appropriate temperature is in the range of 0 to 60° C., more preferably 20 to 60° C. although it varies with other reaction conditions.

When the starting reactant is ester compound (6) wherein $R^4$ is a bulky substituent such as tert-butyl ester or tert-amyl ester, the reaction of step (ix) terminates at the stage of intermediate (77). Then the reaction mixture is subjected to aqueous work-up and acid treatment (as previously described), obtaining hydroxy-lactone compound (66). If the process can be driven all at once to lactonization of step (x) under the reaction conditions of step (ix), more economic merits such as a saving of solvent are available. The starting reactant preferred in this sense is ester compound (6) wherein $R^4$ is a primary or secondary alkyl group.

Through steps (ix) and (x), there is obtained hydroxy-lactone compound (66), which may be converted to the desired monomer (1) through step (xi) mentioned above.

Polymer

A second embodiment of the invention is a polymer or high-molecular-weight compound comprising recurring units derived from the monomer having formula (1) defined above, specifically recurring units having the general formula (2).

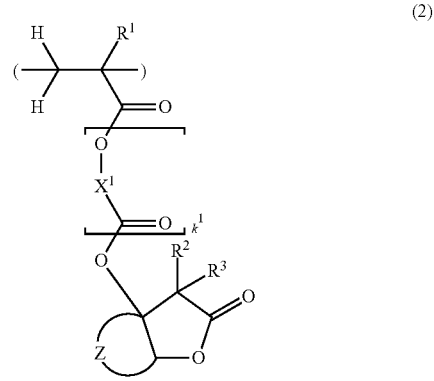

(2)

Herein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent $—CH_2—$ may be replaced by $—O—$ or $—C(=O)—$, $k^1$ is 0 or 1, and Z forms a 5 or 6-membered alicyclic group, which may contain a heteroatom, with the two carbon atoms to which it is attached.

The polymer (2) obtained from the monomer (1) has a fused ring lactone structure resulting from two rings being fused together and is characterized by a polymerizable acyloxy group at β-position of lactone carbonyl group, i.e., internuclear position of fused ring. As long as the inventors know, the present invention is the first discovery of a lactone unit having a polymerizable group at the internuclear position of fused ring, inclusive of synthesis of monomers. Owing to the fused ring structure and a polymerizable group on quaternary carbon at the internuclear position of fused ring, this lactone unit is a fully rigid structural unit having a high carbon density. Accordingly, as long as the relevant unit is used in an appropriate proportion, the resulting polymer (2) has a high glass transition temperature (Tg). When the polymer (2) is used as a base resin to formulate a resist composition, many advantages are expectable including controlled acid diffusion, low roughness, improved exposure latitude, and retention of as-developed film pattern having high strength and hence high etch resistance.

In addition to the units having formula (2), the preferred polymer may further comprise recurring units of at least one type selected from recurring units having the general formulae (A) to (E).

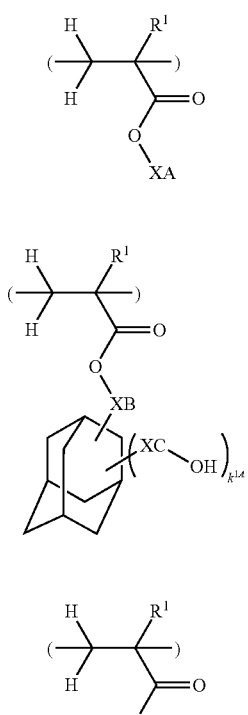

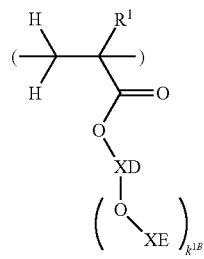

Herein $R^1$ is hydrogen, methyl or trifluoromethyl. XA is an acid labile group. XB and XC are each independently a single bond or a straight or branched, divalent hydrocarbon group of 1 to 4 carbon atoms. XD is a straight, branched or cyclic, di- to pentavalent aliphatic hydrocarbon group of 1 to 16 carbon atoms in which a constituent —$CH_2$— may be replaced by —O— or —C(=O)—. XE is an acid labile group. YA is a substituent group of lactone, sultone or carbonate structure. ZA is hydrogen, a fluoroalkyl group of 1 to 30 carbon atoms or a fluoroalcohol-containing group of 1 to 15 carbon atoms, $k^{1A}$ is an integer of 1 to 3, and $k^{1B}$ is an integer of 1 to 4.

A polymer comprising recurring units of formula (A) is decomposed under the action of acid to generate carboxylic acid so that it may turn alkali soluble. The acid labile group XA may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

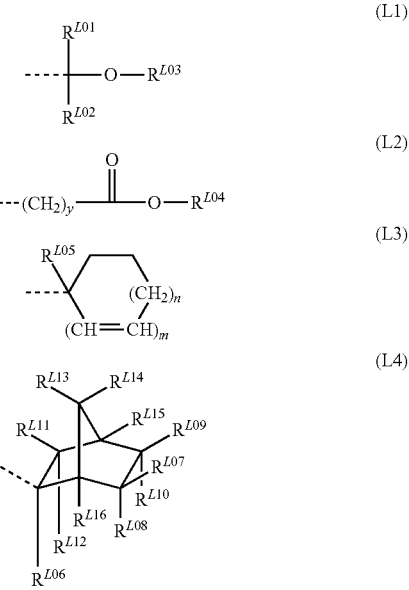

Herein $R^{L01}$ and $R^{L02}$ are each independently hydrogen or a straight, branched or cyclic alkyl group of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C_{10}$ alkyl group or an optionally substituted $C_6$-$C_{20}$ aryl group. $R^{L07}$ to $R^{L16}$ independently represent hydrogen or optionally substituted monovalent hydrocarbon groups of 1 to 15 carbon atoms. Letter y is an integer of 0 to 6, m is equal to 0 or 1, n is equal to 0, 1, 2 or 3, and 2m+n is equal to 2 or 3. The broken line denotes a valence bond.

In formula (L1), exemplary groups of $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. Illustrative examples of the straight, branched or cyclic alkyl groups are as exemplified above for $R^{L01}$ and $R^{L02}$, and examples of the substituted alkyl groups are as shown below.

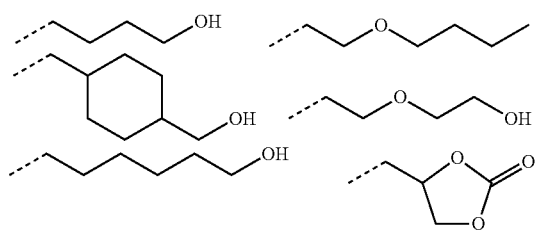

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), examples of the optionally substituted $C_1$-$C_{10}$ alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxyl, alkoxycarbonyl, oxo, amino, alkylamino, cyano, mercapto, alkylthio, sulfo or other groups or in which a methylene moiety is replaced by an oxygen or sulfur atom. Examples of optionally substituted $C_6$-$C_{20}$ aryl groups include phenyl, methylphenyl, naphthyl, anthryl, phenanthryl, and pyrenyl.

In formula (L4), examples of optionally substituted, straight, branched or cyclic $C_1$-$C_{10}$ alkyl groups and optionally substituted $C_6$-$C_{20}$ aryl groups of $R^{L06}$ are the same as exemplified for $R^{L05}$. Exemplary $C_1$-$C_{15}$ monovalent hydrocarbon groups of $R^{L07}$ to $R^{L16}$ include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom(s) to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$ form a ring). Each of $R^{L07}$ to $R^{L16}$ represents a $C_1$-$C_{15}$ divalent hydrocarbon group, typically alkylene, when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, or $R^{L13}$ and $R^{L15}$).

Of the acid labile groups of formula (L1), the straight and branched ones are exemplified by the following groups.

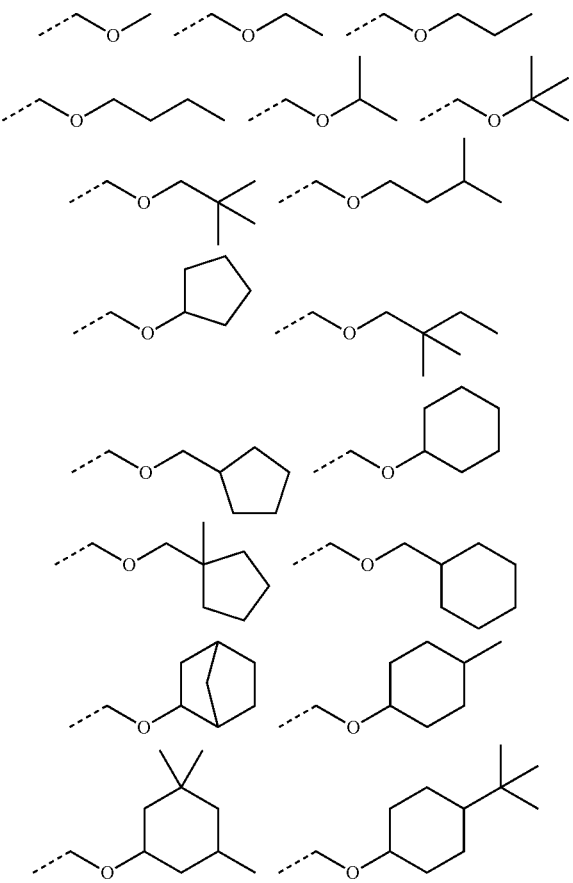

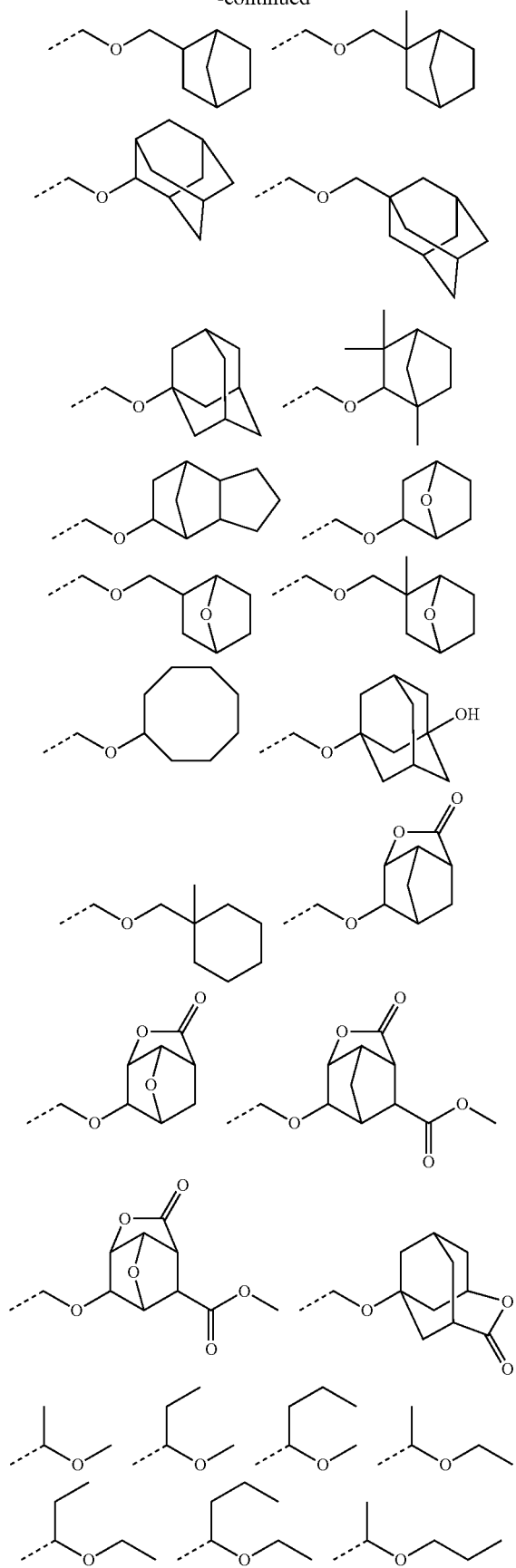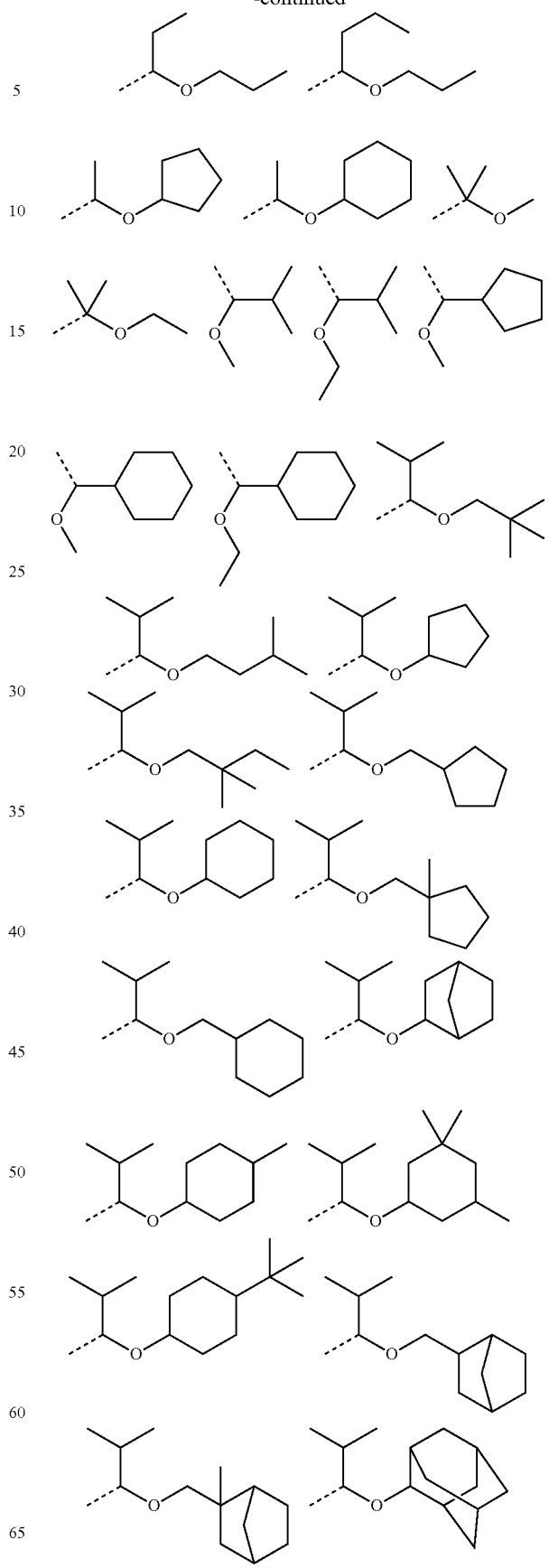

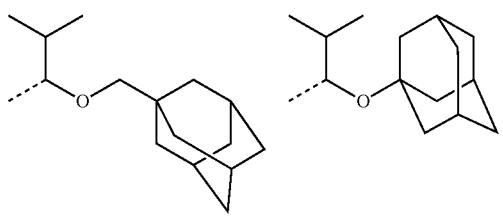
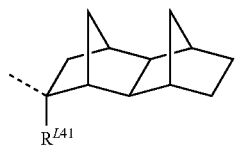

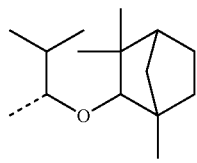

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethyl cyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

(L4-1)

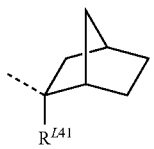

(L4-2)

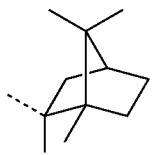

(L4-3)

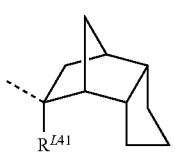

(L4-4)

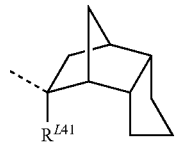

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

(L4-3-1)

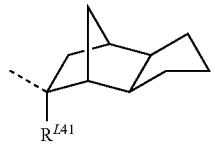

(L4-3-2)

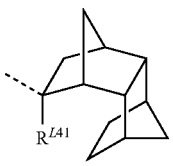

Note that $R^{L41}$ is as defined above.

Similarly, the general formula (L4-4) represents one or a mixture of two or more selected from groups having the following general formulas (L4-4-1) to (L4-4-4).

(L4-4-1)

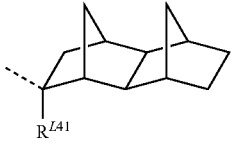

(L4-4-2)

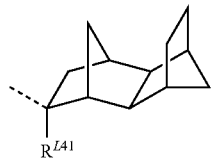

(L4-4-3)

(L4-4-4)

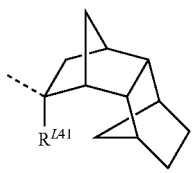

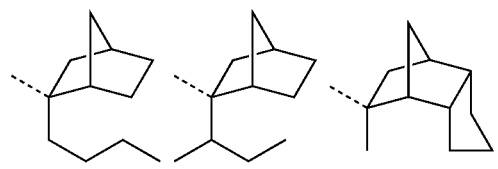

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

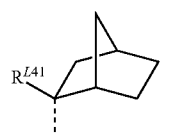

(L4-2-endo)

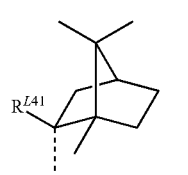

(L4-3-endo)

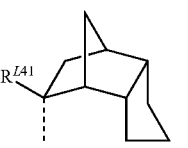

(L4-4-endo)

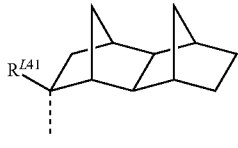

Note that $R^{L41}$ is as defined above.

Illustrative examples of the acid labile group of formula (L4) are given below.

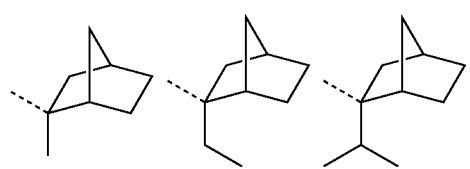

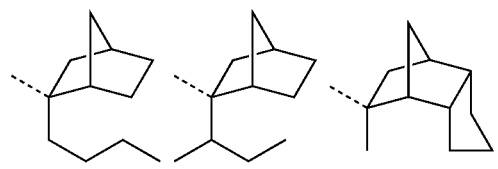

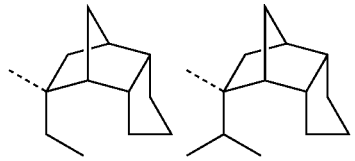

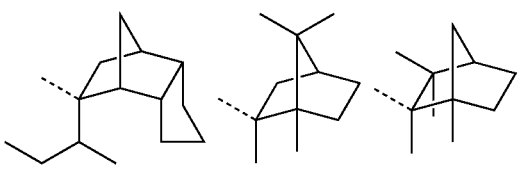

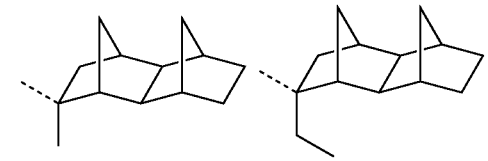

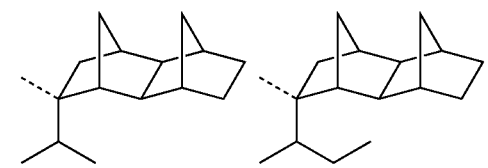

Examples of the tertiary $C_4$-$C_{20}$ alkyl groups, trialkyl-silyl groups in which each alkyl moiety has 1 to 6 carbon atoms, and $C_4$-$C_{20}$ oxoalkyl groups, represented by XA, are as exemplified for $R^{L04}$ and the like.

Illustrative examples of the recurring units having formula (A) are given below, but not limited thereto.

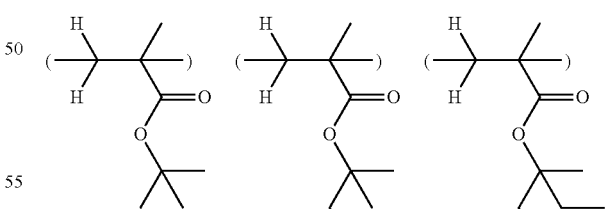

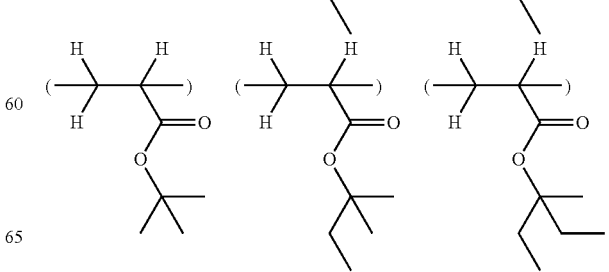

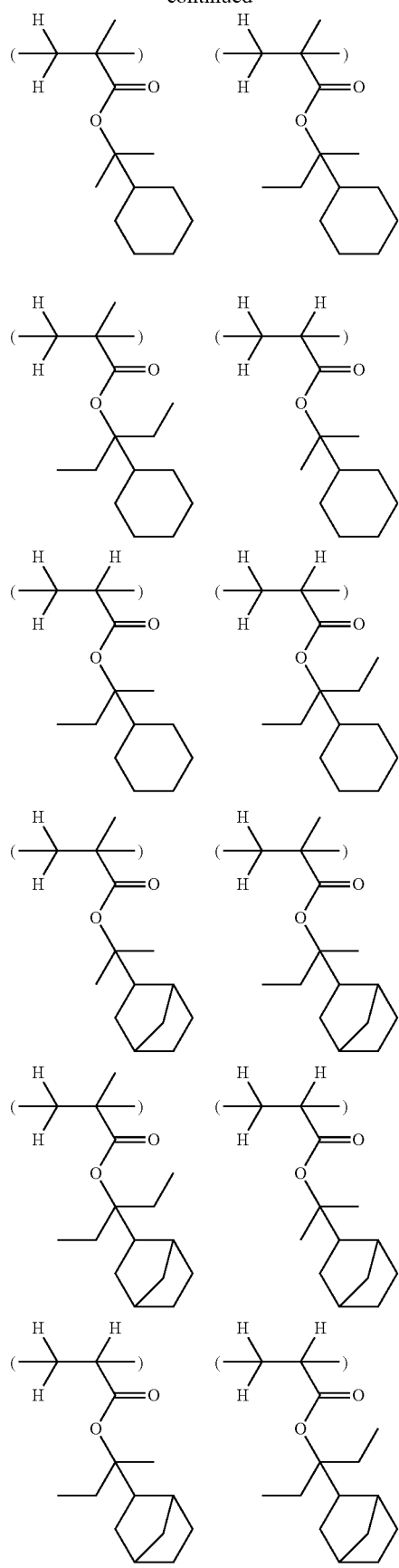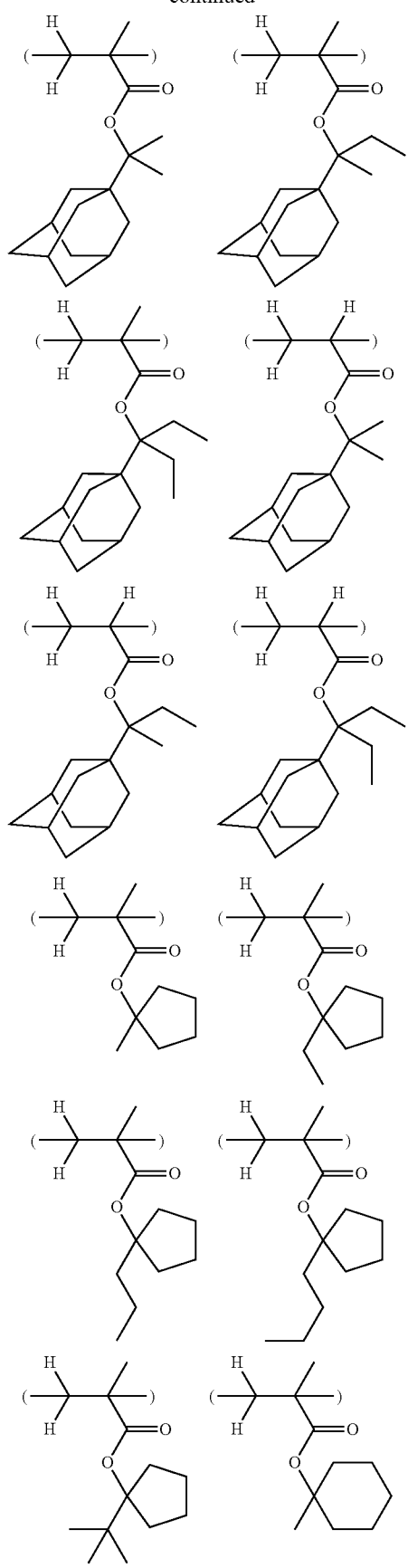

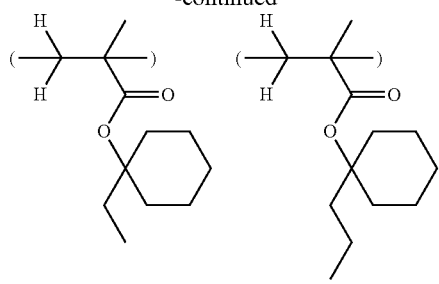
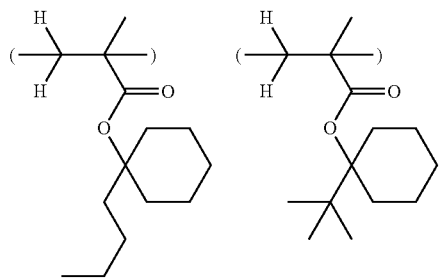
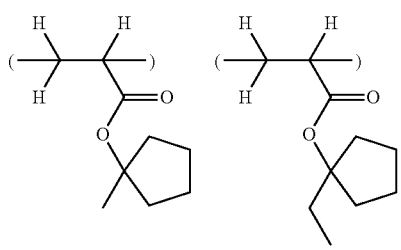
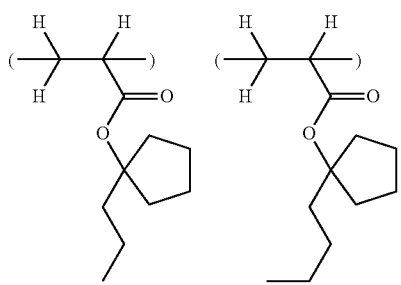
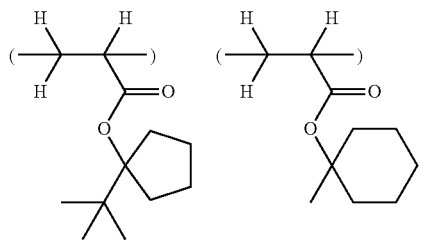
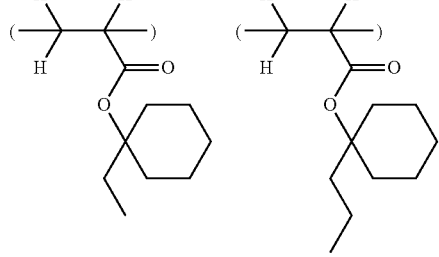
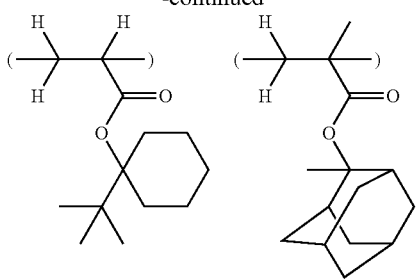
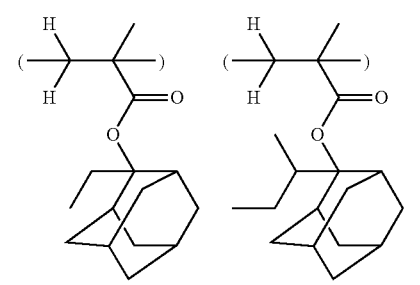
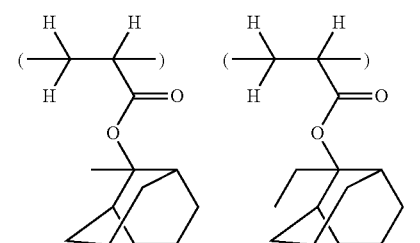
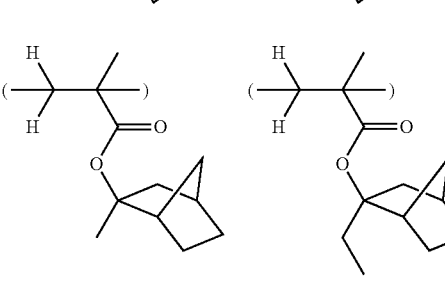
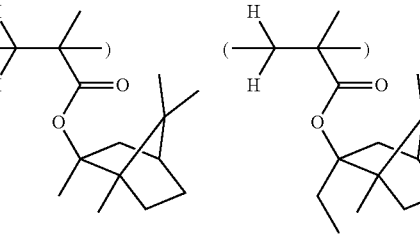
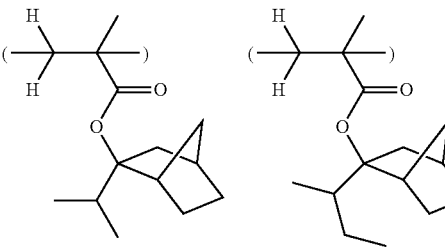

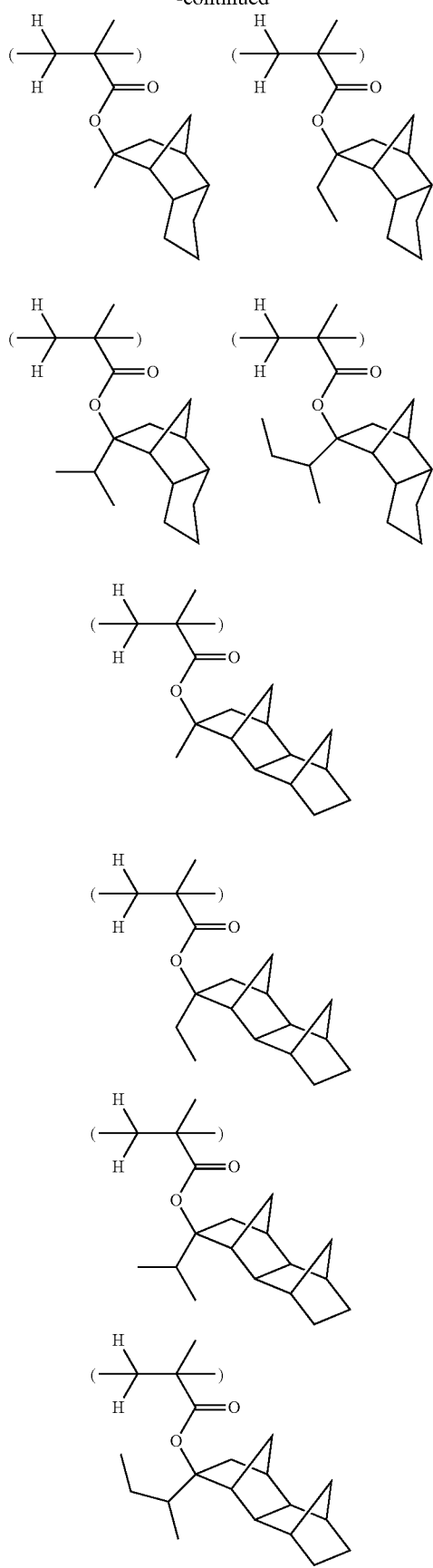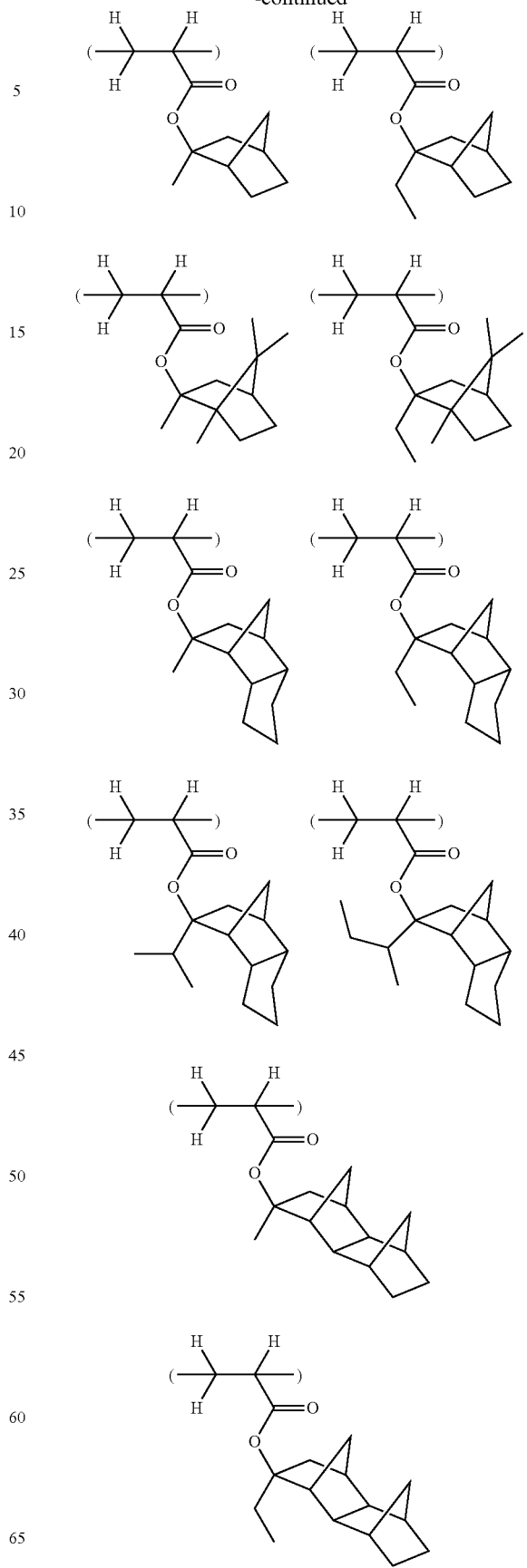

-continued
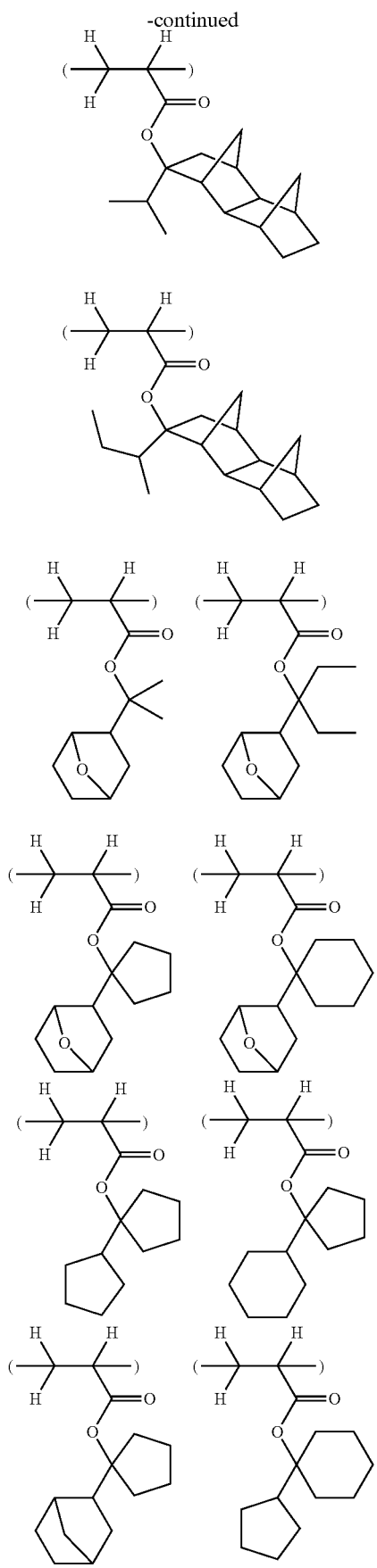
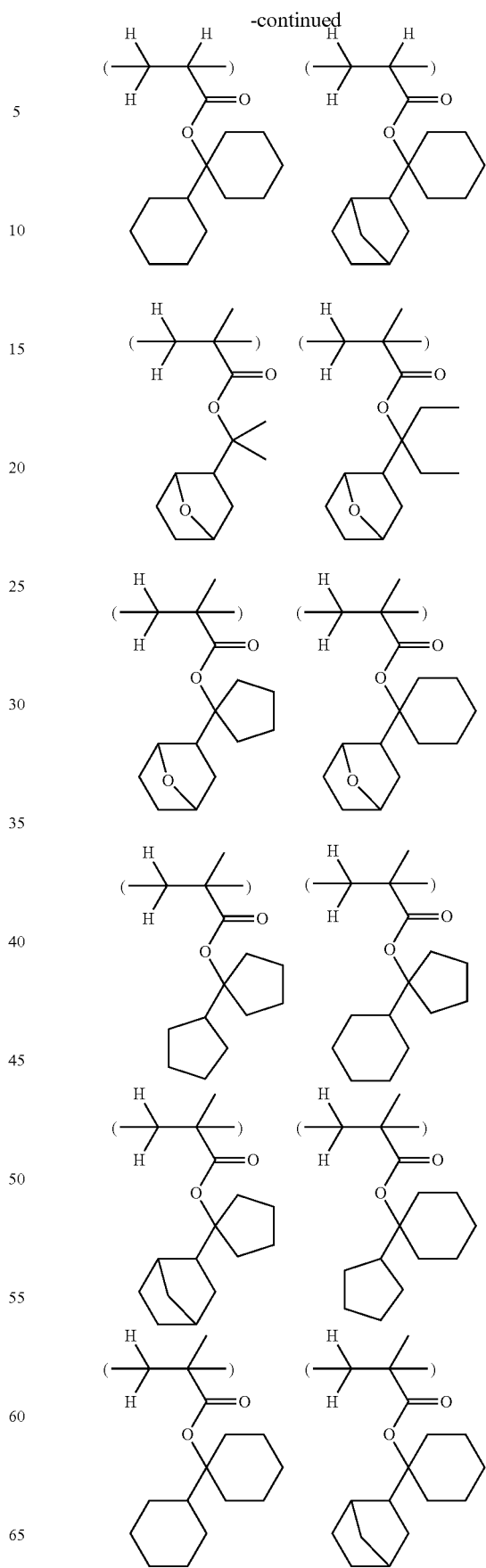

-continued
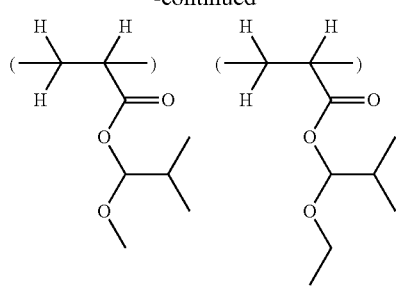
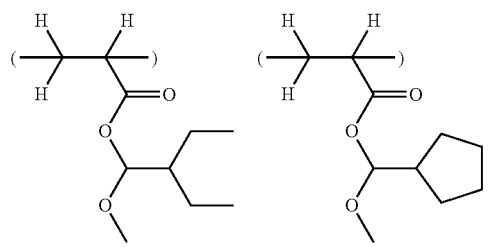
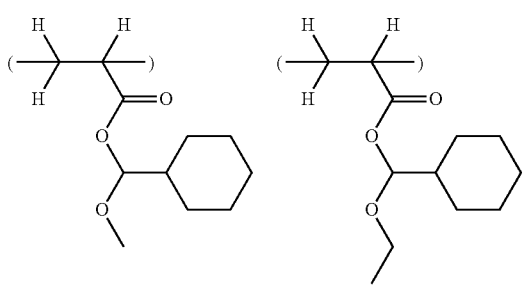
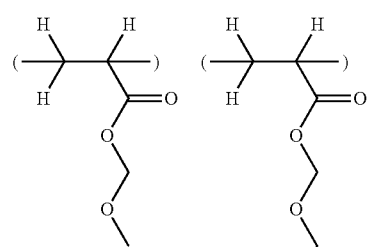
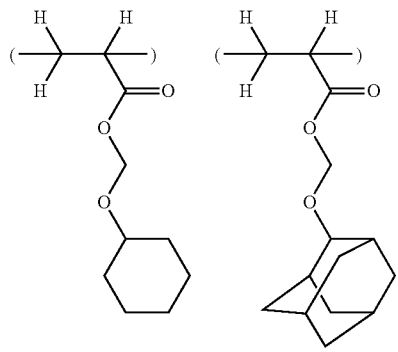
-continued
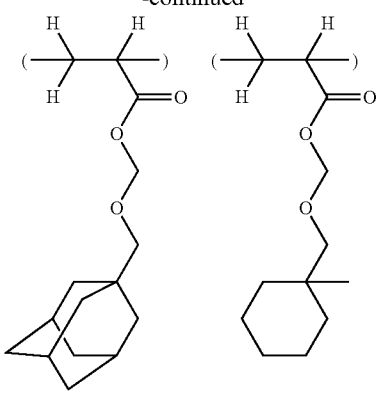
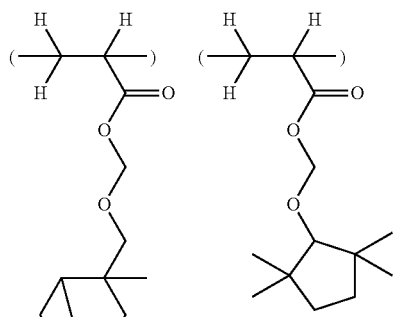
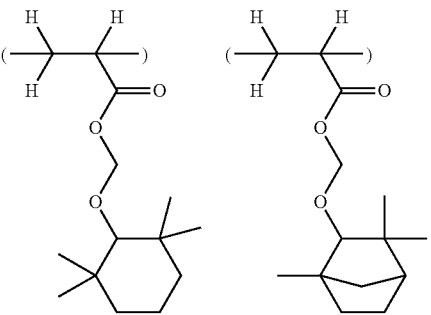
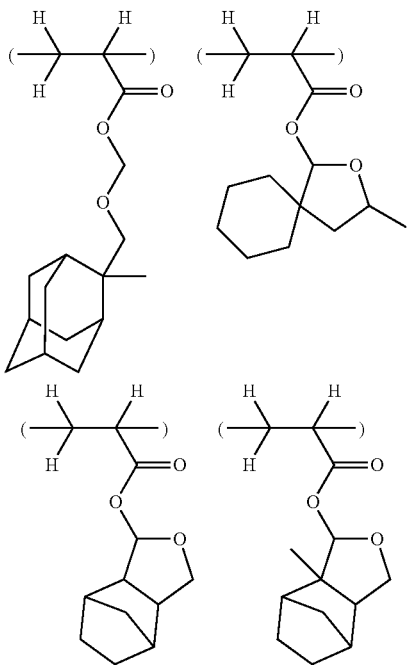

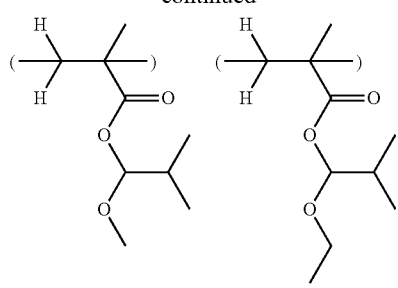
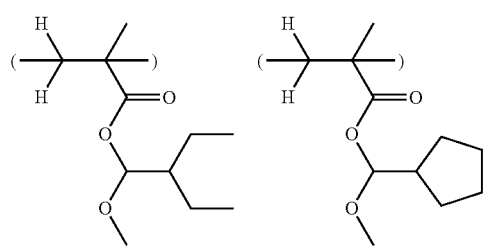
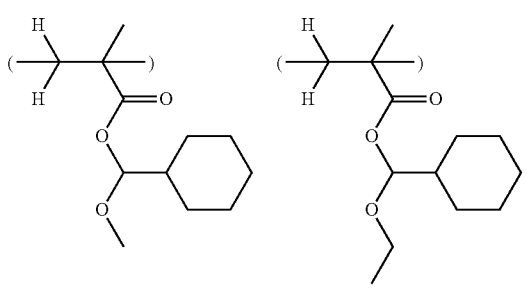
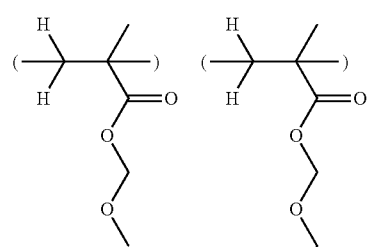
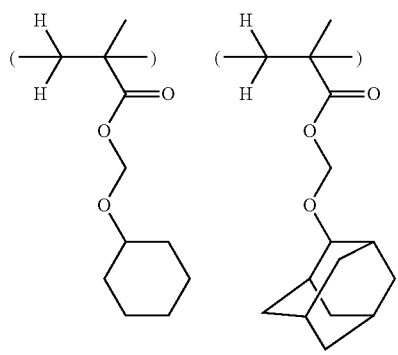
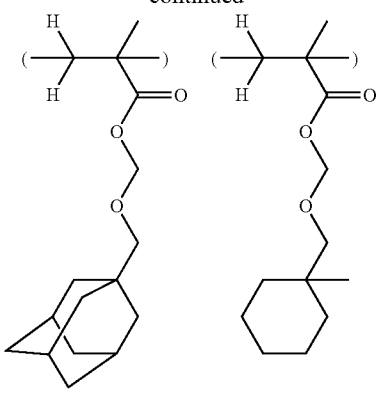
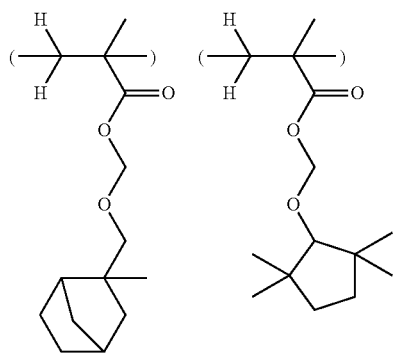
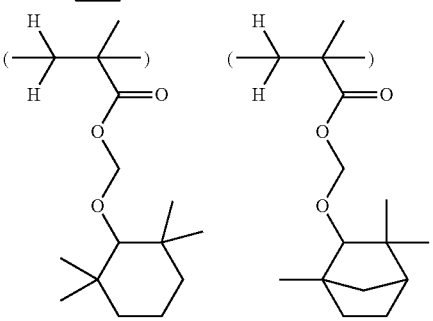
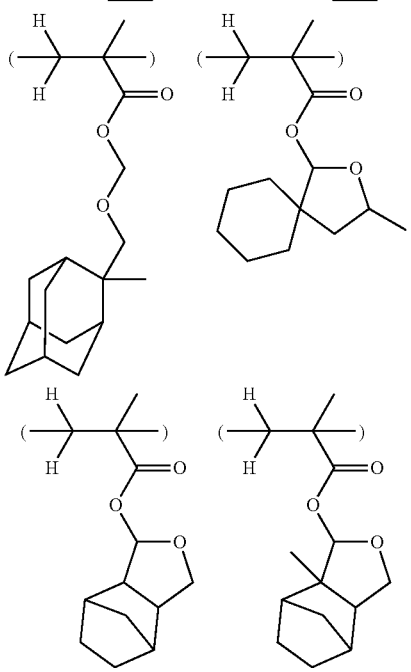

-continued
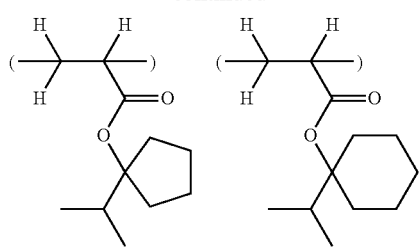
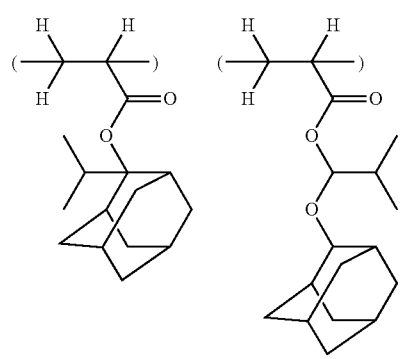
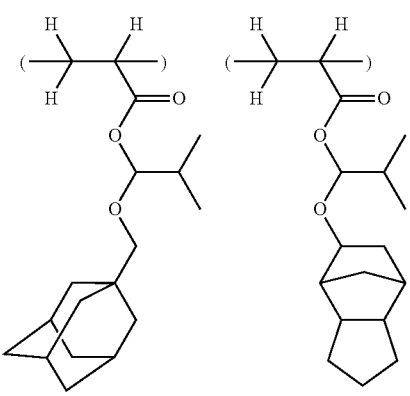
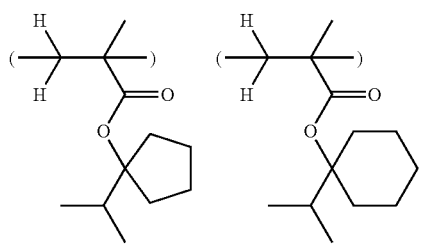
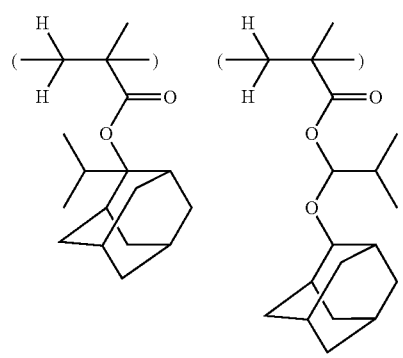
-continued
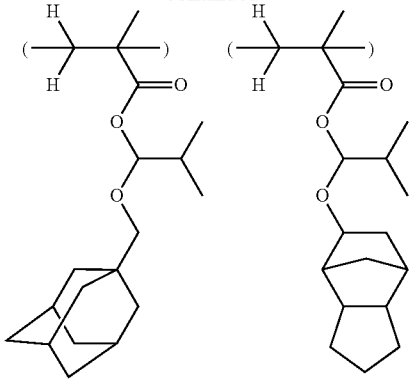
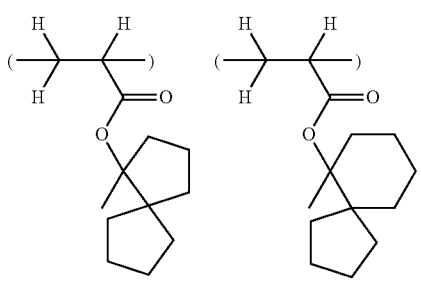
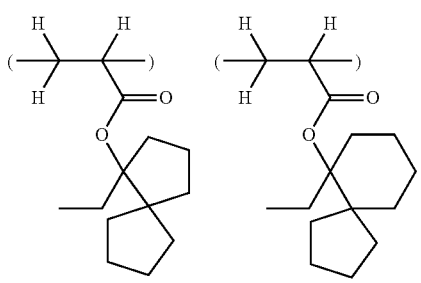
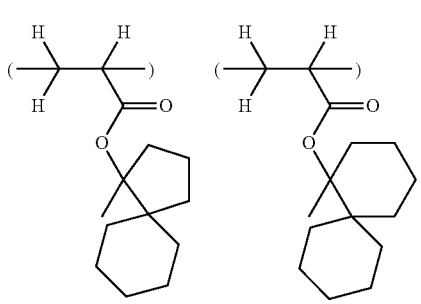
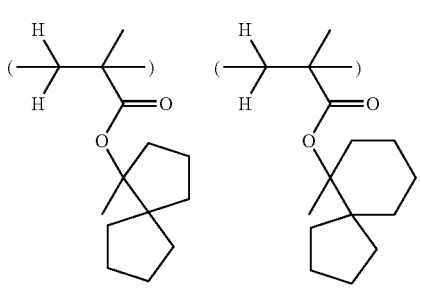

67
-continued
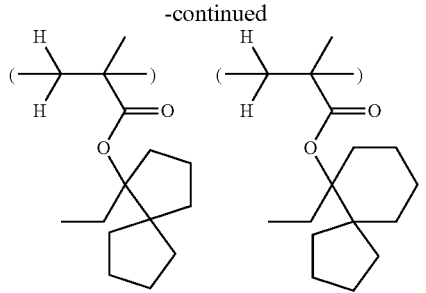
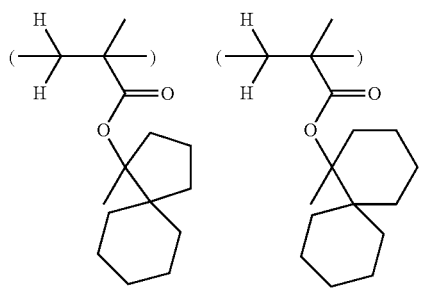
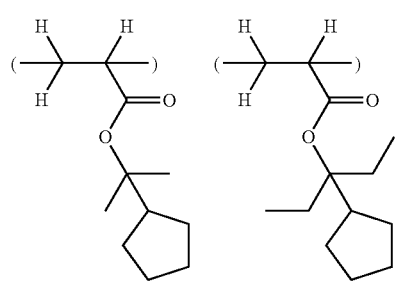
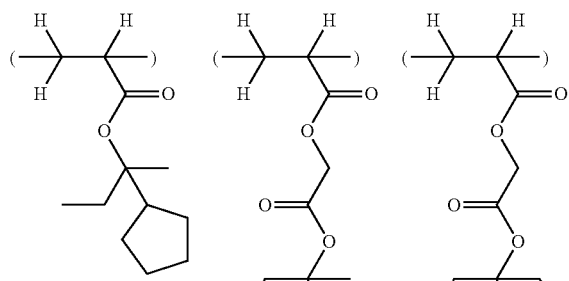
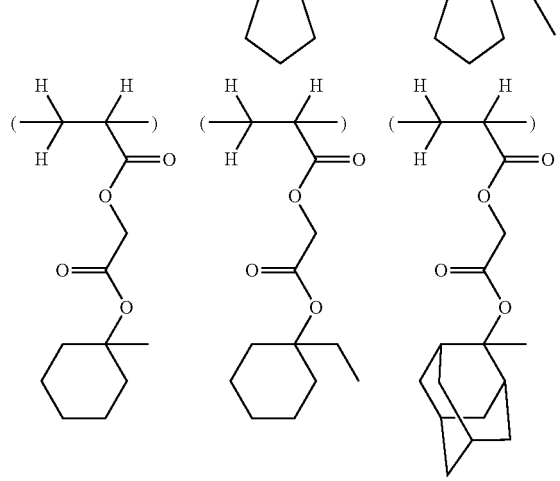
68
-continued
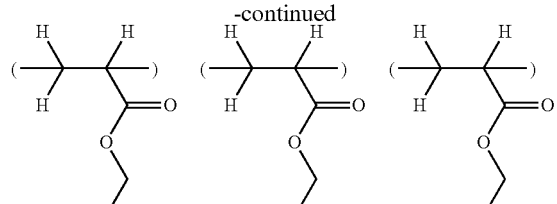
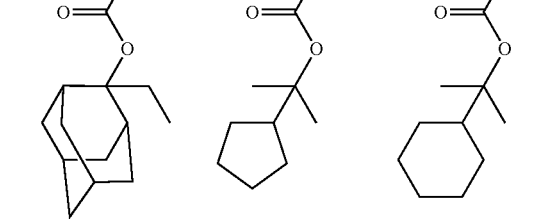
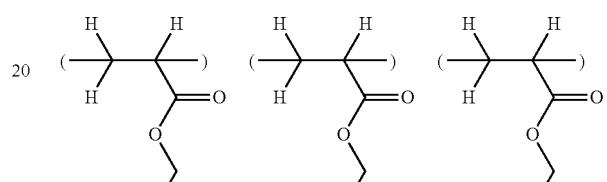
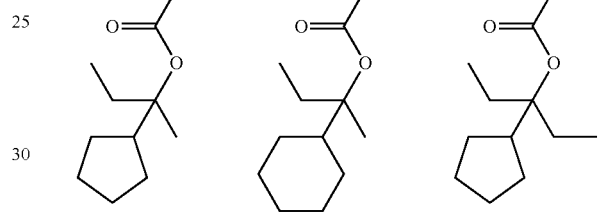
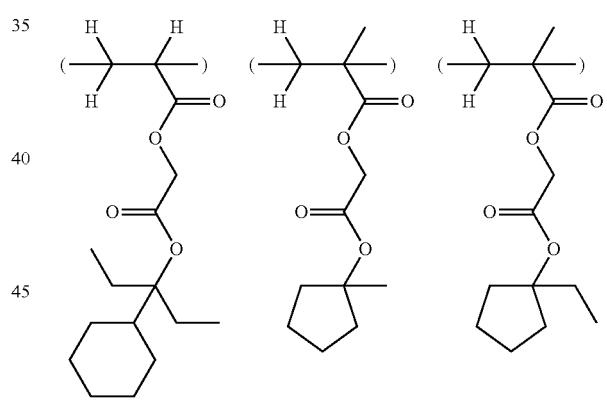
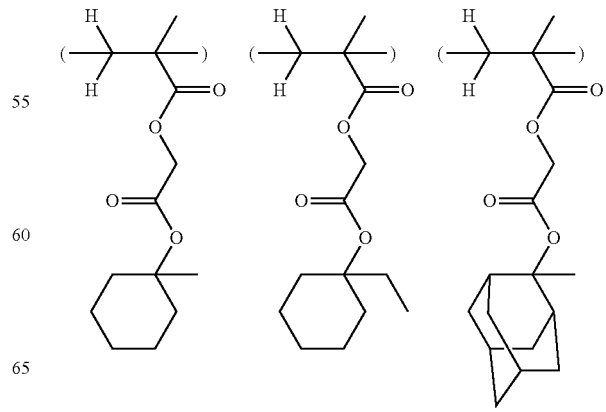

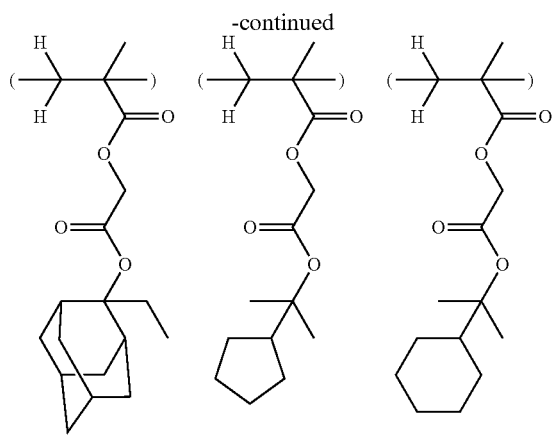
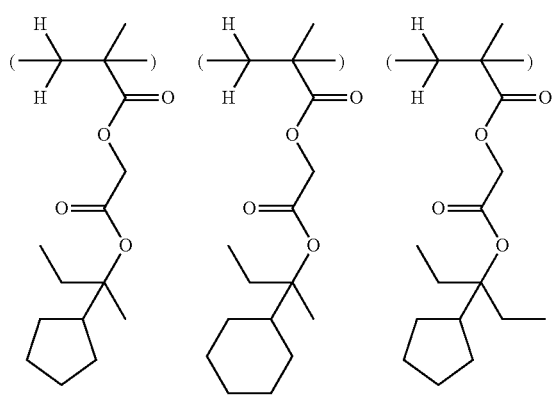
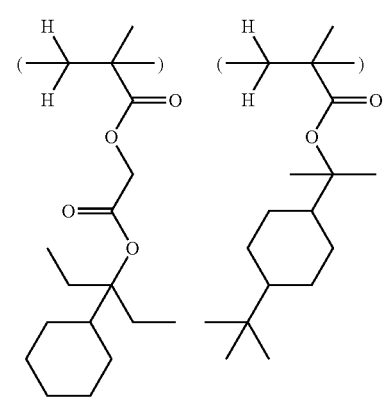
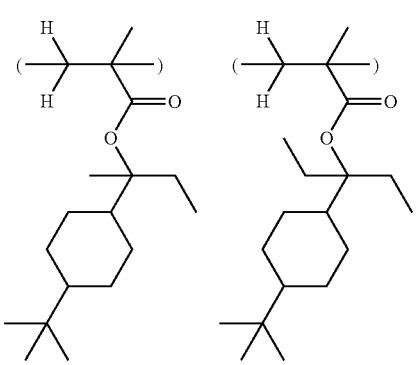
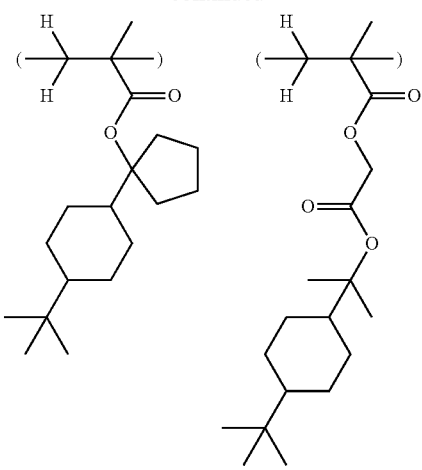
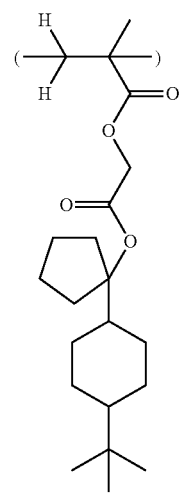
Illustrative examples of the recurring units having formula (B) are given below, but not limited thereto.
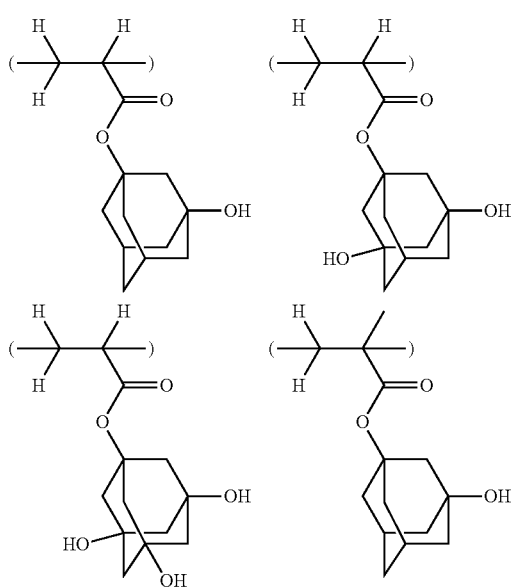

71
-continued
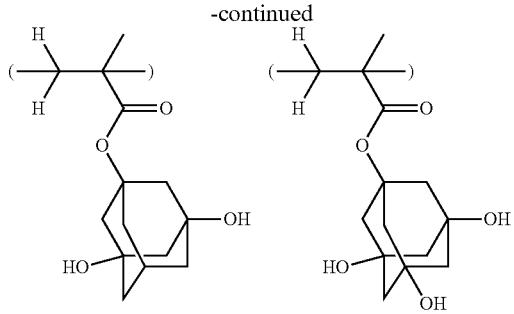
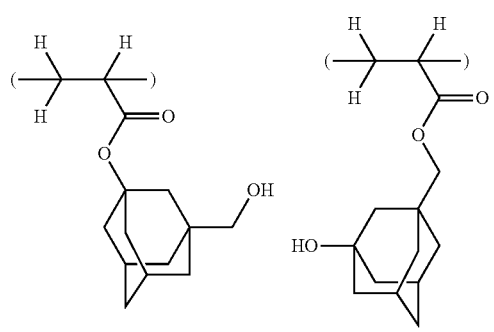
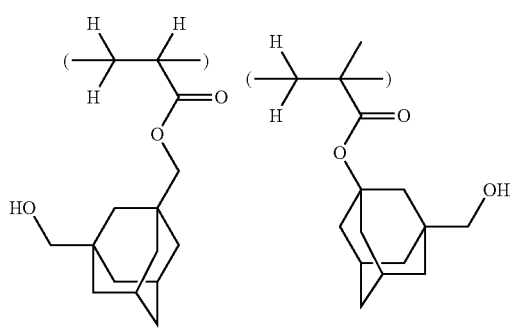
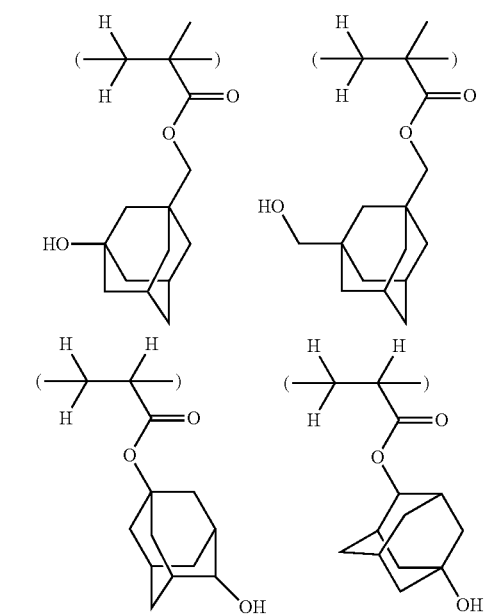
72
-continued
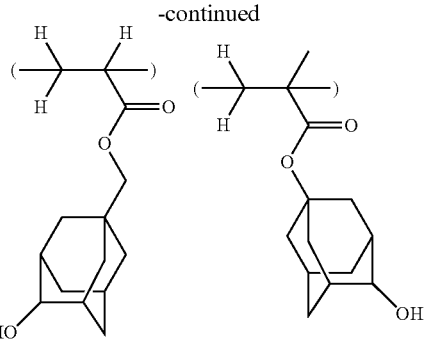
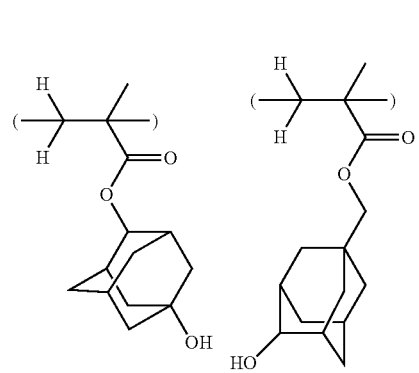
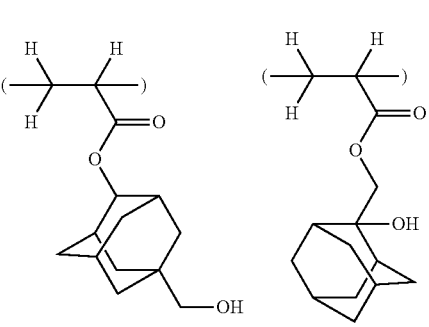
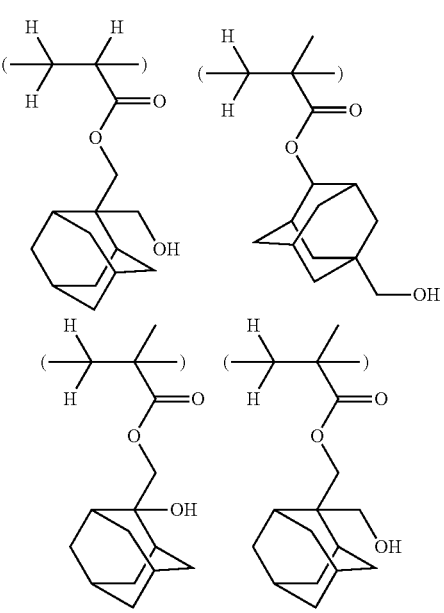

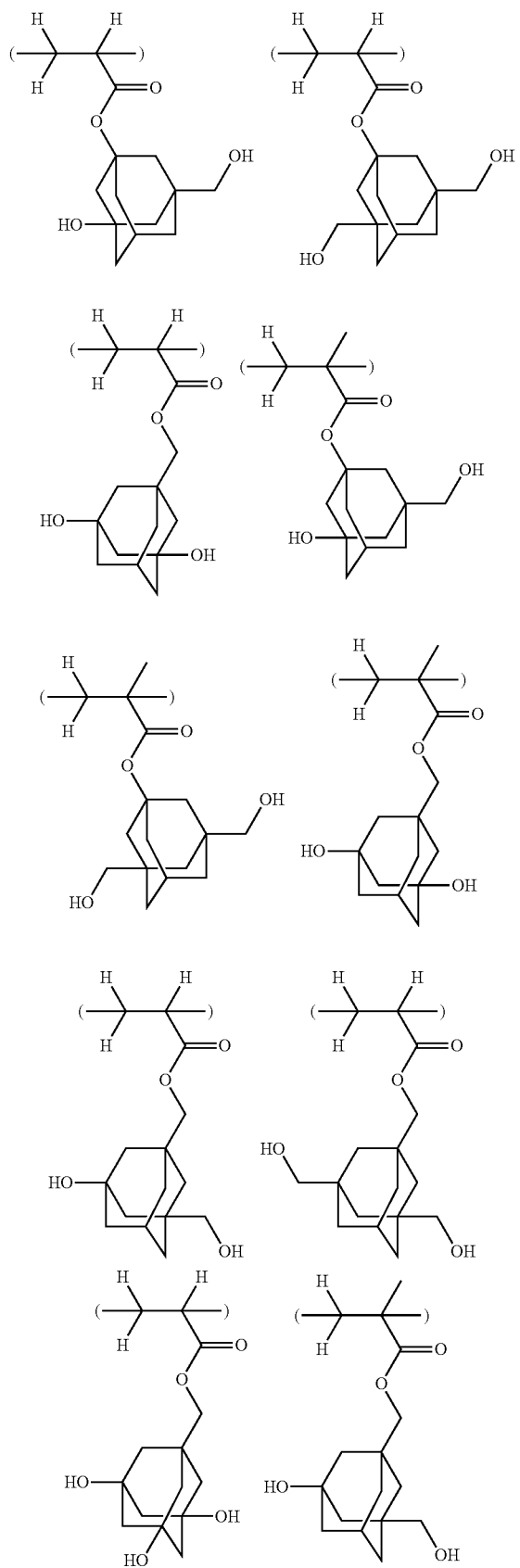
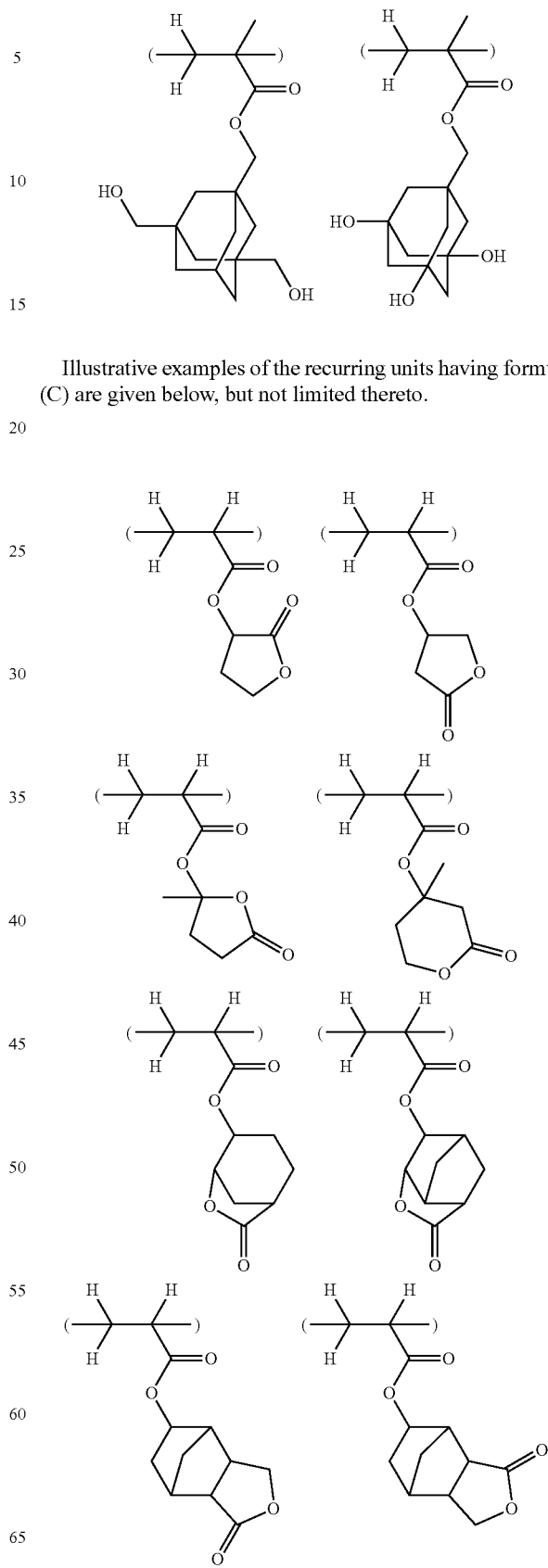
Illustrative examples of the recurring units having formula (C) are given below, but not limited thereto.

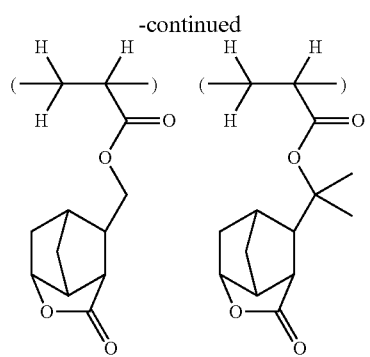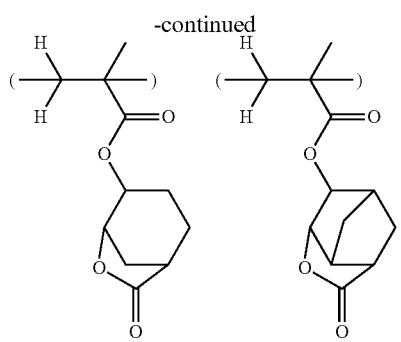

-continued
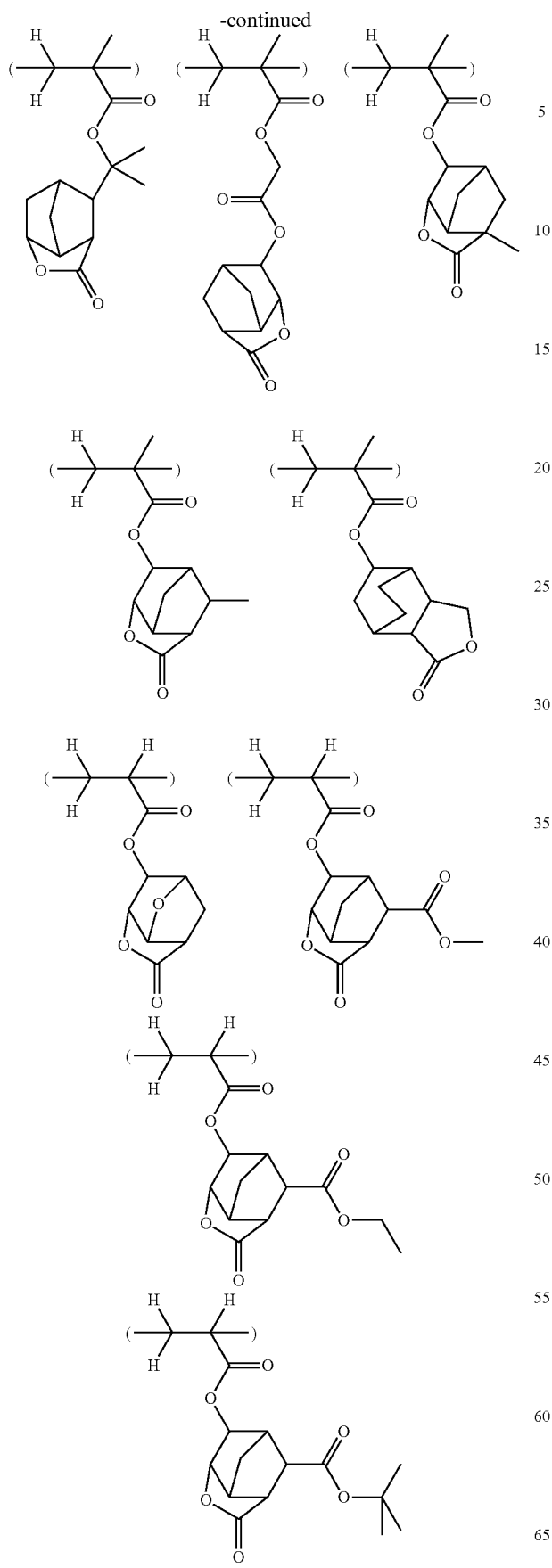
-continued
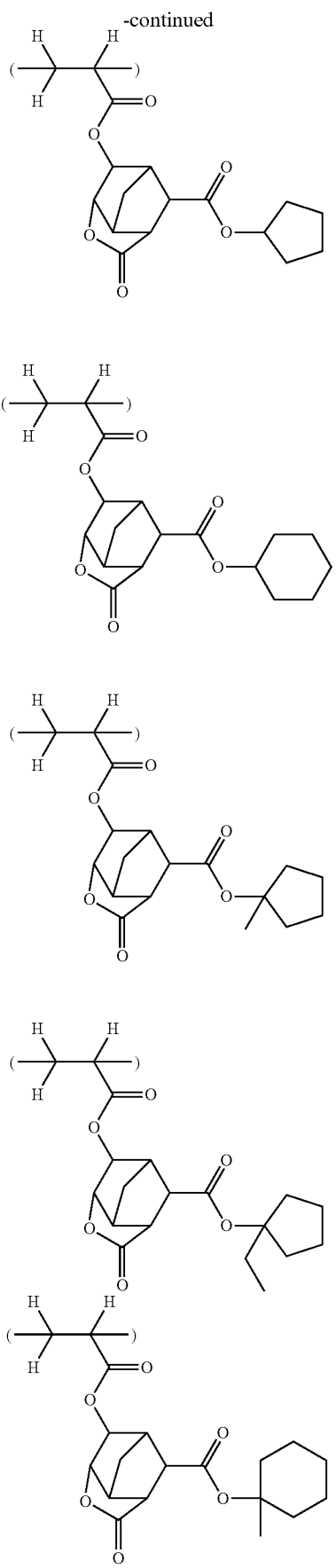

-continued
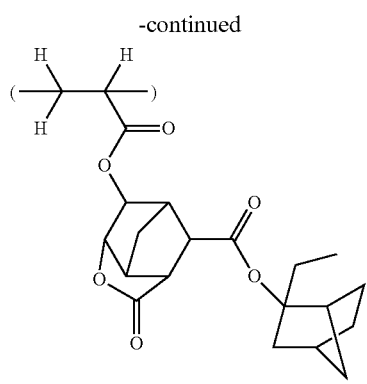
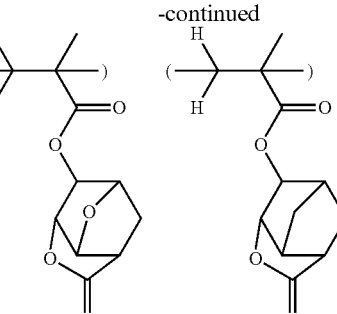
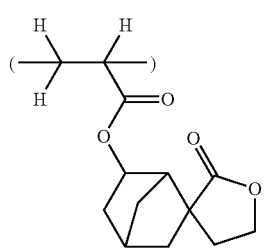
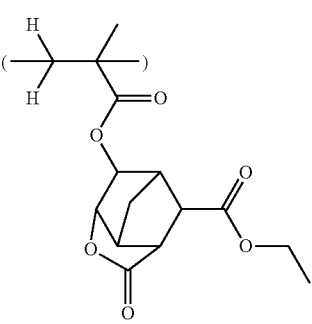
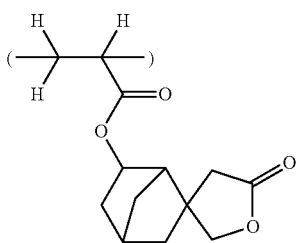
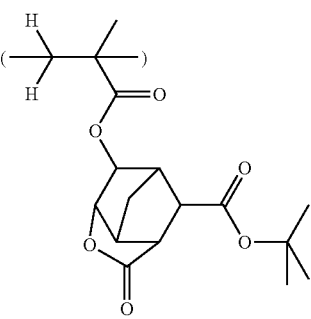
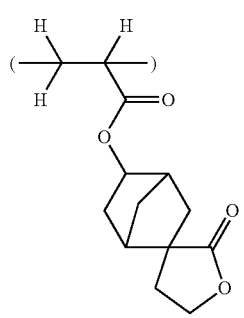
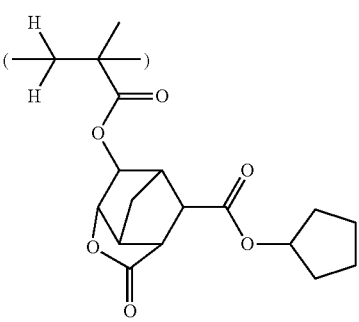
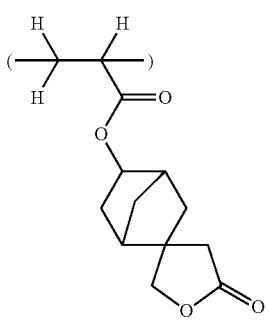
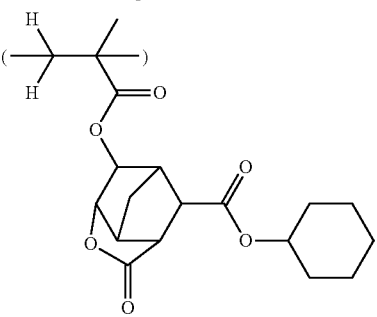

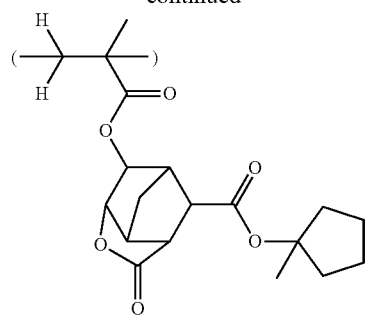
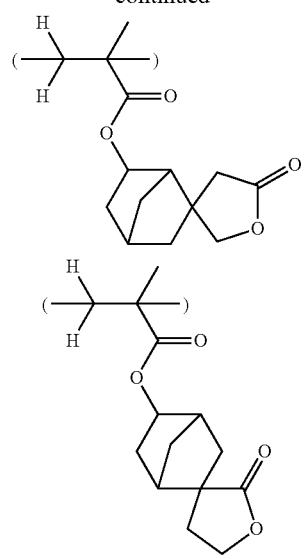

83
-continued
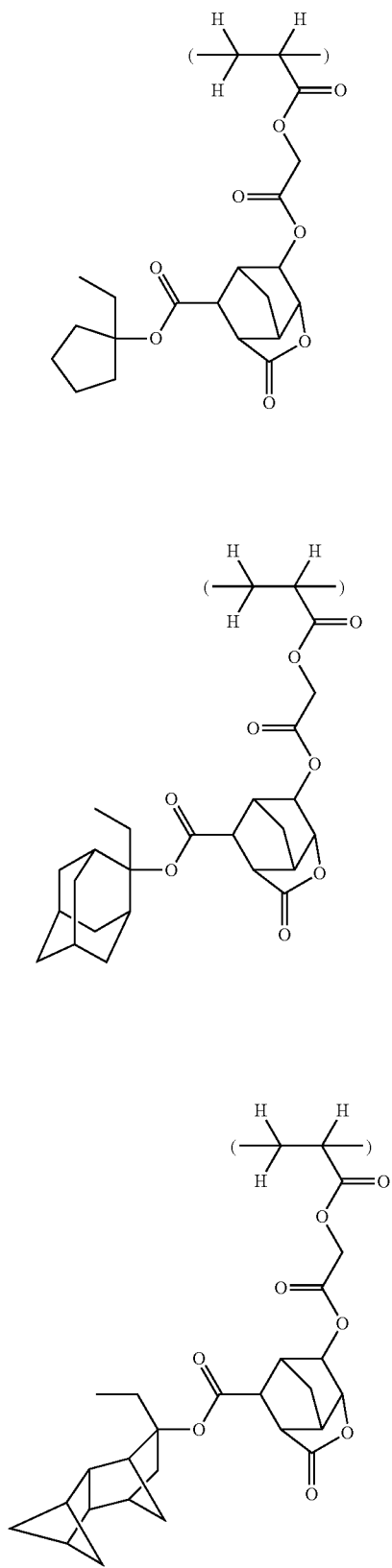
84
-continued
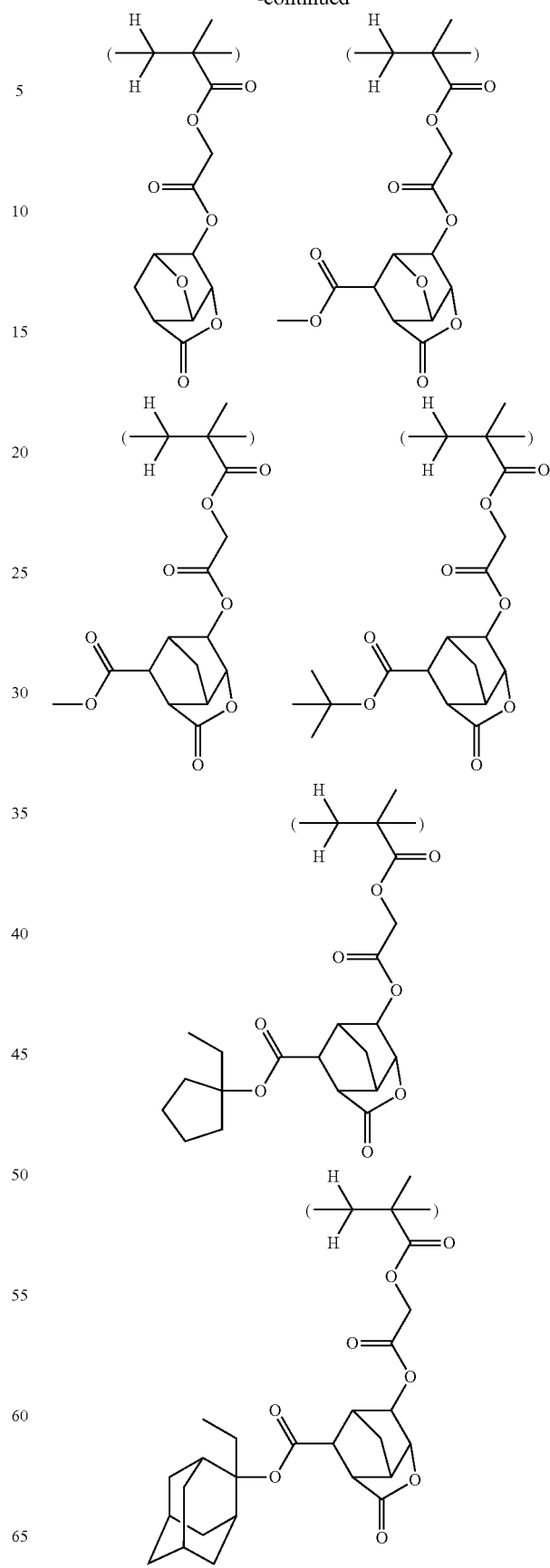

-continued
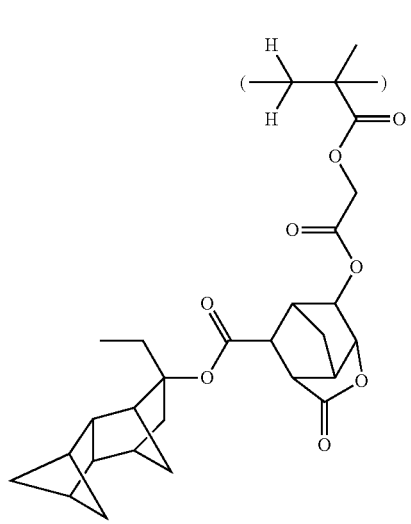
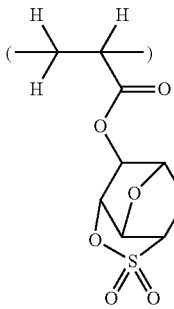
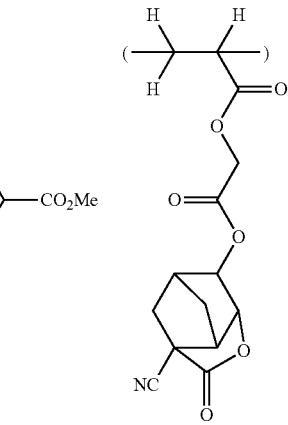
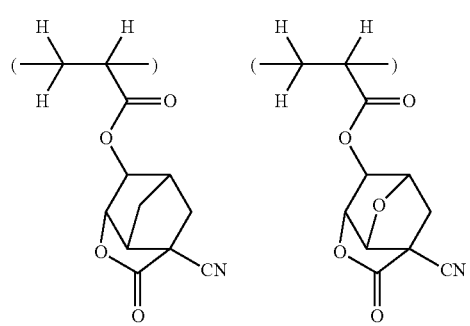
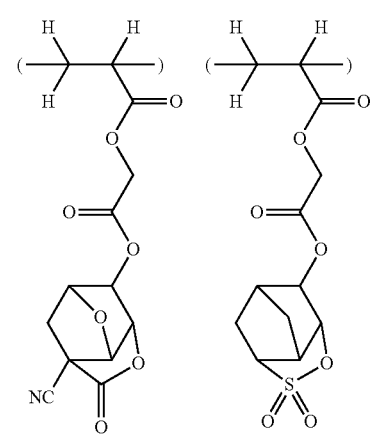
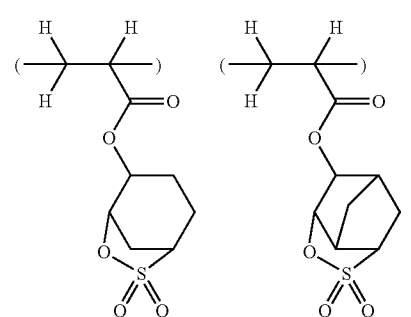
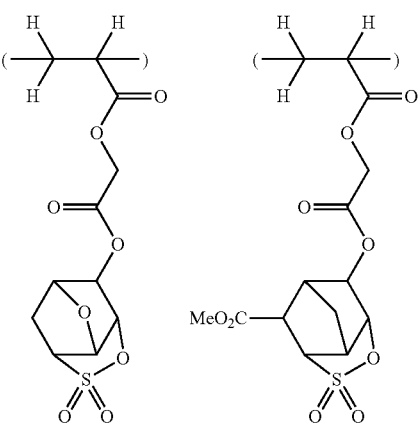
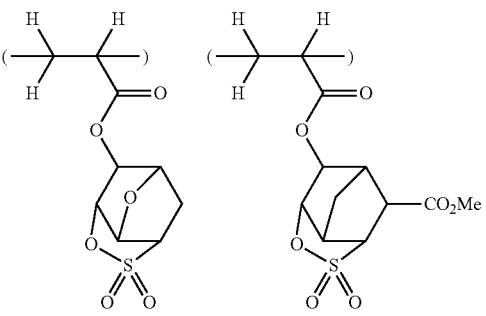
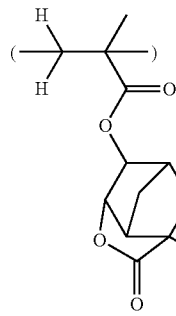
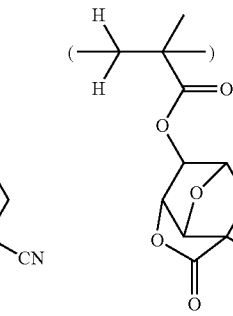

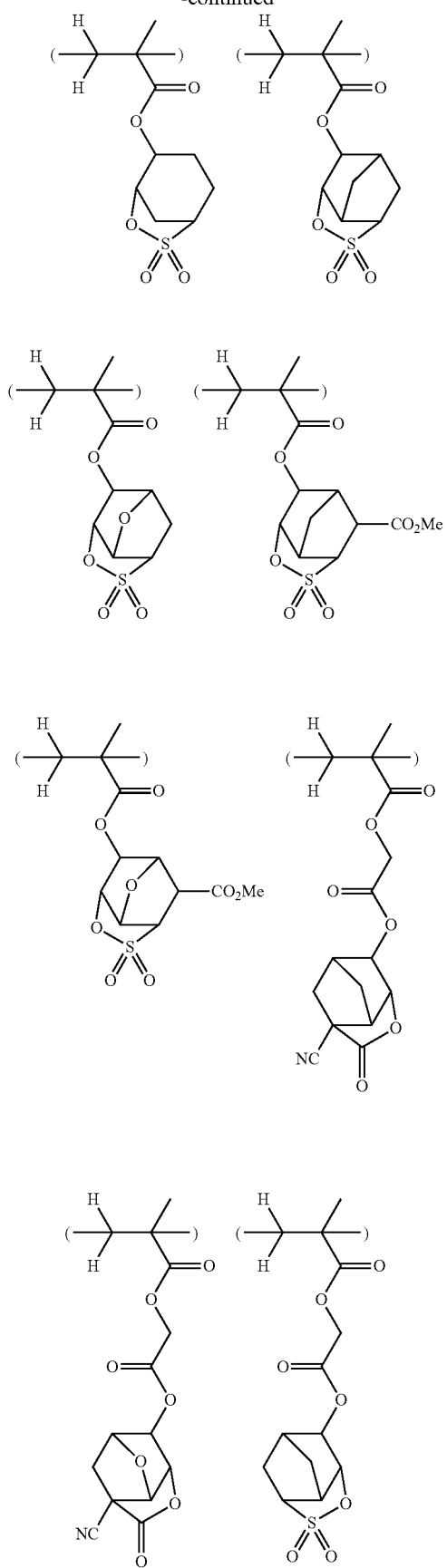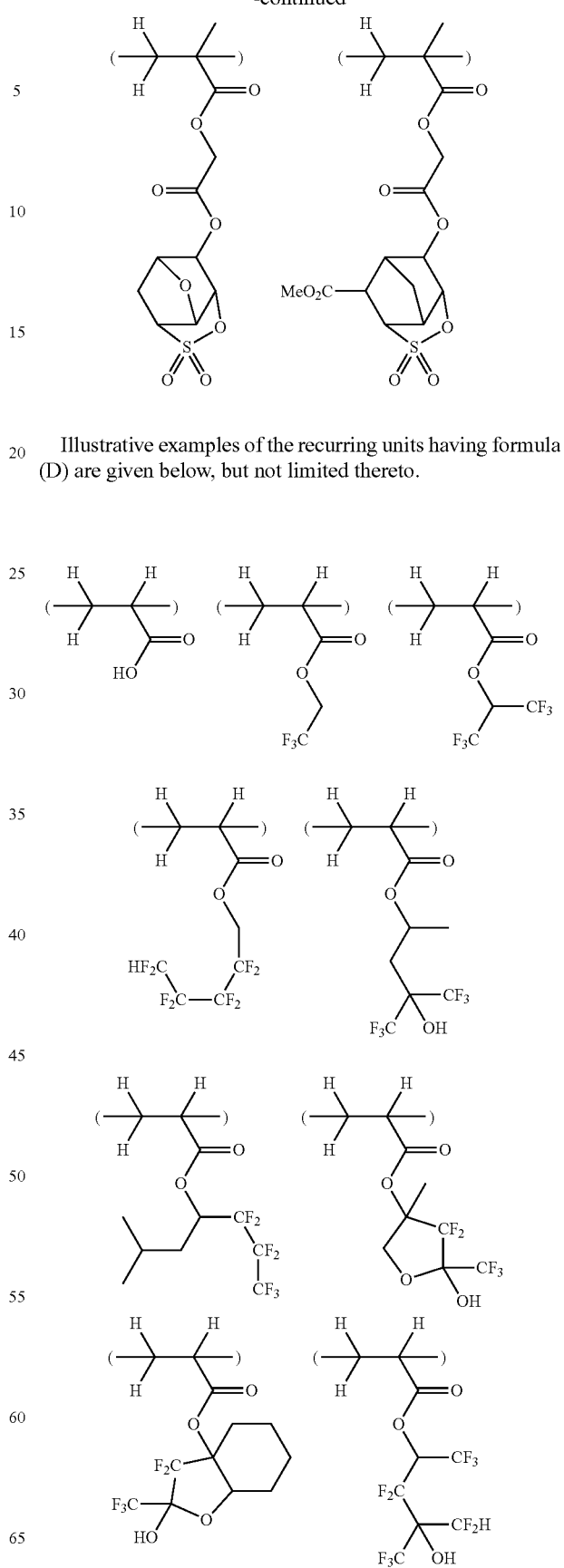
Illustrative examples of the recurring units having formula (D) are given below, but not limited thereto.

-continued
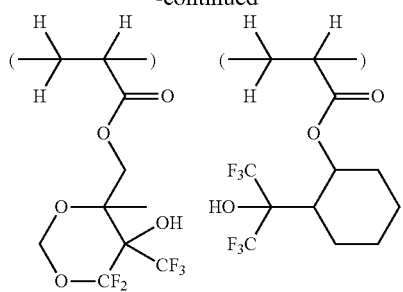
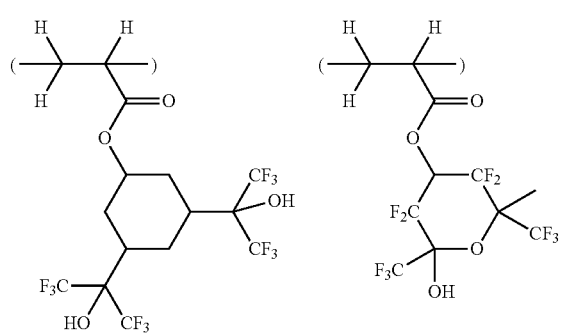
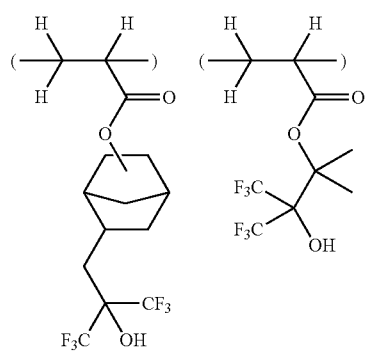
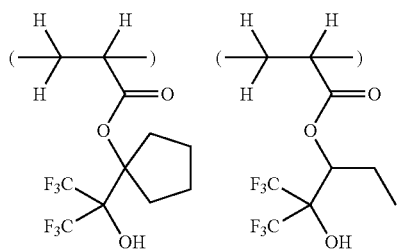
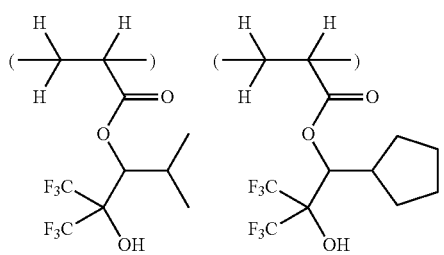
-continued
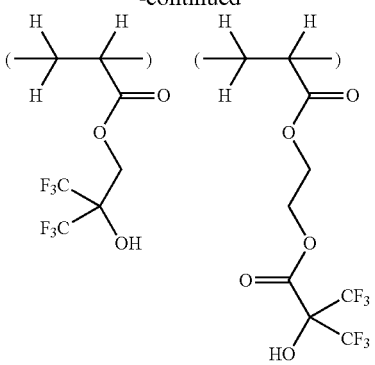
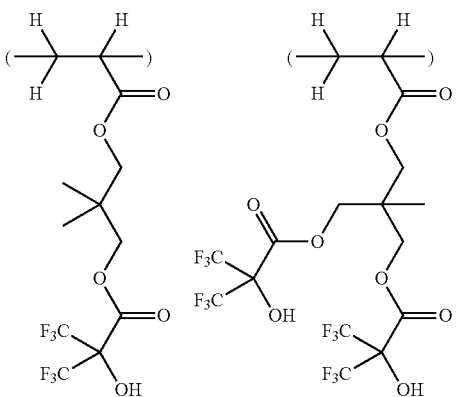
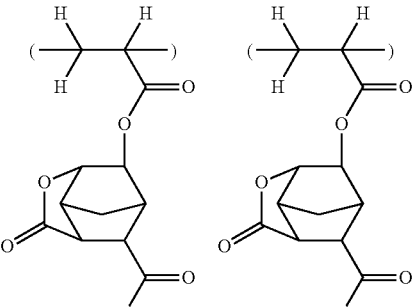
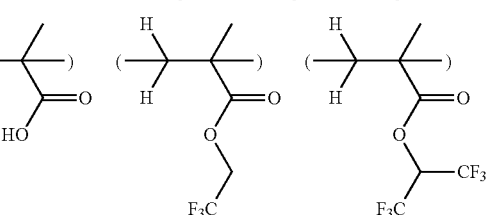
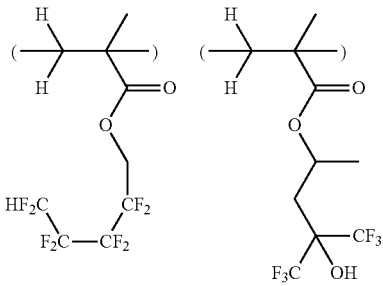

-continued
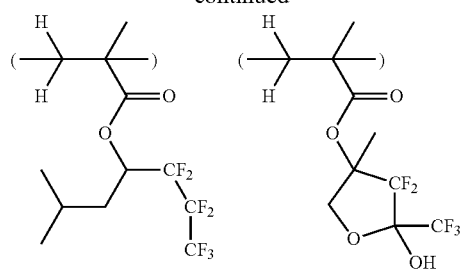
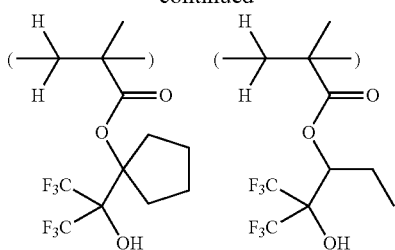
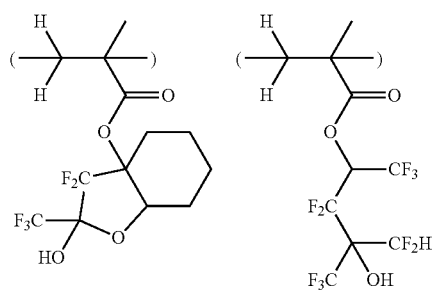
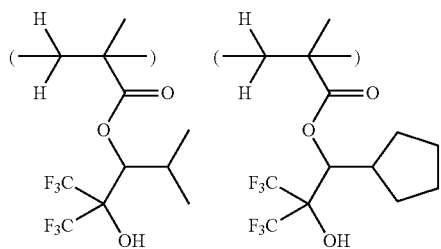
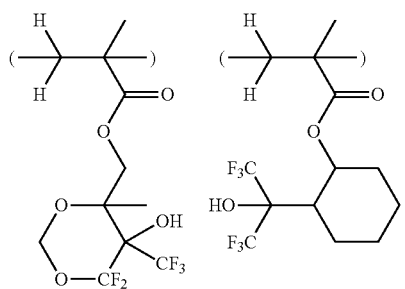
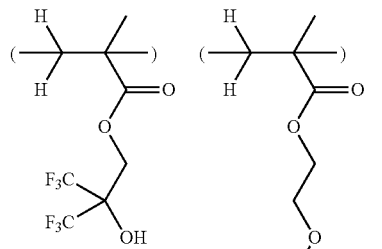
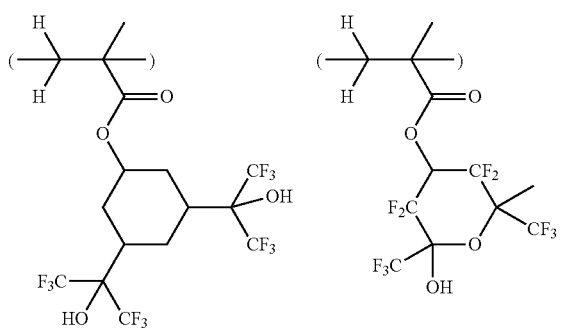
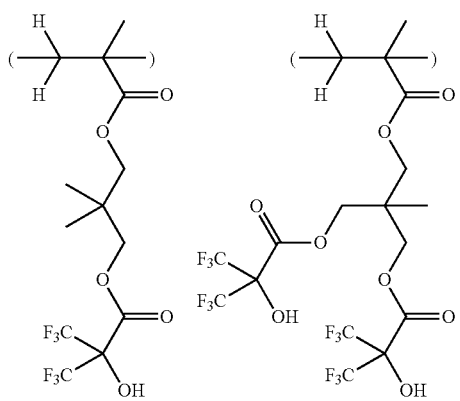
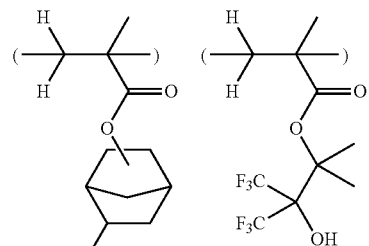
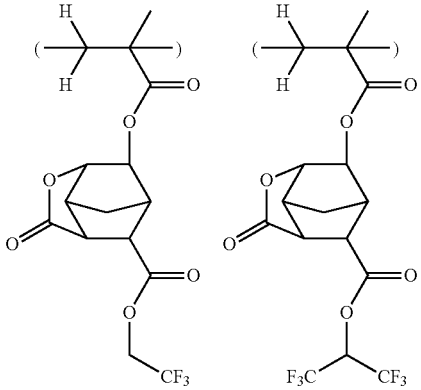

93
-continued
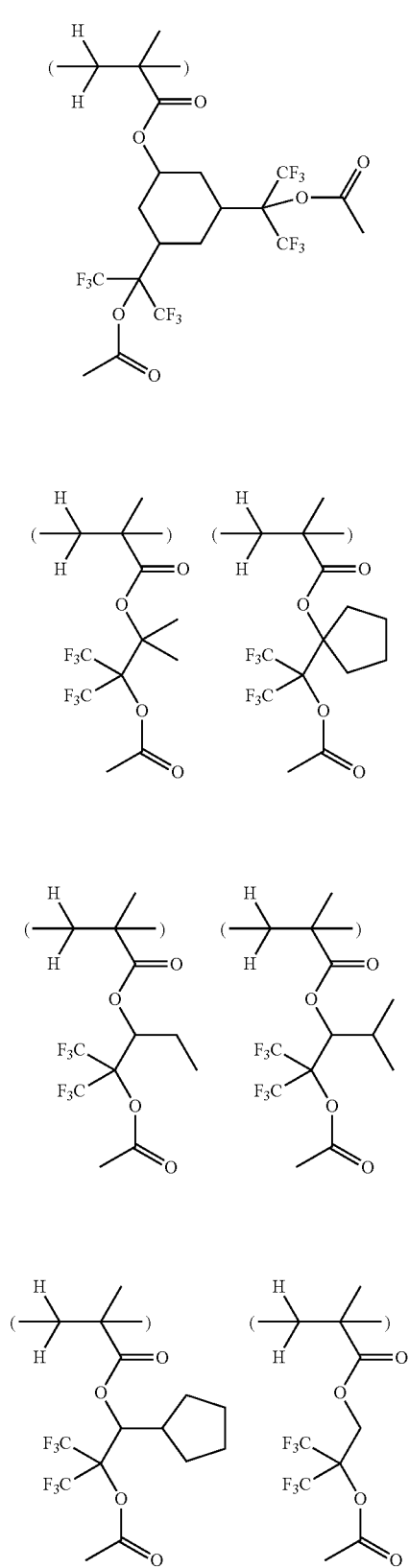
94
-continued
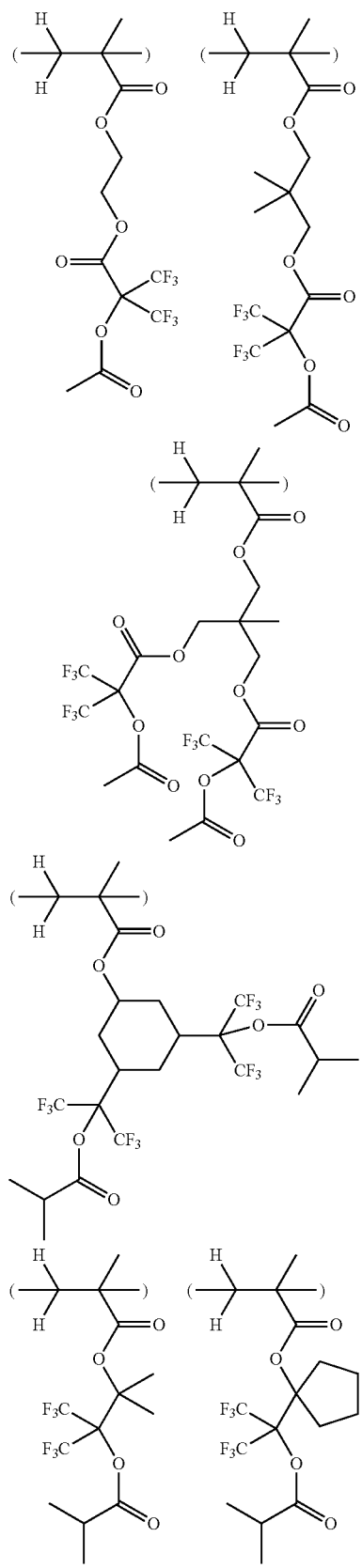

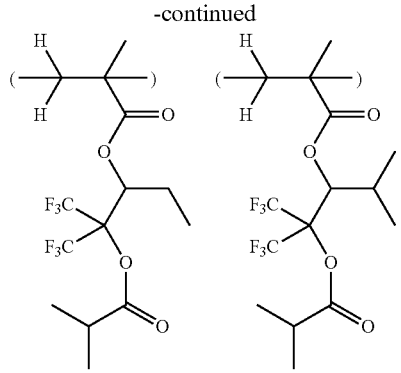
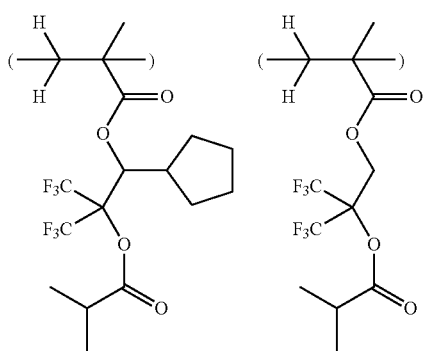
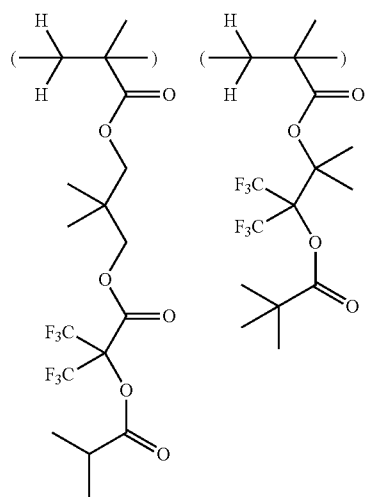
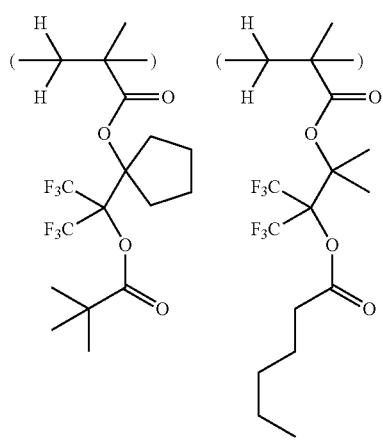

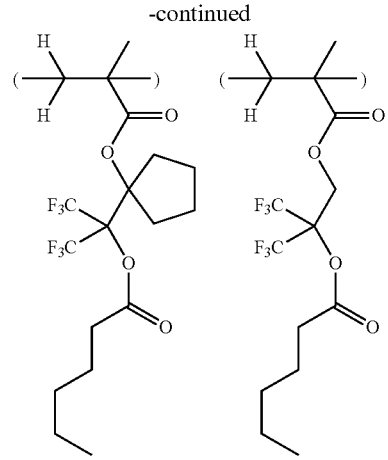

A polymer comprising recurring units of formula (E) is decomposed under the action of acid to generate a hydroxyl group so that its solubility in various solvents may change. The acid labile group XE may be selected from a variety of such groups. Examples of the acid labile group XE are groups of formulae (L1) to (L4), tertiary alkyl groups of 4 to 20 carbon atoms, trialkylsilyl groups in which each alkyl moiety has 1 to 6 carbon atoms, and oxoalkyl groups of 4 to 20 carbon atoms, like the acid labile group XA mentioned above.

Illustrative examples of the recurring units having formula (E) are given below, but not limited thereto.

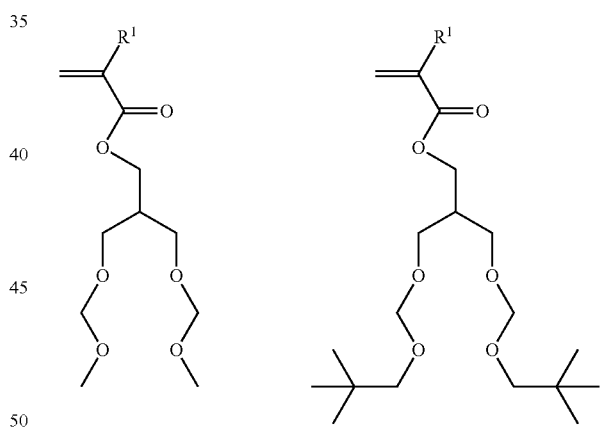
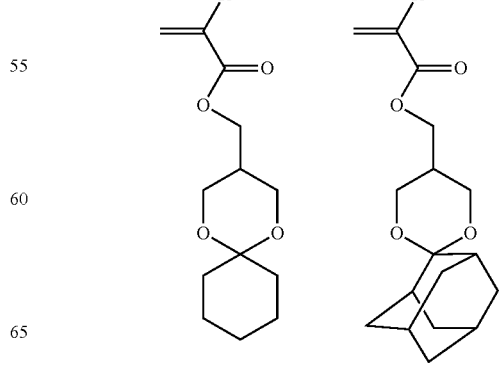

97
-continued
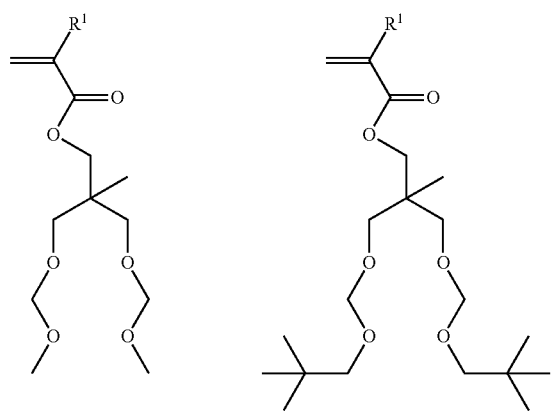
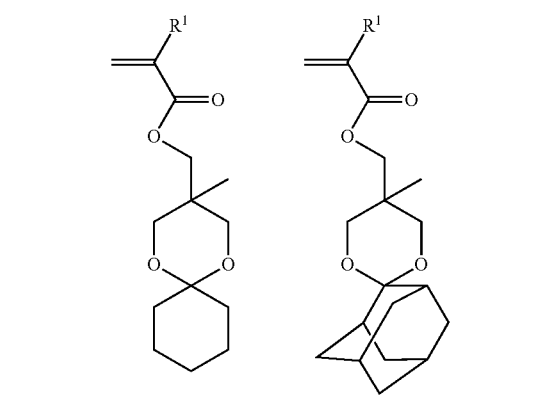
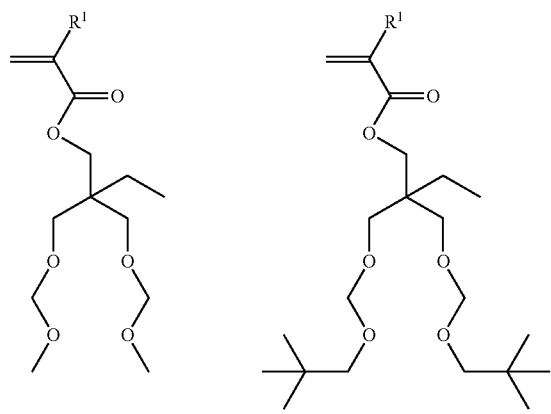
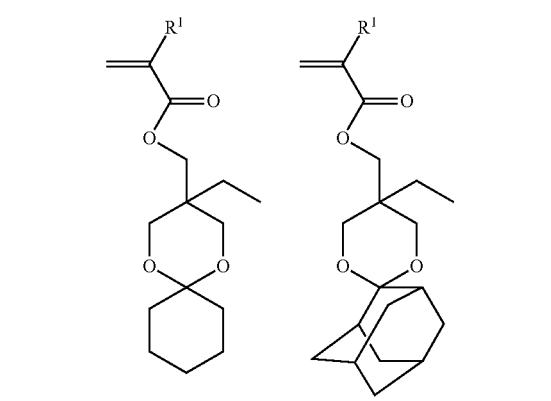
98
-continued
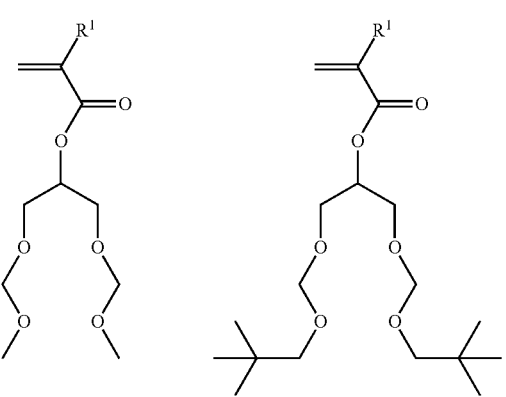
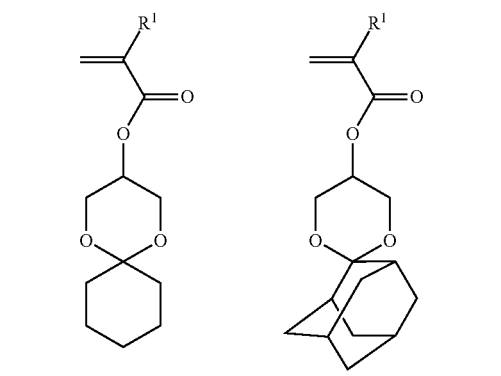
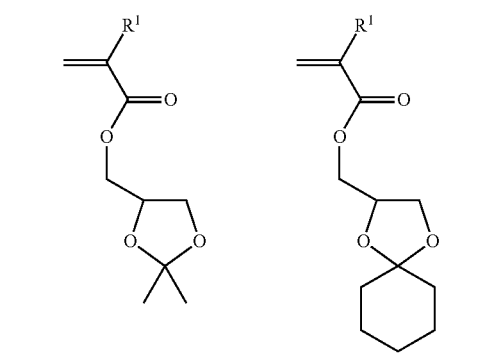
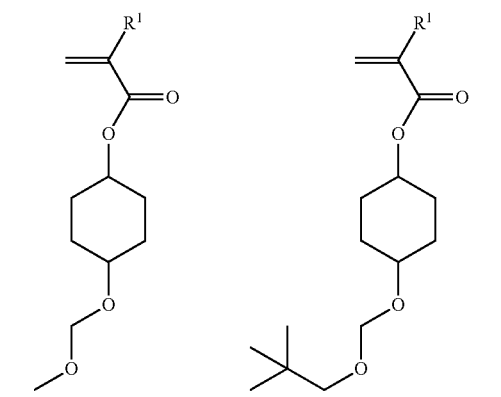

99
-continued
100
-continued
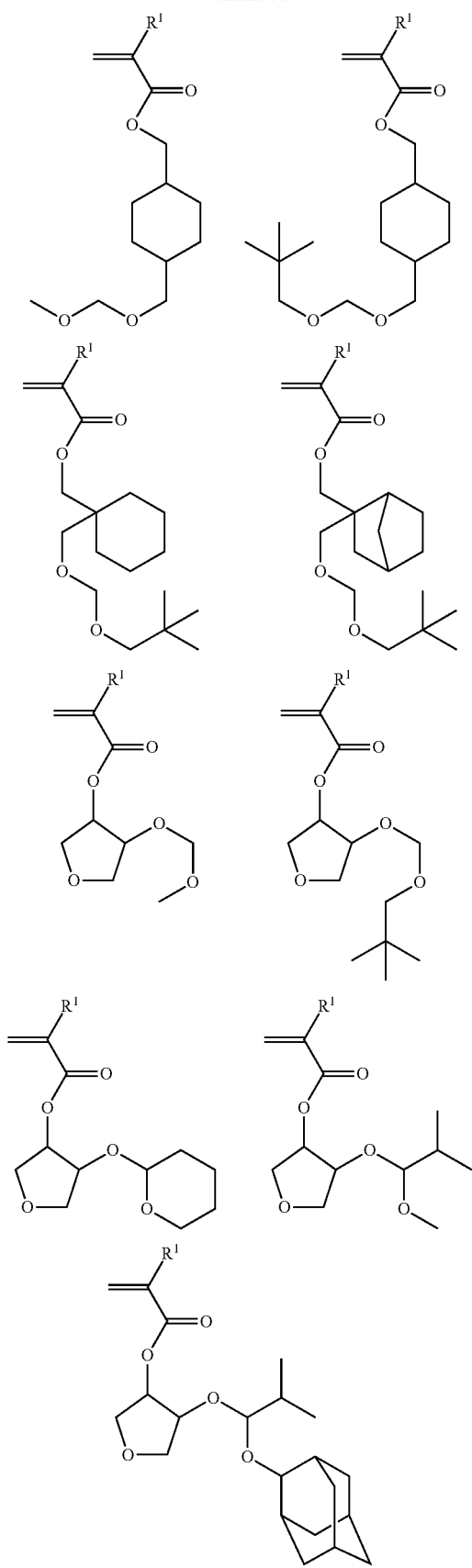
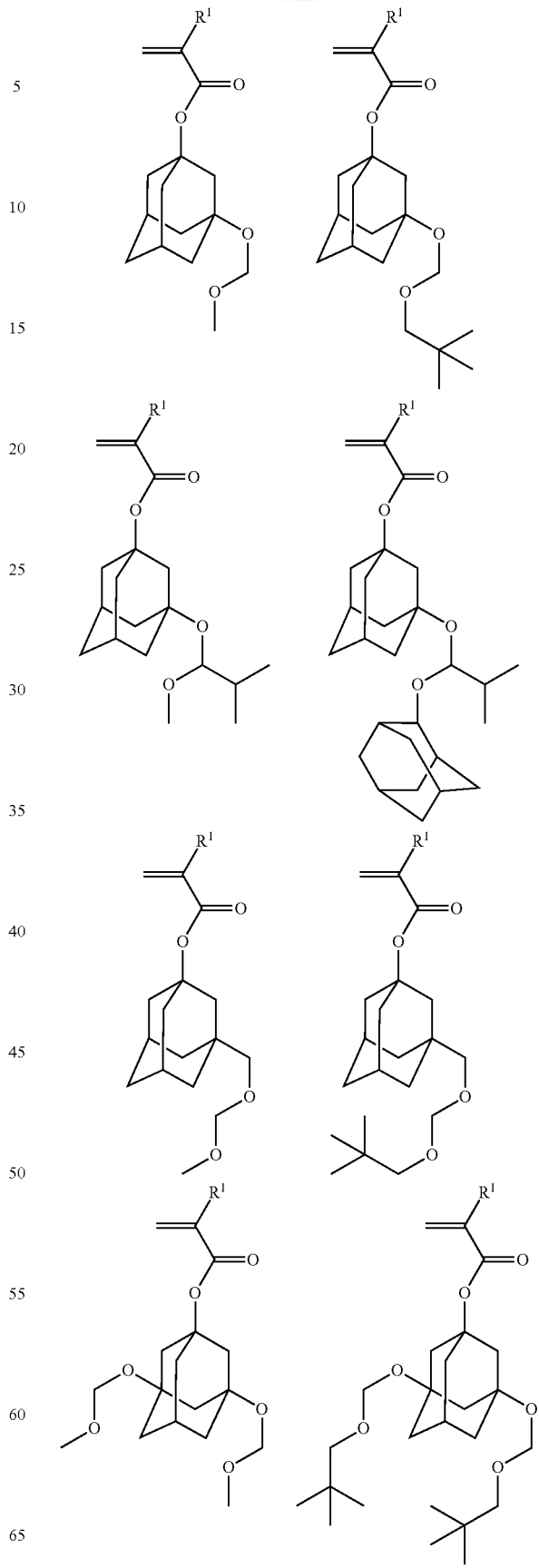

101
-continued
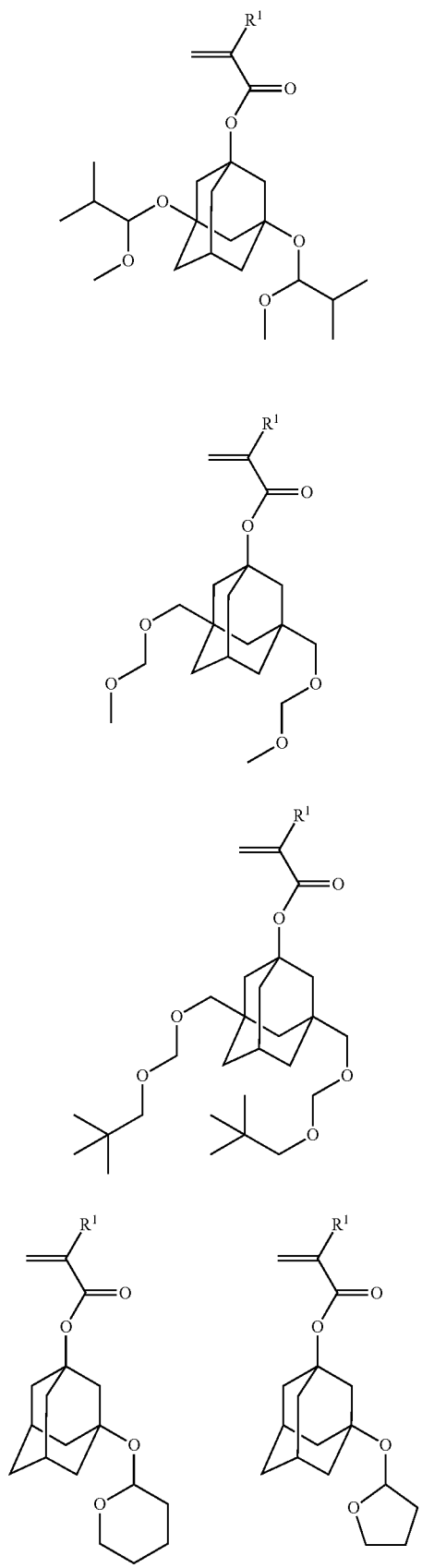
102
-continued
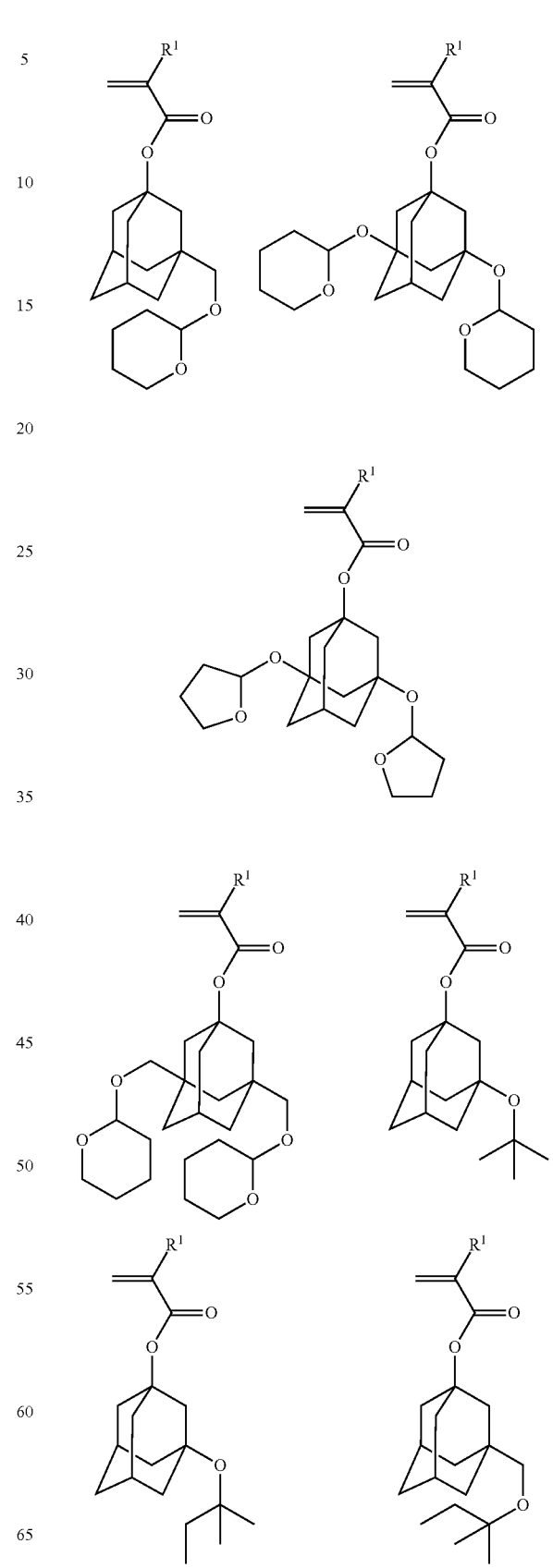

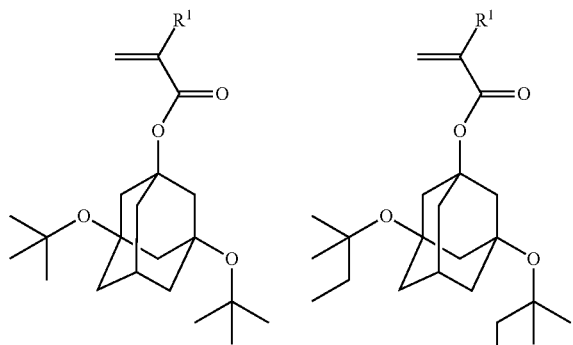
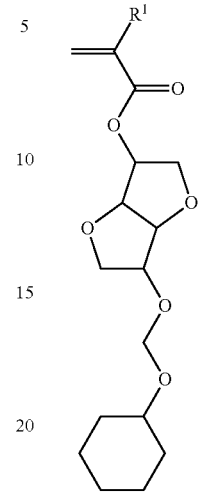
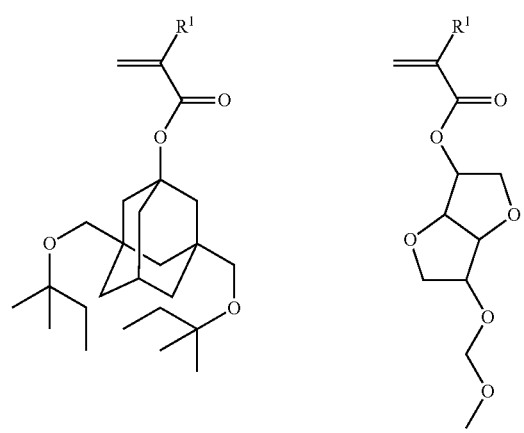
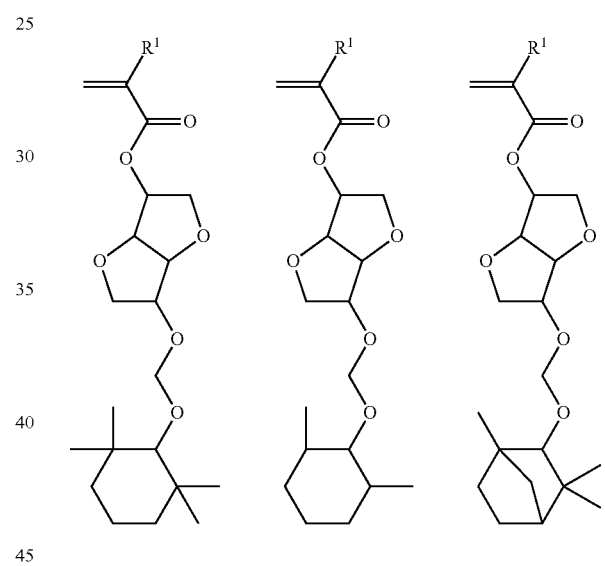
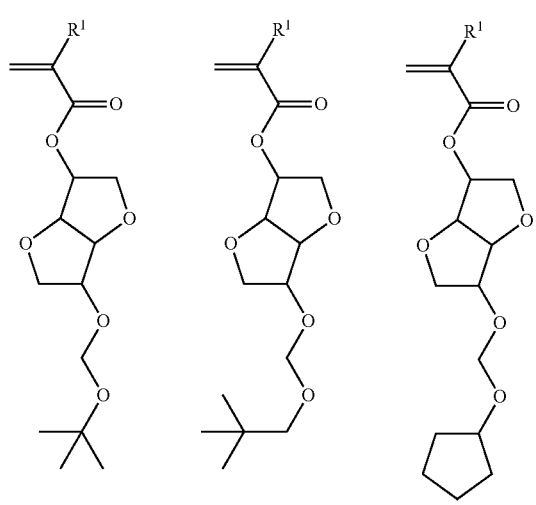
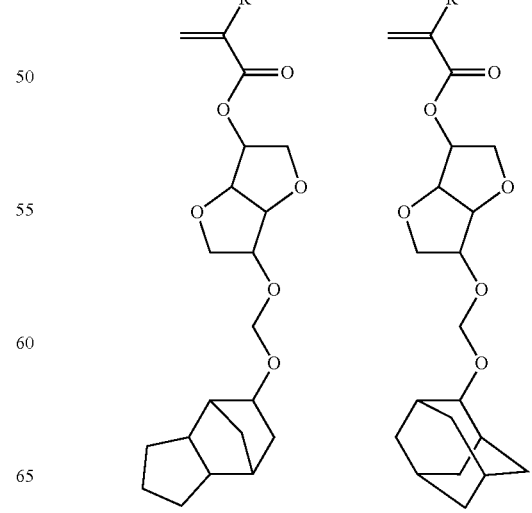

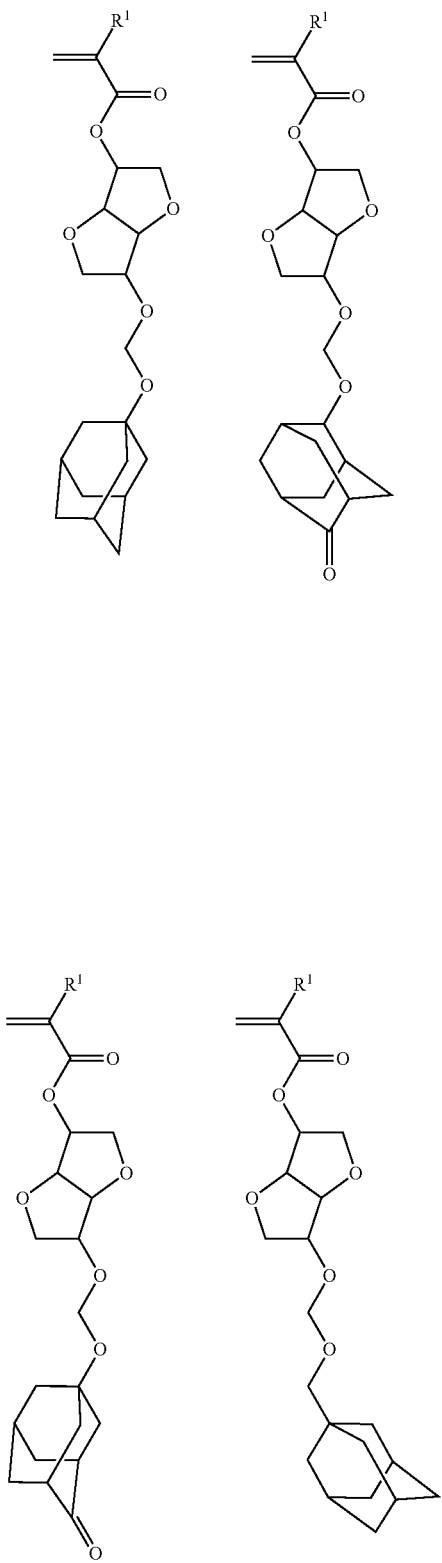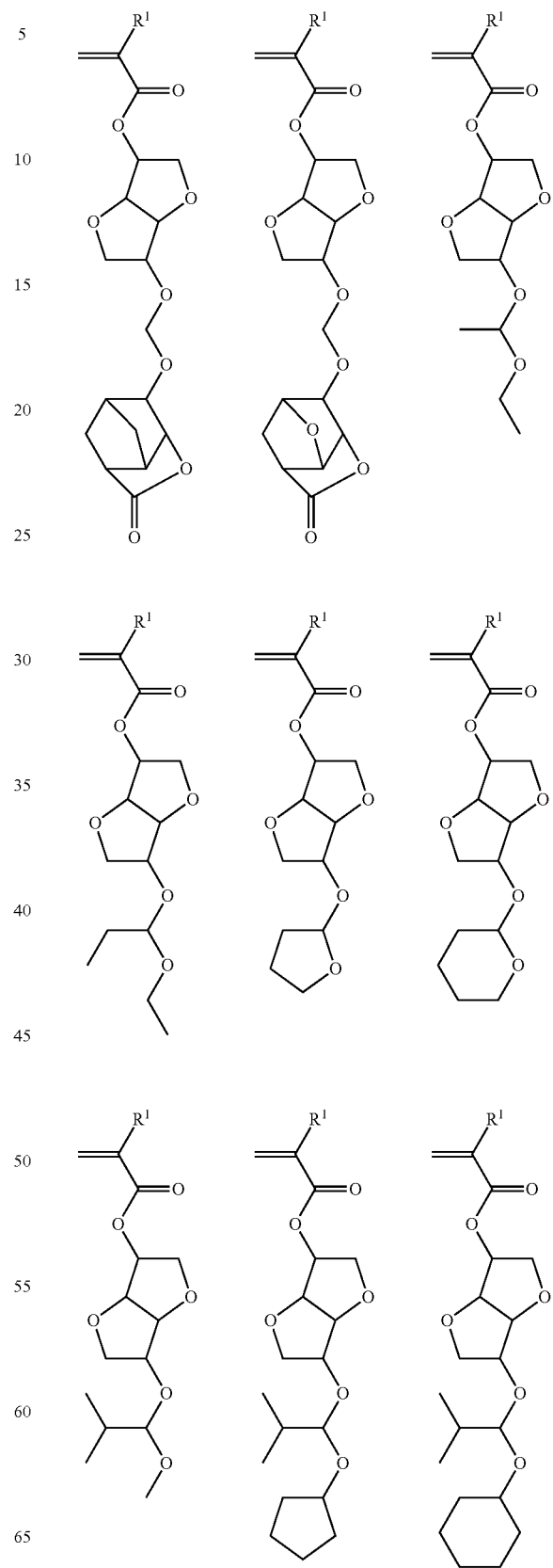

107
-continued
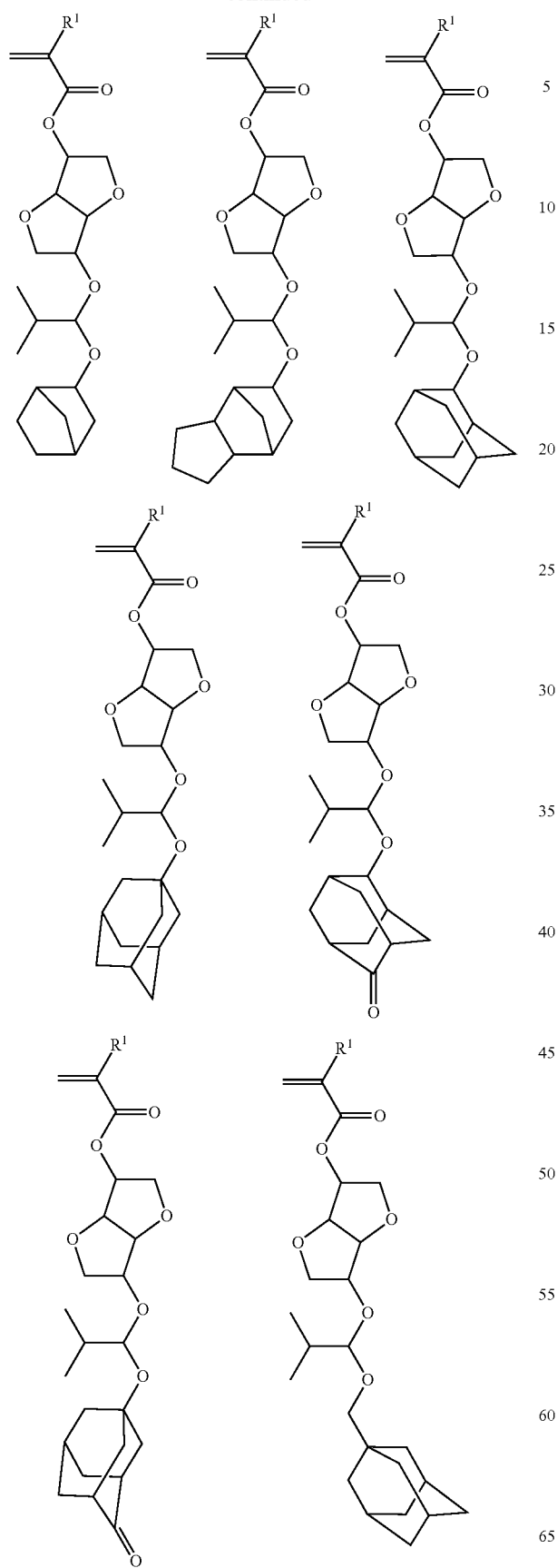
108
-continued
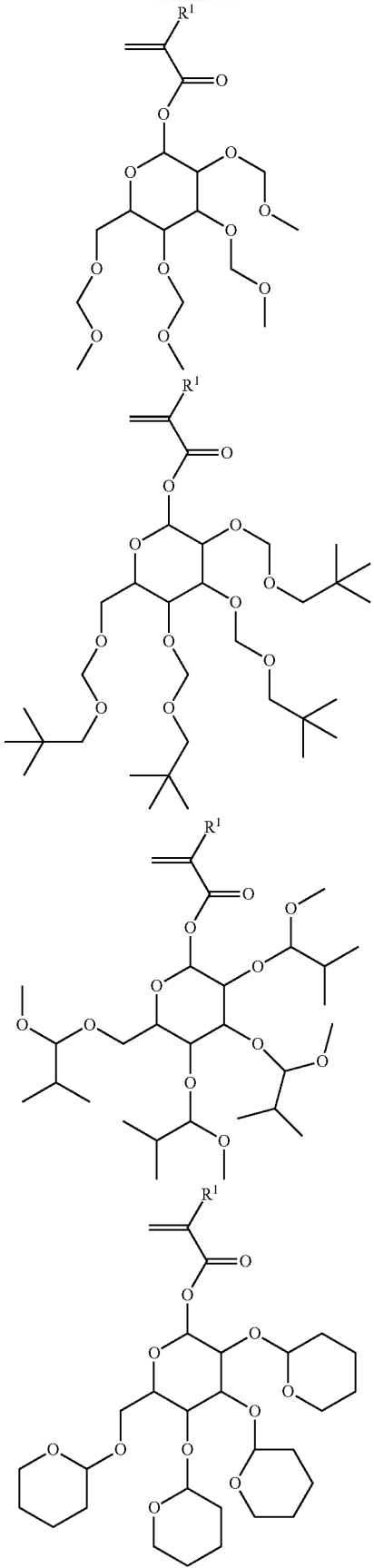

109
-continued
110
-continued
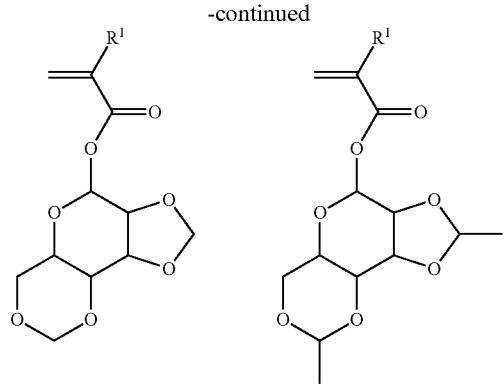
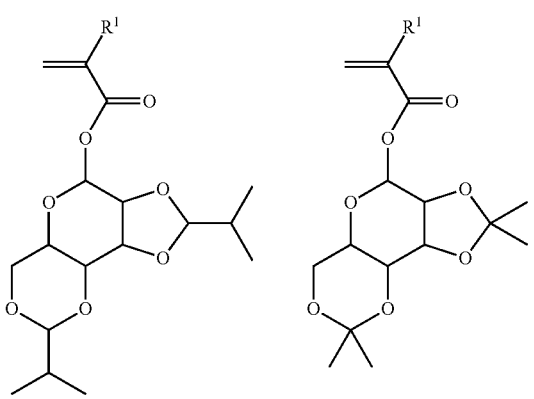
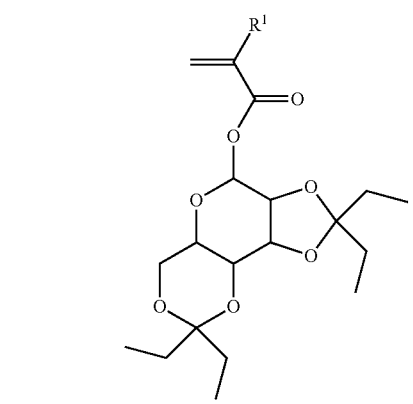
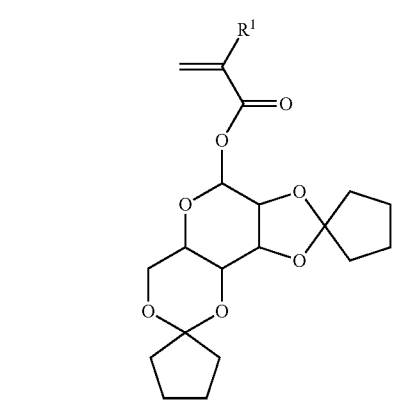
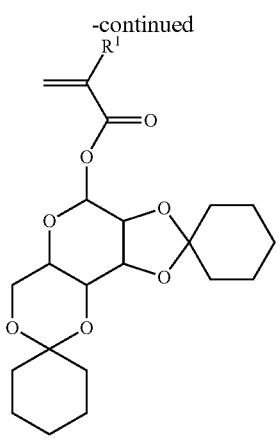
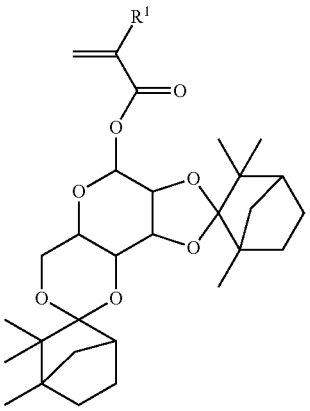
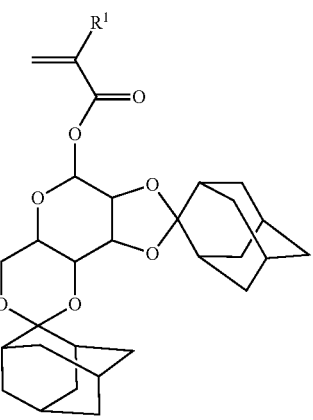
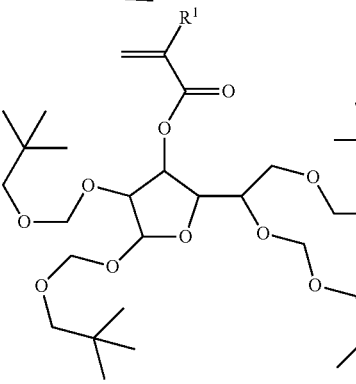

-continued

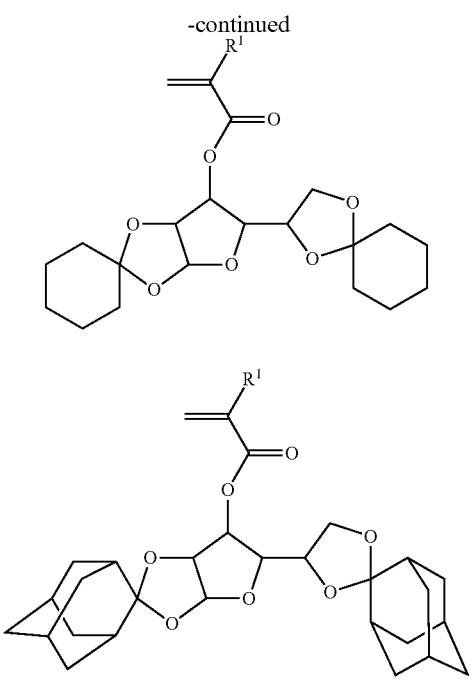

Herein $R^1$ is as defined above.

In a preferred embodiment, the polymer may have further copolymerized therein any of recurring units (d1) to (d3) of sulfonium salt represented by the following general formulae.

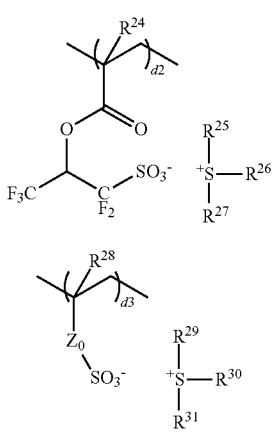

Herein $R^{20}$, $R^{24}$ and $R^{28}$ each are hydrogen or methyl. $R^{21}$ is a single bond, phenylene, —O—$R^{33}$—, or —C(=O)—Y—$R^{33}$— wherein Y is oxygen or NH and $R^{33}$ is a straight, branched or cyclic $C_1$-$C_6$ alkylene group, alkenylene group or phenylene group, which may contain a carbonyl (—CO—), ester (—COO—), ether (—O—) or hydroxyl moiety. $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether moiety, or a $C_6$-$C_{12}$ aryl group, $C_7$-$C_{20}$ aralkyl group, or thiophenyl group. $Z_0$ is a single bond, methylene, ethylene, phenylene, fluorinated phenylene, —O—$R^{32}$—, or —C(=O)—$Z_1$—$R^{32}$— wherein $Z_1$ is oxygen or NH and $R^{32}$ is a straight, branched or cyclic $C_1$-$C_6$ alkylene group, alkenylene group or phenylene group, which may contain a carbonyl, ester, ether or hydroxyl moiety. M is a non-nucleophilic counter ion.

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are a sulfonate which is fluorinated at α-position as represented by the general formula (F-1) and a sulfonate which is fluorinated at α- and β-positions as represented by the general formula (F-2).

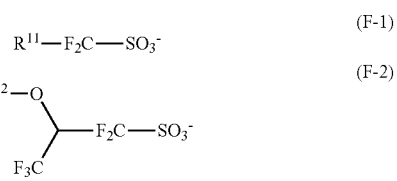

In formula (F-1), $R^{11}$ is hydrogen, or a straight, branched or cyclic $C_1$-$C_{20}$ alkyl group, $C_2$-$C_{20}$ alkenyl group or $C_6$-$C_{20}$ aryl group, which may have an ether, ester, carbonyl moiety, lactone ring or fluorine atom. In formula (F-2), $R^{12}$ is hydrogen, or a straight, branched or cyclic $C_1$-$C_{30}$ alkyl group, acyl group, $C_2$-$C_{20}$ alkenyl group, $C_6$-$C_{20}$ aryl group or aryloxy group, which may have an ether, ester, carbonyl moiety or lactone ring.

Furthermore, recurring units (g) having an oxirane or oxetane ring may be copolymerized. When recurring units (g) having an oxirane or oxetane ring are copolymerized, the exposed region of a resist film is crosslinked, indicating that the exposed region is improved in film retention and etch resistance. Examples of recurring units (g) having an oxirane or oxetane ring are shown below. Note that $R^{41}$ is hydrogen or methyl.

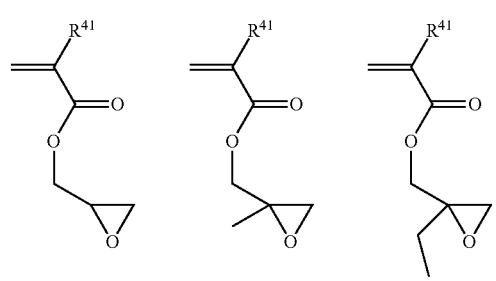

-continued
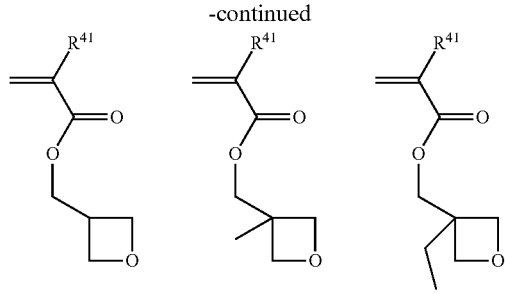
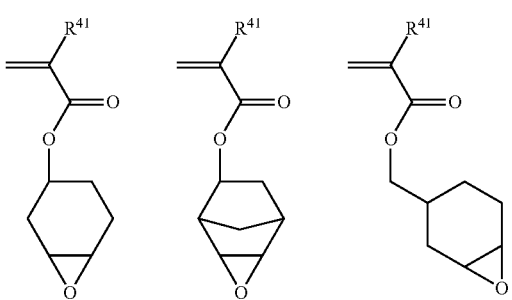
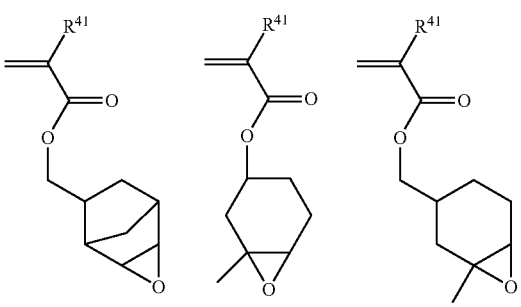
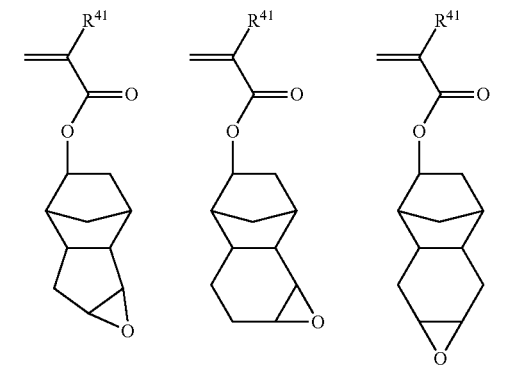
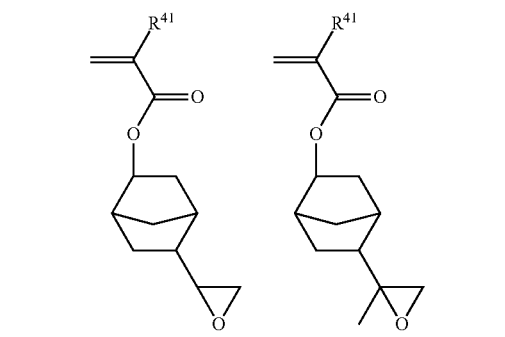
-continued
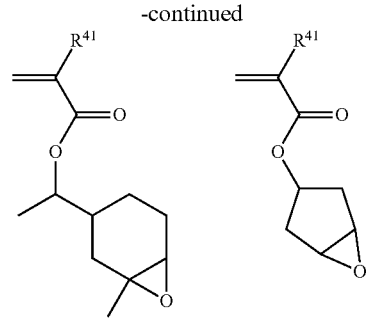
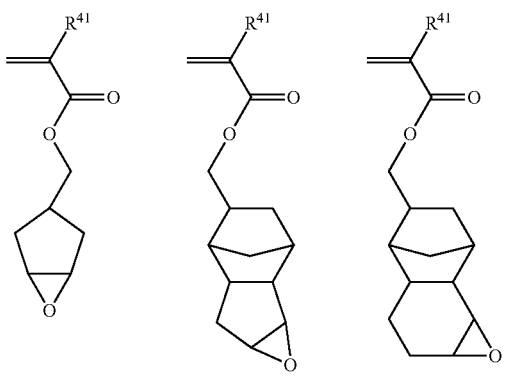
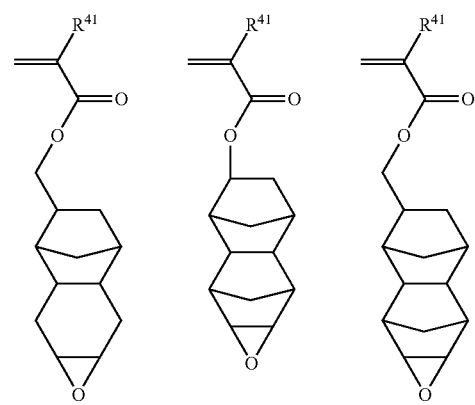
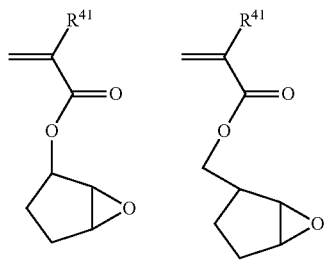
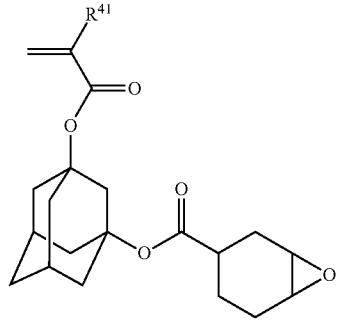

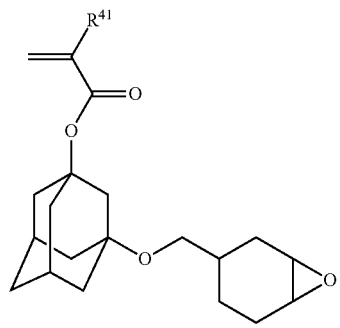
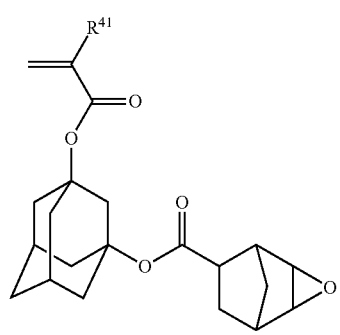
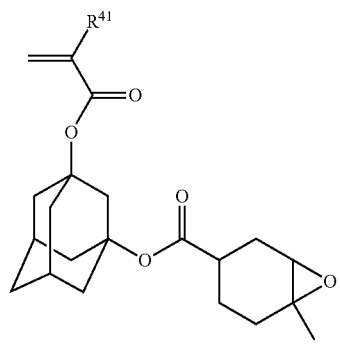
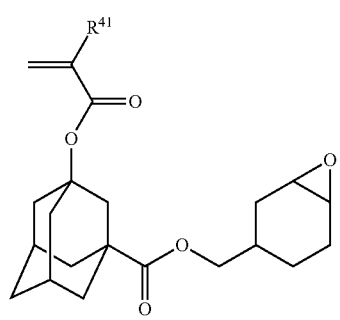
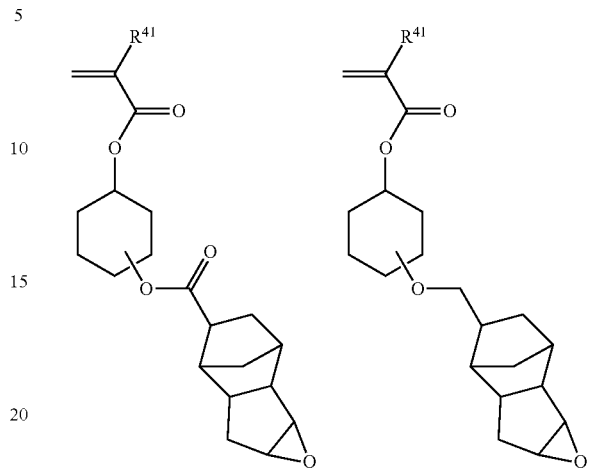
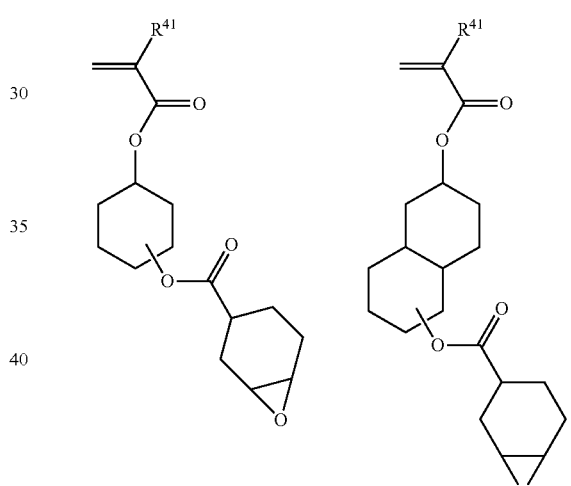
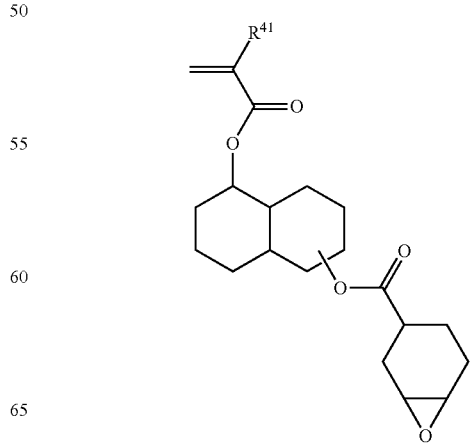

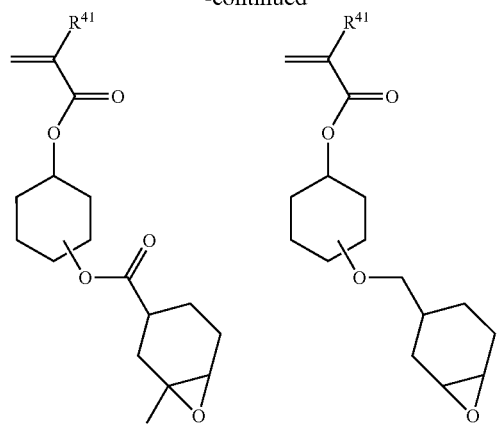
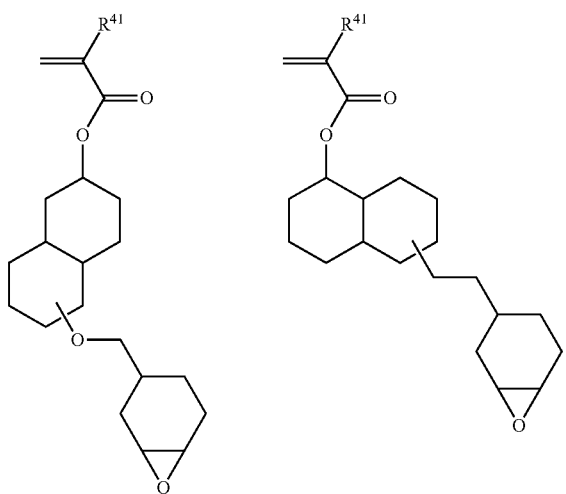
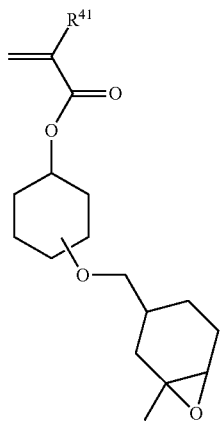
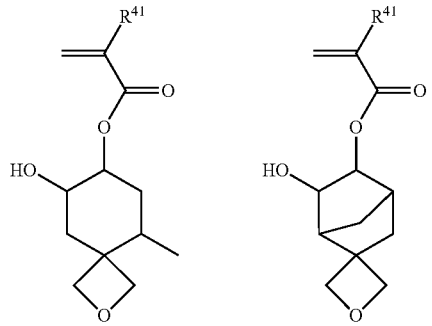
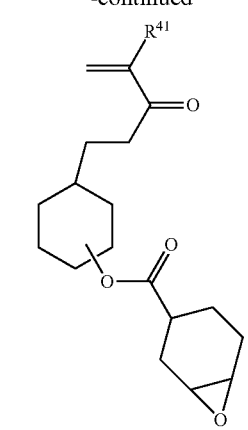

In addition to the foregoing units, the polymer may further comprise recurring units (h) derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers shown below. In the following examples, $R^5$ is hydrogen or methyl, and $R^7$ is hydrogen or $C_1$-$C_{10}$ alkyl.

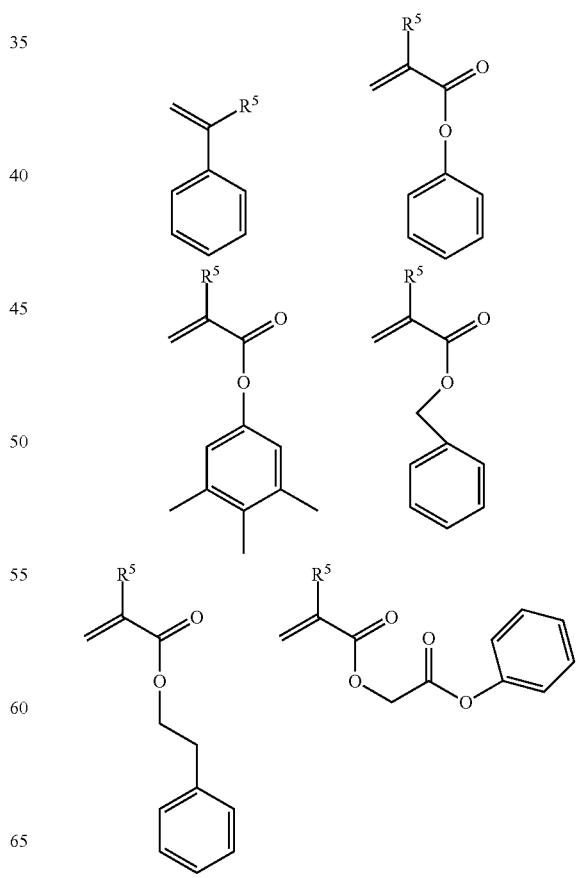

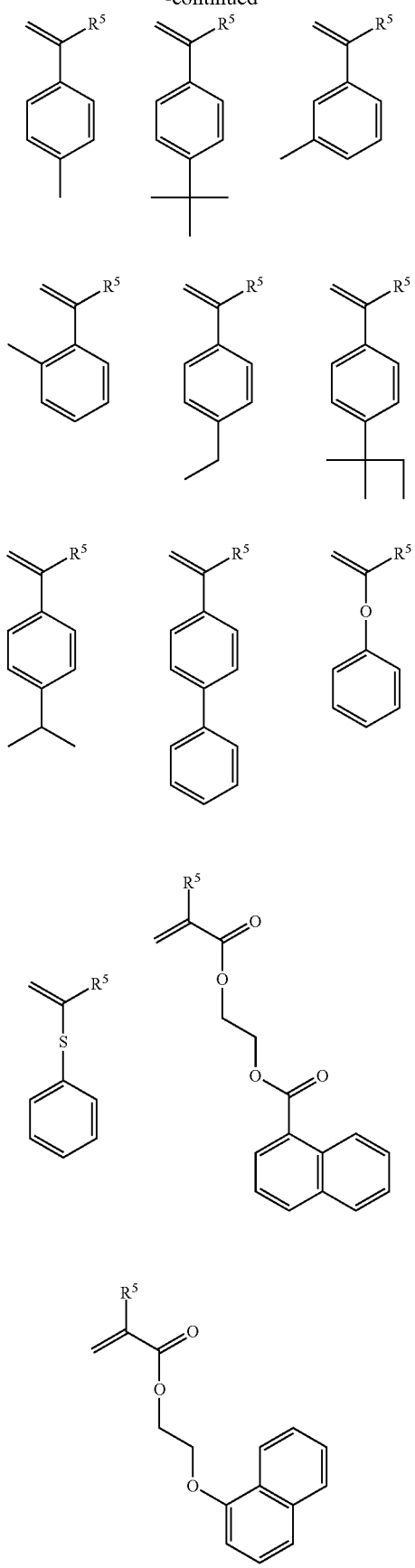

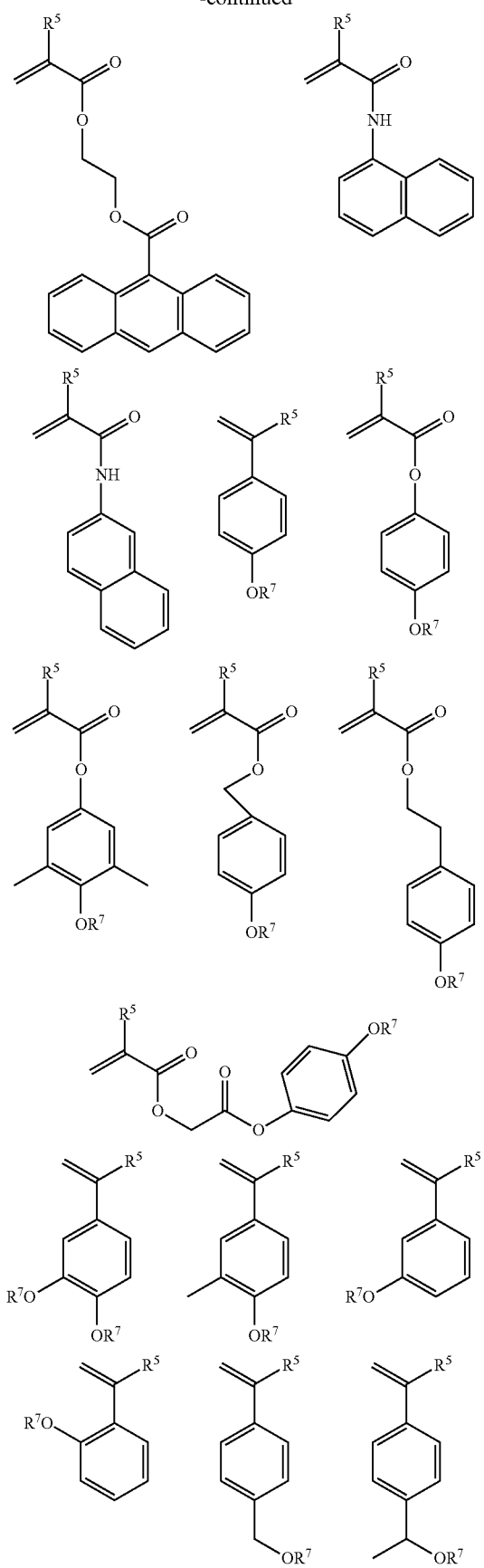
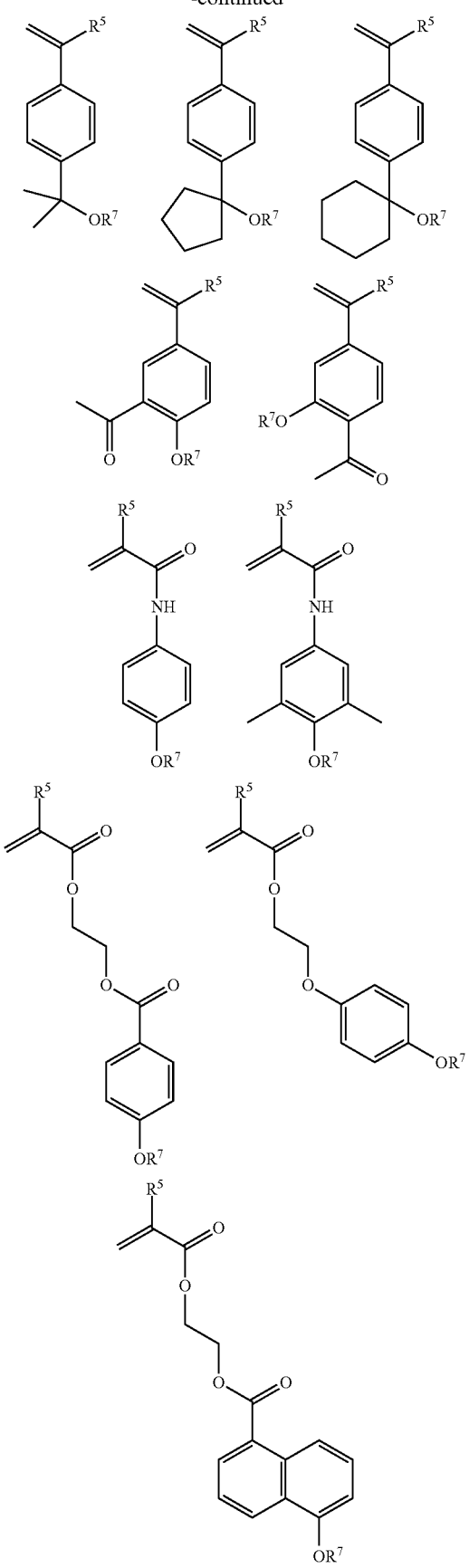

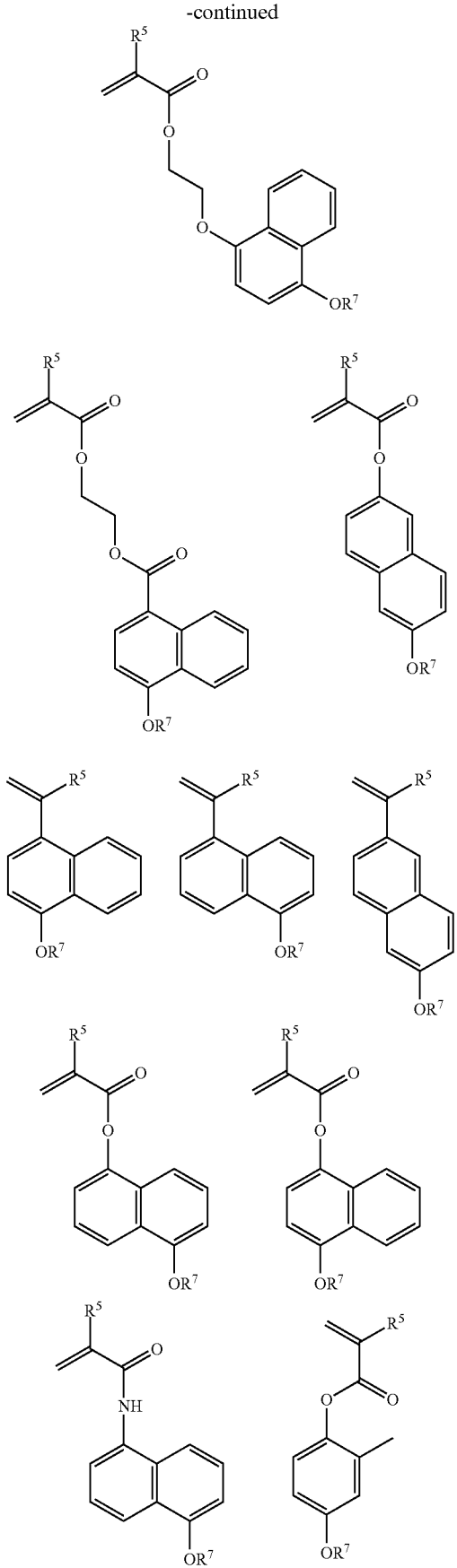

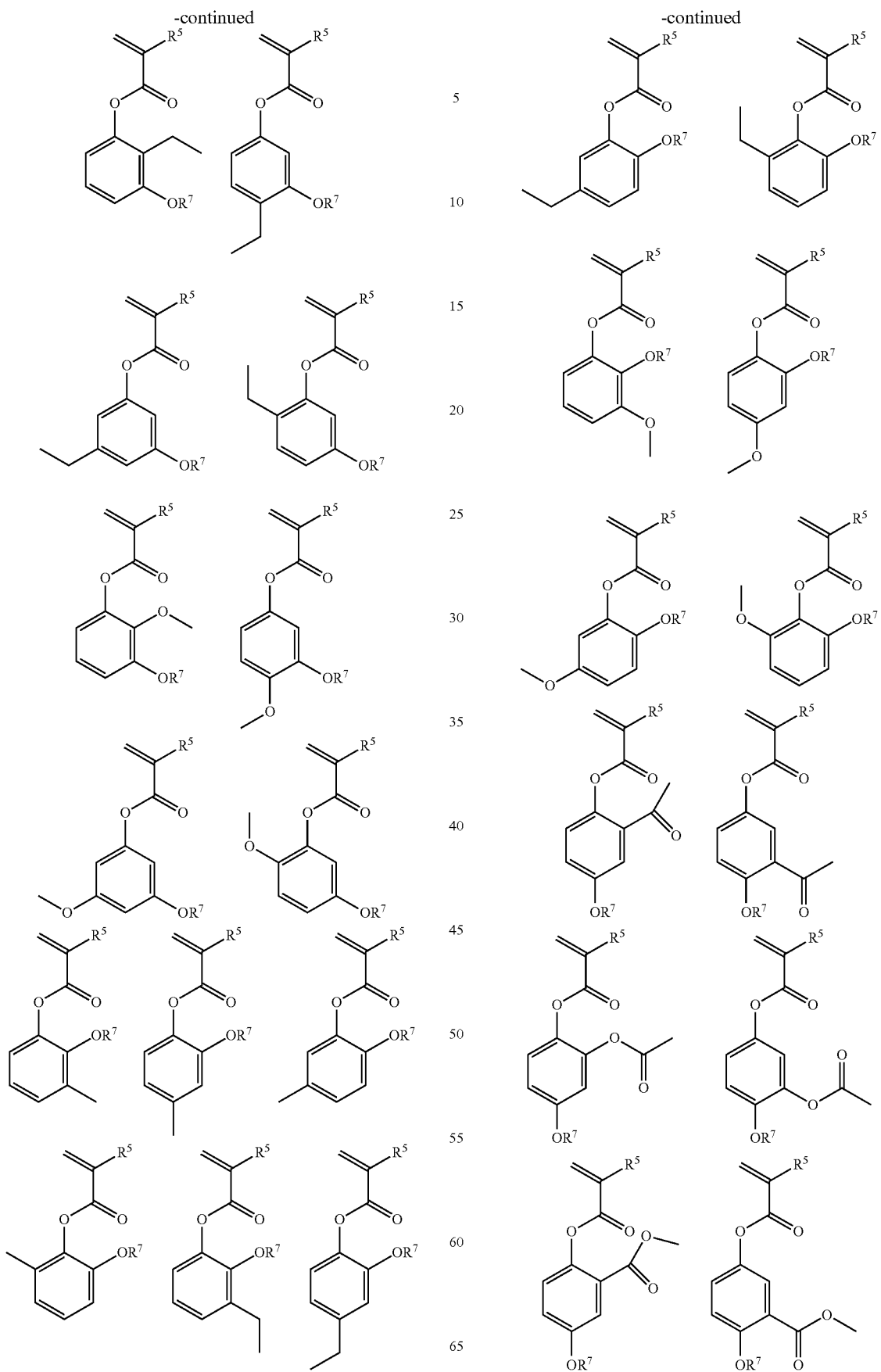

127
-continued
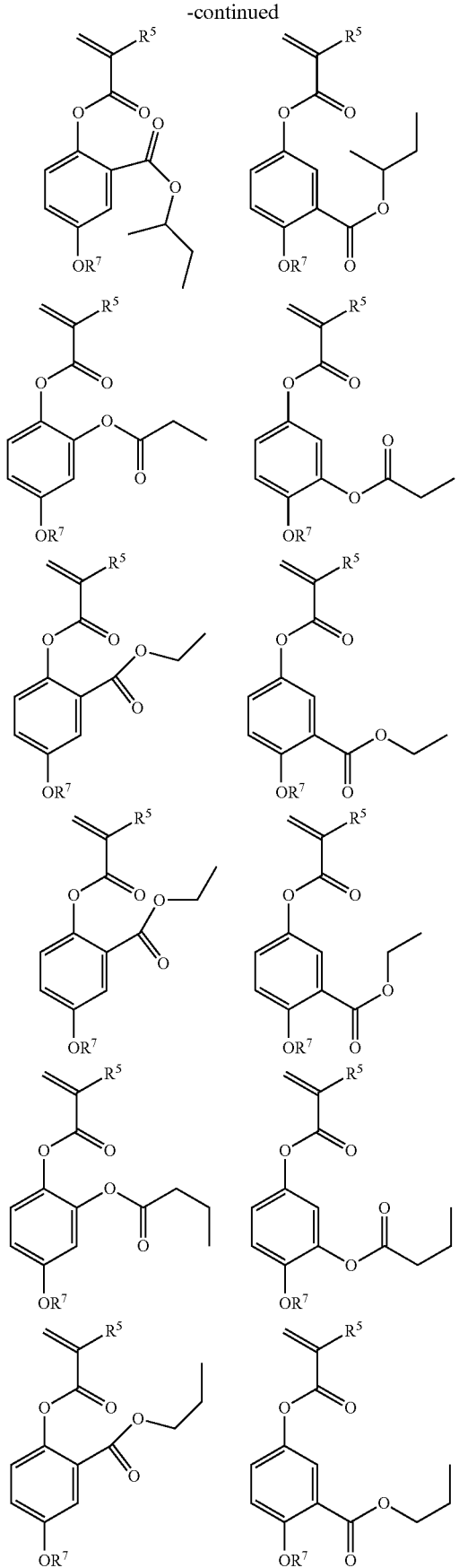
128
-continued
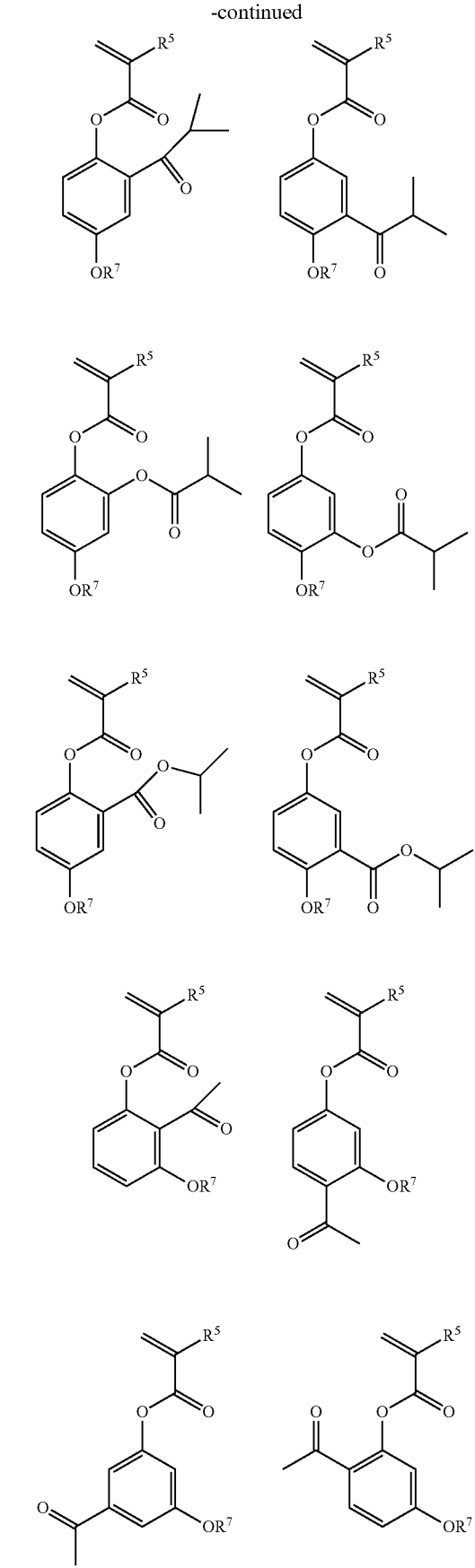

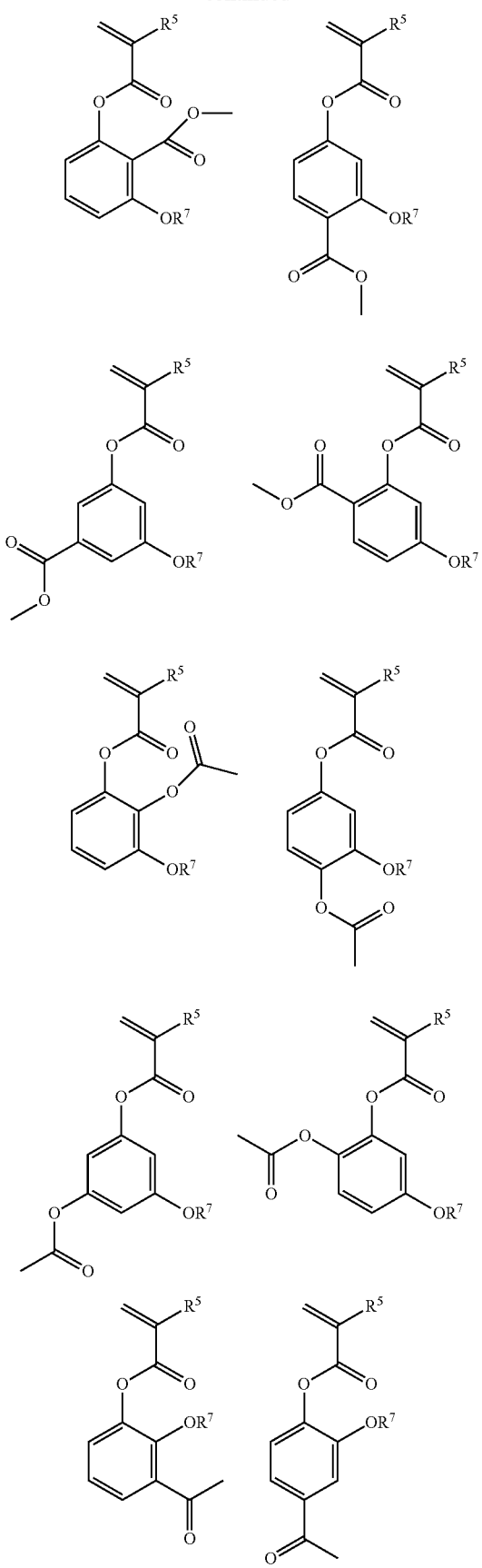
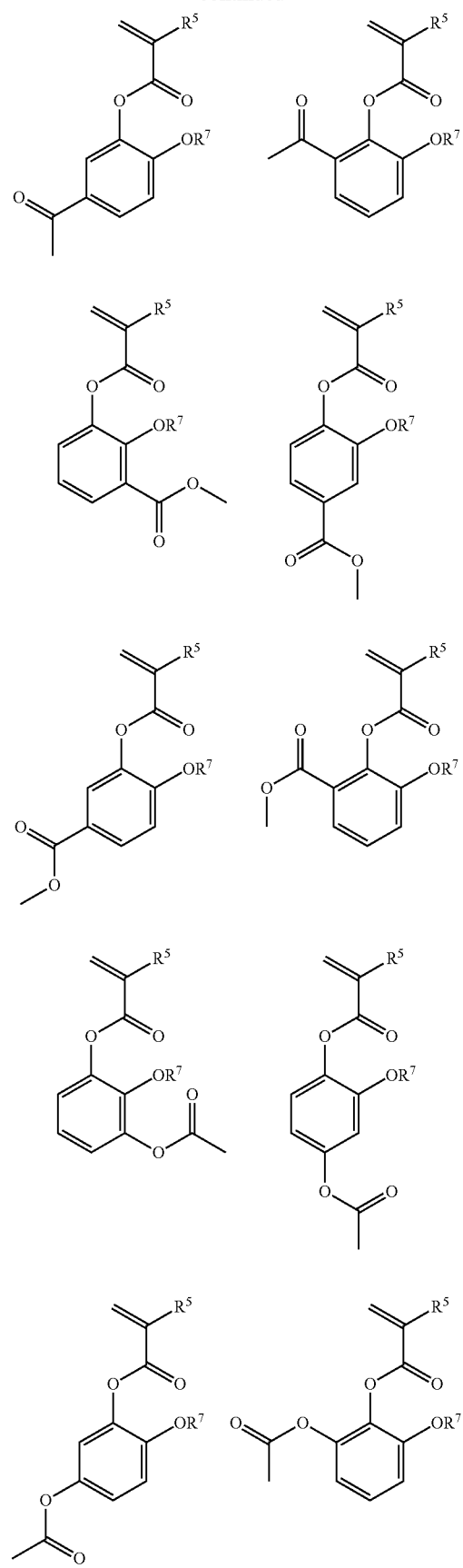

131
-continued
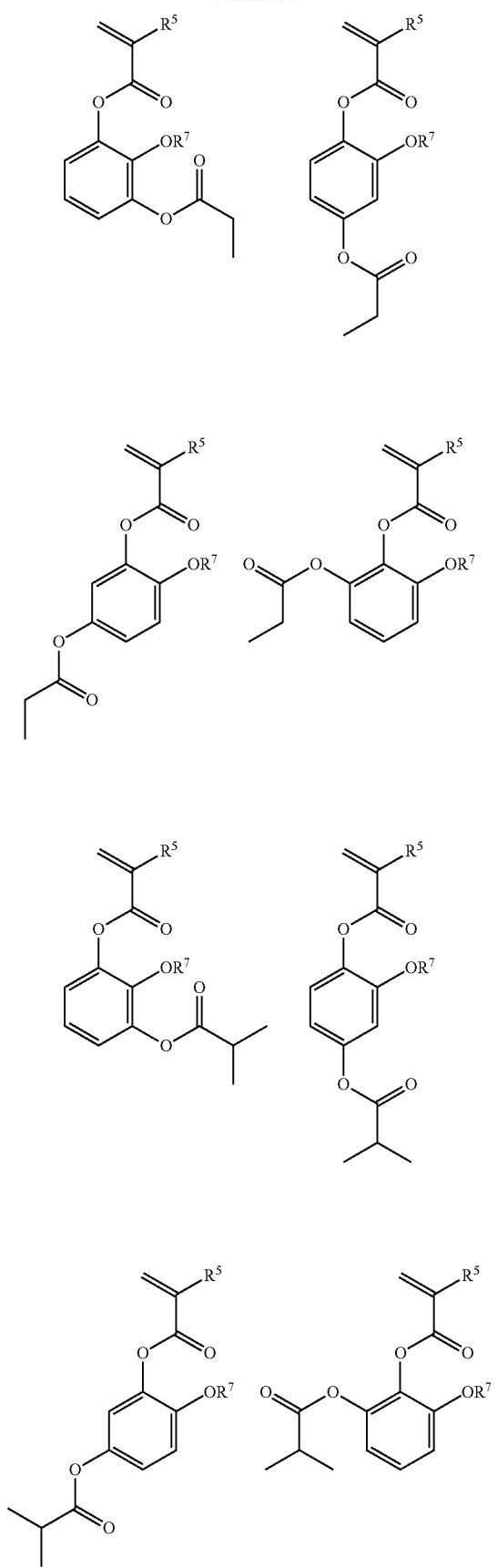
132
-continued
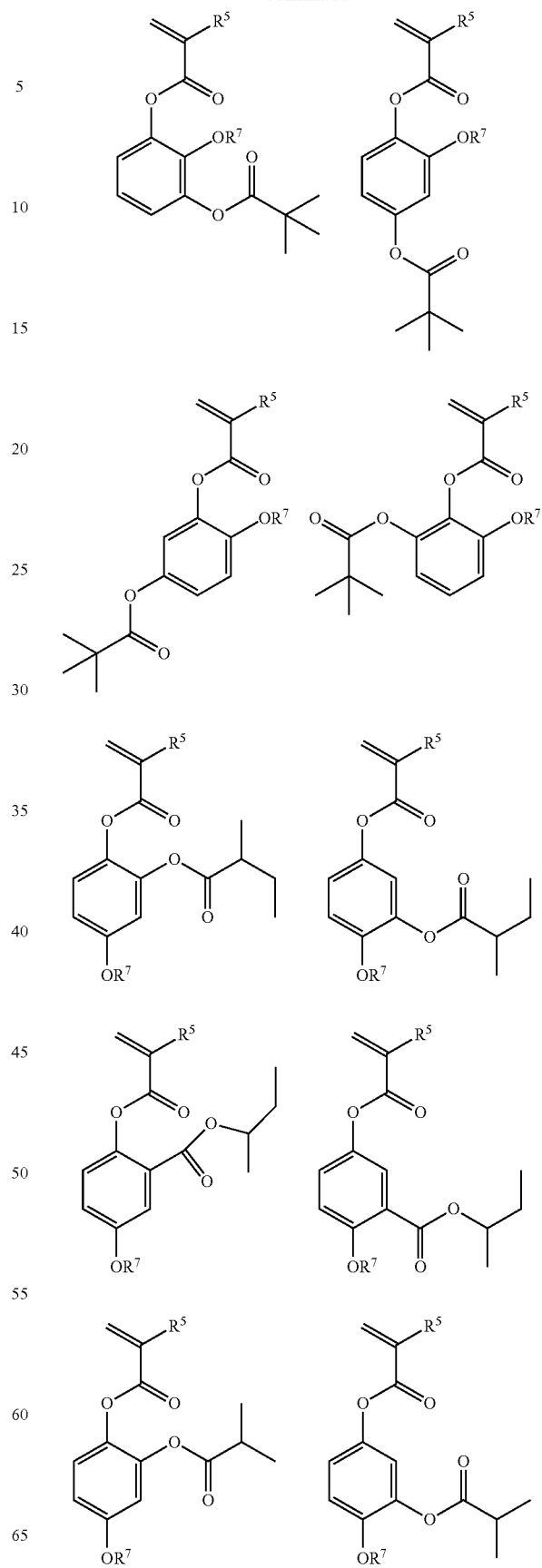

133
-continued
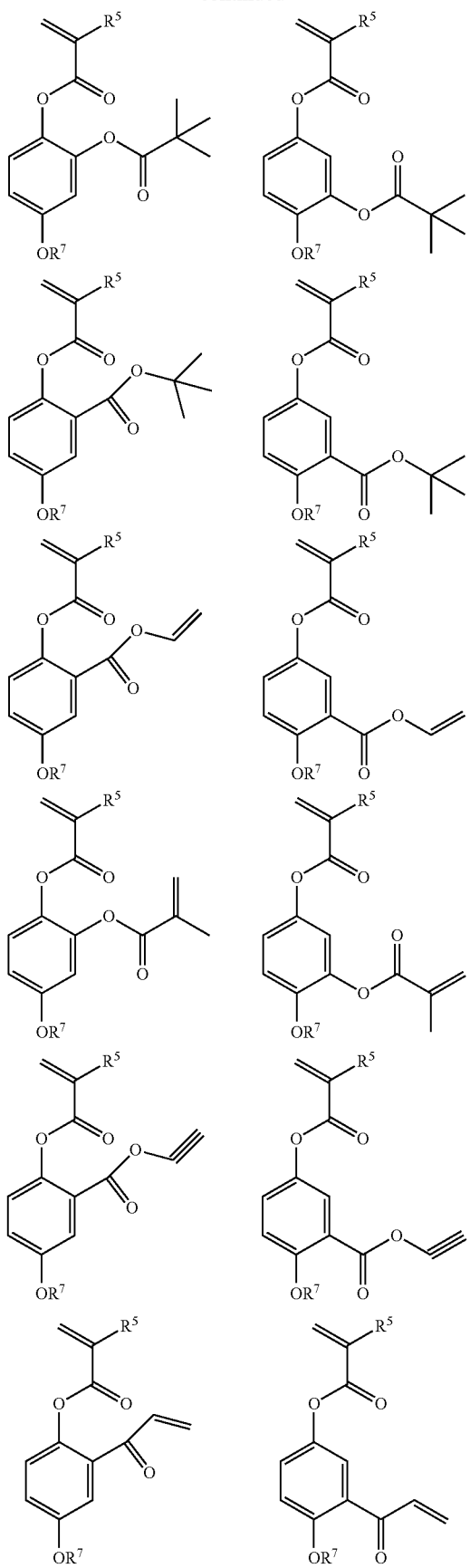
134
-continued
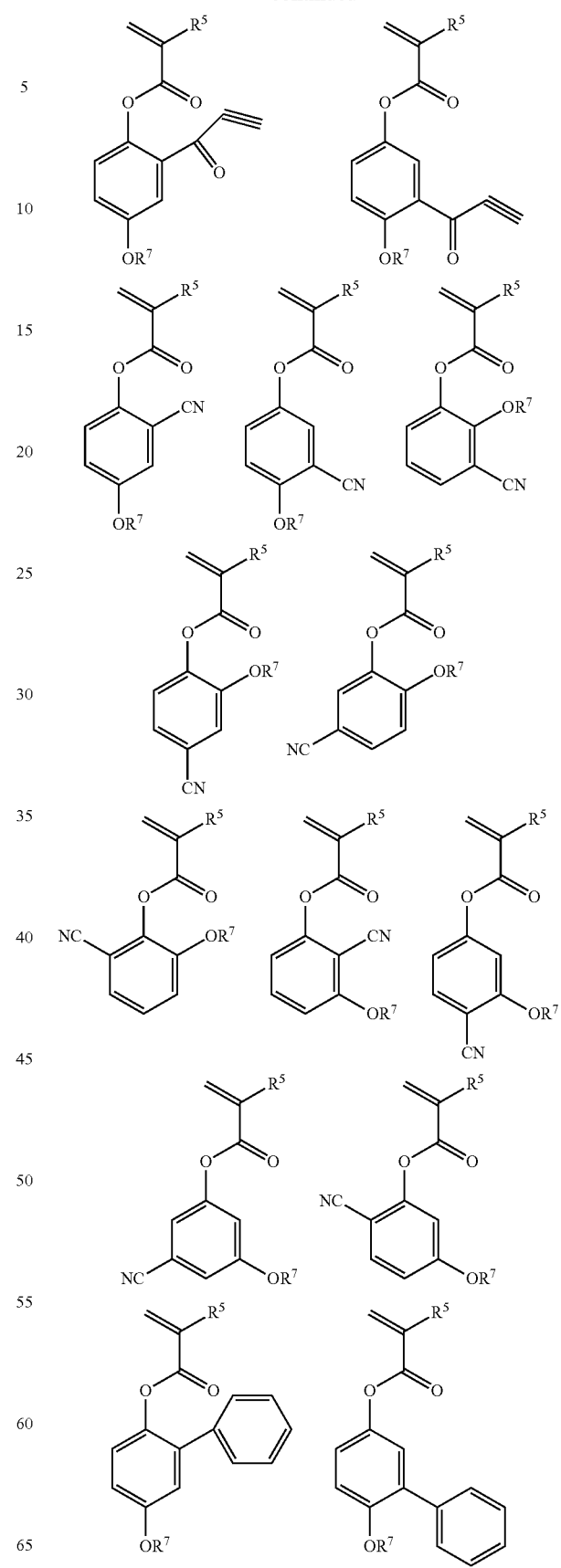

135
-continued
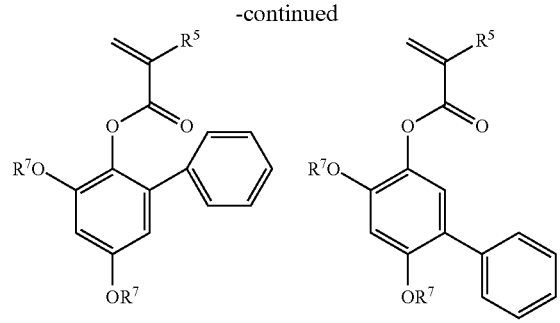
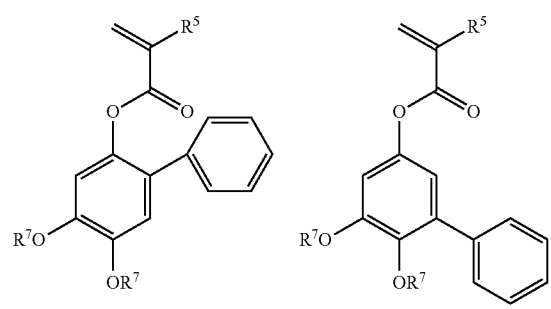
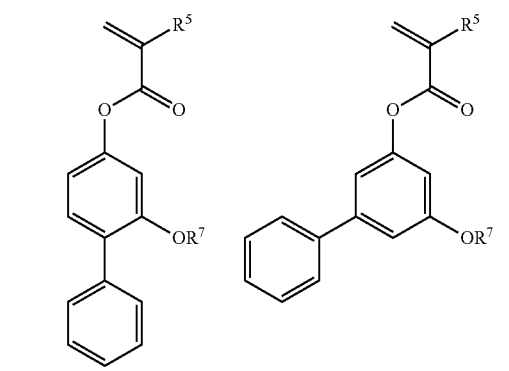
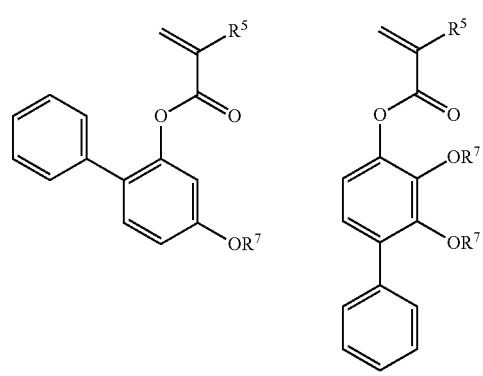
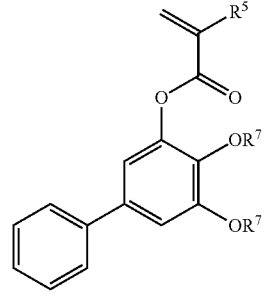
136
-continued
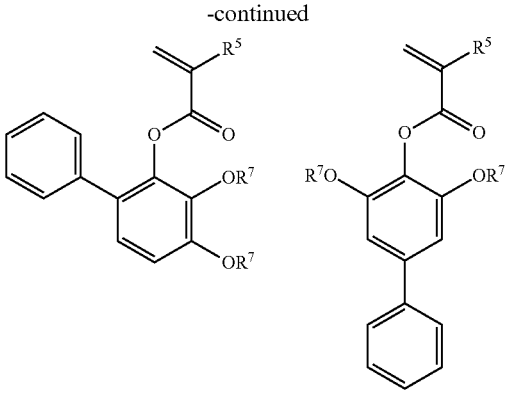
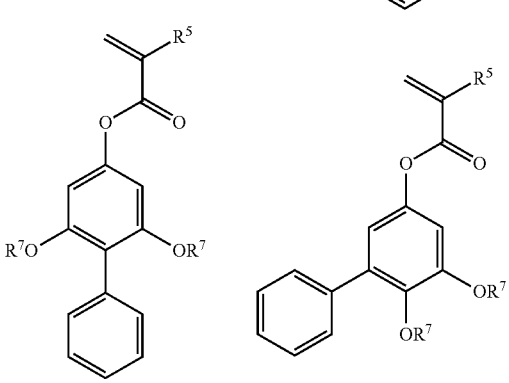
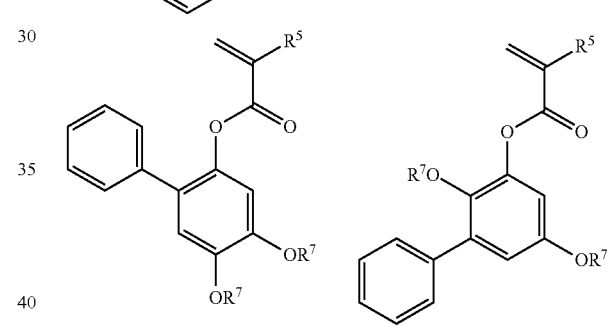
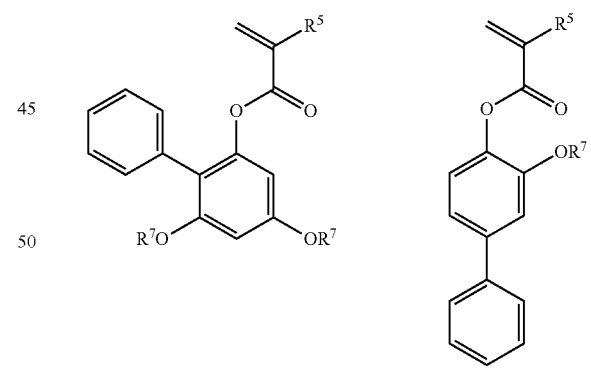
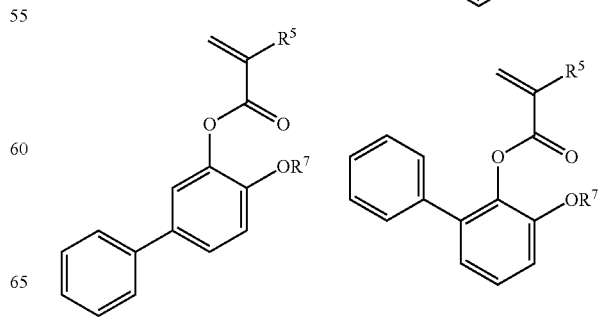

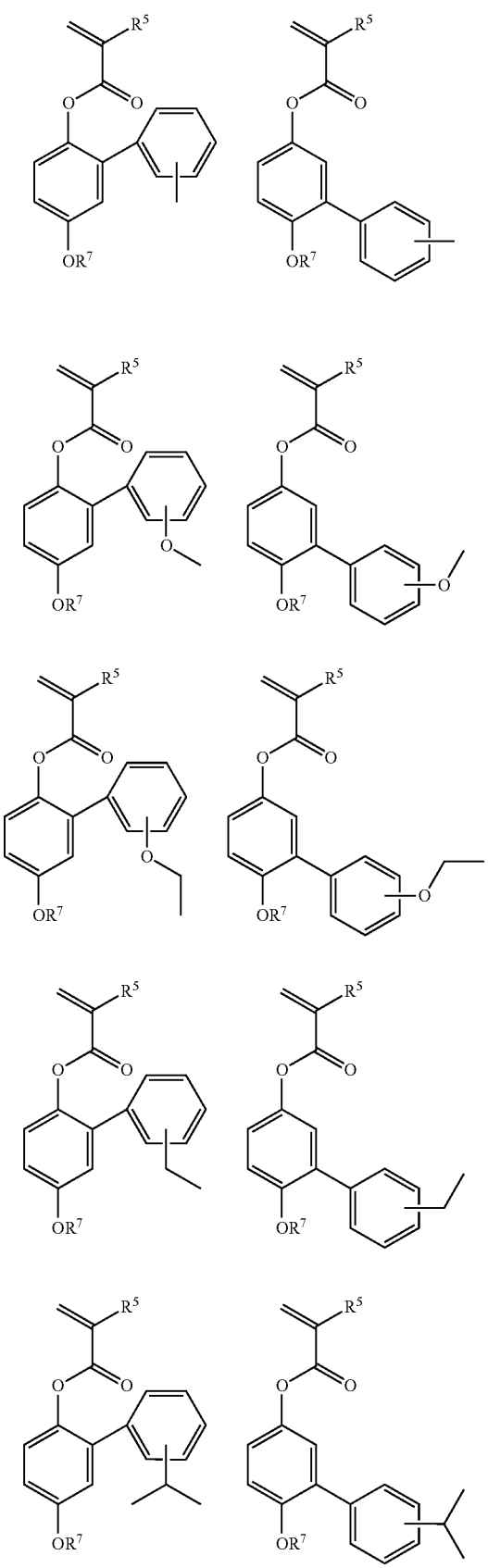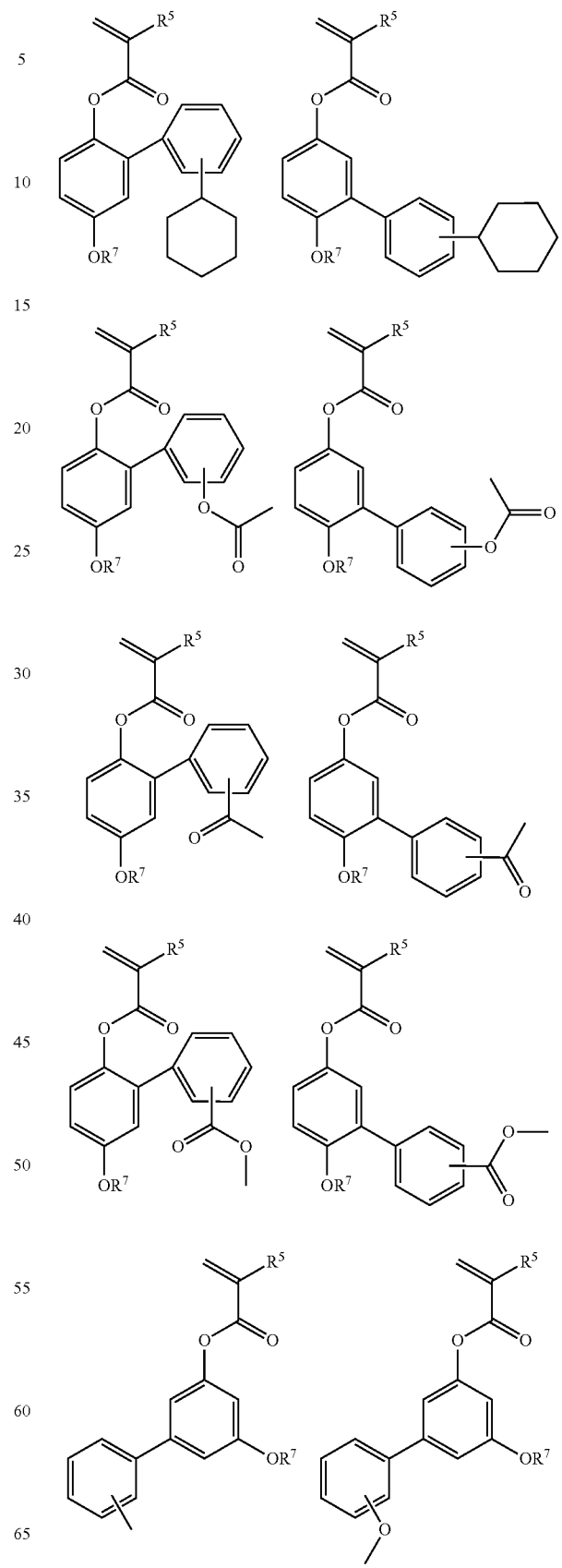

-continued
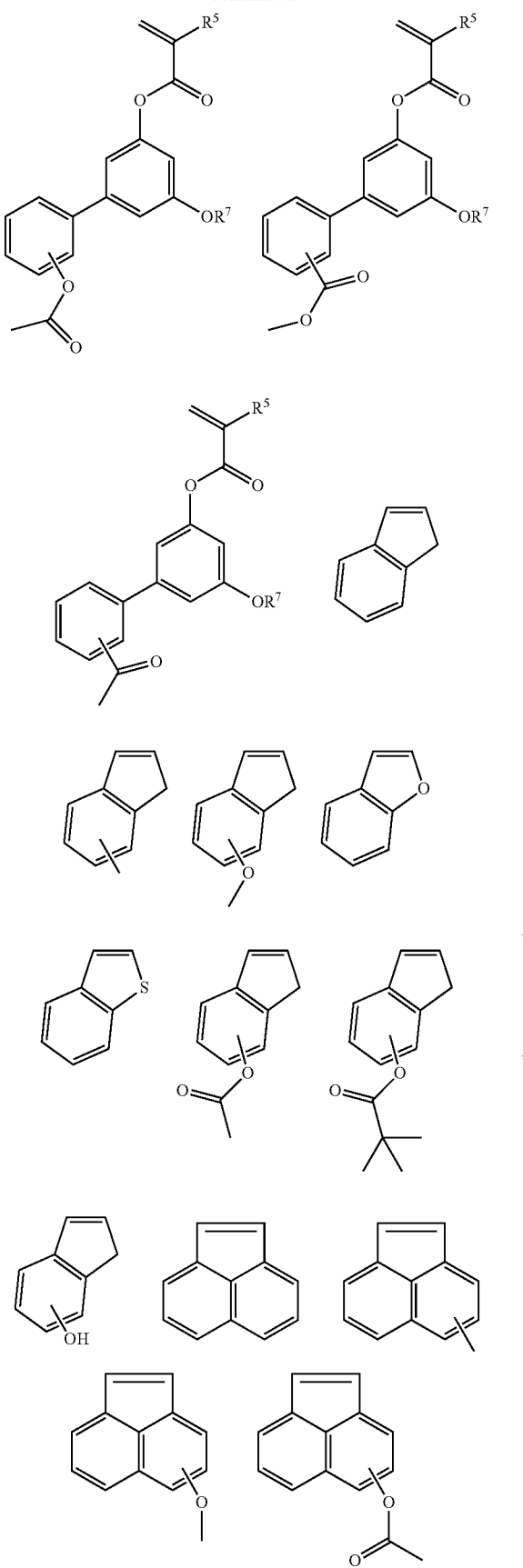
-continued
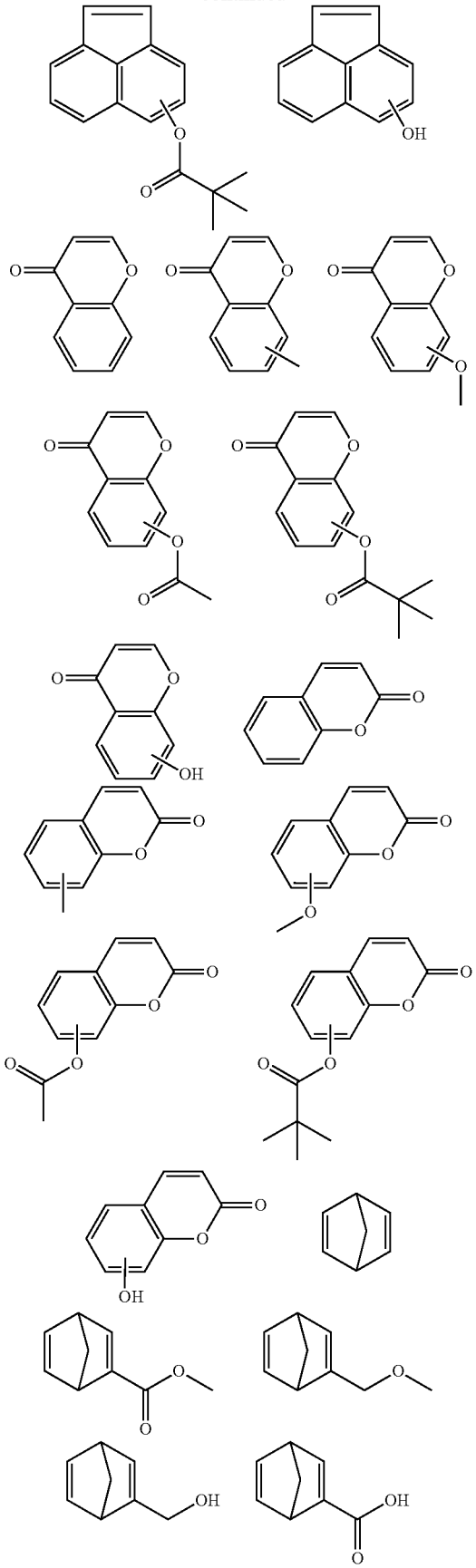

-continued

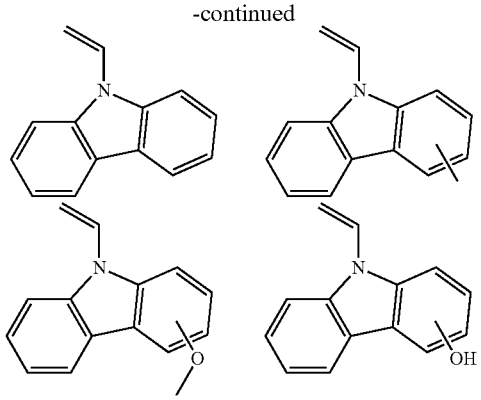

In the polymer, the recurring units derived from the inventive monomer and other monomers are preferably incorporated in the following molar fractions (mol %):

(I) more than 0 mol % to 100 mol %, preferably 5 to 70 mol %, and more preferably 10 to 50 mol % of constituent units of at least one type having formula (2) derived from monomer of formula (1);

(II) 0 mol % to less than 100 mol %, preferably 30 to 95 mol %, and more preferably 50 to 90 mol % of constituent units of at least one type selected from units (A) to (E);

(III) 0 to 30 mol %, preferably 0 to 20 mol %, and more preferably 0 to 10 mol % of constituent units of at least one type selected from units (d1) to (d3); and (IV) 0 to 80 mol %, preferably 0 to 70 mol %, and more preferably 0 to 50 mol % of constituent units derived from one or more other monomers such as units (g) and (h).

The inventive polymer is not limited to the above range.

The polymer may be synthesized by any desired methods, for example, by dissolving one or more monomers corresponding to the selected recurring units in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, a copolymer may be obtained by dissolving hydroxystyrene or hydroxyvinylnaphthalene and another comonomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The polymer should preferably have a weight average molecular weight (Mw) in the range of 1,000 to 500,000, and more preferably 3,000 to 50,000, as measured versus polystyrene standards by GPC using tetrahydrofuran solvent. Outside the range, there may result a loss of etch resistance, a failure to provide a differential dissolution rate before and after exposure, and a lowering of resolution. Also preferably, the polymer has a molecular weight distribution or dispersity (Mw/Mn) of 1.20 to 2.50, more preferably 1.30 to 1.80.

Resist Composition

The polymer is advantageously used as a base resin in a resist composition. Specifically, the polymer is used as a base resin and combined with any desired components including an organic solvent, acid generator, dissolution regulator, basic compound, and surfactant to formulate a resist composition. This resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Inclusion of a dissolution regulator may lead to an increased difference in dissolution rate between exposed and unexposed areas and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified positive resist composition. Typical of the acid generator used herein is a photoacid generator (PAG) capable of generating an acid in response to actinic light or radiation. Preferably the PAG is used in an amount of 0.5 to 30 parts, more preferably 1 to 20 parts by weight per 100 parts by weight of the base resin. The PAG is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used. These compounds may be used alone or in admixture. Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection. Where the base polymer having recurring units (d1), (d2) or (d3) of acid generator copolymerized therein is used, the acid generator of addition type is not essential.

The resist composition may comprise an acid generator having the general formula (Z1) or (Z2) as component (Z).

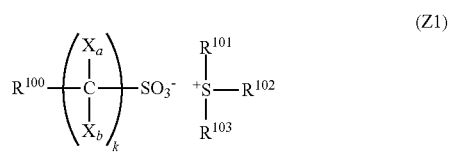

(Z1)

-continued

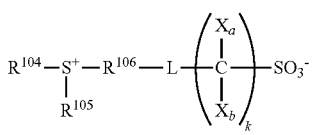
(Z2)

Herein $R^{100}$ is hydrogen, fluorine, or a straight, branched or cyclic $C_1$-$C_{35}$ monovalent hydrocarbon group which may contain a heteroatom. $X_a$ and $X_b$ are each independently hydrogen, fluorine, or trifluoromethyl, k is an integer of 1 to 4. $R^{101}$, $R^{102}$, and $R^{103}$ are each independently a substituted or unsubstituted, straight or branched alkyl, alkenyl or oxoalkyl group of 1 to 10 carbon atoms, or a substituted or unsubstituted aryl, aralkyl or aryloxoalkyl group of 6 to 18 carbon atoms, or any two or more of $R^{101}$, $R^{102}$, and $R^{103}$ may bond together to form a ring with the sulfur atom. $R^{104}$ and $R^{105}$ are each independently a straight, branched or cyclic $C_1$-$C_{20}$ monovalent hydrocarbon group which may be substituted with or separated by a heteroatom. $R^{106}$ is a straight, branched or cyclic $C_1$-$C_{20}$ divalent hydrocarbon group which may be substituted with or separated by a heteroatom. L is a single bond or a straight, branched or cyclic $C_1$-$C_{20}$ divalent hydrocarbon group which may be substituted with or separated by a heteroatom.

Preferred as component (Z) are acid generators having the general formulae (Z3) and (Z4).

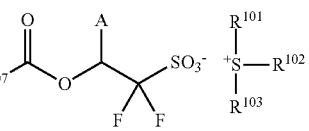
(Z3)

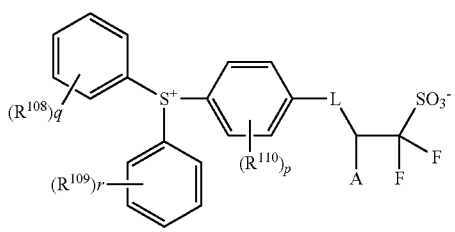
(Z4)

Herein A is hydrogen or trifluoromethyl. $R^{101}$, $R^{102}$, and $R^{103}$ are each independently a substituted or unsubstituted, straight or branched alkyl, alkenyl or oxoalkyl group of 1 to 10 carbon atoms, or a substituted or unsubstituted aryl, aralkyl or aryloxoalkyl group of 6 to 18 carbon atoms, or any two or more of $R^{101}$, $R^{102}$, and $R^{103}$ may bond together to form a ring with the sulfur atom. $R^{107}$ is a straight, branched or cyclic $C_1$-$C_{35}$ monovalent hydrocarbon group which may contain a heteroatom. $R^{108}$, $R^{109}$, and $R^{110}$ are each independently hydrogen or a straight, branched or cyclic $C_1$-$C_{20}$ monovalent hydrocarbon group which may be separated by a heteroatom. Each of q and r is an integer of 0 to 5, p is an integer of 0 to 4. L is a single bond or a straight, branched or cyclic $C_1$-$C_{20}$ divalent hydrocarbon group which may be substituted with or separated by a heteroatom.

When component (Z) is an acid generator having formula (Z3) or (Z4), preferably formula (Z3) or (Z4) wherein A is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of component (Z) are shown below.

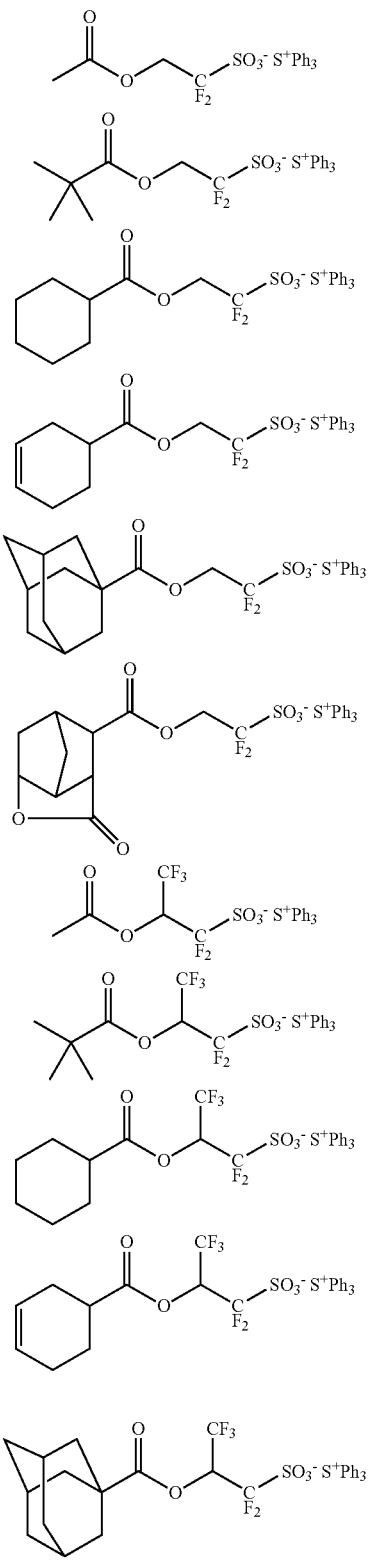

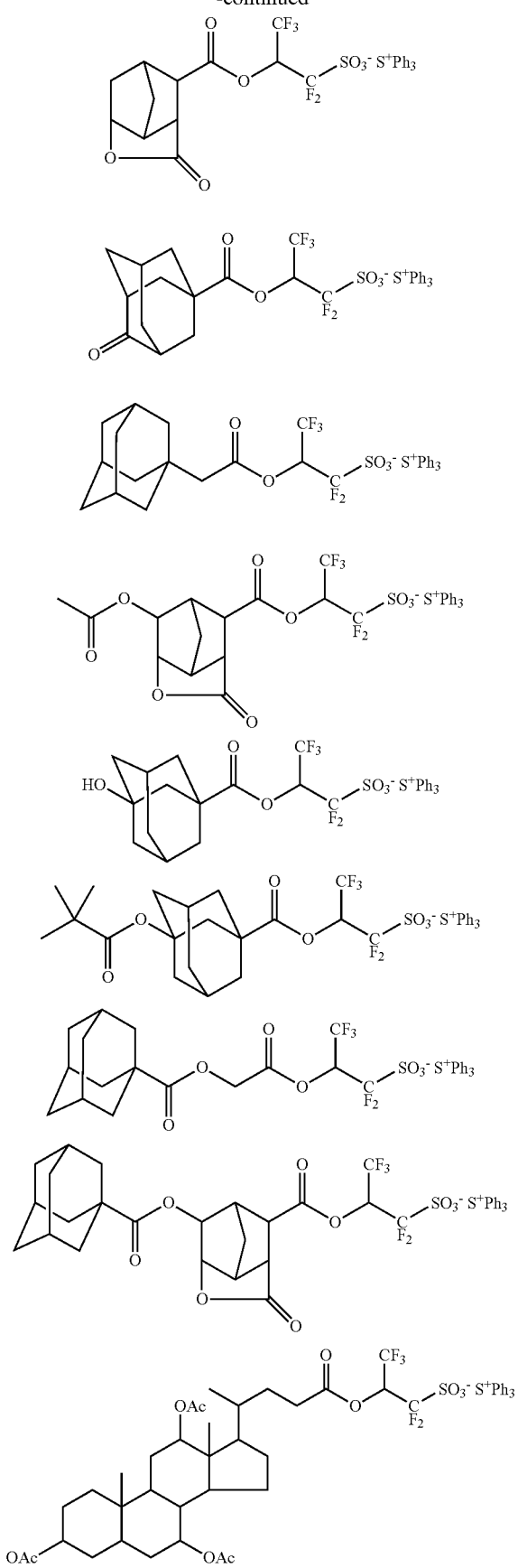
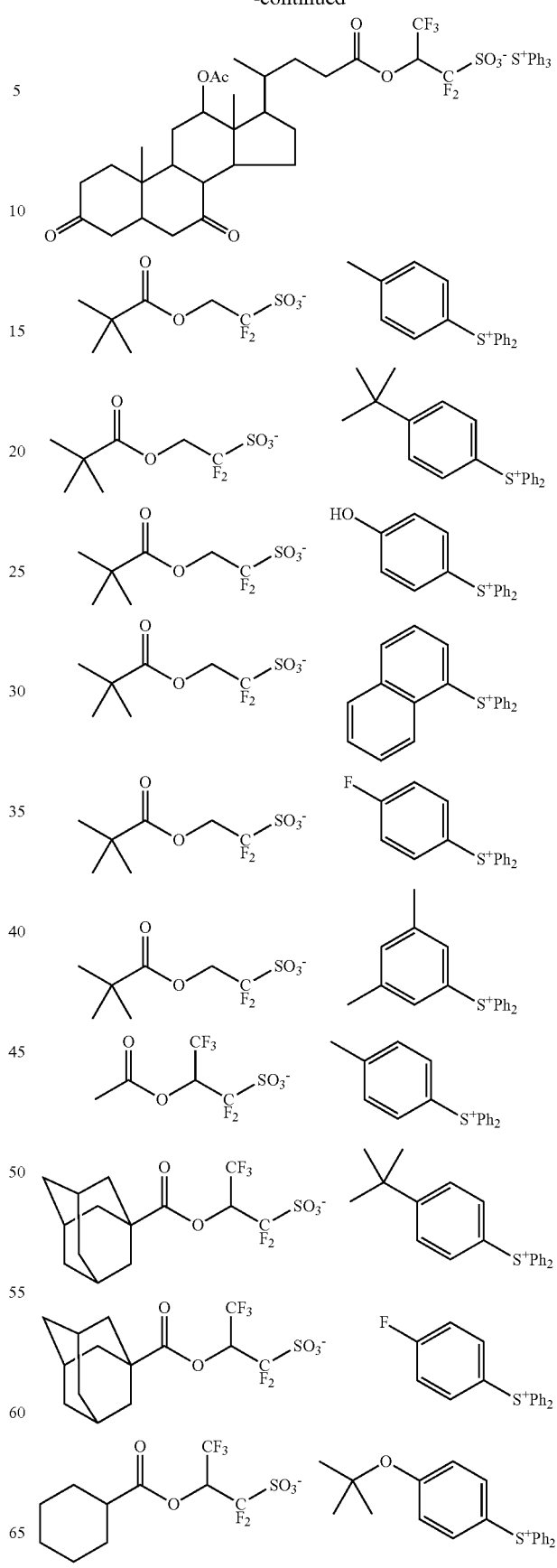

147
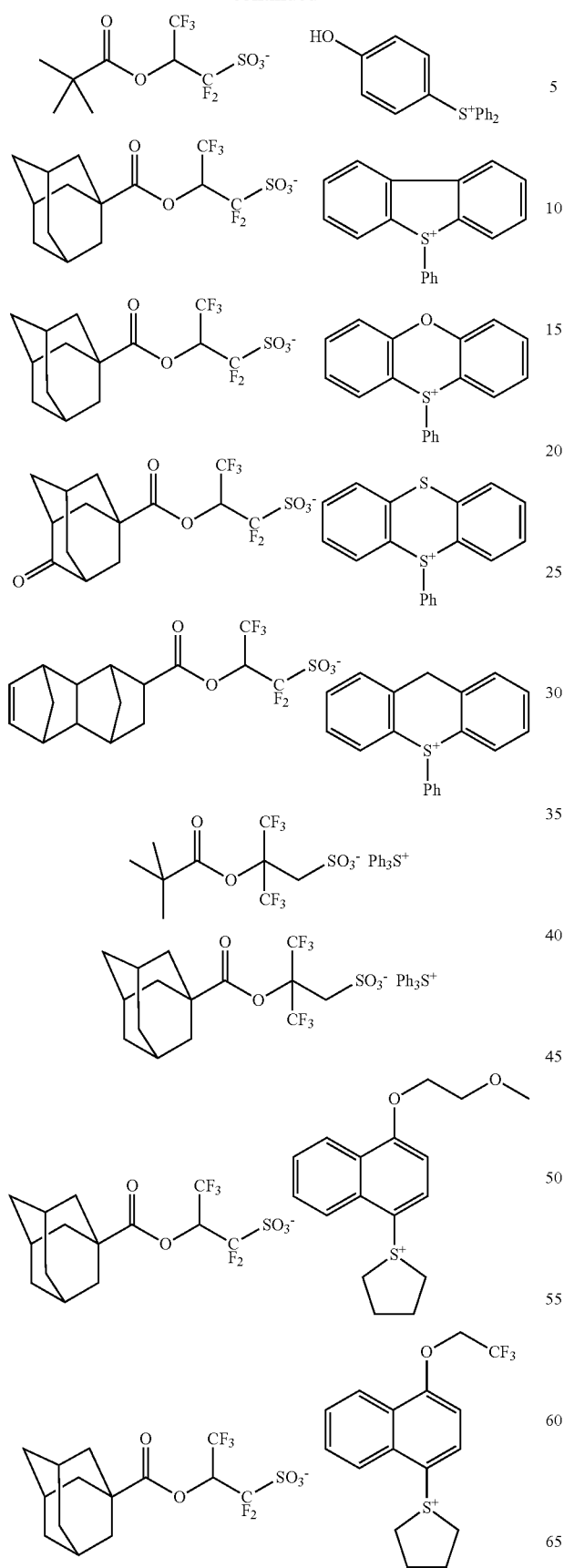
148
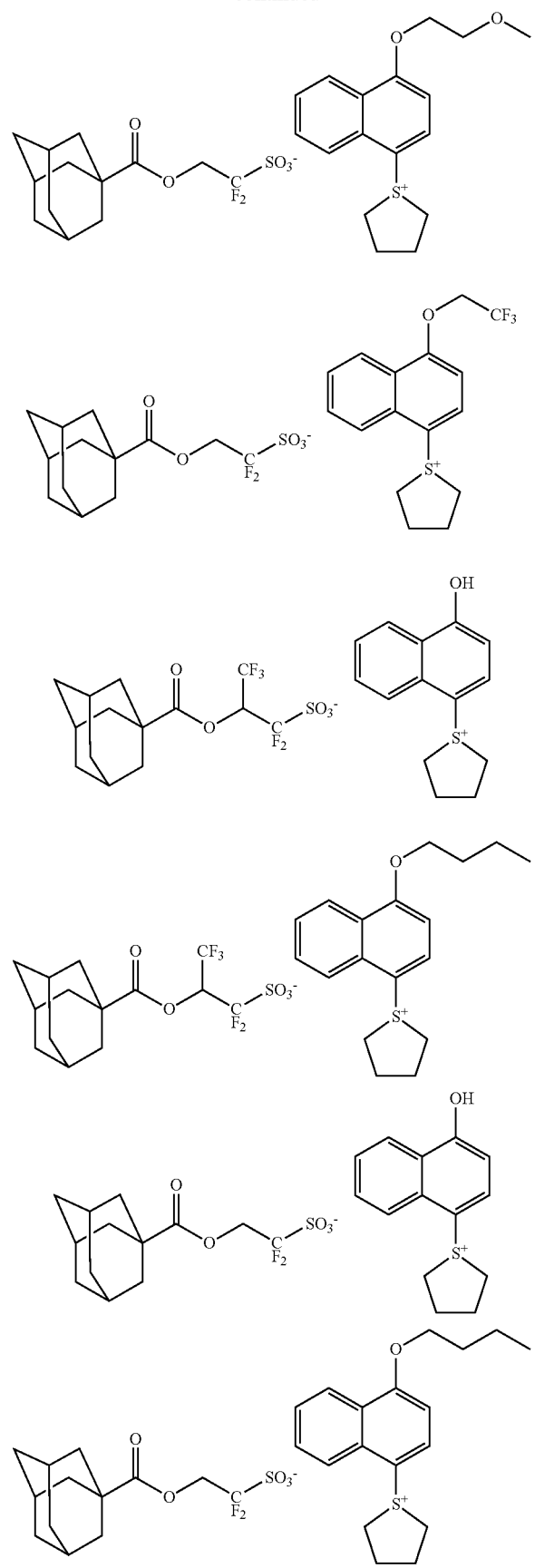

149
-continued
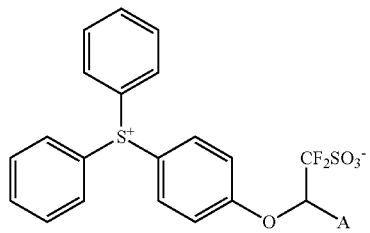
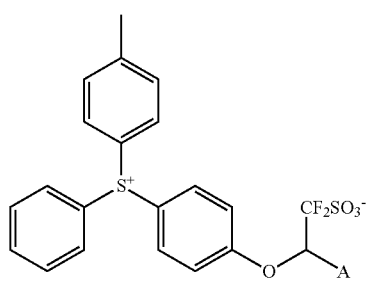
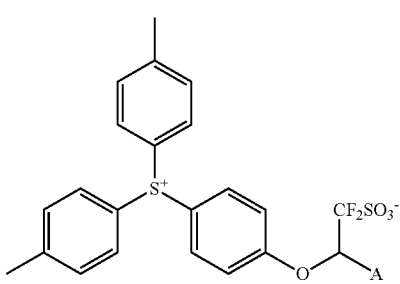
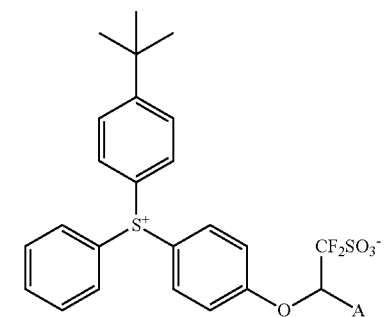
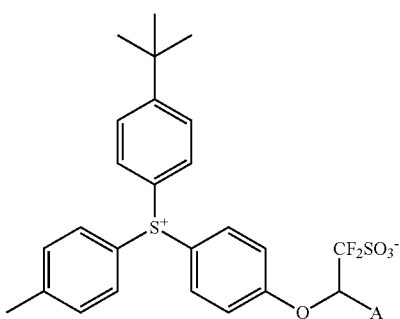
150
-continued
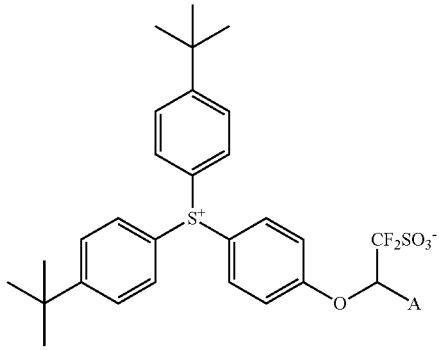
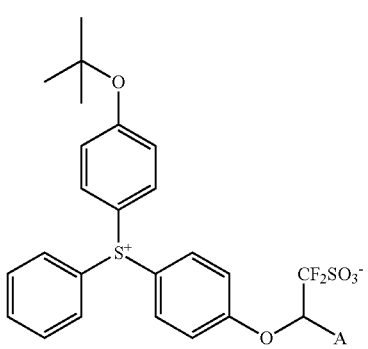
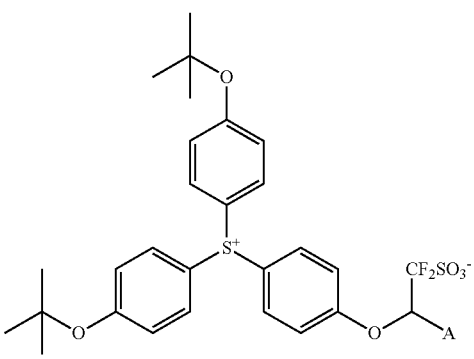
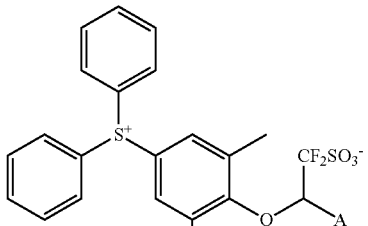
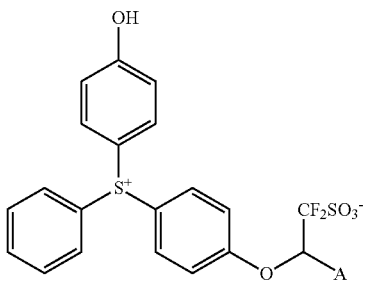

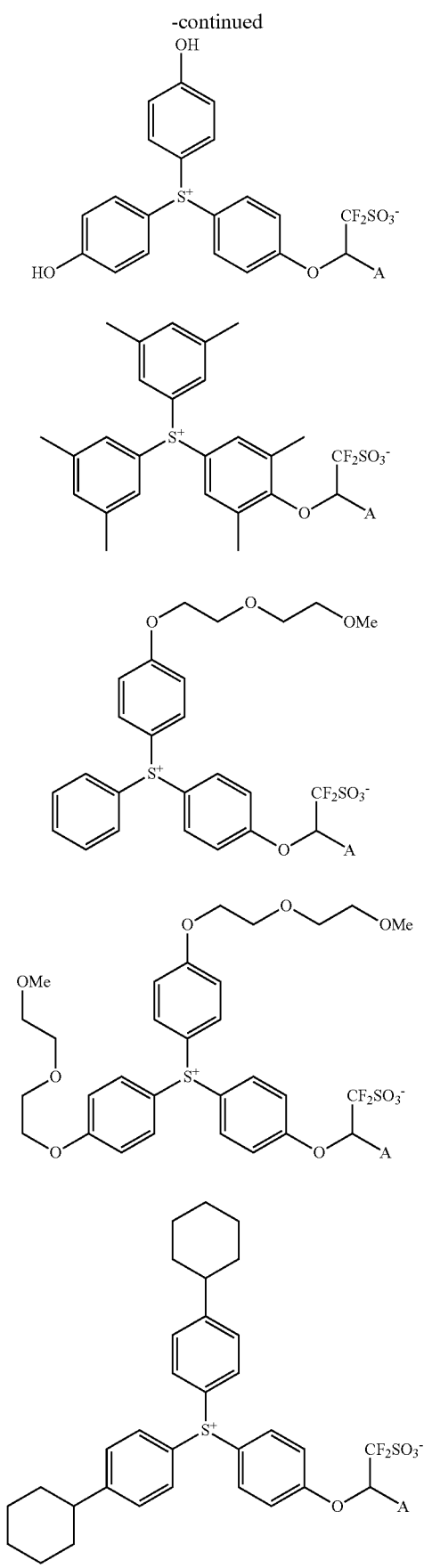
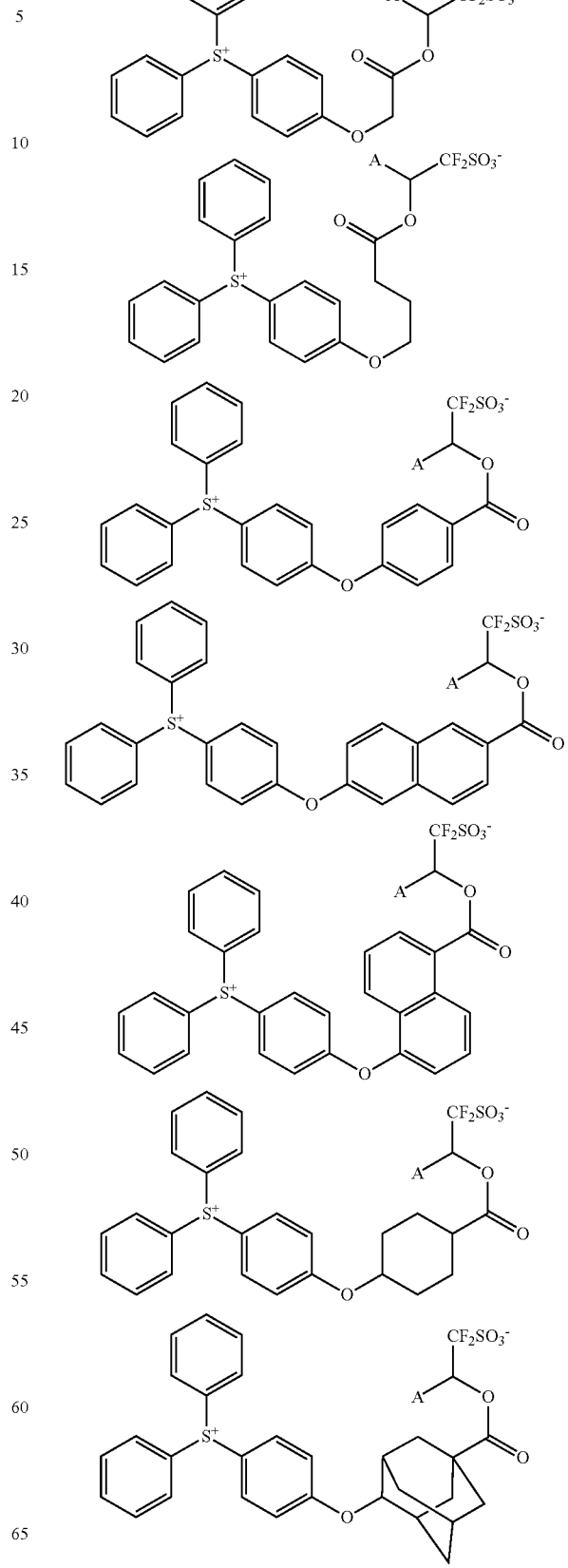

-continued

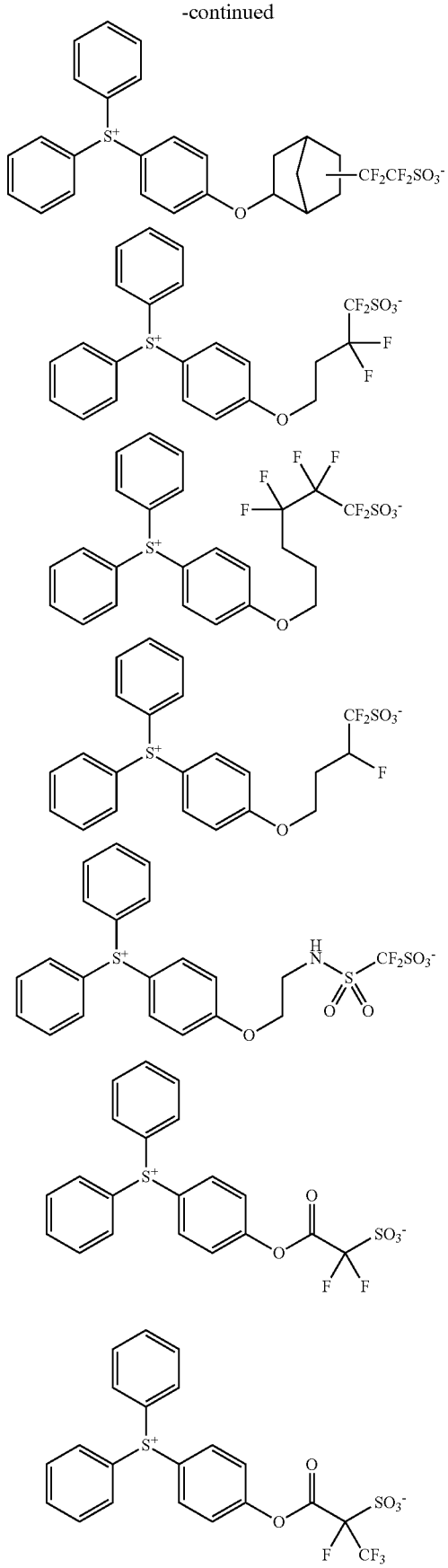

In the above formulae, A is hydrogen or trifluoromethyl.

In addition to the inventive polymer, the resist composition may further comprise at least one component selected from among an organic solvent, basic compound, dissolution regulator, surfactant, and acetylene alcohol.

Suitable organic solvents include those described in JP-A 2008-111103, paragraphs [0144] to [0145] (U.S. Pat. No. 7,537,880), for example, ketones such as cyclohexanone, cyclopentanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monoethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

Examples of the basic compound used herein include primary, secondary, and tertiary amine compounds as described in JP-A 2008-111103, paragraphs [0146] to [0164], specifically amine compounds having a hydroxyl, ether, ester, lactone, cyano or sulfonic ester group, and compounds having a carbamate group as described in JP 3790649.

Onium salts such as sulfonium salts, iodonium salts and ammonium salts of sulfonic acids which are not fluorinated at α-position as described in US 2008153030 (JP-A 2008-158339) and similar onium salts of carboxylic acids as described in JP-A 2013-037092 may be used as the quencher. Where an α-position non-fluorinated sulfonic acid salt or carboxylic acid salt and an α-position fluorinated sulfonic acid, imide acid, and methide acid generated by a PAG are co-present, salt exchange occurs to generate an α-position non-fluorinated sulfonic acid or carboxylic acid. Since this α-position non-fluorinated sulfonic acid or carboxylic acid has an insufficient acid strength to induce deprotection reaction to the resist resin, the relevant sulfonium salt, iodonium salt or ammonium salt functions as a quencher. In particular, since sulfonium salts and iodonium salts of an α-position non-fluorinated sulfonic acid and a carboxylic acid are photodecomposable, those portions receiving a high light intensity are reduced in quenching capability and increased in the concentration of an α-position fluorinated sulfonic acid, imide acid, or methide acid. This enables to form a pattern having an improved contrast in exposed area, further improved focus margin or DOF and satisfactory dimensional control.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Illustrative, non-limiting examples of the α-position non-fluorinated sulfonic acid salt and carboxylic acid salt are given below.

155
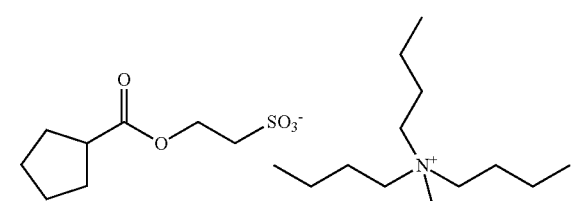
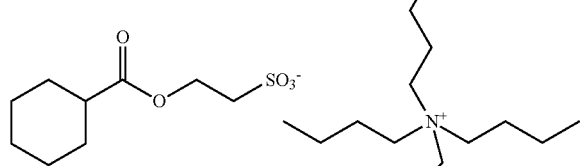
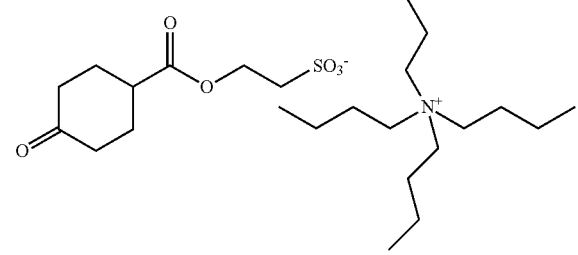
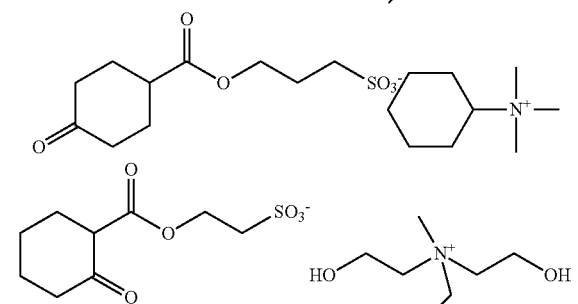
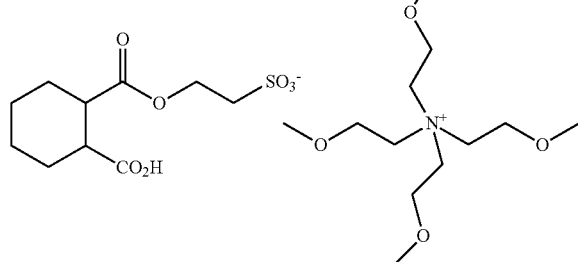
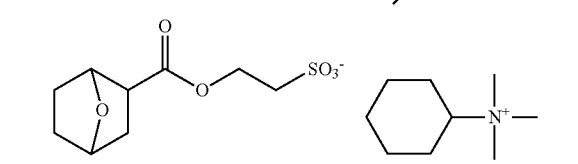
156
-continued
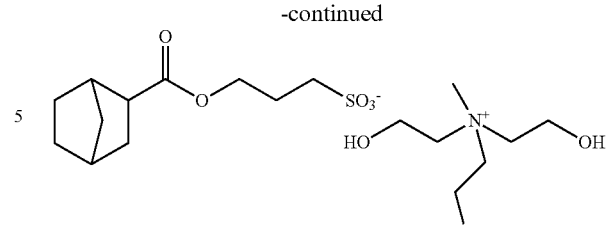
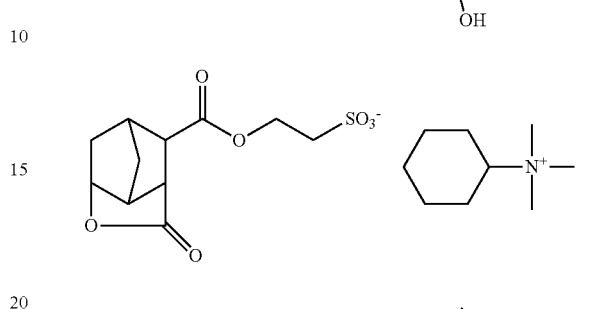
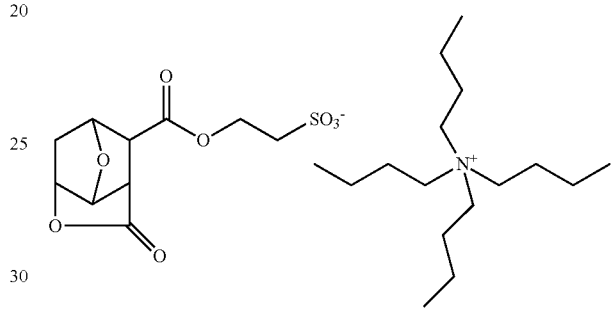
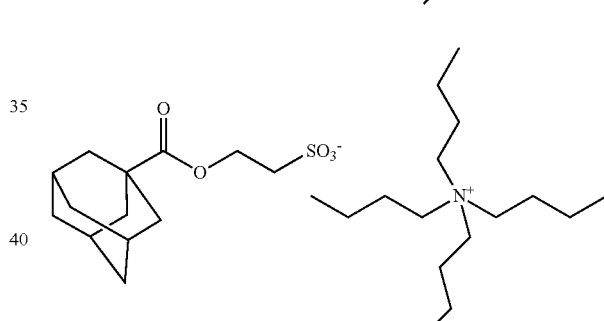
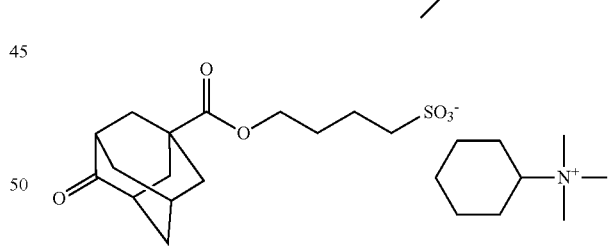
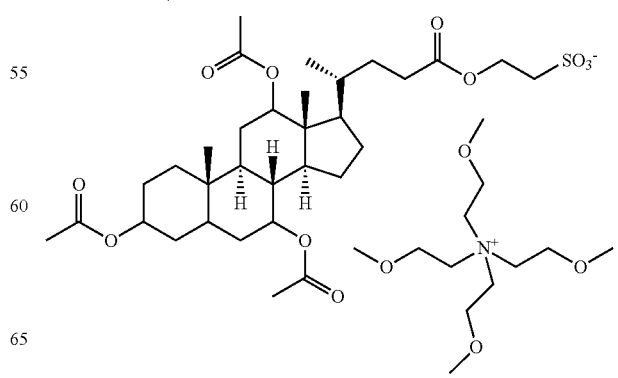

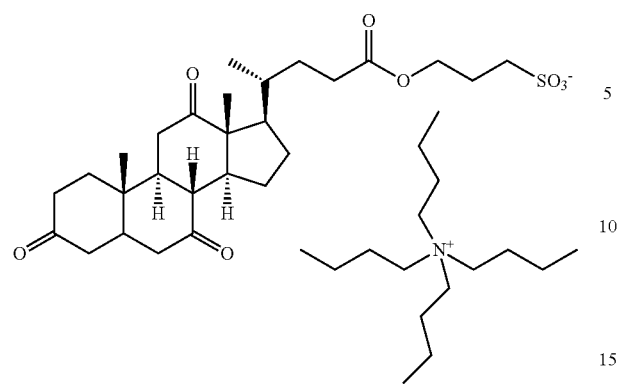
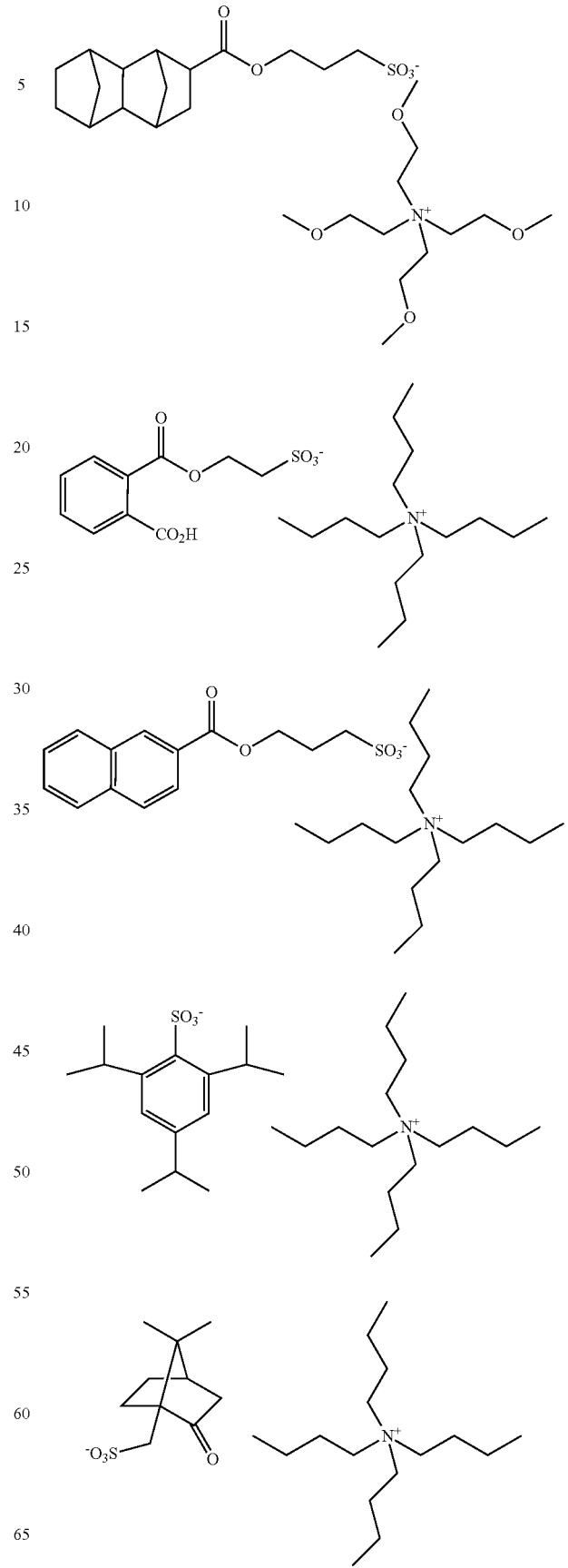

159
-continued
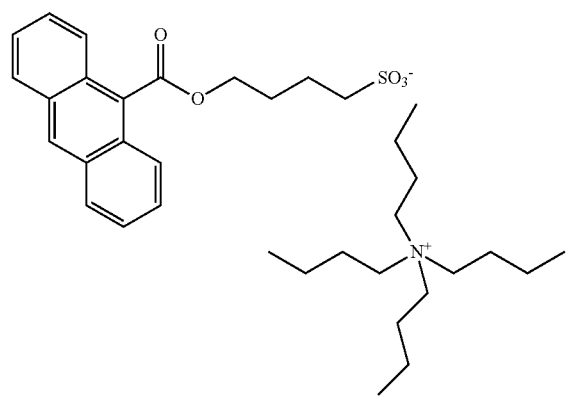
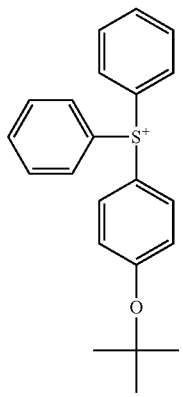
160
-continued
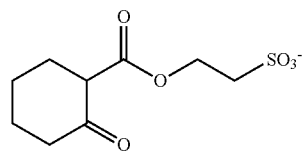
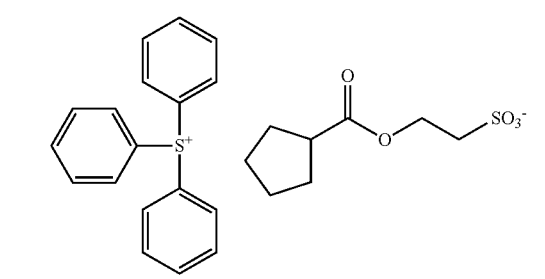
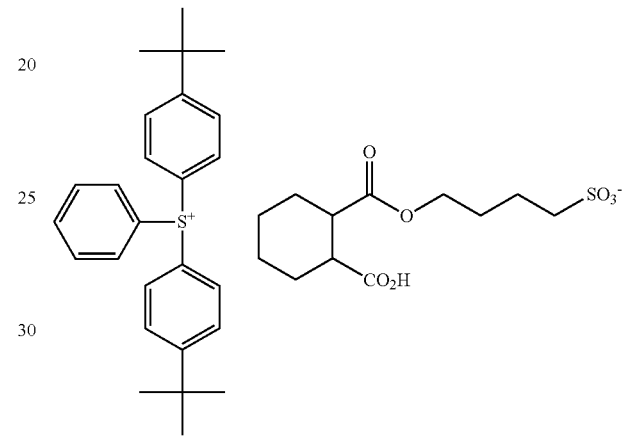
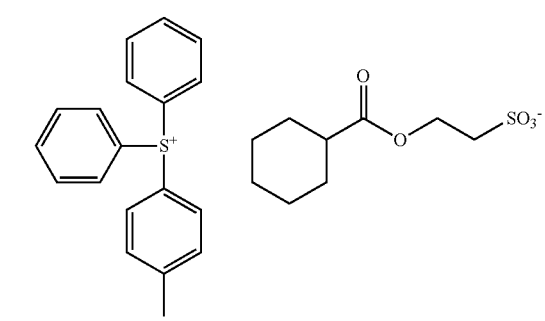
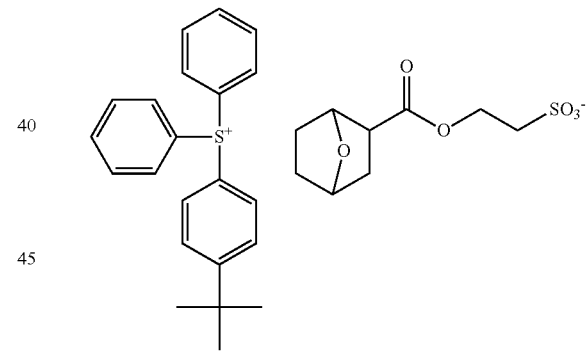
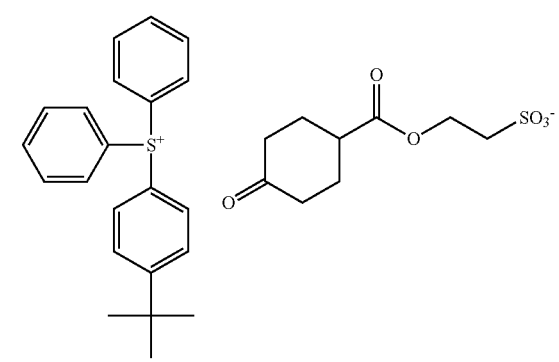
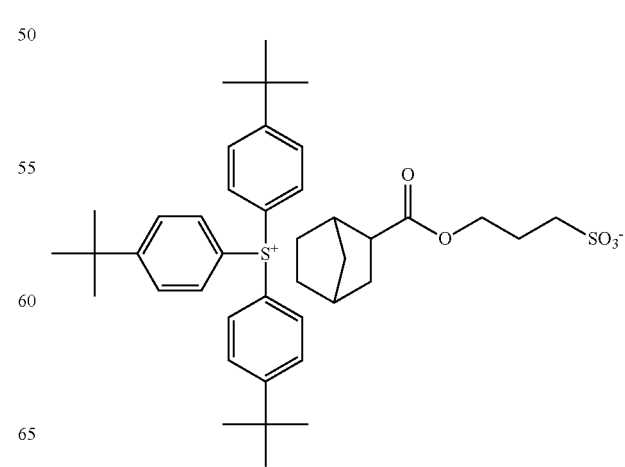
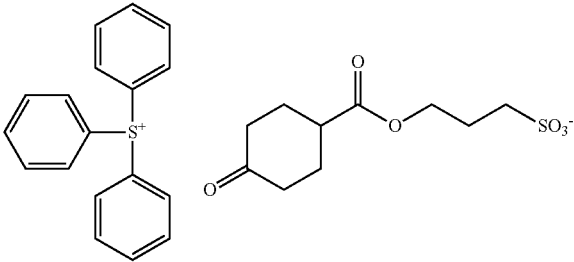

161
-continued
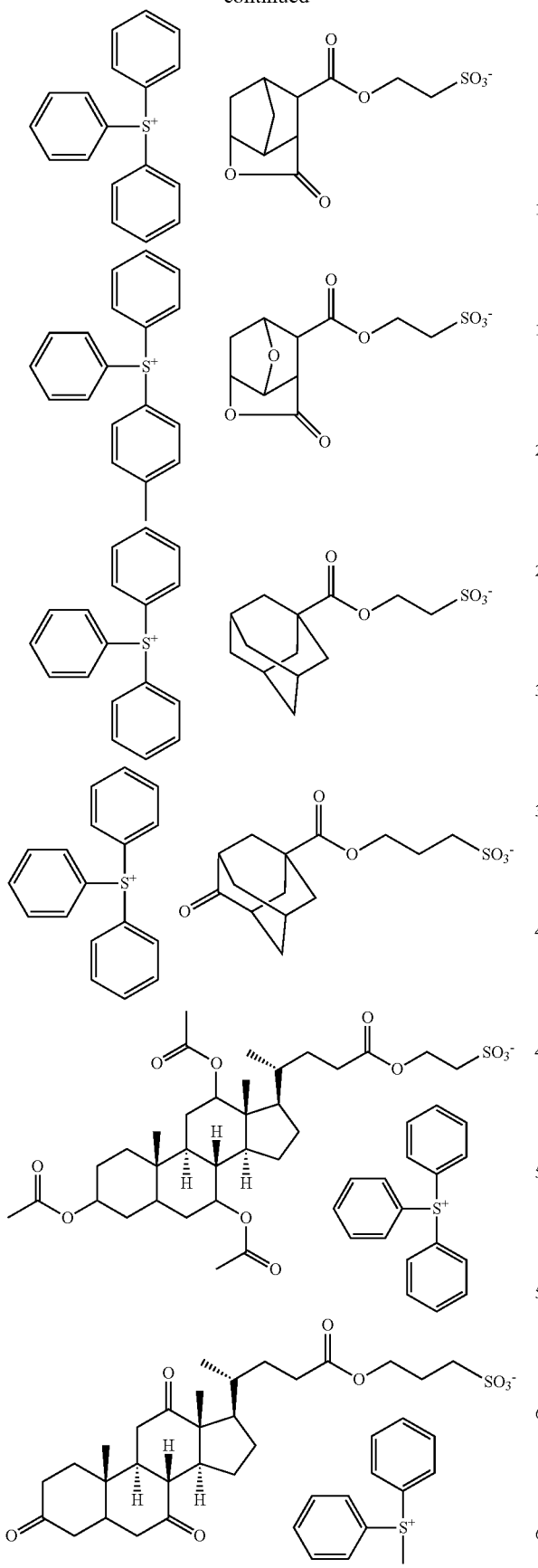
162
-continued
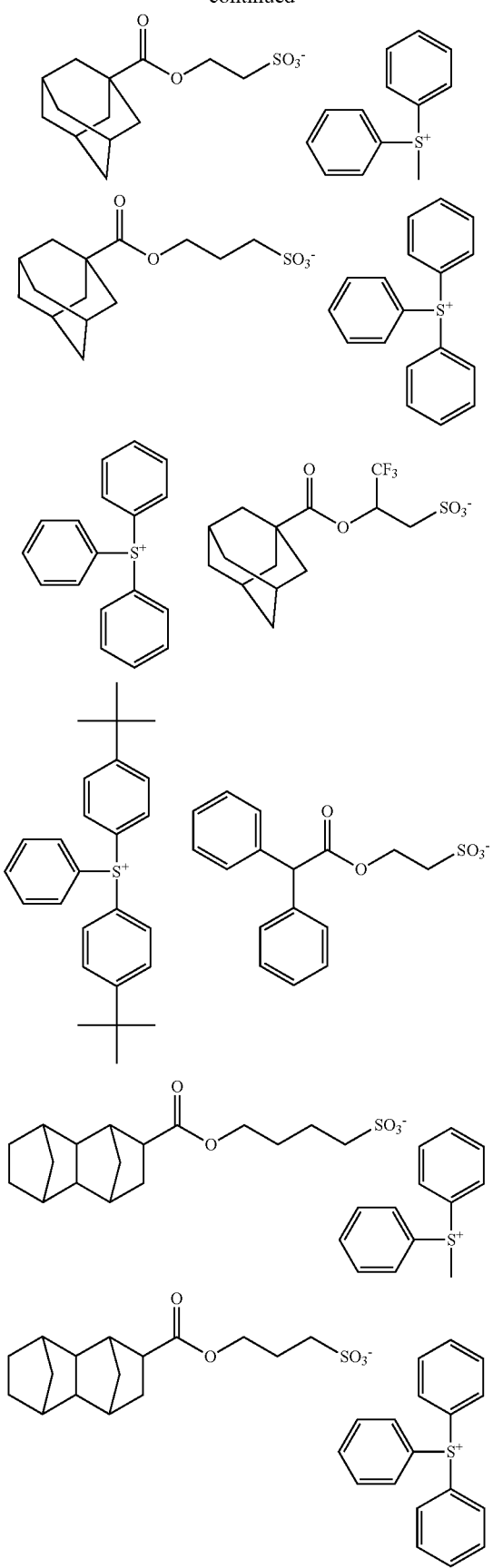

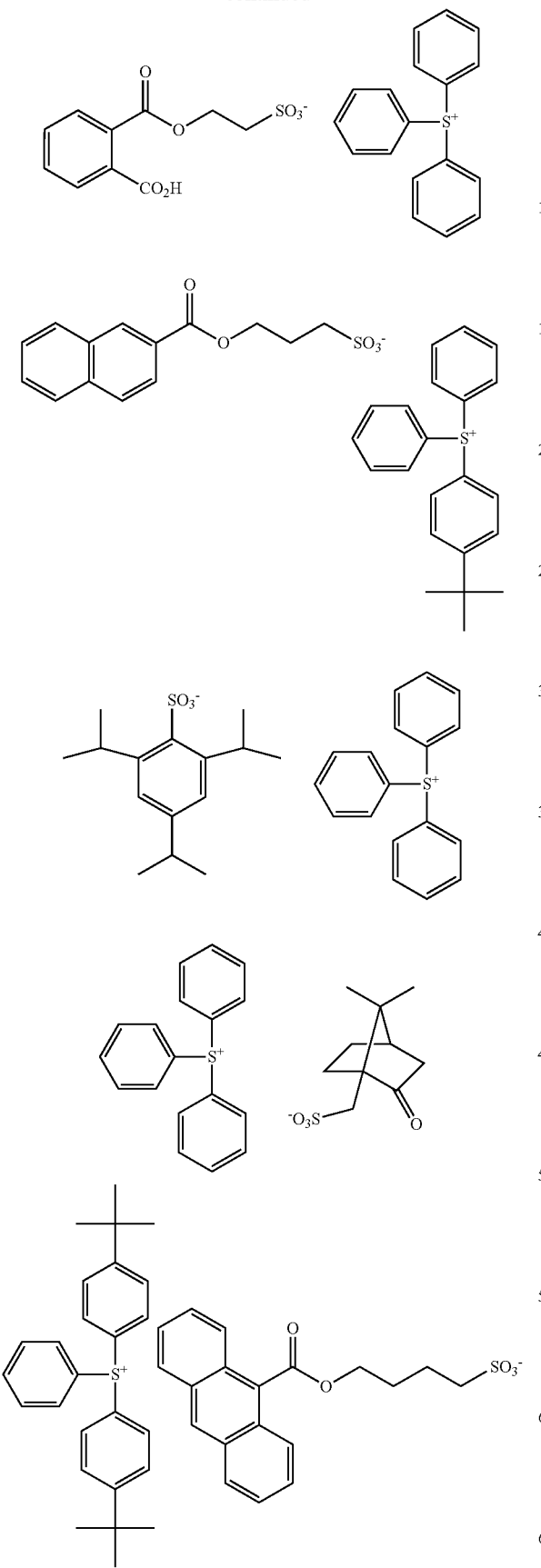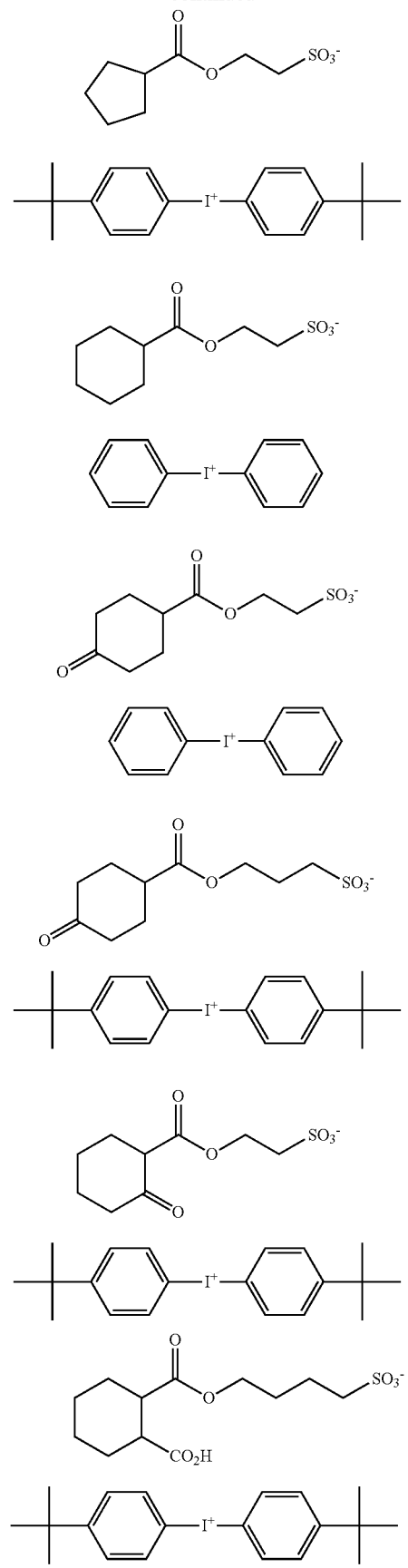

165
-continued
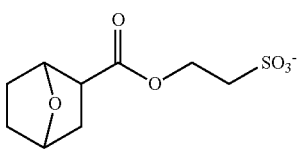
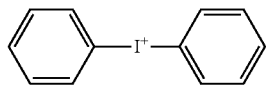
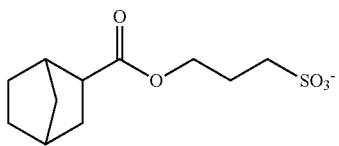
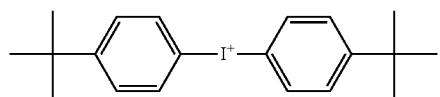
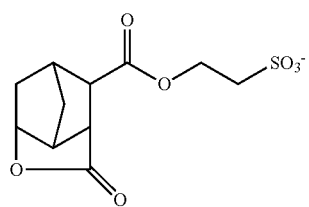
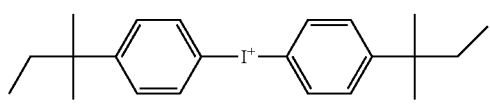
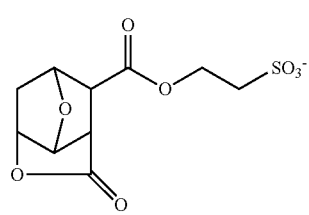
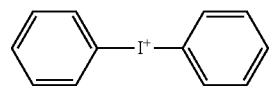
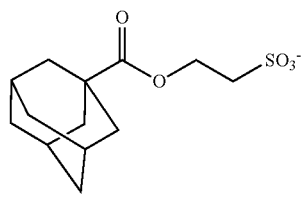
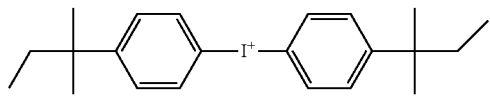
166
-continued
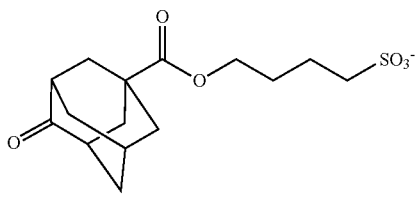
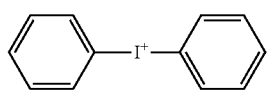
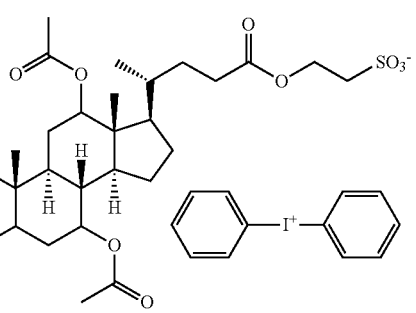
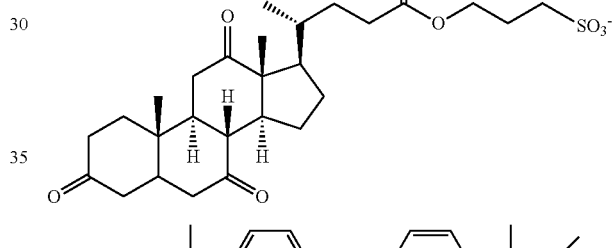
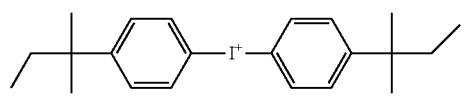
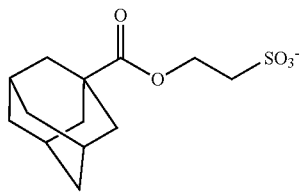
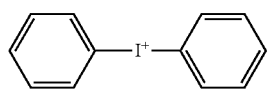
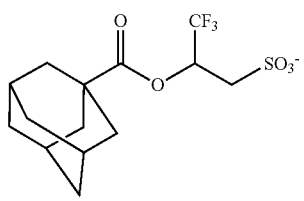
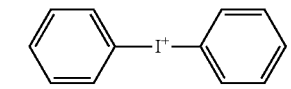

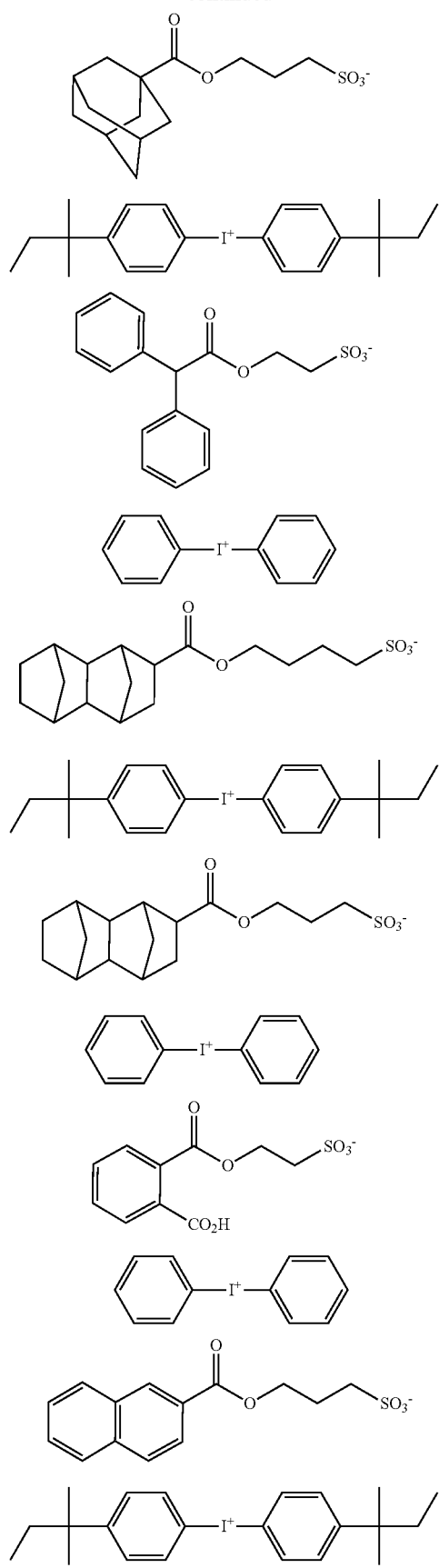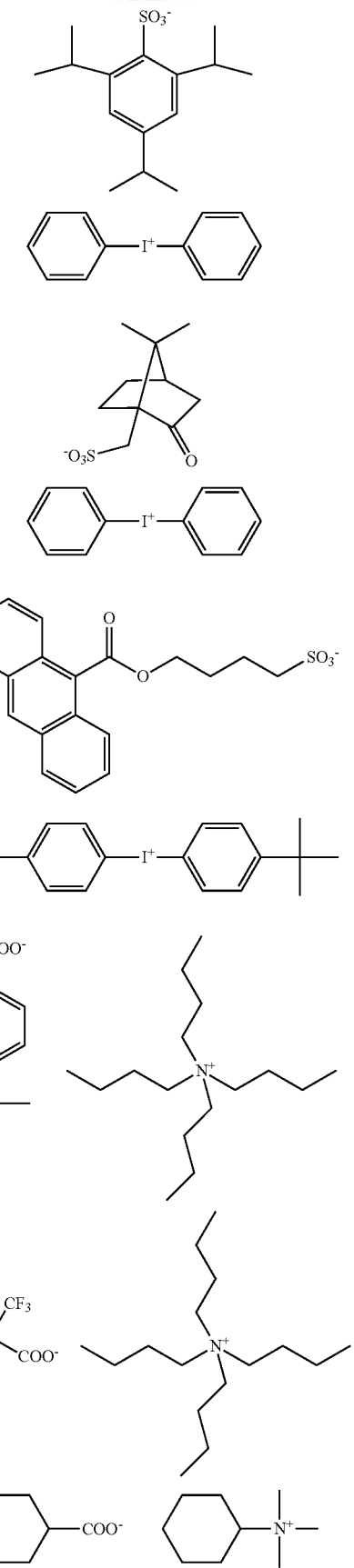

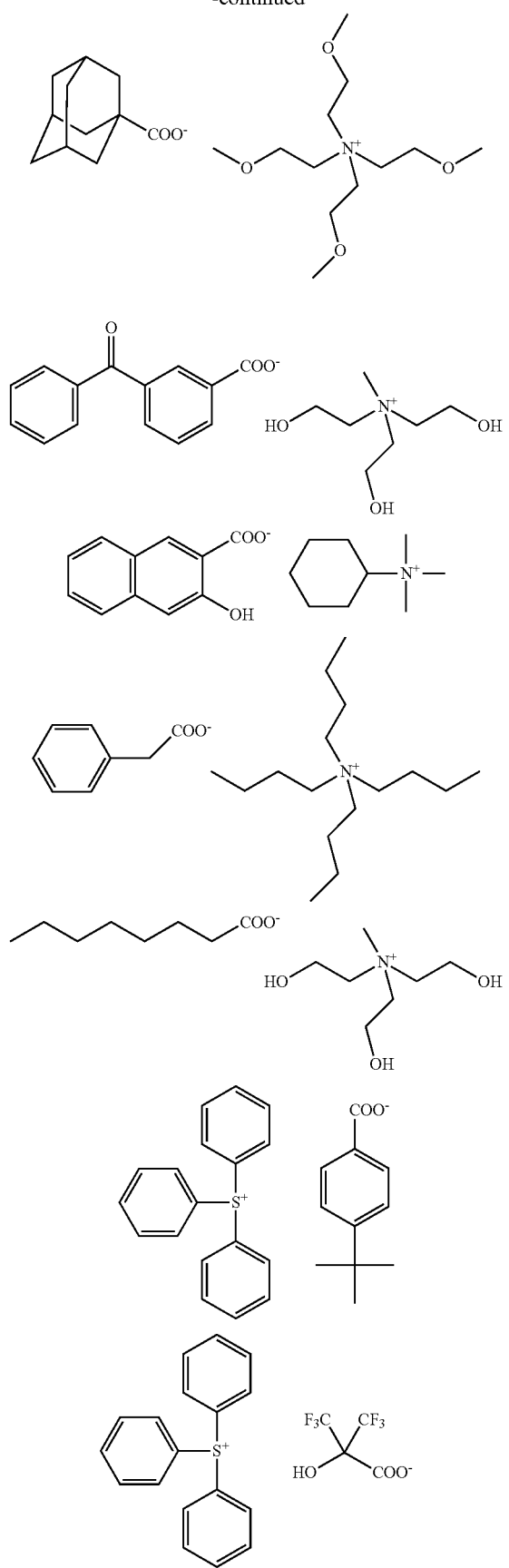
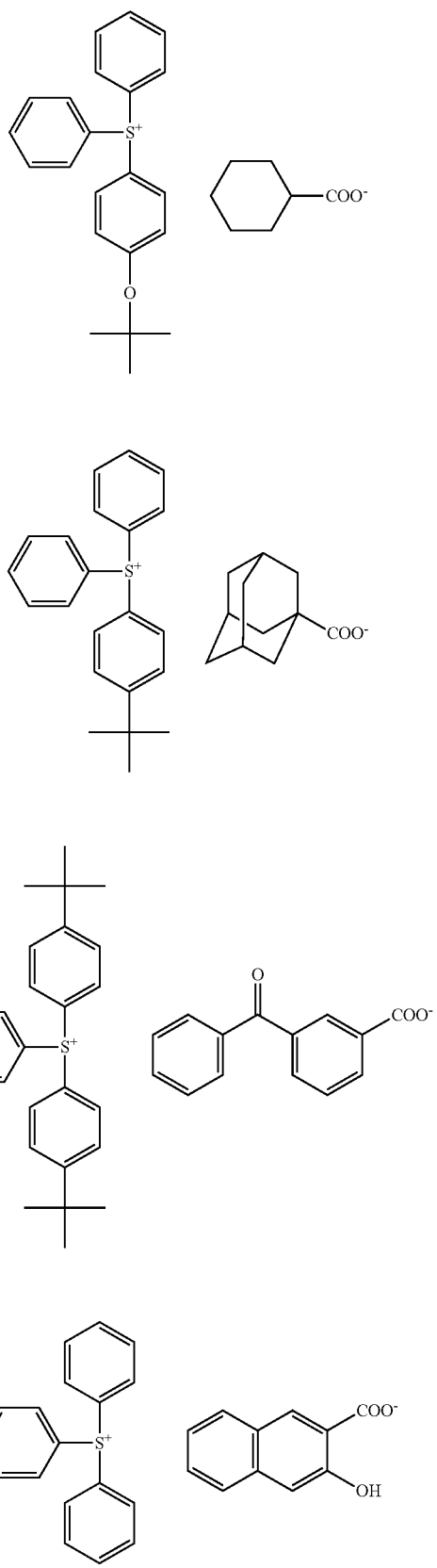

171
-continued
172
-continued
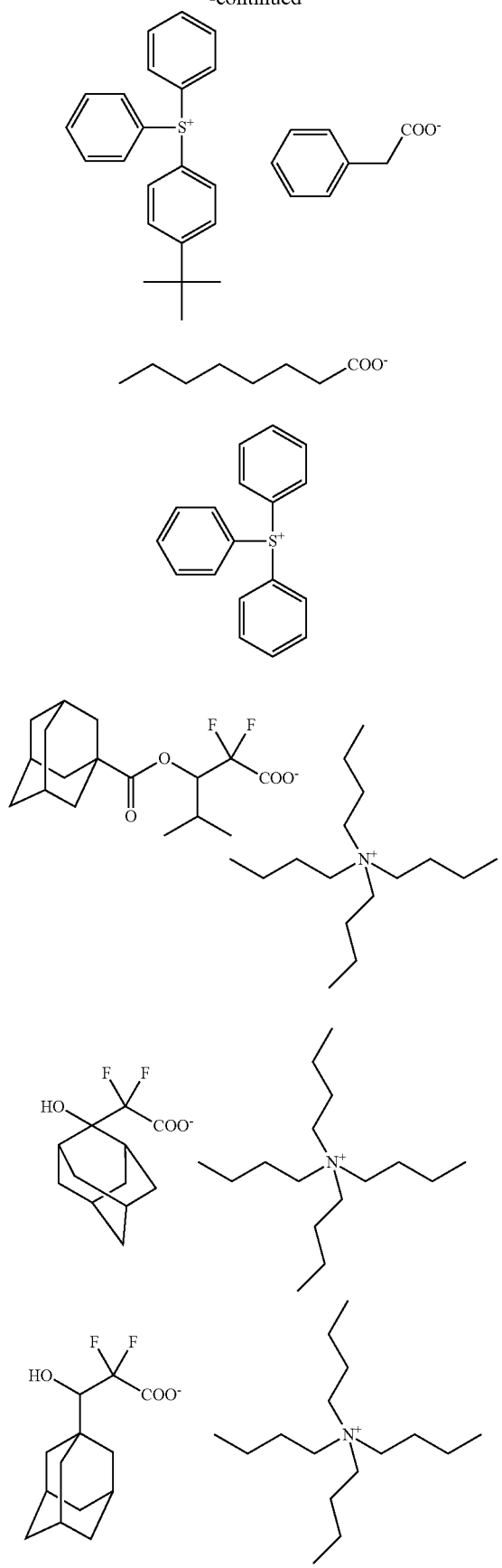
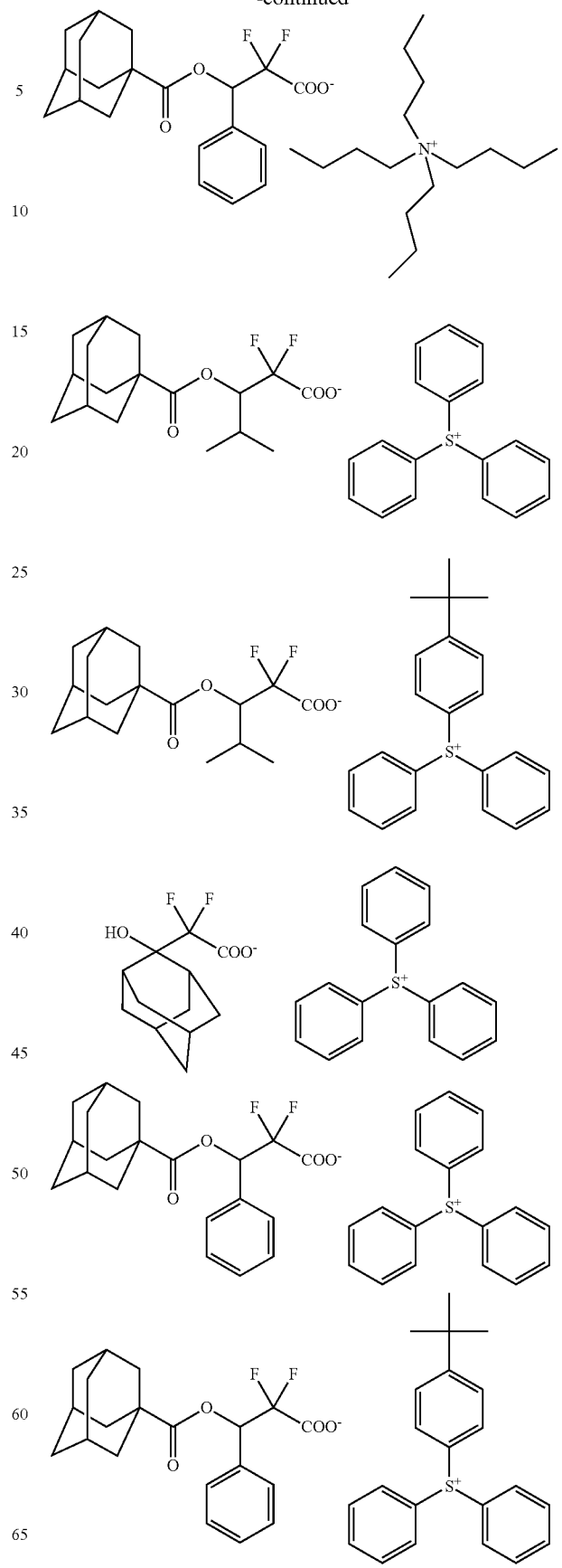

-continued

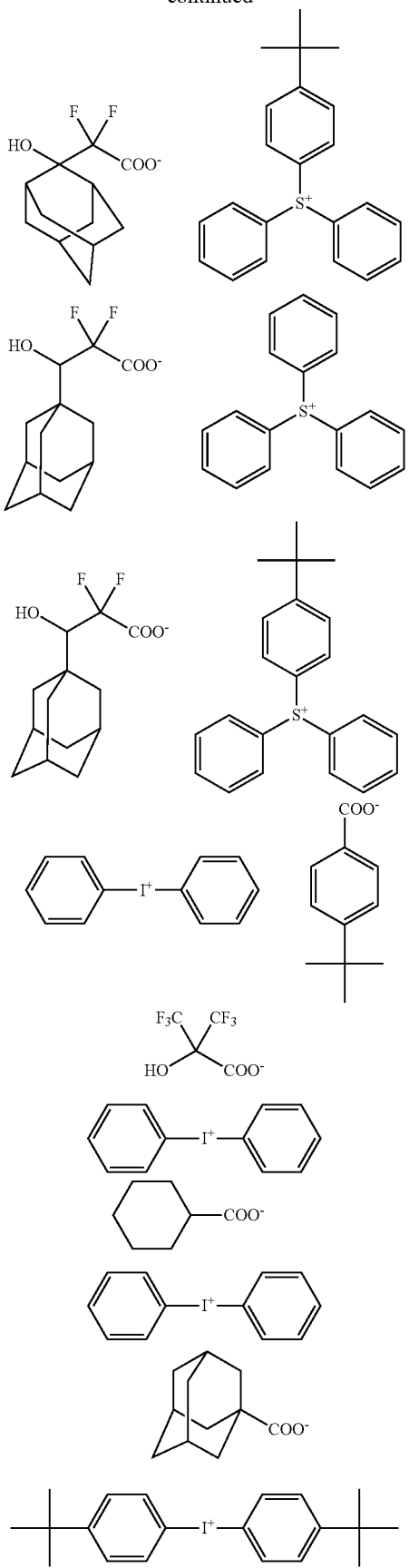

-continued

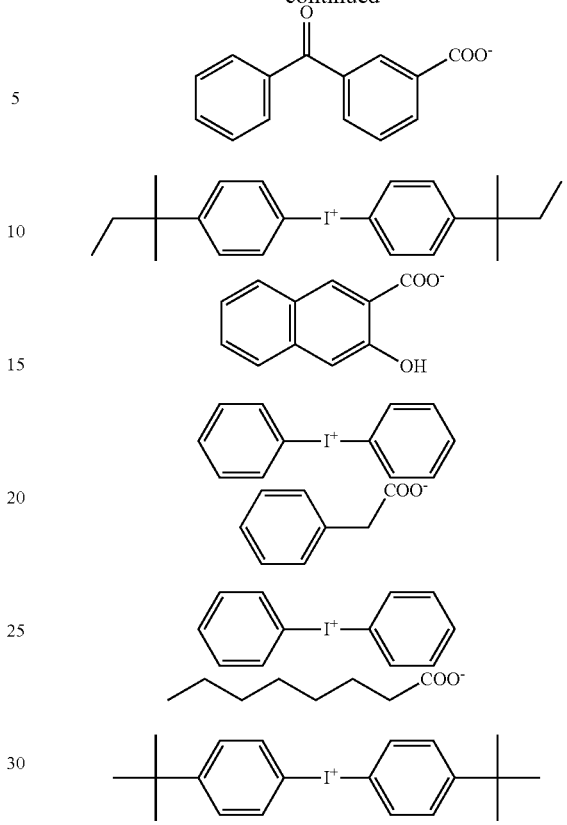

Exemplary surfactants are described in JP-A 2008-111103, paragraphs [0165] to [0166]. Exemplary dissolution regulators are described in JP-A 2008-122932 (US 2008090172), paragraphs [0155] to [0178], and exemplary acetylene alcohols in paragraphs [0179] to [0182].

Notably, an appropriate amount of the organic solvent used is 50 to 10,000 parts, preferably 100 to 5,000 parts by weight, an appropriate amount of the dissolution regulator is 0 to 50 parts, preferably 0 to 40 parts by weight, and an appropriate amount of the basic compound is 0 to 100 parts, preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. This additive may be used in the topcoatless immersion lithography. These additives have a specific structure with a 1,1,1,3,3,3-hexafluoro-2-propanol residue and are described in JP-A 2007-297590, JP-A 2008-111103, JP-A 2008-122932, and JP-A 2012-128067. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, any hole pattern opening failure after development, and bridging of a line-and-space pattern. An appropriate amount of the water repellency improver is 0.1 to 20 parts, preferably 0.5 to 10 parts by weight per 100 parts by weight of the base resin.

Process

When the resist composition of the invention, typically a chemically amplified resist composition comprising a polymer having recurring units of formula (2) and an acid labile group, an acid generator, a basic compound, and an organic solvent is used to form a variety of integrated circuits, any well-known lithography processes are applicable. The process generally involves coating, heat treatment (or prebake), exposure, heat treatment (PEB), and development. If necessary, any additional steps may be added.

The process of forming a positive pattern using an aqueous alkaline solution as developer is well known in the art, for example, from JP-A 2011-231312, paragraphs [0138] to [0146].

Figure 1B:
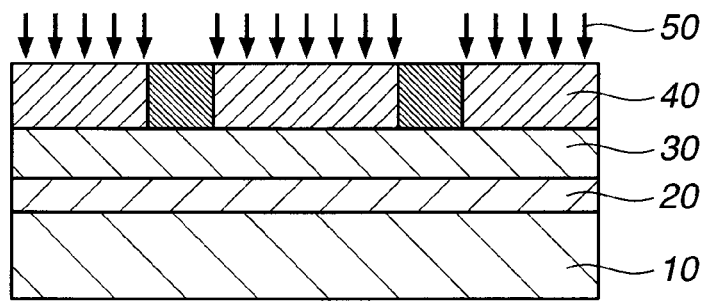
Figure 1C:
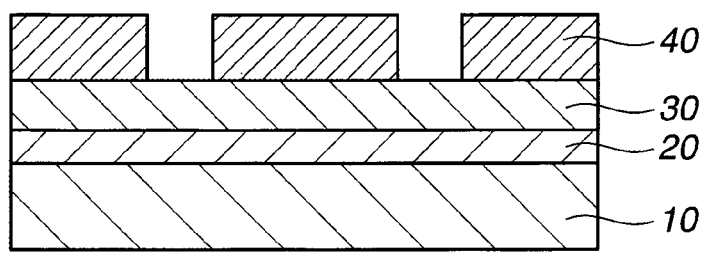

The process of forming a negative pattern using an organic solvent as developer is illustrated in FIG. 1. First, the resist composition is coated on a substrate to form a positive resist film thereon. Specifically, a resist film 40 of a resist composition is formed on a processable substrate 20 disposed on a substrate 10 directly or via an intermediate intervening layer 30 as shown in FIG. 1 (A). The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 300 seconds, especially 15 to 200 seconds.

The substrate 10 used herein is generally a silicon substrate. The processable substrate (or target film) 20 used herein includes $SiO_2$, SiN, SiON, SiOC, p-Si, α-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Next comes exposure depicted at 50 in FIG. 1 (B). For the exposure, preference is given to high-energy radiation having a wavelength of 140 to 250 nm, EUV having a wavelength of 13.5 nm, EB, and especially ArF excimer laser radiation of 193 nm. The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves prebaking a resist film and exposing the resist film to light through a projection lens, with water introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue. While the protective film must dissolve in the organic solvent developer, the polymer comprising recurring units derived from a monomer having a 1,1,1,3,3,3-hexafluoro-2-propanol residue dissolves in organic solvent developers. In particular, protective film-forming materials having 1,1,1,3, 3,3-hexafluoro-2-propanol residues as described in JP-A 2007-025634, 2008-003569, 2008-81716, and 2008-111089 readily dissolve in organic solvent developers.

In the protective film-forming composition, an amine compound or amine salt or a polymer having copolymerized therein recurring units containing an amine group or amine salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful protective film materials having an amino group or amine salt copolymerized are described in JP-A 2007-316448. The amine compound or amine salt may be selected from the compounds enumerated as the basic compound to be added to the resist composition. An appropriate amount of the amine compound or amine salt added is 0.01 to 10 parts, preferably 0.02 to 8 parts by weight per 100 parts by weight of the base resin.

After formation of the photoresist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface edges of holes or lines of a hole or line-and-space pattern after development are bridged. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

A further embodiment of the invention is a process for forming a pattern by applying a resist composition comprising a polymer comprising recurring units having formula (2), an acid generator, and an organic solvent onto a substrate, baking the composition to form a resist film, forming a protective film on the resist film, exposing the resist film to high-energy radiation to define exposed and unexposed regions, baking, and applying an organic solvent developer to the coated substrate to form a negative pattern wherein the unexposed region of resist film and the protective film are dissolved and the exposed region of resist film is not dissolved. The protective film is preferably formed from a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

With respect to the recurring units having a 1,1,1,3,3,3-hexafluoro-2-propanol residue, those monomers having a —C(CF$_3$)(OH) group, i.e., a carbon atom having CF, and OH radicals bonded thereto are preferably selected among the exemplary monomers listed for the recurring unit (D) (some monomers on pages 59 and 60). The amino group-containing compound may be selected from the exemplary amine compounds (to be added to photoresist compositions) described in JP-A 2008-111103, paragraphs [0146] to [0164]. As the amine salt-containing compound, salts of the foregoing amine compounds with carboxylic acid or sulfonic acid may be used.

Suitable alcohols of at least 4 carbon atoms include 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether.

Exposure is preferably performed in an exposure dose of about 1 to 200 mJ/cm$^2$, more preferably about 10 to 100 mJ/cm$^2$. This is followed by baking (PEB) on a hot plate at 60 to 150° C. for 1 to 5 minutes, preferably at 80 to 120° C. for 1 to 3 minutes.

Thereafter the exposed resist film is developed in a developer consisting of an organic solvent for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1 (C). The developer used herein is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof. A surfactant may be added to the developer while it may be selected from the same surfactants listed for the resist composition.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. Suitable aromatic solvents include toluene, xylene, ethylbenzene, isopropylbenzene, tert-butylbenzene, and mesitylene. The solvents may be used alone or in admixture.

While rinsing is effective for mitigating collapse and defect formation in the resist pattern, rinsing is not essential. If the rinsing step is omitted, the amount of solvent used in the process may be reduced.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

EXAMPLE

Synthesis Examples and Examples of the invention are given below by way of illustration and not by way of limitation. The abbreviation "pbw" is parts by weight. For all polymers, Mw and Mn are determined versus polystyrene standards by GPC using tetrahydrofuran (THF) solvent.

Synthesis Example 1

Synthesis of Monomers

A series of monomers and polymerizable acyloxy-ketone compounds as monomer precursor were synthesized according to the following formulation.

Synthesis Example 1

1-1

Synthesis of Methacryloyloxyketone 1

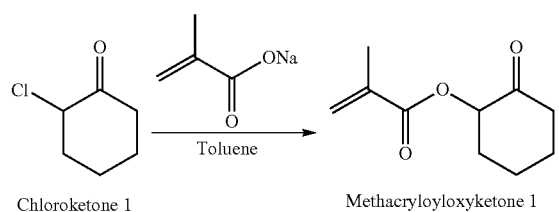

Chloroketone 1                Methacryloyloxyketone 1

Chloroketone 1 (297 g) was added to a suspension of sodium methacrylate (300 g) in toluene (3,000 mL), which was aged at 90° C. for 40 hours. The reaction solution was cooled whereupon water (1,000 mL) was added to quench the reaction. This was followed by standard aqueous workup and solvent distillation. On vacuum distillation, 384 g of Methacryloyloxyketone 1 was obtained (yield 94%).

b.p.: 72° C./10 Pa $^1$H-NMR (600 MHz in DMSO-$d_6$): δ=1.53 (1H, m), 1.71 (1H, m), 1.76-1.86 (2H), 1.88 (3H, s), 1.98 (1H, m), 2.24 (1H, m), 2.28 (1H, m), 2.54 (1H, ddd), 5.25 (1H, dd), 5.71 (1H, m), 6.06 (1H, m) ppm Synthesis Example 1-1-2

Synthesis of Monomer 1

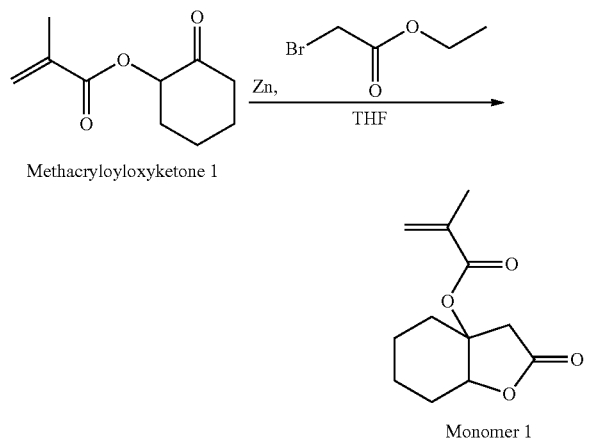

In a nitrogen atmosphere, zinc powder (36 g) was suspended in THF (400 mL). Then 1,2-dibromoethane (4.7 g) and chlorotrimethylsilane (0.8 g) were added to the suspension, which was heated under reflux for 30 minutes for activating zinc. To the activated zinc-THF suspension, a mixture of Methacryloyloxyketone 1 (98 g), ethyl bromoacetate (84 g) and THF (100 mL) was added dropwise at 55° C., followed by aging at 60° C. for 2 hours. Under ice cooling, 10% aqueous hydrochloric acid (110 g) was added to quench the reaction. This was followed by standard aqueous workup. After the solvent was distilled off, the product was purified by silica gel column chromatography, obtaining 82 g (yield 73%) of Monomer 1.

IR (D-ATR): ν=2940, 2867, 1788, 1717, 1636, 1455, 1378, 1362, 1325, 1302, 1292, 1255, 1211, 1162, 1120, 1072, 1041, 1021, 984, 952, 940, 905, 852, 835, 815, 720, 698, 657 cm$^{-1}$ $^1$H-NMR (600 MHz in DMSO-$d_6$): δ=1.31-1.52 (4H), 1.64 (1H, m), 1.84 (3H, s), 1.94-2.08 (3H), 2.94 (1H, d), 3.14 (1H, d), 4.62 (1H, dd), 5.70 (1H, m), 6.03 (1H, m) ppm Synthesis Example 1-1-3

Synthesis of Monomer 1 (Alternative Route)

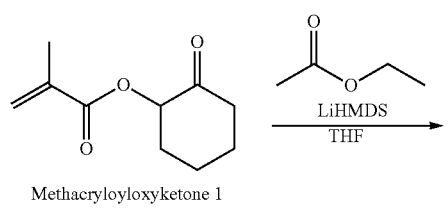

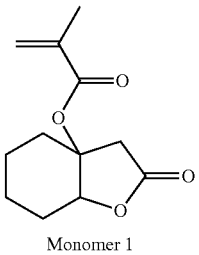

Monomer 1 was synthesized by reacting Methacryloyloxyketone 1 of Synthesis Example 1-1-1 with lithium enolate prepared from ethyl acetate.

A THF solution (78 mL) of 1.3M lithium hexamethyldisilazide was cooled at −50° C., to which ethyl acetate (5.3 g) was added dropwise. Stirring was continued at the temperature for 10 minutes. To the resulting enolate solution kept at −40° C., a solution of Methacryloyloxyketone 1 (9.1 g) in THF (10 mL) was added dropwise. Stirring was continued at −40° C. for 30 minutes. With cooling interrupted, the solution was warmed up to 0° C. over 4 hours, after which 10% aqueous hydrochloric acid (10 g) was added to quench the reaction. This was followed by standard aqueous workup and solvent distillation. The product was purified by silica gel column chromatography, obtaining 7.8 g (yield 70%) of Monomer 1.

Synthesis Example 1-2-1

Synthesis of Methacryloyloxyketone 2

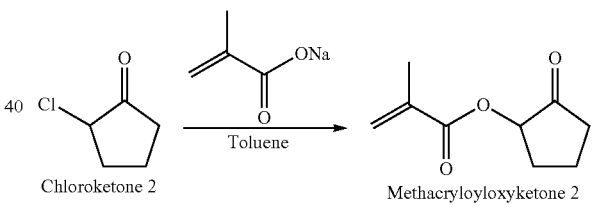

Methacryloyloxyketone 2 was synthesized by the same procedure as in Synthesis Example 1-1-1 aside from using Chloroketone 2 as the reactant. Yield 91%.

b.p.: 64° C./10 Pa $^1$H-NMR (600 MHz in CDCl$_3$): δ=1.85-1.92 (2H), 1.94 (3H, s), 2.11 (1H, m), 2.23 (1H, m), 2.37 (1H, m), 2.44 (1H, m), 5.11 (1H, m), 5.61 (1H, m), 6.15 (1H, m) ppm Synthesis Example 1-2-2

Synthesis of Monomer 2

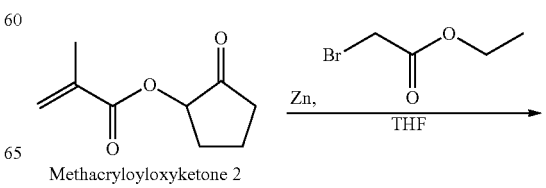

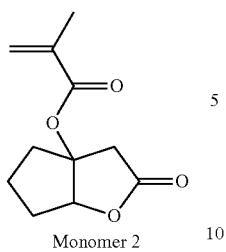

Monomer 2

Monomer 2 was synthesized by the same procedure as in Synthesis Example 1-1-2 aside from using Methacryloyloxyketone 2 as the reactant. Yield 69%.

IR (D-ATR): ν=2970, 2876, 1785, 1717, 1636, 1450, 1407, 1379, 1328, 1301, 1280, 1222, 1163, 1130, 1117, 1095, 1049, 1015, 987, 964, 911, 876, 864, 843, 725, 650, 584 cm$^{-1}$ $^1$H-NMR (600 MHz in DMSO-d$_6$): δ=1.64 (1H, m), 1.72-1.80 (2H), 1.86 (3H, s), 1.88-2.00 (2H), 2.22 (1H, m), 3.03 (2H, m), 4.96 (1H, m), 5.70 (1H, m), 6.05 (1H, m) ppm Synthesis Example 1-3-1

Synthesis of Methacryloyloxyacetoxyketone 1

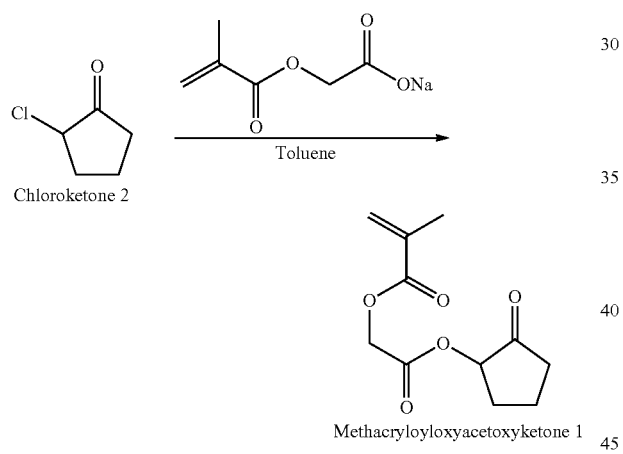

Methacryloyloxyacetoxyketone 1 was synthesized by the same procedure as in Synthesis Example 1-2-1 aside from using sodium methacryloyloxyacetate as the reactant. Yield 87%.

Synthesis Example 1-3-2

Synthesis of Monomer 3

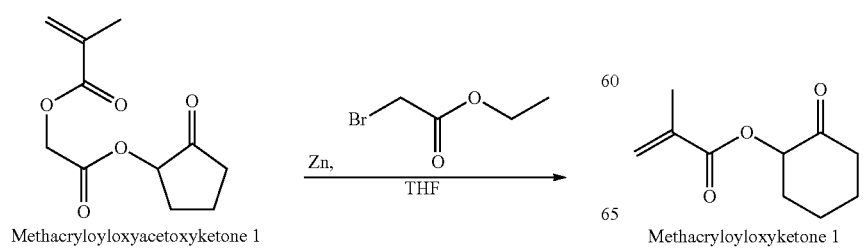

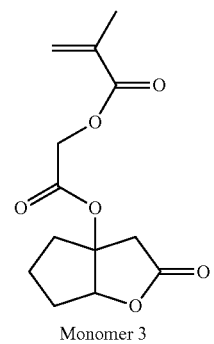

Monomer 3

Monomer 3 was synthesized by the same procedure as in Synthesis Example 1-1-2 aside from using Methacryloyloxyacetoxyketone 1 as the reactant. Yield 61%.

Synthesis Example 1-4

Synthesis of Monomer 4

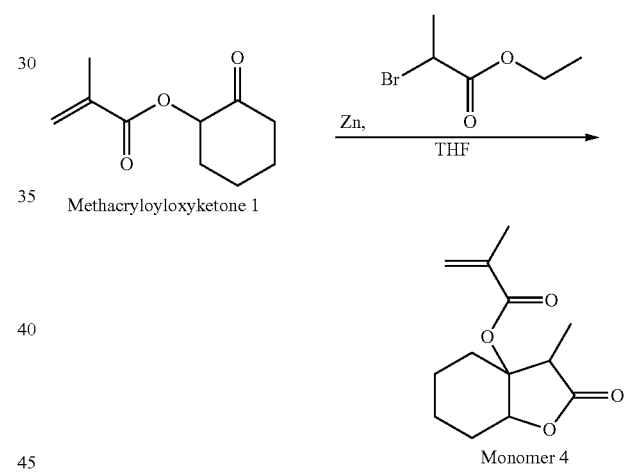

Monomer 4

Monomer 4 was synthesized by the same procedure as in Synthesis Example 1-1-2 aside from using ethyl 2-bromopropionate as the reactant. Yield 70%.

Synthesis Example 1-5

Synthesis of Monomer 5

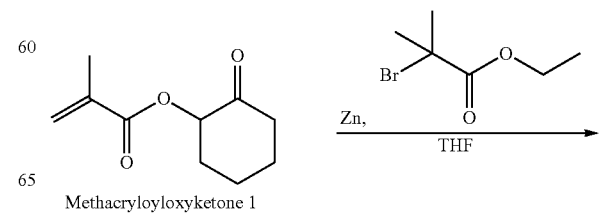

-continued

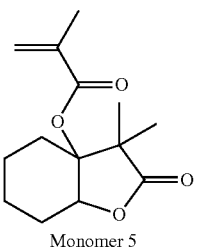

Monomer 5

Monomer 5 was synthesized by the same procedure as in Synthesis Example 1-1-2 aside from using ethyl 2-bromoisobutyrate as the reactant. Yield 71%.

Synthesis Example 1-6-1

Synthesis of Acryloyloxyketone 1

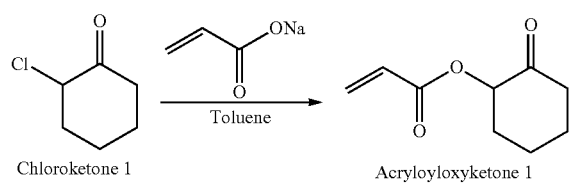

Chloroketone 1                Acryloyloxyketone 1

Acryloyloxyketone 1 was synthesized by the same procedure as in Synthesis Example 1-1-1 aside from using sodium acrylate as the reactant. Yield 89%.

Synthesis Example 1-6-2

Synthesis of Monomer 6

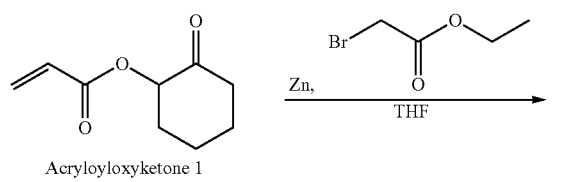

Acryloyloxyketone 1

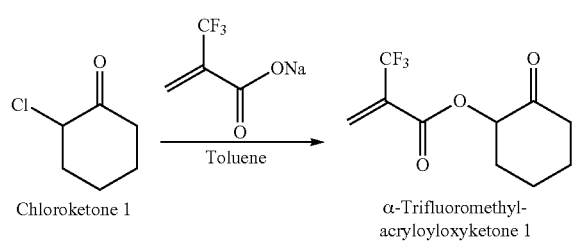

Monomer 6

Monomer 6 was synthesized by the same procedure as in Synthesis Example 1-1-2 aside from using Acryloyloxyketone 1 as the reactant. Yield 60%.

Synthesis Example 1-7-1

Synthesis of α-Trifluoromethylacryloyloxyketone 1

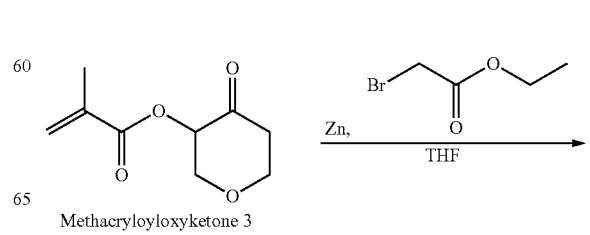

Chloroketone 1                α-Trifluoromethyl-
                              acryloyloxyketone 1

α-Trifluoromethylacryloyloxyketone 1 was synthesized by the same procedure as in Synthesis Example 1-1-1 aside from using sodium α-trifluoromethylacrylate as the reactant. Yield 79%.

Synthesis Example 1-7-2

Synthesis of Monomer 7

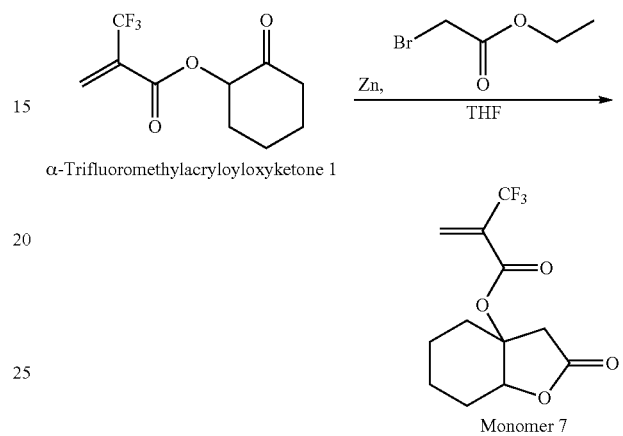

α-Trifluoromethylacryloyloxyketone 1

Monomer 7

Monomer 7 was synthesized by the same procedure as in Synthesis Example 1-1-2 aside from using α-Trifluoromethylacryloyloxyketone 1 as the reactant. Yield 55%.

Synthesis Example 1-8-1

Synthesis of Methacryloyloxyketone 3

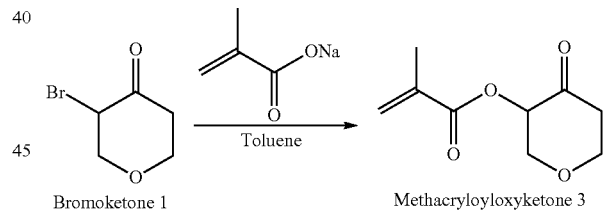

Bromoketone 1                 Methacryloyloxyketone 3

Methacryloyloxyketone 3 was synthesized by the same procedure as in Synthesis Example 1-1-1 aside from using Bromoketone 1 as the reactant. Yield 82%.

Synthesis Example 1-8-2

Synthesis of Monomer 8

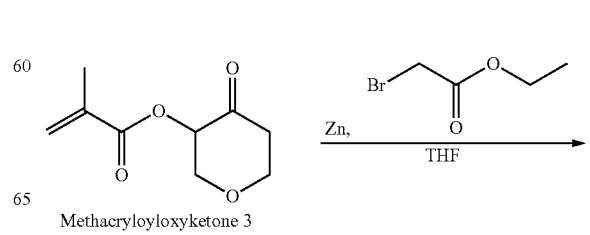

Methacryloyloxyketone 3

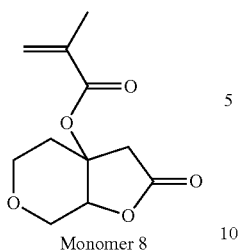

Monomer 8

Monomer 8 was synthesized by the same procedure as in Synthesis Example 1-1-2 aside from using Methacryloyloxyketone 3 as the reactant. Yield 74%.

Synthesis Example 1-9-1

Synthesis of Methacryloyloxyketone 4

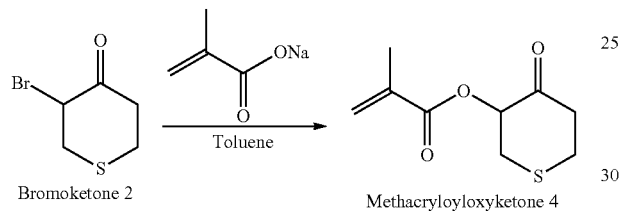

Methacryloyloxyketone 4 was synthesized by the same procedure as in Synthesis Example 1-1-1 aside from using Bromoketone 2 as the reactant. Yield 83%.

Synthesis Example 1-9-2

Synthesis of Monomer 9

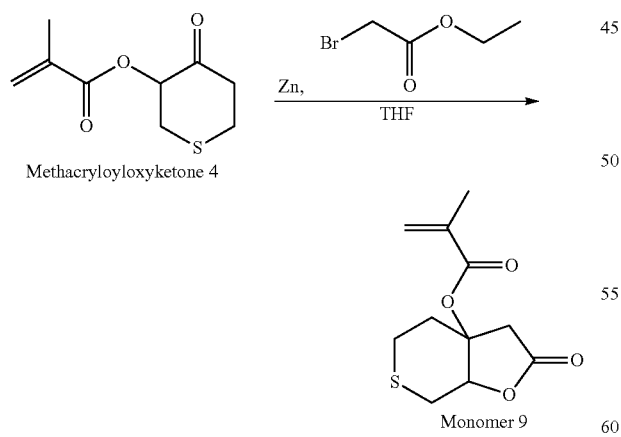

Monomer 9 was synthesized by the same procedure as in Synthesis Example 1-1-2 aside from using Methacryloyloxyketone 4 as the reactant. Yield 69%.

A list of Monomers 1 to 9 obtained in Synthesis Example 1 are shown by the structural formula.

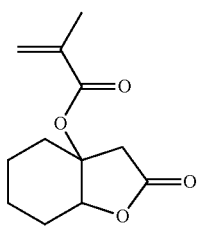

Monomer 1

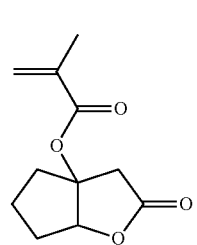

Monomer 2

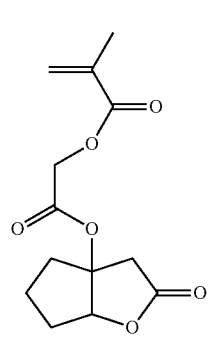

Monomer 3

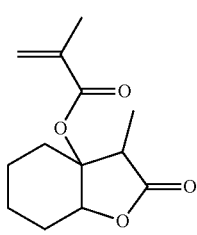

Monomer 4

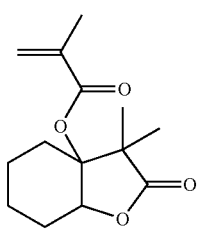

Monomer 5

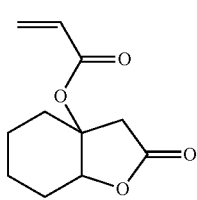

Monomer 6

-continued

Monomer 7

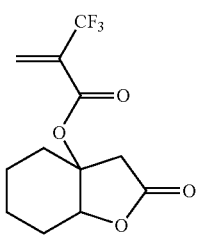

Monomer 8

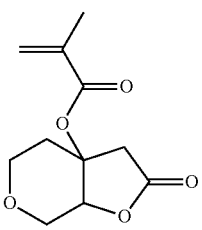

Monomer 9

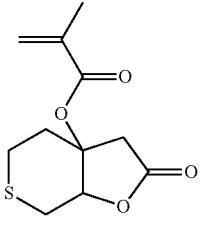

Synthesis Example 2

Synthesis of Polymers

A series of polymers for use in resist compositions were synthesized by dissolving selected monomers in propylene glycol monomethyl ether acetate (PGMEA), copolymerization reaction, crystallizing from methanol, repeatedly washing with methanol, isolation and drying. The composition of a polymer was analyzed by $^1$H-NMR spectroscopy, and the Mw and Mw/Mn determined by GPC. The polymers are designated Resist Polymers 1 to 18 and Comparative Resist Polymers 1 to 7.

Resist Polymer 1
Mw=8,500
Mw/Mn=1.67

-continued

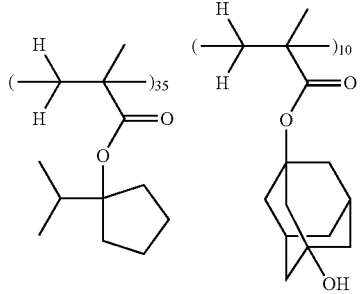

Resist Polymer 2
Mw=8,400
Mw/Mn=1.65

Polymer 2

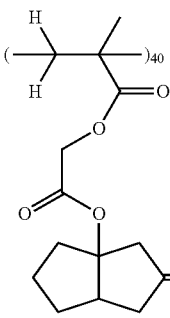 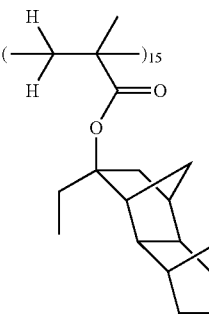

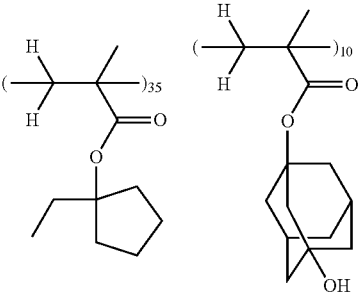

Resist Polymer 3
Mw=8,300
Mw/Mn=1.67

Polymer 3

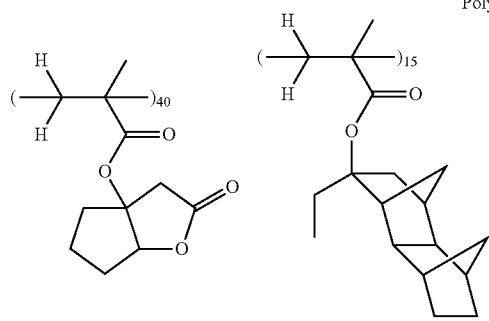

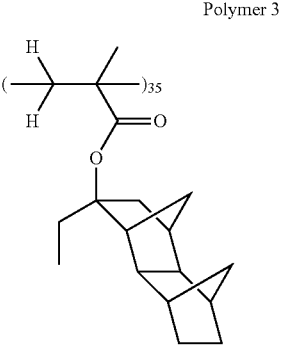

Polymer 1

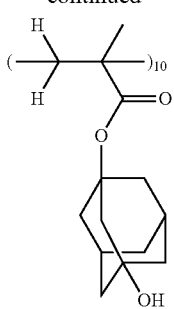
Resist Polymer 4
Mw=8,300
Mw/Mn=1.67
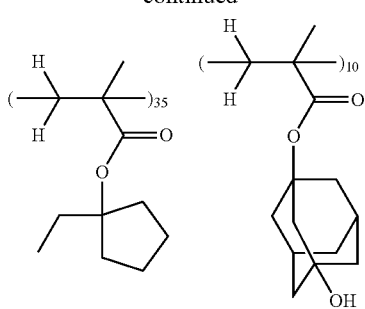
Resist Polymer 6
Mw=8,600
Mw/Mn=1.61
Polymer 4
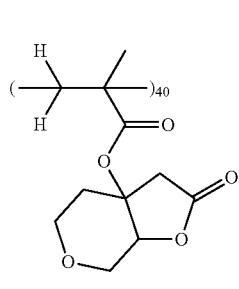 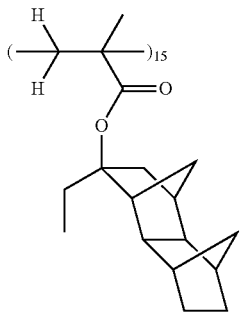
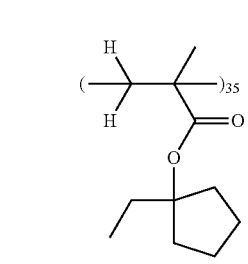 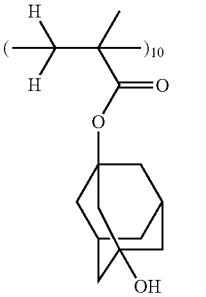
Resist Polymer 5
Mw=8,500
Mw/Mn=1.66
Polymer 6
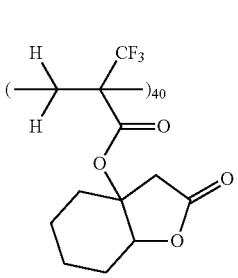 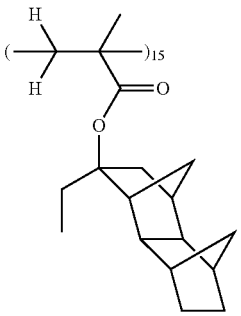
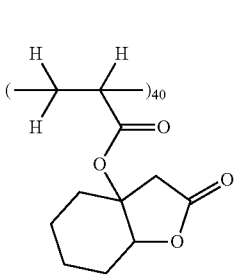 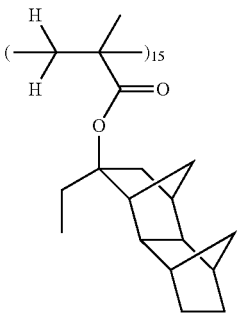
Resist Polymer 7
Mw=8,400
Mw/Mn=1.67
Polymer 5
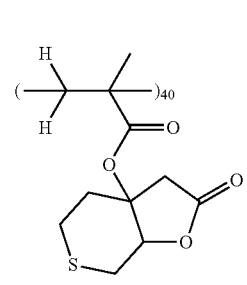 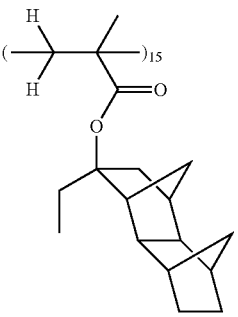
Polymer 7

-continued
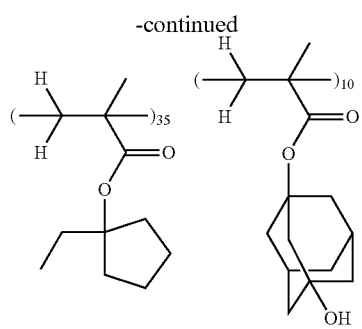
Resist Polymer 8
Mw=8,500
Mw/Mn=1.62
Polymer 8
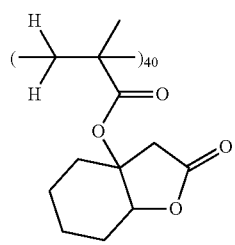
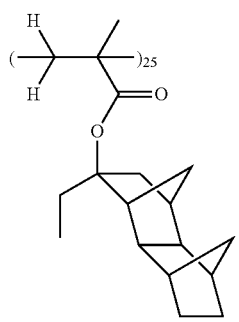
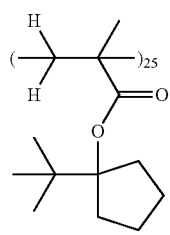
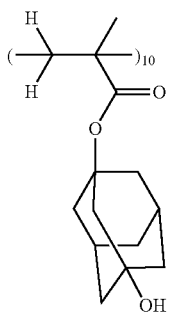
Resist Polymer 9
Mw=8,500
Mw/Mn=1.64
Polymer 9
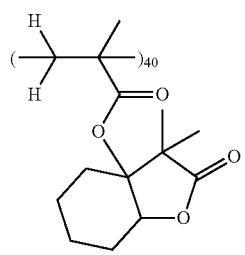
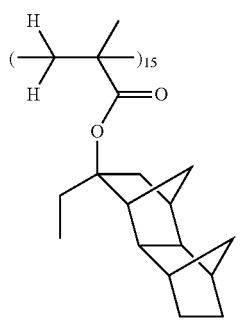
-continued
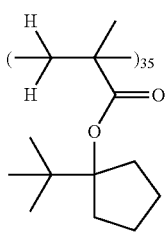
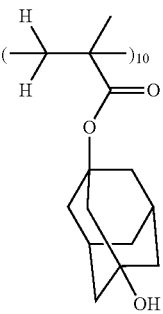
Resist Polymer 10
Mw=8,600
Mw/Mn=1.62
Polymer 10
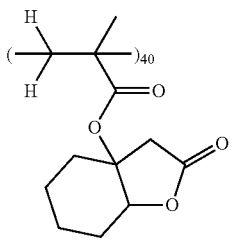
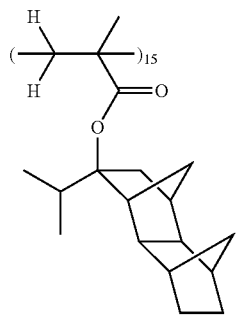
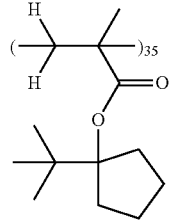
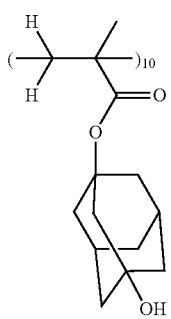
Resist Polymer 11
Mw=8,300
Mw/Mn=1.61
Polymer 11
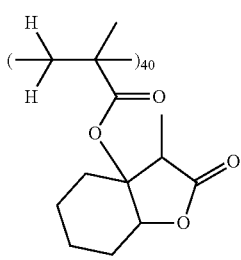
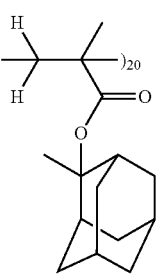

-continued
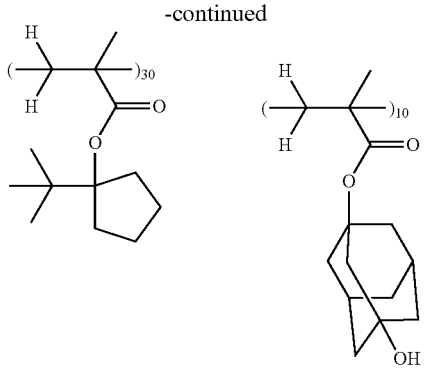
Resist Polymer 12
Mw=8,500
Mw/Mn=1.63
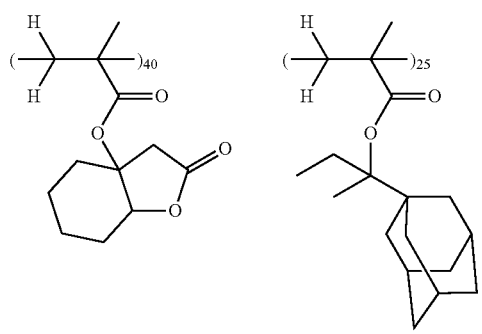
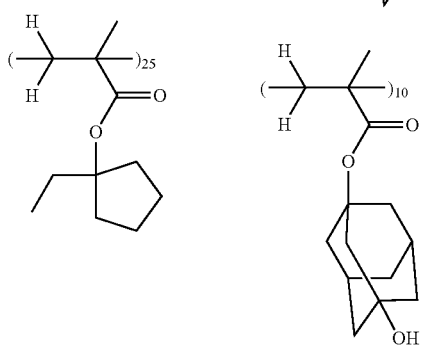
Resist Polymer 13
Mw=8,600
Mw/Mn=1.66
Polymer 12
Polymer 13
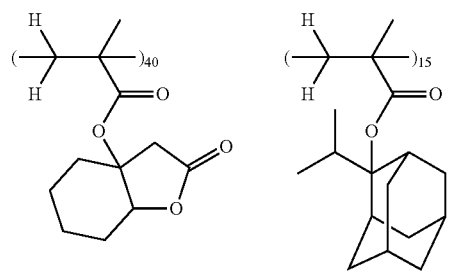
-continued
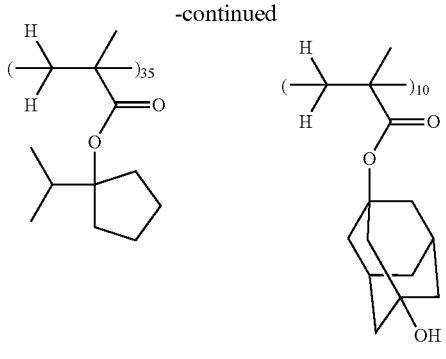
Resist Polymer 14
Mw=8,400
Mw/Mn=1.61
Polymer 14
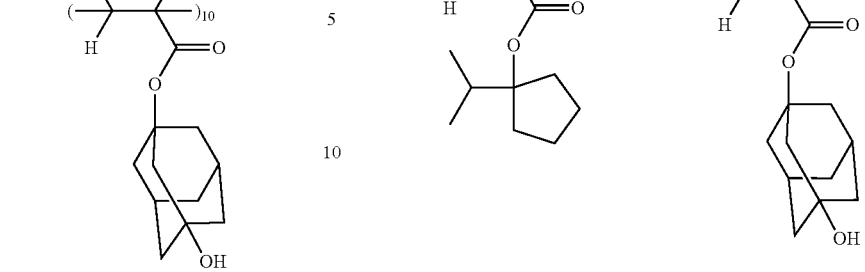
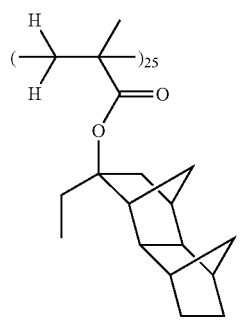
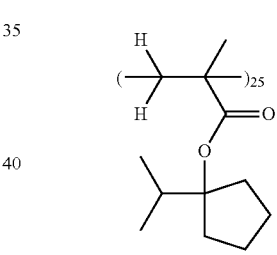
Resist Polymer 15
Mw=8,300
Mw/Mn=1.58
Polymer 15
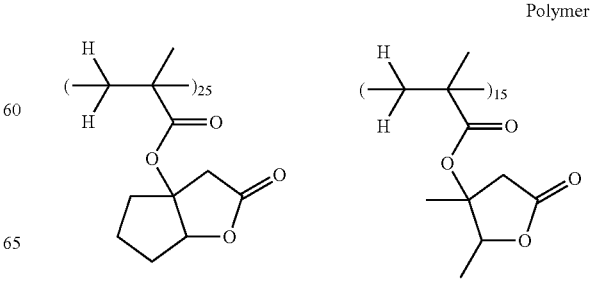
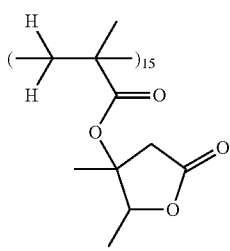

-continued
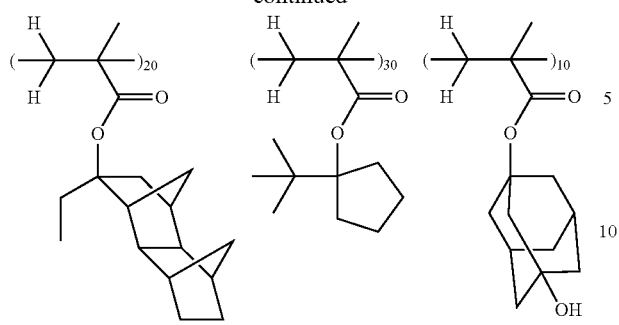
Resist Polymer 16
Mw=8,300
Mw/Mn=1.58
Polymer 16
-continued
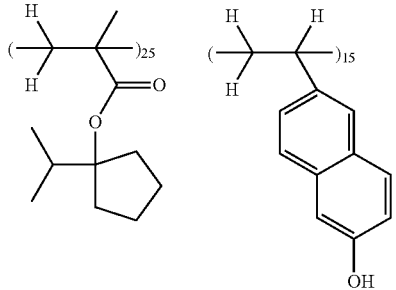
Resist Polymer 18
Mw=8,800
Mw/Mn=1.68
Polymer 18
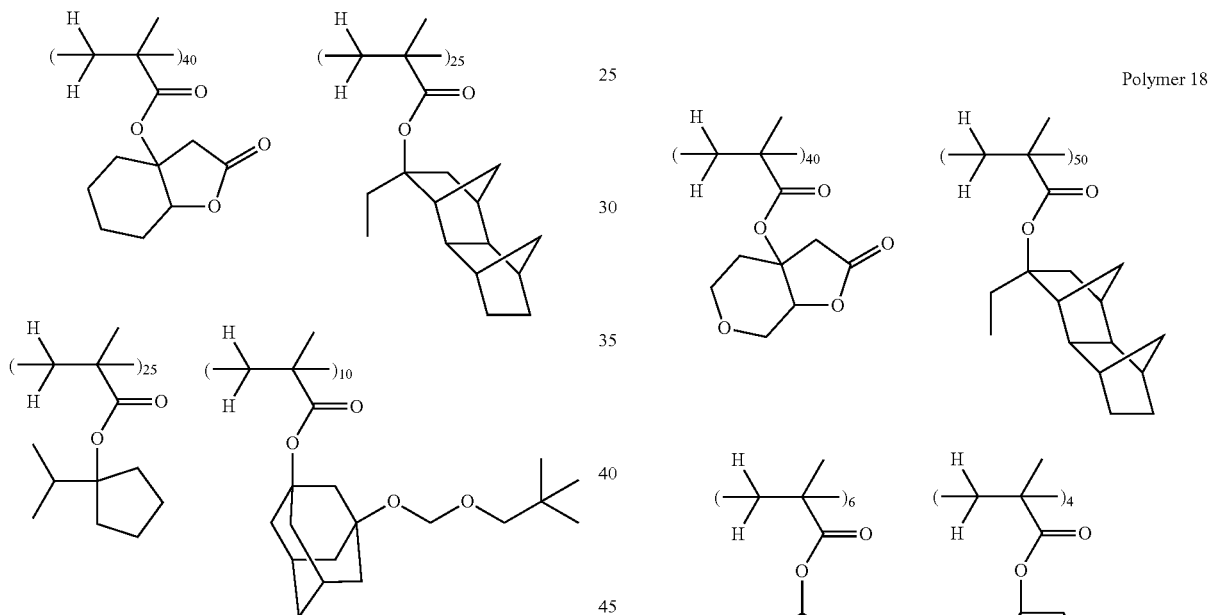
Resist Polymer 17
Mw=8,300
Mw/Mn=1.61
Polymer 17
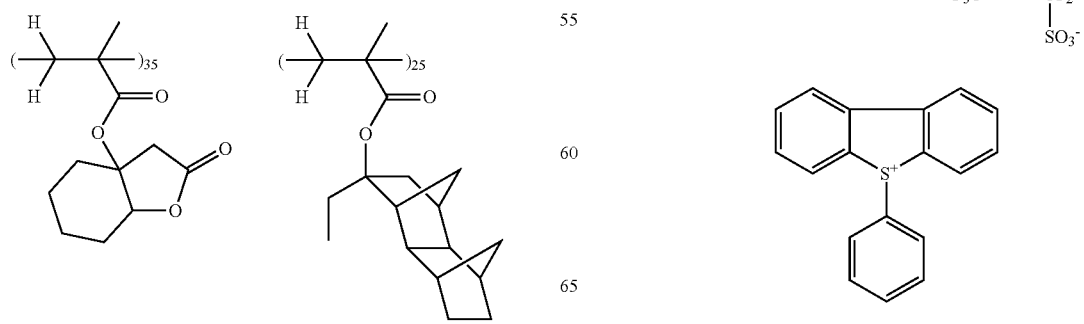
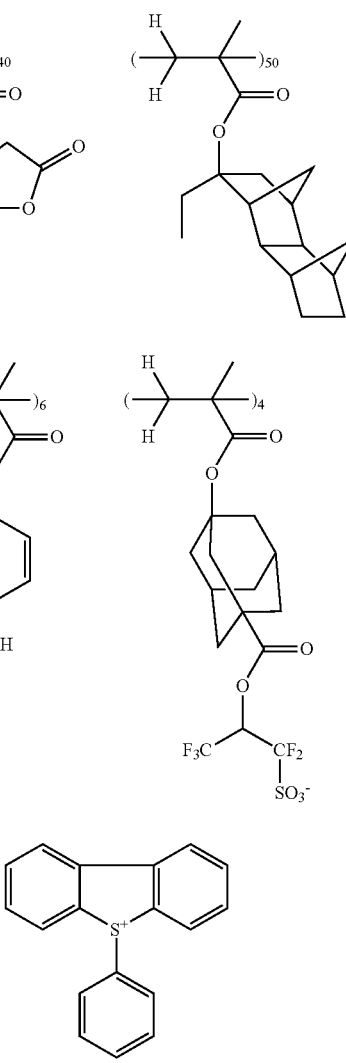
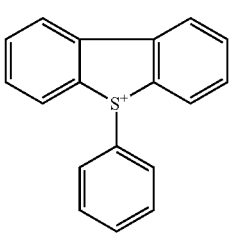

Comparative Resist Polymer 1
  Mw=8,600
  Mw/Mn=1.62
Comparative Polymer 1
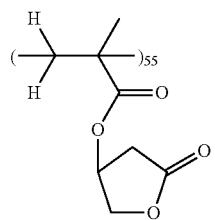
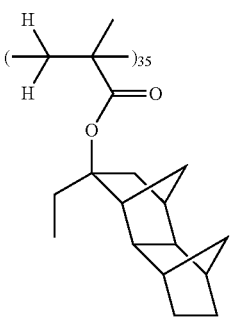
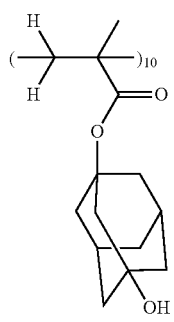
Comparative Resist Polymer 2
  Mw=8,500
  Mw/Mn=1.63
Comparative Polymer 2
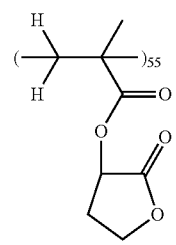
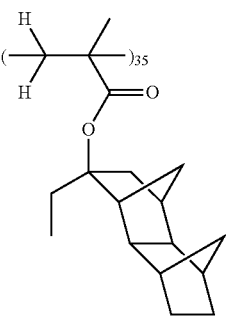
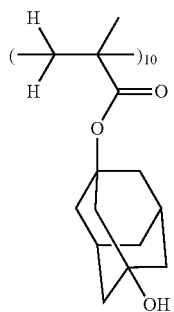
Comparative Resist Polymer 3
  Mw=8,700
  Mw/Mn=1.65
Comparative Polymer 3
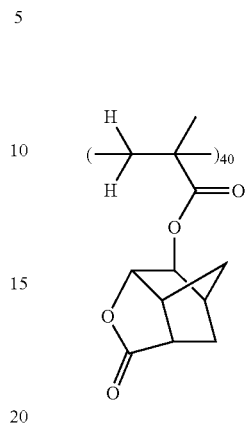
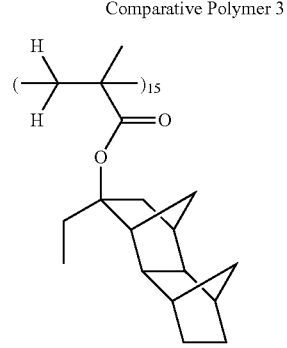
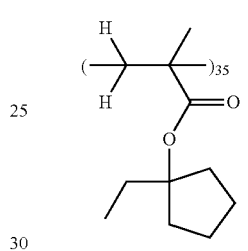
Comparative Resist Polymer 4
  Mw=8,600
  Mw/Mn=1.62
Comparative Polymer 4
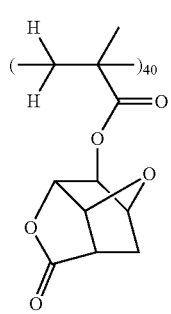
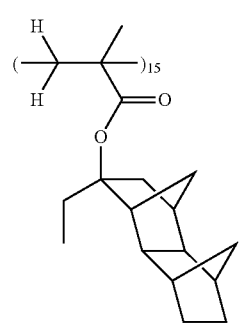
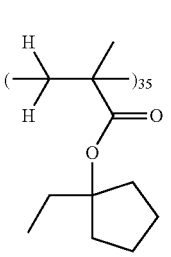
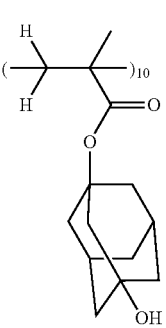

Comparative Resist Polymer 5
 Mw=8,400
 Mw/Mn=1.66

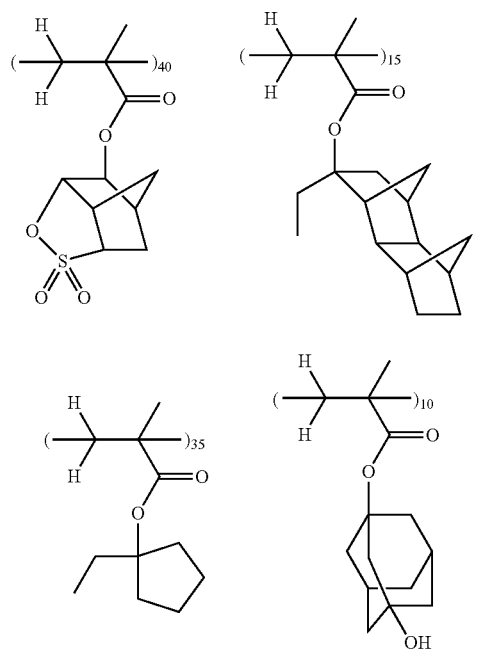

Comparative Polymer 5

Comparative Resist Polymer 6
 Mw=8,600
 Mw/Mn=1.63

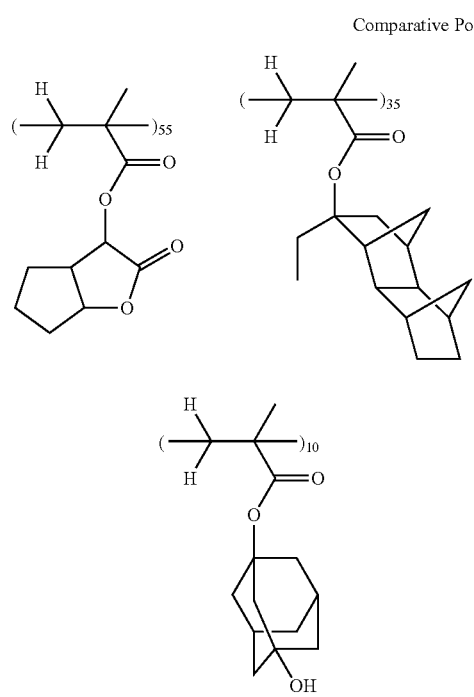

Comparative Polymer 6

Comparative Resist Polymer 7
 Mw=8,400
 Mw/Mn=1.59

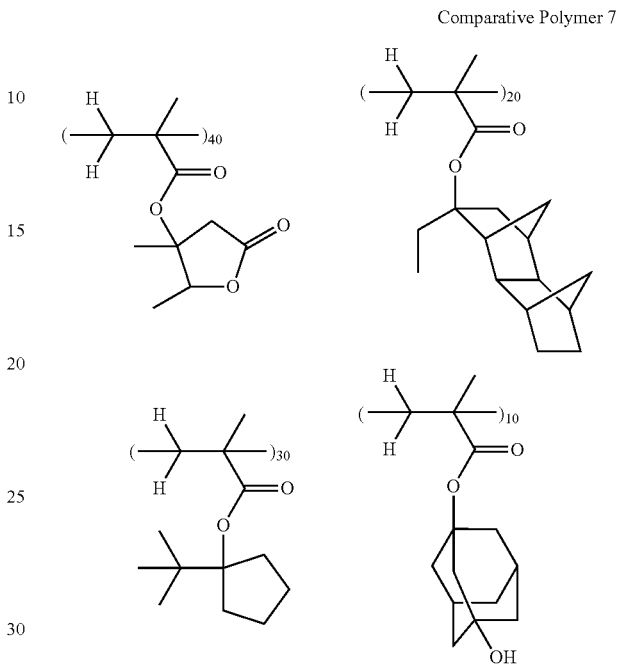

Comparative Polymer 7

Examples 1-1 to 1-19 and Comparative Examples 1-1 to 1-9

Preparation of Resist Composition

Resist compositions R-1 to R-19 and Comparative Resist compositions R-20 to R-28 in solution form were prepared by dissolving a polymer (Resist Polymers 1 to 18 or Comparative Resist Polymers 1 to 7) as base resin, photoacid generator, sensitivity adjustor, and water-repellent polymer in a solvent in accordance with the formulation of Table 1 and filtering through a Teflon® filter with a pore size of 0.2 μm. The photoacid generator (PAG-1 to 4), sensitivity adjustor (Q-1 to 6), water-repellent polymer (SF-1, 2), and solvent used herein are identified below.

Photoacid Generator: PAG-1 to 4 Shown Below

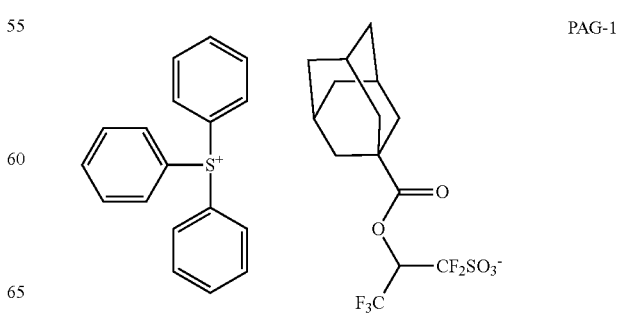

PAG-1

-continued
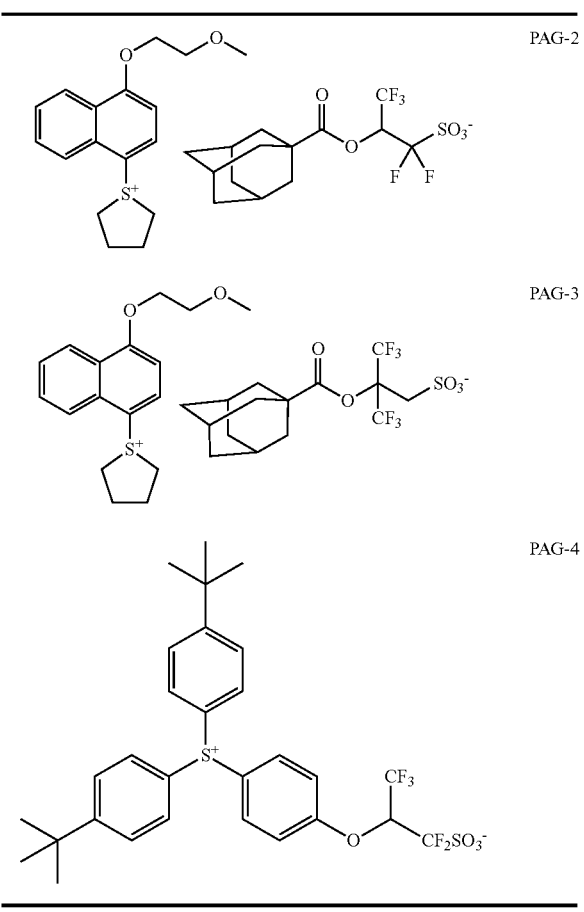
Sensitivity Adjustor: Q-1 to 6 Shown Below
-continued
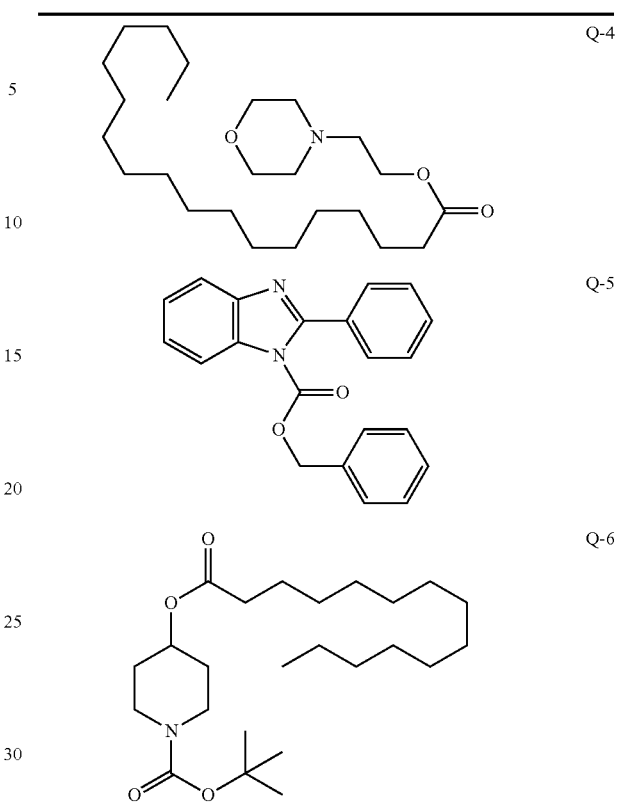
Water-Repellent Polymer: SF-1 and 2 Shown Below
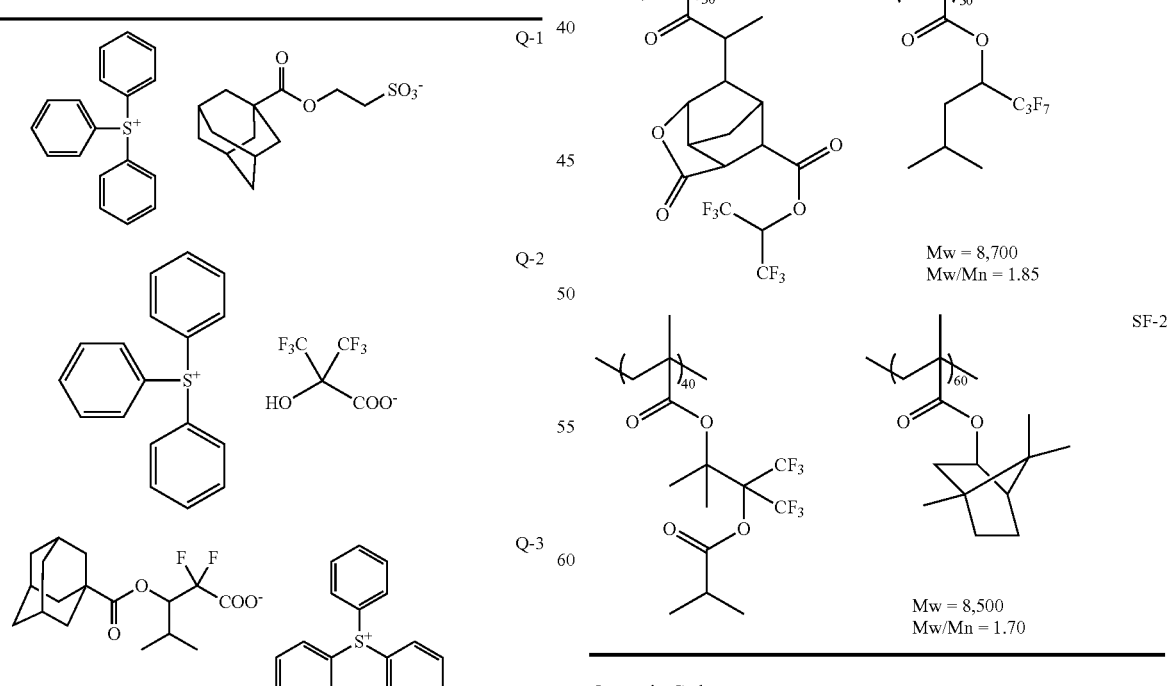
Organic Solvent:
  PGMEA (propylene glycol monomethyl ether acetate)
  GBL (γ-butyrolactone)

TABLE 1

|  | Resist | Resin (pbw) | PAG (pbw) | Sensitivity adjustor (pbw) | Water-repellent polymer (pbw) | Solvent (pbw) |
|---|---|---|---|---|---|---|
| Example 1-1 | R-1 | Polymer 1 (100) | PAG-1 (10.0) | Q-1 (1.5) | SF-1 (6.0) | PGMEA (2,000) GLB (500) |
| 1-2 | R-2 | Polymer 2 (100) | PAG-2 (12.5) | Q-5 (1.5) | SF-1 (6.0) | PGMEA (2,000) GLB (500) |
| 1-3 | R-3 | Polymer 3 (100) | PAG-1 (10.0) | Q-4 (1.5) | SF-1 (6.0) | PGMEA (2,000) GLB (500) |
| 1-4 | R-4 | Polymer 4 (100) | PAG-2 (12.5) | Q-5 (1.5) | SF-1 (6.0) | PGMEA (2,000) GLB (500) |
| 1-5 | R-5 | Polymer 5 (100) | PAG-1 (10.0) | Q-2 (1.5) | SF-1 (6.0) | PGMEA (2,000) GLB (500) |
| 1-6 | R-6 | Polymer 6 (100) | PAG-2 (12.5) | Q-6 (1.5) | SF-1 (6.0) | PGMEA (2,000) GLB (500) |
| 1-7 | R-7 | Polymer 7 (100) | PAG-4 (10.0) | Q-4 (1.5) | SF-1 (6.0) | PGMEA (2,000) GLB (500) |
| 1-8 | R-8 | Polymer 3 (100) | PAG-1 (10.0) | Q-4 (1.5) | SF-2 (6.0) | PGMEA (2,000) GLB (500) |
| 1-9 | R-9 | Polymer 8 (100) | PAG-2 (12.5) | Q-6 (1.5) | SF-2 (6.0) | PGMEA (2,000) GLB (500) |
| 1-10 | R-10 | Polymer 9 (100) | PAG-3 (12.5) | Q-6 (1.5) | SF-2 (6.0) | PGMEA (2,000) GLB (500) |
| 1-11 | R-11 | Polymer 10 (100) | PAG-4 (10.0) | Q-3 (1.5) | SF-2 (6.0) | PGMEA (2,000) GLB (500) |
| 1-12 | R-12 | Polymer 11 (100) | PAG-3 (12.5) | Q-5 (1.5) | SF-2 (6.0) | PGMEA (2,000) GLB (500) |
| 1-13 | R-13 | Polymer 12 (100) | PAG-4 (10.0) | Q-6 (1.5) | SF-2 (6.0) | PGMEA (2,000) GLB (500) |
| 1-14 | R-14 | Polymer 13 (100) | PAG-4 (10.0) | Q-4 (1.5) | SF-2 (6.0) | PGMEA (2,000) GLB (500) |
| 1-15 | R-15 | Polymer 14 (100) | PAG-2 (12.5) | Q-6 (1.5) | SF-2 (6.0) | PGMEA (2,000) GLB (500) |
| 1-16 | R-16 | Polymer 15 (100) | PAG-4 (10.0) | Q-3 (1.5) | SF-2 (6.0) | PGMEA (2,000) GLB (500) |
| 1-17 | R-17 | Polymer 16 (100) | PAG-3 (12.5) | Q-6 (1.5) | SF-2 (6.0) | PGMEA (2,000) GLB (500) |
| 1-18 | R-18 | Polymer 17 (100) | PAG-1 (10.0) | Q-1 (1.5) | SF-2 (6.0) | PGMEA (2,000) GLB (500) |
| 1-19 | R-19 | Polymer 18 (100) | — | Q-1 (1.5) | SF-2 (6.0) | PGMEA (2,000) GLB (500) |
| Comparative Example 1-1 | R-20 | Comparative Polymer 1 (100) | PAG-1 (10.0) | Q-1 (1.5) | SF-1 (6.0) | PGMEA (2,000) GLB (500) |
| 1-2 | R-21 | Comparative Polymer 2 (100) | PAG-2 (12.5) | Q-5 (1.5) | SF-1 (6.0) | PGMEA (2,000) GLB (500) |
| 1-3 | R-22 | Comparative Polymer 3 (100) | PAG-1 (10.0) | Q-1 (1.5) | SF-1 (6.0) | PGMEA (2,000) GLB (500) |
| 1-4 | R-23 | Comparative Polymer 4 (100) | PAG-2 (12.5) | Q-5 (1.5) | SF-1 (6.0) | PGMEA (2,000) GLB (500) |
| 1-5 | R-24 | Comparative Polymer 5 (100) | PAG-1 (10.0) | Q-1 (1.5) | SF-1 (6.0) | PGMEA (2,000) GLB (500) |
| 1-6 | R-25 | Comparative Polymer 1 (100) | PAG-1 (10.0) | Q-1 (1.5) | SF-2 (6.0) | PGMEA (2,000) GLB (500) |
| 1-7 | R-26 | Comparative Polymer 2 (100) | PAG-3 (12.5) | Q-6 (1.5) | SF-2 (6.0) | PGMEA (2,000) GLB (500) |
| 1-8 | R-27 | Comparative Polymer 6 (100) | PAG-3 (12.5) | Q-6 (1.5) | SF-2 (6.0) | PGMEA (2,000) GLB (500) |
| 1-9 | R-28 | Comparative Polymer 7 (100) | PAG-4 (10.0) | Q-3 (1.5) | SF-2 (6.0) | PGMEA (2,000) GLB (500) |

Examples 2-1 to 2-7 and Comparative Examples 2-1 to 2-5

ArF Lithography Patterning Test 1: Evaluation of Positive Pattern

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-1 to R-7) or comparative resist composition (R-20 to R-24) shown in Table 1 was spin coated, then baked on a hot plate at 100° C. for 60 seconds to form a resist film of 80 nm thick.

Using an ArF excimer laser immersion lithography stepper NSR-610C (Nikon Corp., NA 1.30, a 0.98/0.78, dipole opening 20 deg., azimuthally polarized illumination, dipole illumination), exposure was performed through a 6% halftone phase shift mask bearing a line pattern with a space width of 40 nm and a pitch of 80 nm (on-wafer size). After the exposure, the wafer was baked (PEB) at the temperature shown in Table 2 for 60 seconds and puddle developed in an aqueous solution of 2.38 wt % tetramethylammonium hydroxide (TMAH) for 30 seconds. The wafer was rinsed with deionized water and spin dried, forming a line-and-space pattern.

A variation in line width of the line-and-space pattern as developed was measured under TDSEM S-9380 (Hitachi Hitechnologies, Ltd.) and reported as line width roughness (LWR).

Evaluation of Sensitivity

As an index of sensitivity, the optimum dose (Eop, mJ/cm$^2$) which provided an L/S pattern with a space width of 40 nm and a pitch of 80 nm was determined. A smaller dose value indicates a higher sensitivity.

Evaluation of Exposure Latitude (EL)

The exposure dose which provided an L/S pattern with a space width of 40 nm±10% (i.e., 36 nm to 44 nm) was determined. EL (%) is calculated from the exposure doses according to the following equation:

$$EL\ (\%)=(|E1-E2|/Eop)\times 100$$

wherein E1 is an exposure dose which provides an L/S pattern with a space width of 36 nm and a pitch of 80 nm, E2 is an exposure dose which provides an L/S pattern with a space width of 44 nm and a pitch of 80 nm, and Eop is the optimum exposure dose which provides an L/S pattern with a space width of 40 nm and a pitch of 80 nm.

Evaluation of Line Width Roughness (LWR)

The L/S pattern formed by exposure in the optimum dose (determined in the sensitivity evaluation) was observed under TDSEM S-9380 (Hitachi Hitechnologies, Ltd.). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Table 2.

TABLE 2

|  |  | Resist | PEB temp. (° C.) | Eop (mJ/cm$^2$) | EL (%) | LWR (nm) | Pattern profile |
|---|---|---|---|---|---|---|---|
| Example | 2-1 | R-1 | 90 | 42 | 18.6 | 3.4 | rectangular |
|  | 2-2 | R-2 | 90 | 44 | 17.9 | 3.3 | rectangular |
|  | 2-3 | R-3 | 90 | 41 | 17.7 | 3.4 | rectangular |
|  | 2-4 | R-4 | 90 | 45 | 19.1 | 3.2 | rectangular |
|  | 2-5 | R-5 | 90 | 42 | 18.6 | 3.3 | rectangular |
|  | 2-6 | R-6 | 90 | 41 | 18.2 | 3.2 | rectangular |
|  | 2-7 | R-7 | 90 | 44 | 17.9 | 3.2 | rectangular |
| Comparative Example | 2-1 | R-20 | 90 | 45 | 13.4 | 4.3 | rectangular |
|  | 2-2 | R-21 | 90 | 43 | 10.6 | 4.5 | T-top |
|  | 2-3 | R-22 | 90 | 42 | 11.8 | 4.7 | rectangular |
|  | 2-4 | R-23 | 90 | 42 | 10.4 | 4.4 | T-top |
|  | 2-5 | R-24 | 90 | 43 | 8.9 | 4.8 | collapsed |

Examples 3-1 to 3-12 and Comparative Examples 3-1 to 3-4

ArF Lithography Patterning Test 2: Evaluation of Negative Pattern by Organic Solvent Development On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-8 to R-19, R-25 to R-28) shown in Table 1 was spin coated, then baked on a hot plate at 100° C. for 60 seconds to form a resist film of 100 nm thick.

Using an ArF excimer laser immersion lithography stepper NSR-610C (Nikon Corp., NA 1.30, σ 0.98/0.78, 4/5 annular illumination), exposure was performed through a 6% halftone phase shift mask bearing a pattern with a pitch of 100 nm and a line width of 50 nm (on-wafer size). After the exposure, the wafer was baked (PEB) at the temperature shown in Table 3 for 60 seconds and developed. Specifically, butyl acetate was injected from a development nozzle while the wafer was spun at 30 rpm for 3 seconds, which was followed by stationary puddle development for 27 seconds. The wafer was rinsed with 4-methyl-2-pentanol, spin dried, and baked at 100° C. for 20 seconds to evaporate off the rinse liquid. On solvent development, the unexposed region of resist film shielded by the mask was dissolved in the developer. This image reversal formed an L/S pattern having a space width of 50 nm and a pitch of 100 nm.

Evaluation of Sensitivity, EL and LWR

For each of the resist compositions, the optimum dose Eop (mJ/cm$^2$), EL and LWR were evaluated as in ArF lithography patterning test 1. The results are shown in Table 3.

TABLE 3

|  |  | Resist | PEB temp. (° C.) | Eop (mJ/cm$^2$) | EL (%) | LWR (nm) | Pattern profile |
|---|---|---|---|---|---|---|---|
| Example | 3-1 | R-8 | 90 | 29 | 18.8 | 3.4 | rectangular |
|  | 3-2 | R-9 | 90 | 28 | 18.9 | 3.3 | rectangular |
|  | 3-3 | R-10 | 90 | 28 | 19.7 | 3.4 | rectangular |
|  | 3-4 | R-11 | 85 | 26 | 20.3 | 3.1 | rectangular |
|  | 3-5 | R-12 | 90 | 28 | 19.3 | 3.3 | rectangular |
|  | 3-6 | R-13 | 85 | 27 | 18.6 | 3.2 | rectangular |
|  | 3-7 | R-14 | 85 | 28 | 19.4 | 3.2 | rectangular |
|  | 3-8 | R-15 | 90 | 30 | 18.8 | 3.5 | rectangular |
|  | 3-9 | R-16 | 90 | 28 | 20.4 | 3.0 | rectangular |
|  | 3-10 | R-17 | 90 | 27 | 18.6 | 3.3 | rectangular |
|  | 3-11 | R-18 | 90 | 28 | 18.8 | 3.5 | rectangular |
|  | 3-12 | R-19 | 90 | 26 | 18.5 | 3.5 | rectangular |
| Comparative Example | 3-1 | R-25 | 90 | 29 | 11.9 | 5.1 | T-top |
|  | 3-2 | R-26 | 90 | 30 | 10.2 | 5.5 | T-top |
|  | 3-3 | R-27 | 90 | 28 | 8.6 | 6.3 | collapsed |
|  | 3-4 | R-28 | 90 | 28 | 12.9 | 4.2 | rectangular |

As seen from the results of Tables 2 and 3, the resist compositions within the scope of the invention are not only effective for forming positive patterns using conventional alkaline developers, but also effective for forming negative patterns via organic solvent development. In either case, L/S patterns of satisfactory profile with minimal roughness (LWR) and improved exposure latitude were obtained.

Examples 4-1 to 4-3 and Comparative Examples 4-1 to 4-2

Etch Resistance Test

On a silicon wafer which had been surface treated in hexamethyldisilazane (HMDS) gas phase at 90° C. for 60 seconds, the resist solution (R-8, R-9, R-10, R-25 or R-27) in Table 1 was spin-coated and baked (PAB) on a hot plate at 100° C. for 60 seconds, forming a resist film of 100 nm thick. Using an ArF excimer laser scanner (NSR-307E by Nikon Corp., NA 0.85), the entire surface of the wafer was subjected to open-frame exposure. The exposure was in a dose of 50 mJ/cm$^2$ so that the PAG might generate sufficient acid to induce deprotection reaction. This was followed by bake (PEB) at 120° C. for 60 seconds for converting the base resin in the resist film to the deprotected state. The portion where the base resin is deprotected corresponds to the insoluble region in negative tone development. A reduction of resist film thickness by exposure and PEB was determined and divided by the initial film thickness, with the result being reported as PEB shrinkage (%).

Further, the resist film was developed for 30 seconds using butyl acetate as developer. The thickness of the resist film after development was measured. A dissolution rate (nm/sec) was computed from a difference between the film thickness after PEB and the film thickness after development. A lower PEB shrinkage or lower dissolution rate is preferable in that a film thickness necessary for dry etching is retained, or the initial film thickness can be reduced, which is advantageous in terms of resolution. The results are shown in Table 4.

TABLE 4

|  |  | Resist | PEB shrinkage (%) | Dissolution rate (nm/sec) |
|---|---|---|---|---|
| Example | 4-1 | R-8 | 10 | 0.13 |
|  | 4-2 | R-9 | 12 | 0.16 |
|  | 4-3 | R-10 | 14 | 0.17 |
| Comparative Example | 4-1 | R-25 | 24 | 0.17 |
|  | 4-2 | R-27 | 24 | 0.23 |

It is evident from Table 4 that the resist compositions within the scope of the invention show a low PEB shrinkage, indicating that a resist film of sufficient thickness is retained after development.

Japanese Patent Application No. 2014-097347 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the general formula (1):

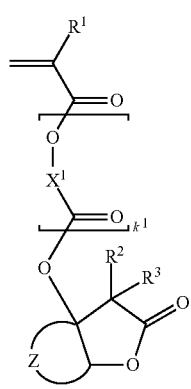

wherein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, and Z forms a 5 or 6-membered alicyclic group, which may contain a heteroatom, with the two carbon atoms to which it is attached.

2. A polymer comprising recurring units having the general formula (2):

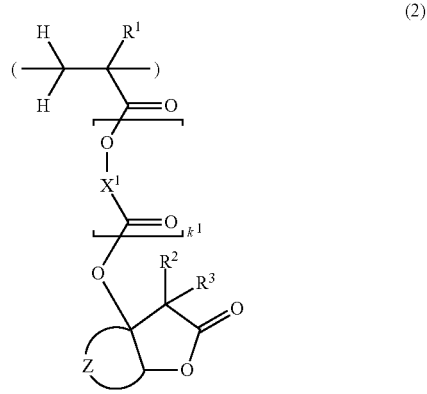

wherein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, and Z forms a 5 or 6-membered alicyclic group, which may contain a heteroatom, with the two carbon atoms to which it is attached.

3. The polymer of claim 2, further comprising recurring units of at least one type selected from recurring units having the general formulae (A) to (E):

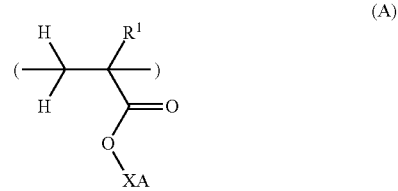

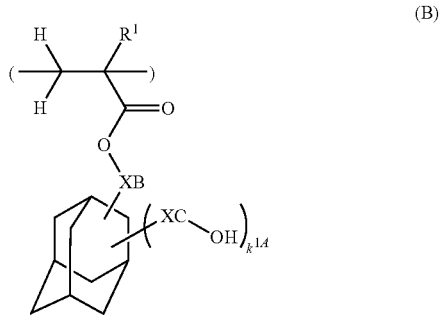

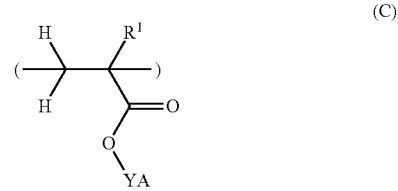

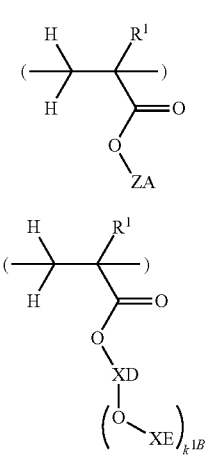

wherein R¹ is hydrogen, methyl or trifluoromethyl, XA is an acid labile group, XB and XC are each independently a single bond or a straight or branched, divalent hydrocarbon group of 1 to 4 carbon atoms, XD is a straight, branched or cyclic, di- to pentavalent aliphatic hydrocarbon group of 1 to 16 carbon atoms in which a constituent —$CH_2$— may be replaced by —O— or —C(=O)—, XE is an acid labile group, YA is a substituent group of lactone, sultone or carbonate structure, ZA is hydrogen, a fluoroalkyl group of 1 to 30 carbon atoms or a fluoroalcohol-containing group of 1 to 15 carbon atoms, $k^{1A}$ is an integer of 1 to 3, and $k^{1B}$ is an integer of 1 to 4.

4. The polymer of claim 2, further comprising recurring units of at least one type selected from sulfonium salt units (d1) to (d3) represented by the following general formula:

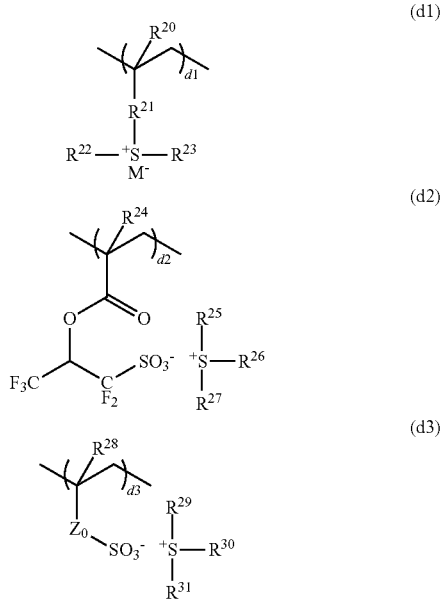

wherein $R^{20}$, $R^{24}$, and $R^{28}$ each are hydrogen or methyl; $R^{21}$ is a single bond, phenylene, —O—$R^{33}$—, or —C(=O)—Y—$R^{33}$—, wherein Y is oxygen or NH and $R^{33}$ is a straight, branched or cyclic $C_1$-$C_6$ alkylene group, alkenylene group or phenylene group, which may contain a carbonyl (—CO—), ester (—COO—), ether (—O—), or hydroxyl moiety; $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether moiety, a $C_6$-$C_{12}$ aryl group, a $C_7$-$C_{20}$ aralkyl group, or a thiophenyl group; $Z_0$ is a single bond, methylene, ethylene, phenylene, fluorinated phenylene, —O—$R^{32}$—, or —C(=O)—$Z_1$—$R^{32}$—, wherein $Z_1$ is oxygen or NH, and $R^{32}$ is a straight, branched or cyclic $C_1$-$C_6$ alkylene group, alkenylene group or phenylene group, which may contain a carbonyl, ester, ether or hydroxyl moiety; and M⁻ is a non-nucleophilic counter ion.

5. A resist composition comprising a base resin containing the polymer of claim 4, and an organic solvent.

6. A resist composition comprising a base resin containing the polymer of claim 2, an acid generator, and an organic solvent.

7. A pattern forming process comprising the steps of applying the resist composition of claim 6 onto a substrate, prebaking to form a resist film, exposing the resist film to high-energy radiation, baking, and developing the exposed resist film in a developer.

8. The process of claim 7 wherein an aqueous alkaline solution is used as the developer in the developing step to form a positive pattern wherein the exposed region of resist film is dissolved away and the unexposed region of resist film is not dissolved.

9. The process of claim 7 wherein an organic solvent is used as the developer in the developing step to form a negative pattern wherein the unexposed region of resist film is dissolved away and the exposed region of resist film is not dissolved.

10. The process of claim 9 wherein the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

11. The process of claim 7 wherein the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

12. A method for preparing a monomer having the general formula (1), comprising the steps of reacting a compound having the general formula (6) with a base or metal to form a metal enolate reagent, and reacting it with an acyloxyketone having the general formula (5):

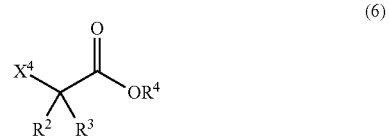

-continued

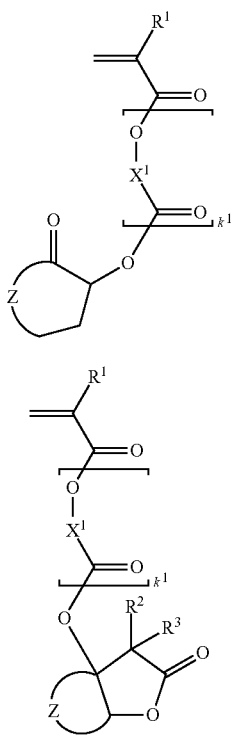

(5)

(1)

wherein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, Z forms a 5 or 6-membered alicyclic group, which may contain a heteroatom, with the two carbon atoms to which it is attached, $X^4$ is hydrogen or halogen, and $R^4$ is a straight, branched or cyclic, monovalent hydrocarbon group of 1 to 10 carbon atoms.

13. The method of claim 12 wherein the acyloxyketone having the general formula (5) is obtained by reacting a cycloalkanone compound having the general formula (3) with an esterifying agent having the general formula (4):

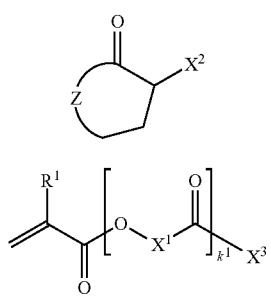

(3)

(4)

wherein $R^1$, $X^1$, Z and $k^1$ are as defined above, $X^2$ is halogen or hydroxyl, $X^3$ is —$OM^b$, halogen, hydroxyl or —$OR^{14}$, $M^b$ is Li, Na, K, $Mg_{1/2}$, $Ca_{1/2}$ or substituted or unsubstituted ammonium, and $R^{14}$ is methyl, ethyl or a group of the formula (9):

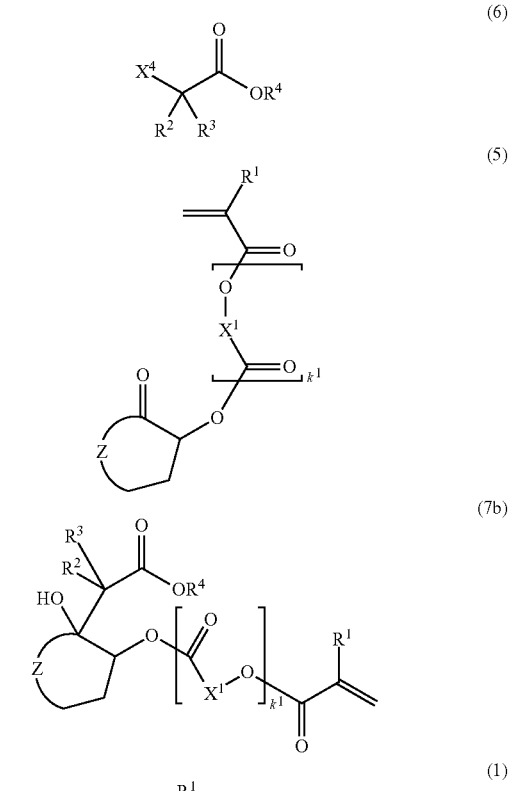

(9)

wherein $R^1$, $X^1$ and $k^1$ are as defined above, and the broken line denotes a valence bond.

14. A method for preparing a monomer having the general formula (1), comprising the steps of reacting a compound having the general formula (6) with a base or metal to form a metal enolate reagent, reacting it with an acyloxyketone having the general formula (5), isolating a hydroxy ester compound having the general formula (7b), and treating it with an acid:

(6)

(5)

(7b)

(1)

wherein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, Z forms a 5 or 6-membered alicyclic group, which may contain a heteroatom, with the two carbon atoms to which it is attached, $X^4$ is hydrogen or halogen, and $R^4$ is a straight, branched or cyclic, monovalent hydrocarbon group of 1 to 10 carbon atoms.

15. A method for preparing a monomer having the general formula (1), comprising the step of reacting a hydroxylactone compound having the general formula (66) with an esterifying agent having the general formula (88):

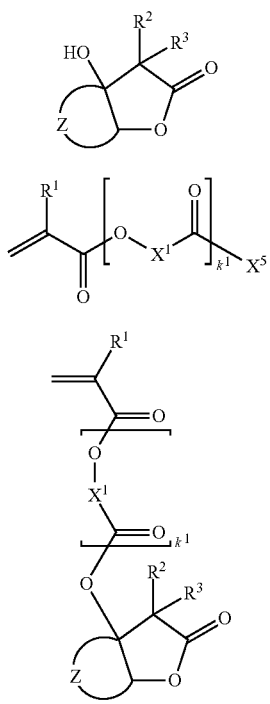

wherein $R^1$ is hydrogen, methyl or trifluoromethyl, $R^2$ and $R^3$ are each independently hydrogen or a straight, branched or cyclic, monovalent hydrocarbon group of 1 to 10 carbon atoms, $R^2$ and $R^3$ may bond together to form an alicyclic group of 5 to 10 carbon atoms, which may be separated by an oxygen atom or have a carbon chain, with the carbon atom to which they are attached, $X^1$ is a straight, branched or cyclic, divalent hydrocarbon group of 1 to 20 carbon atoms in which a constituent —$CH_2$— may be replaced by —O— or —C(=O)—, $k^1$ is 0 or 1, Z forms a 5 or 6-membered alicyclic group, which may contain a heteroatom, with the two carbon atoms to which it is attached, $X^5$ is halogen, hydroxyl or —$OR^{14}$, and $R^{14}$ is methyl, ethyl or a group of the formula (9):

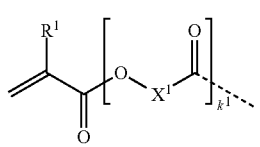

wherein $R^1$, $X^1$ and $k^1$ are as defined above, and the broken line denotes a valence bond.

16. The method of claim 15 wherein the hydroxylactone compound having the general formula (66) is obtained from reaction of a ketone compound of the general formula (33) wherein $P^1$ is a protective group with a compound having the general formula (6) and a base or metal to form a hydroxy ester compound having the general formula (44), deprotection of protective group $P^1$, and acid treatment:

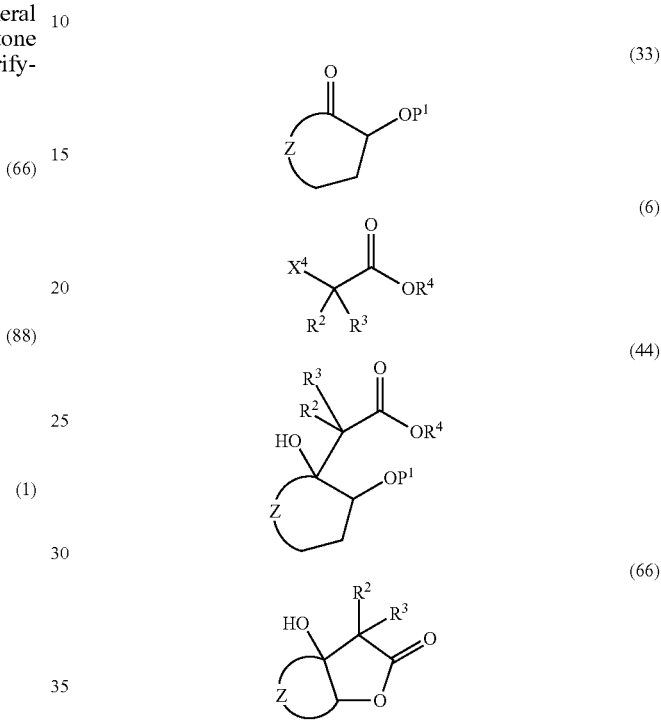

wherein $R^2$, $R^3$ and Z are as defined above, $P^1$ is a protective group, $X^4$ is hydrogen or halogen, and $R^4$ is a straight, branched or cyclic, monovalent hydrocarbon group of 1 to 10 carbon atoms.

17. The method of claim 15 wherein the hydroxylactone compound having the general formula (66) is obtained from reaction of a ketone compound of the general formula (33) wherein $P^1$ is hydrogen with a compound having the general formula (6) and a base or metal:

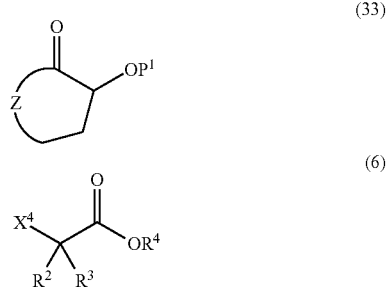

wherein $R^2$, $R^3$ and Z are as defined above, $P^1$ is hydrogen, $X^4$ is hydrogen or halogen, and $R^4$ is a straight, branched or cyclic, monovalent hydrocarbon group of 1 to 10 carbon atoms.

* * * * *